(12) United States Patent
Falco

(10) Patent No.: US 7,071,383 B2
(45) Date of Patent: Jul. 4, 2006

(54) CHIMERIC GENES AND METHODS FOR INCREASING THE LYSINE AND THREONINE CONTENT OF THE SEEDS OF PLANTS

(75) Inventor: Saverio Carl Falco, Arden, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 591 days.

(21) Appl. No.: 10/023,066

(22) Filed: Dec. 17, 2001

(65) Prior Publication Data

US 2003/0056242 A1 Mar. 20, 2003

Related U.S. Application Data

(60) Division of application No. 08/823,771, filed on Mar. 24, 1997, now Pat. No. 6,459,019, which is a division of application No. 08/474,633, filed on Jun. 7, 1995, now Pat. No. 5,773,691, which is a continuation-in-part of application No. 08/178,212, filed as application No. PCT/US93/02480 on Mar. 18, 1993, now abandoned, which is a continuation-in-part of application No. 07/855,414, filed on Mar. 19, 1992, now abandoned.

(51) Int. Cl.
*A01H 5/00* (2006.01)
*C12N 15/82* (2006.01)

(52) U.S. Cl. .................. 800/298; 800/278; 800/287
(58) Field of Classification Search ............... 800/298, 800/278, 287, 281
See application file for complete search history.

(56) References Cited

U.S. PATENT DOCUMENTS

| 4,886,878 A | * | 12/1989 | Larkins et al. ............. 536/2.6 |
| 5,024,944 A | * | 6/1991 | Collins et al. ............ 435/172.3 |
| 5,367,110 A | * | 11/1994 | Galili et al. ................ 300/205 |

FOREIGN PATENT DOCUMENTS

| EP | 0 435 132 | 7/1991 |
| EP | 0 485 970 | 11/1991 |
| WO | WO 89/11789 | 12/1989 |
| WO | 8911789 | * 12/1989 |
| WO | WO 93/1910 | 9/1993 |
| WO | WO 95/15392 | 6/1995 |
| WO | WO 95/34672 | 12/1995 |
| WO | WO 96/19588 | 6/1996 |

OTHER PUBLICATIONS

Doyle, J.J. et al. (1986) J. Biol. Chem 261:9228–9236.*
Casan et al (1986) J. Biol Chem 26(3):1052–1057.*
Mertz (1964) Science 145:279–280.*
Brochetto–Braga et al (1992) Plant Physiol 98:1139–1147.*
Guerde et al (1990) Mole Gen Genet 221 306–314.*
Jacobs et al (1985) Nature 313:806–810.*
Pedersen et al (1986) J Biol Chem 261(14):6279–6284.*
Leonard et al (1984) Nature 311:626–631.*
Matsudaira (1987) J Biol Chem 262(21):10035–10038.*
Matsudaira (1990) Methods in Enzymol. 182:602–613.*
Lewin (1987) Science 237:1570.*
Bonnassie et al (1990) Nucleic Acids Res. 18(21):6421.*
Mertz, E., *Science*, 145, 279–280, 1964.
Nelson, *Science*, 150, 1469–1470, 1965.
Deutscher, D. *Adv. Exp. Medicine and Biology*, 105, 281–300, 1978.
Vasal, S.K., et al., Proceedings of the 3rd Seed Protecin Symposium, Gatersleben, Aug. 31–Sep. 2, 1983.
Giovanelli, J. et al, *Plant Physiol*, 90, 1584–1599, 1989.
Shaul, O. et al, *Plant Journal*, 2, 203–209, 1992.
Perl et al, *Plant Mol. Biol.*, 19, 815–823, 1992.
Shaul, O., *Plant Physiol.*, 100, 1157–1163, 1992
Brochetto–Braga, M.R. et al, *Plant Physiol.*, 98, 1139–1147, 1992.
Doyle, JJ. et al, *J. Biol. Chem.*, 261, 9228–9236, 1986.
Altenbach, et al, *Plant Mol. Biol.*, 8, 239–250, 1987.
Altenbach, et al, *Plant Mol. Biol.*, 13, 513–522, 1989.
Glassman, et al, PCT Patent Application PCT/US89/01309, 1989.
Galili, et al, Abstr. 422 from *Thrid Int'l Cong. of Int. Soc. Plant Mol. Biol.*, 1991.
Richard, et al, *J. Bacteriology*, 166, 297–300, 1986.
Bonnassie, et al, *Nucleic Acids Research*, 18, 6421, 1990.
Yeh, et al, *Mol. Gen. Genet.*, 212, 105–111, 1988.
Katinka et al, *Proc. Nat'l. Acad. Sci. USA*, 77, 5730–5733, 1980.
Zakin et al, *J. Biol. Chem.*, 258, 3028–3031, 1983.
Rafalski et al, *J. Biol. Chem.*, 263, 2146–2151, 1988.
Bright, et al, *Nature*, 299, 278–279, 1982.
Rognes, et al, *Planta*, 157, 32–38, 1983.
Arruda, et al, *Plant Physiol.*, 76, 442–446, 1984.
Hibbard, et al, *Planta*, 148, 183–187, 1980.
Diedrich, et al, *Theor. Appl. Genet.* , 79, 209–215, 1990.
Dotson, et al, *Planta*, 182, 546–552, 1990.
Frankard, et al, *Theor. Appl. Genet.*, 82, 273–282, 1991.
Wilson, et al. *Plant Physiol.*, 97, 1323–1328, 1991.
Kaneko, et al, *J. Biol. Chem.*, 265, 17451–17455, 1990.
Frisch, et al, *Mol. Gen. Genet.*, 228, 287–293, 1991.
Cassan, et al. *J. Biol. Chem.*, 261, 1052–1057, 1986.
Negrutui et al, *Theor. Appl. Genet.*, 68, 11–20, 1984.
Theze, et al, *J. Bacteriol.*, 117, 133–143, 1974.
Giovanelli, et al, *Plant Physiol.*, 90, 1577–1583, 1989.

(Continued)

*Primary Examiner*—Elizabeth F. McElwain

(57) ABSTRACT

This invention relates to four chimeric genes, a first encoding lysine-insensitive aspartokinase (AK), which is operably linked to a plant chloroplast transit sequence, a second encoding lysine-insensitive dihydrodipicolinic acid synthase (DHDPS), which is operably linked to a plant chloroplast transit sequence, a third encoding a lysine-rich protein, and a fourth encoding a plant lysine ketoglutarate reductase, all operably linked to plant seed-specific regulatory sequences. Methods for their use to produce increased levels of lysine or threonine in the seeds of transformed plants are provided. Also provided are transformed plants wherein the seeds accumulate lysine or threonine to higher levels than untransformed plants.

8 Claims, 25 Drawing Sheets

OTHER PUBLICATIONS

Karchi, H. et al., Lysine synthesis and catabolism are coordinately regulated during tobacco seed development, Proc. Natl. Acad. Sci. USA, Plant Biology, 91, 2577–2581, Mar. 1994.

Ghislain, M. et al., A dinucleotide mutation in dihydrodipicolinate synthase of Nicotiana sylvestris leads to lysine overproduction, The Plant Journal, 8(5), 733–743, 1995.

Silk, Gregg W. et al., Cloning and expression of the soybean DapA gene encoding dihydrodipicolinate synthase, Plant Molecular Biology, 26, 289–993, 1994.

Brinch–Pedersen, Henrick et al., Engineering of the aspartate family biosynthetic pathway in barley (Hordeum vulgare L.) by transformation with heterologous genes encoding feed–back–insensitive aspartate kinase and dihydrodipicolinate synthase, Plant Molecular Biology, 32, 611–620, 1996.

Pisabarro, A. et al., A Cluster of Three Genes (dapA, orf2, and dapB) of Brevibacterium lactofermentum Encodes Dihydrodipicolinates Synthase, Dihydrodipicolinate Reductase, and a Third Polypeptide of Unknown Function, Journal of Bacteriology, 175, No. 9, 2743–2749, May 1993.

Arruda, P. et al., Lysine–Ketoglutarate Reductase Activity in Developing Maize Endosperm, Plant Physiology, vol., 69, pp. 988–989, 1982.

National Center for Biotechnology Information General Identifier No. 2052507, Accession No. U95759, Jan. 16, 1998, S. Epelbaum et al.

* cited by examiner

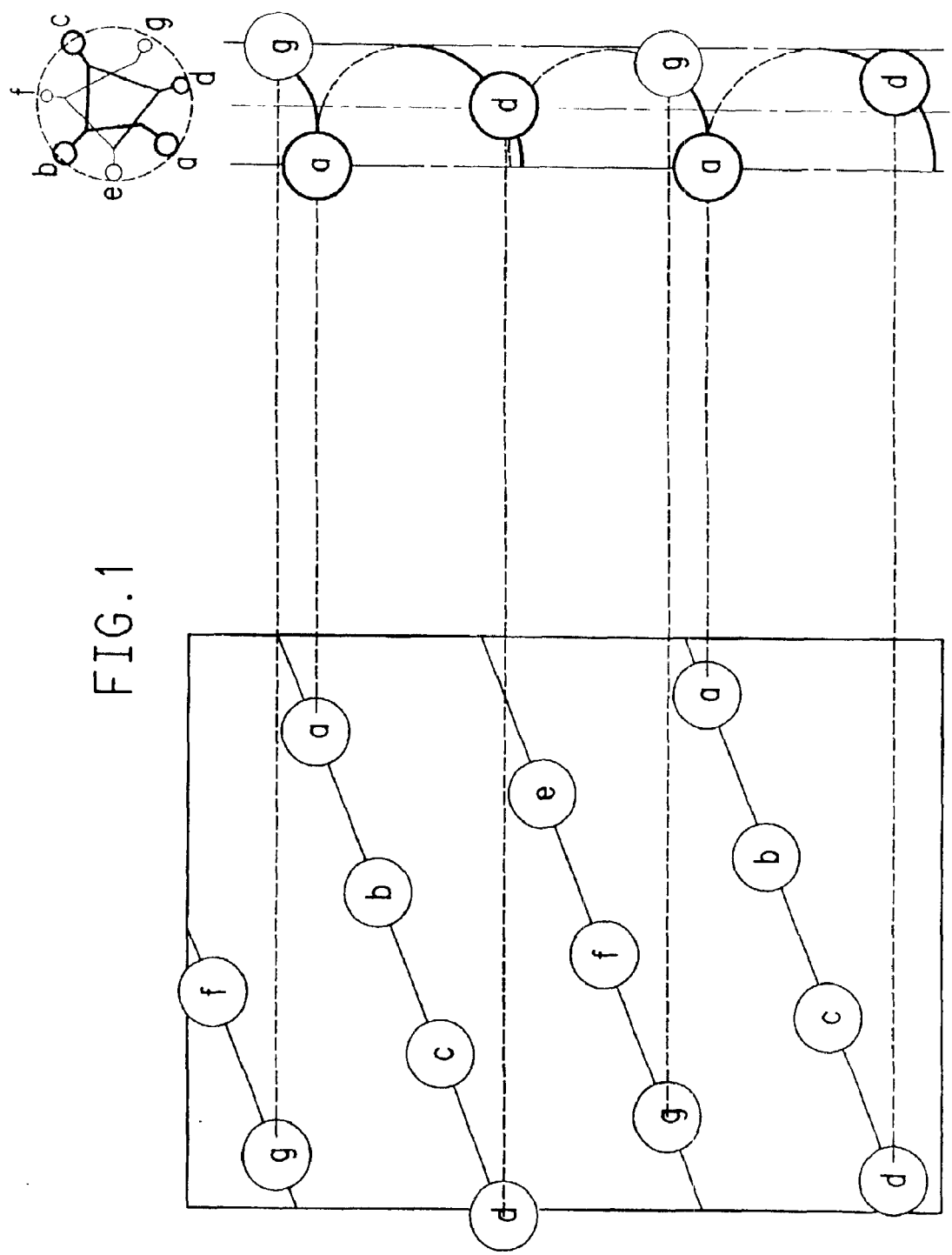

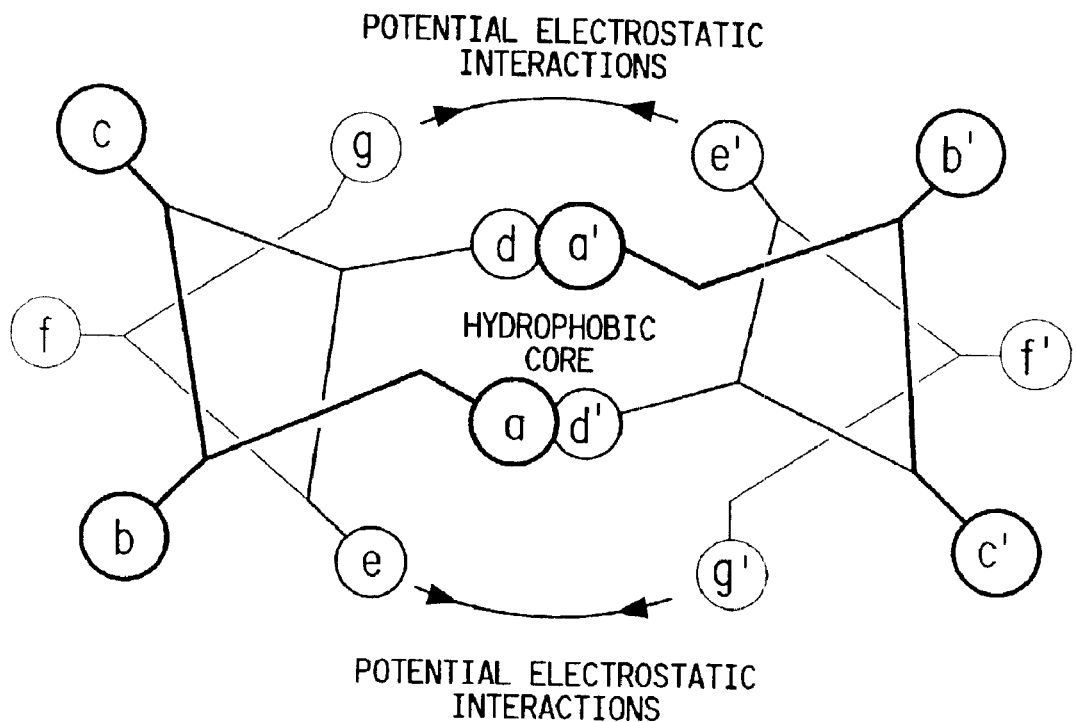
FIG.2A
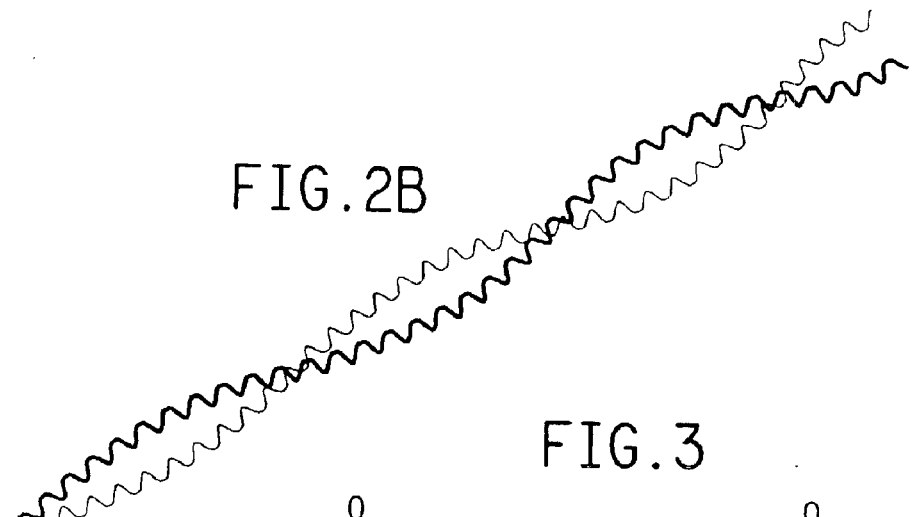
FIG.2B
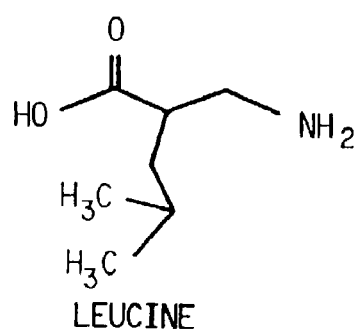
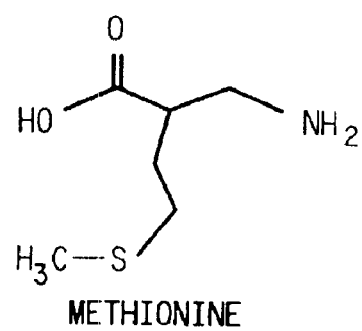
FIG.3

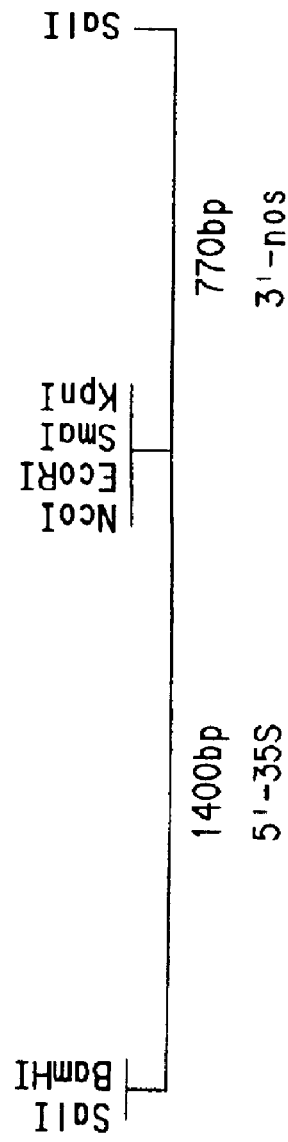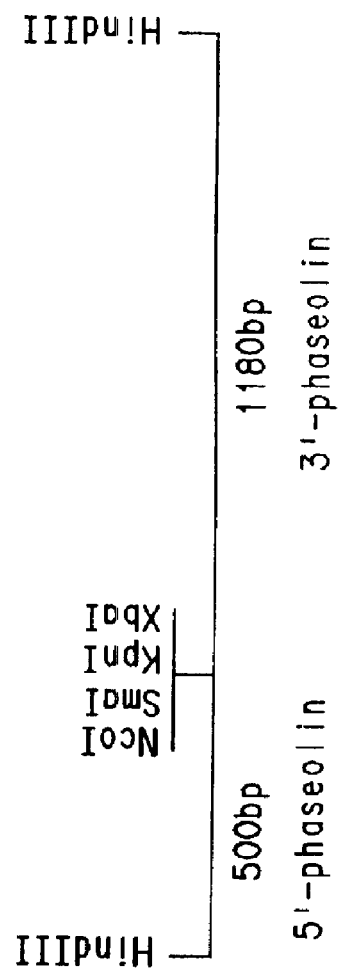

FIG.9

```
SEQ ID NO:104    19 KKSGVLILGAGRVXRPAADFLASVRTISSQQWYKTYFGADSEEKTDVHVI 68
                    ..:.|::|.|.|.|..|..||.
S. cerevisiae SDH 1 MGKNVLLLGSGFVAQPVIDTLAA................NDDINVT 30

69 VASLYLKDAKETVEGISDVEAVRLDVSDSESLLKYVSQVDVVLSLLPASC 118
                    ||..:|..:|.|::..|:..|:..|.|||.|...|.|.:|||:||:|.:|
                 31 VACRTLANA.QALAKPSGSKAISLDVTDDSALDKVLADNDVVISLIPYTF 79

119 HA 120
                    |:
                 80 HP 81

SEQ ID NO:105    1 KHTATLLEFGDIKNGQTTAMAKTVGIPAAIGALLLIEDKIKTRGVLRPL 50
                   .:.||.:|:||:.    ..||.|||.|.|.||.    :::::|.||.|:.|.
S. cerevisiae SDH 374 TRTSTLVDYGKV...GGYSSMAATVGYPVAIATKFVLDGTIKGPGLLAPY 420

51 EAEVYLPALDIL.QAYGIKLMEKAE 74
                    .:|.||..||||..:||||.|||.||
                421 SPEINDPIMKELKDKYGIYLKEKTVA 446
```

FIG. 13

```
       NCOI           EARI        BSPHI   STOP  ASP718       ECORI              BASE GENE
       CATGGAGGAGAAGATGAAAAA      GCTC GAAGAGAAGATGAAGGCTATGAGGAGAAAGATGAAGAAGCTTGAGGAGAAAAGATGAAGAAGTCATGAAGTGAAGGTACCG
       CTCCTCTTCTACTTTTTCTA            GCTTCTCTTCTACTTCCGATACTCCTCTTTCTACTTCTTCGA
       M  E  E  K  M  K  K         L    E  E  K  M  K  K  V  M  K

OLIGONUCLEOTIDE INSERTS

GCTGGAAGAAAAGATGAAGGCTATGGAGGAGAAAGATGAAGAAGCTTGAGGAGAAAAGATGAAGAAG
       CGACCTTCTTTTCTACTTCCGATACCTCCTCTTTCTACTTCTTCGAACTCCTTTTCTACTTCTTC
        L  E  E  K  M  K  A  M  E  E  K  M  K  K  L  E  E  K  M  K  K

↓ OLIGOS LIGATED INTO EARI CUT BASE GENE

NCOI            EARI                                                                                                
       CATGGAGGAGAAGATGAAAAA GCTGGAAGAAAAGATGAAGGCTATGGAGGAGAAAGATGAAGAAGCTTGAGGAGAAAAGATGAAGAAG          
       CTCCTCTTCTACTTTTTCTA CGACCTTCTTTTCTACTTCCGATACCTCCTCTTTCTACTTCTTCGAACTCCTTTTCTACTTCTTC
       M  E  E  K  M  K  K  L  E  E  K  M  K  A  M  E  E  K  M  K  K  W  L  E  E  K  M  K  K  L

EARI                      BSPHI          ASP718  ECORI
       CGAAGAGAAGATGAAGGCTTCTCTTCTACTTCCAGTAGTTCATGAAGTGAAGGTACCG               CLONE pSK34
       GCTTCTCTTCTACTTCCGAAGAGAAGATGAAGGTCATCAAGTACTTCACTTCCATGGCTTAA
            E  E  K  M  K  K  V  M  K
```

CHIMERIC GENES AND METHODS FOR INCREASING THE LYSINE AND THREONINE CONTENT OF THE SEEDS OF PLANTS

This is a divisional of Ser. No. 08/823,771, filed on Mar. 24, 1997, now U.S. Pat. No. 6,459,019, which is a divisional of Ser. No. 08/474,633, filed on Jun. 7, 1995, now U.S. Pat. No. 5,773,691, which is a continuation-in-part of Ser. No. 08/178,212, filed on Jan. 6, 1994, now abandoned, which was the national filing of PCT/US93/02480, filed on Mar. 18, 1993 and which is a continuation-in-part of Ser. No. 07/855,414, filed on Mar. 19, 1992 now abandoned.

TECHNICAL FIELD

This invention relates to four chimeric genes, a first encoding lysine-insensitive aspartokinase (AK), which is operably linked to a plant chloroplast transit sequence, a second encoding lysine-insensitive dihydrodipicolinic acid synthase (DHDPS), which is operably linked to a plant chloroplast transit sequence, a third encoding a lysine-rich protein, and a fourth encoding a plant lysine ketoglutarate reductase, all operably linked to plant seed-specific regulatory sequences. Methods for their use to produce increased levels of lysine or threonine in the seeds of transformed plants are provided. Also provided are transformed plants wherein the seeds accumulate lysine or threonine to higher levels than untransformed plants.

BACKGROUND OF THE INVENTION

Human food and animal feed derived from many grains are deficient in some of the ten essential amino acids which are required in the animal diet. In corn (*Zea mays* L.), lysine is the most limiting amino acid for the dietary requirements of many animals. Soybean (*Glycine max* L.) meal is used as an additive to corn based animal feeds primarily as a lysine supplement. Thus an increase in the lysine content of either corn or soybean would reduce or eliminate the need to supplement mixed grain feeds with lysine produced via fermentation of microbes.

Plant breeders have long been interested in using naturally occuring variations to improve protein quality and quantity in crop plants. Maize lines containing higher than normal levels of lysine (70%) have been identified [Mertz et al. (1964) *Science* 145:279, Mertz et al. (1965) *Science* 150:1469–70]. However, these lines which incorporate a mutant gene, opaque-2, exhibit poor agronomic qualities (increased susceptibility to disease and pests, 8–14% reduction in yield, low kernel weight, slower drying, lower dry milling yield of flaking grits, and increased storage problems) and thus are not commercially useful [Deutscher (1978) *Adv. Exp. Medicine and Biology* 105:281–300]. Quality Protein Maize (QPM) bred at CIMMYT using the opaque-2 and sugary-2 genes and associated modifiers has a hard endosperm and enriched levels of lysine and tryptophan in the kernels [Vasal, S. K., et al. *Proceedings of the 3rd seed protein symposium,* Gatersleben, Aug. 31–Sep. 2, 1983]. However, the gene pools represented in the QPM lines are tropical and subtropical. Quality Protein Maize is a genetically complex trait and the existing lines are not easily adapted to the dent germplasm in use in the United States, preventing the adoption of QPM by corn breeders.

The amino acid content of seeds is determined primarily (90–99%) by the amino acid composition of the proteins in the seed and to a lesser extent (1–10%) by the free amino acid pools. The quantity of total protein in seeds varies from about 10% of the dry weight in cereals to 20–40% of the dry weight of legumes. Much of the protein-bound amino acids is contained in the seed storage proteins which are synthesized during seed development and which serve as a major nutrient reserve following germination. In many seeds the storage proteins account for 50% or more of the total protein.

To improve the amino acid composition of seeds genetic engineering technology is being used to isolate, and express genes for storage proteins in transgenic plants. For example, a gene from Brazil nut for a seed 2S albumin composed of 26% sulfur-containing amino acids has been isolated [Altenbach et al. (1987) *Plant Mol. biol.* 8:239–250] and expressed in the seeds of transformed tobacco under the control of the regulatory sequences from a bean phaseolin storage protein gene. The accumulation of the sulfur-rich protein in the tobacco seeds resulted in an up to 30% increase in the level of methionine in the seeds [Altenbach et al. (1989) *Plant Mol. biol.* 13:513–522]. However, no plant seed storage proteins similarly enriched in lysine relative to average lysine content of plant proteins have been identified to date, preventing this approach from being used to increase lysine.

An alternative approach is to increase the production and accumulation of specific free amino acids such as lysine via genetic engineering technology. However, little guidance is available on the control of the biosynthesis and metabolism of lysine in the seeds of plants.

Lysine, along with threonine, methionine and isoleucine, are amino acids derived from aspartate, and regulation of the biosynthesis of each member of this family is interconnected. Regulation of the metabolic flow in the pathway appears to be primarily via end products. The first step in the pathway is the phosphorylation of aspartate by the enzyme aspartokinase (AK), and this enzyme has been found to be an important target for regulation in many organisms. However, detailed physiological studies on the flux of 4-carbon molecules through the aspartate pathway have been carried out in the model plant system *Lemna paucicostata* [Giovanelli et al. (1989) *Plant Physiol.* 90:1584–1599]. The authors state "These data now provide definitive evidence that the step catalyzed by aspartokinase is not normally an important site for regulation of the entry of 4-carbon units into the aspartate family of amino acids [in plants]."

The aspartate family pathway is also believed to be regulated at the branch-point reactions. For lysine this is the condensation of aspartyl β-semialdehyde with pyruvate catalyzed by dihydrodipicolinic acid synthase (DHDPS), while for threonine and methionine the reduction of aspartyl β-semialdehyde by homoserine dehydrogenase (HDH) followed by the phosphorylation of homoserine by homoserine kinase (HK) are important points of control.

The *E. coli* dapA gene encodes a DHDPS enzyme that is about 20-fold less sensitive to inhibition by lysine than than a typical plant DHDPS enzyme, e.g., wheat germ DHDPS. The *E. coli* dapA gene has been linked to the 35S promoter of Cauliflower Mosaic Virus and a plant chloroplast transit sequence. The chimeric gene was introduced into tobacco cells via transformation and shown to cause a substantial increase in free lysine levels in leaves [Glassman et al. (1989) PCT Patent Appl. PCT/US89/01309, Shaul et al. (1992) *Plant Jour.* 2:203–209, Galili et al. (1992) EPO Patent Appl. 91119328.2]. However, the lysine content of the seeds was not increased in any of the transformed plants described in these studies. The same chimeric gene was also introduced into potato cells and lead to small increases in free lysine in leaves, roots and tubers of regenerated plants [Galili et al. (1992) EPO Patent Appl. 91119328.2, Perl et al. (1992) *Plant Mol. Biol.* 19:815–823]. These workers have also reported on the introduction of an *E. coli* lysC gene that encodes a lysine-insensitive AK enzyme into tobacco cells via transformation [Galili et al. (1992) Eur. Patent Appl. 91119328.2; Shaul et al. (1992) Plant Physiol. 100:1157–1163]. Expression of the *E. coli* enzyme results in increases in the levels of free threonine in the leaves and seeds of transformed plants. Crosses of plants expressing *E. coli* DHDPS and AK resulted in progeny that accumulated more free lysine in leaves than the parental DHDPS plant, but less free threonine in leaves than the parental AK plant. No evidence for increased levels of free lysine in seeds was presented.

The limited understanding of the details of the regulation of the biosynthetic pathway in plants makes the application of genetic engineering technology, particularly to seeds, uncertain. There is little information available on the source of the aspartate-derived amino acids in seeds. It is not known, for example, whether they are synthesized in seeds, or transported to the seeds from leaves, or both, from most plants. In addition, free amino acids make up only a small fraction of the total amino acid content of seeds. Therefore, over-accumulation of free amino acids must be many-fold in order to significantly affect the total amino acid composition of the seeds. Furthermore, little is known about catabolism of free amino acids in seeds. Catabolism of free lysine has been observed in developing endosperm of corn and barley. The first step in the catabolism of lysine is believed to be catalyzed by lysine-ketoglutarate reductase [Brochetto-Braga et al. (1992) *Plant Physiol.* 98:1139–1147]. Whether such catabolic pathways are widespread in plants and whether they affect the level of accumulation of free amino acids is unknown. Finally, the effects of over-accumulation of a free amino acid such as lysine or threonine on seed development and viability is not known.

Before this patent application no method to increase the level of lysine or threonine, or any other amino acid, in seeds via genetic engineering was known. Furthermore, no examples of seeds having increased lysine or threonine levels obtained via genetic engineering were known before the invention described herein. Thus, there is a need for genes, chimeric genes, and methods for expressing them in seeds so that an over-accumulation of free amino acids in seeds will result in an improvement in nutritional quality.

SUMMARY OF THE INVENTION

This invention concerns an isolated nucleic acid fragment comprising:
(a) a first nucleic acid subfragment encoding apartokinase which is substantially insensitive to inhibition by lysine; and
(b) a second nucleic acid subfragment encoding dihydrodipicolinic acid synthase which is substantially insensitive to inhibition by lysine.

The invention also concerns an isolated nucleic acid fragment comprising a nucleic acid subfragment encoding lysine ketoglutarate reductase.

Further disclosed herein is a nucleic acid fragment comprising
(a) a first chimeric gene wherein a nucleic acid fragment encoding aspartokinase which is substantially insensitive to inhibition by lysine is operably linked to a plant chloroplast transit sequence and to a seed-specific regulatory sequence; and
(b) a second chimeric gene wherein a nucleic acid fragment encoding dihydrodipicolinic acid synthase which is substantially insensitive to inhibition by lysine is operably linked to a plant chloroplast transit sequence and to a seed-specific regulatory sequence.

Additionally disclosed is an isolated nucleic acid fragment comprising:
(a) a first chimeric gene wherein a nucleic acid fragment comprising a nucleotide sequence essentially similar to the sequence shown in SEQ ID NO:1: encoding *E. coli* AKIII, said nucleic acid fragment encoding a lysine-insensitive variant of *E. coli* AKIII and further characterized in that at least one of the following conditions is met:
(1) the amino acid at position 318 is an amino acid other than threonine, or
(2) the amino acid at position 352 is an amino acid other than methionine is operably linked to a plant chloroplast transit sequence and to a seed-specific regulatory sequence and
(b) a second chimeric gene wherein a nucleic acid fragment derived from a bacteria encoding dihydrodipicolinic acid synthase is operably linked to a plant chloroplast transit sequence and to a seed-specific regulatory sequence; and
(c) a third chimeric gene wherein a nucleic acid fragment encoding part or all of lysine ketoglutarate reductase is operably linked in the sense or antisense orientation to a seed-specific regulatory sequence.

Also disclosed is an isolated nucleic acid fragment comprising at least one nucleotide sequence essentially similar to the sequence shown in SEQ ID NO:1 encoding *E. coli* AKIII, said nucleic acid fragment encoding a lysine-insensitive variant of *E. coli* AKIII and further characterized in that at least one of the following conditions is met:
(a) the amino acid at position 318 is an amino acid other than threonine, or
(b) the amino acid at position 352 is an amino acid other than methionine.

Also claimed is an embodiment wherein the nucleic acid fragment discussed herein is operably linked to a plant chloroplast transit sequence and to a seed-specific regulatory sequence.

Plants and seeds comprising in their genomes the described nucleic acid fragments and/or genes are also disclosed.

The invention also concerns a method for increasing the threonine content of the seeds of plants, and plants produced by such method wherein the plant is capable of transmitting said chimeric gene to a progeny plant and wherein the progeny plant has the ability to produce levels of free threonine at least two times greater than the free threonine levels of untransformed plants, which method comprises:
(a) transforming plant cells with the above described chimeric gene;
(b) growing fertile mature plants from the transformed plant cells obtained from step (a) under conditions suitable to obtain seeds; and
(c) selecting from the progeny seed of step (b) for those seeds containing increased levels of threonine.

Also described is a method for increasing the lysine content of the seeds of plants and plants produced by such methods wherein the plant is capable of transmitting said nucleic acid fragment to a progeny plant and wherein the progeny plant has the ability to produce levels of free lysine at least two times greater than free lysine levels of plants not containing the nucleic acid fragment, which method comprises:

(a) transforming plant cells with the above described nucleic acid fragments;

(b) growing fertile mature plants from the transformed plant cells obtained from step (a) under conditions suitable to obtain seeds; and (c) selecting from the progeny seed of step (b) those seeds containing increased levels of lysine.

Further disclosed is an isolated nucleic acid fragment comprising:

(a) a first nucleic acid subfragment encoding apartokinase which is substantially insensitive to inhibition by lysine; and (b) a second nucleic acid subfragment encoding dihydrodipicolinic acid synthase which is substantially insensitive to inhibition by lysine; and (c) a third nucleic acid subfragment encoding a lysine-rich protein wherein the weight percent lysine is at least 15%.

Also disclosed herein are an isolated nucleic acid fragment comprising:

(a) a first chimeric gene wherein a nucleic acid fragment comprising a nucleotide sequence essentially similar to the sequence shown in SEQ ID NO:1: encoding *E. coli* AKIII, said nucleic acid fragment encoding a lysine-insensitive variant of *E. coli* AKIII and further characterized in that at least one of the following conditions is met:

(1) the amino acid at position 318 is an amino acid other than threonine, or (2) the amino acid at position 352 is an amino acid other than methionine is operably linked to a plant chloroplast transit sequence and to a seed-specific regulatory sequence and (b) a second chimeric gene wherein a nucleic acid fragment derived from a bacteria encoding dihydrodipicolinic acid synthase is operably linked to a plant chloroplast transit sequence and to a seed-specific regulatory sequence; and (c) a third chimeric gene wherein a nucleic acid fragment encoding a lysine-rich protein wherein the weight percent lysine is at least 15% is operably linked to a seed-specific regulatory sequence.

Further disclosed herein is an isolated nucleic acid fragment, and plants and seeds containing such fragment, comprising:

(a) a first chimeric gene wherein a nucleic acid fragment comprising a nucleotide sequence essentially similar to the sequence shown in SEQ ID NO:1: encoding *E. coli* AKIII, said nucleic acid fragment encoding a lysine-insensitive variant of *E. coli* AKIII and further characterized in that at least one of the following conditions is met:

(1) the amino acid at position 318 is an amino acid other than threonine, or (2) the amino acid at position 352 is an amino acid other than methionine is operably linked to a plant chloroplast transit sequence and to a seed-specific regulatory sequence and (b) a second chimeric gene wherein a nucleic acid fragment derived from a bacteria encoding dihydrodipicolinic acid synthase is operably linked to a plant chloroplast transit sequence and to a seed-specific regulatory sequence; and (c) a third chimeric gene wherein a nucleic acid fragment encoding a lysine-rich protein comprising n heptad units (d e f g a b c), each heptad being either the same or different, wherein:

n is at least 4;

a and d are independently selected from the group consisting of Met, Leu, Val, Ile and Thr;

e and g are independently selected from the group consisting of the acid/base pairs Glu/Lys, Lys/Glu, Arg/Glu, Arg/Asp, Lys/Asp, Glu/Arg, Asp/Arg and Asp/Lys; and b, c and f are independently any amino acids except Gly or Pro and at least two amino acids of b, c and f in each heptad are selected from the group consisting of Glu, Lys, Asp, Arg, His, Thr, Ser, Asn, Ala, Gln and Cys, said nucleic acid fragment is operably linked to a seed-specific regulatory sequence.

Further disclosed herein is an isolated nucleic acid fragment, and plants and seeds containing such fragment, comprising:

(a) a first chimeric gene wherein a nucleic acid fragment comprising a nucleotide sequence essentially similar to the sequence shown in SEQ ID NO:1: encoding *E. coli* AKIII, said nucleic acid fragment encoding a lysine-insensitive variant of *E. coli* AKIII and further characterized in that at least one of the following conditions is met:

(1) the amino acid at position 318 is an amino acid other than threonine, or (2) the amino acid at position 352 is an amino acid other than methionine is operably linked to a plant chloroplast transit sequence and to a seed-specific regulatory sequence; and (b) a second chimeric gene wherein a nucleic acid fragment derived from a bacteria encoding dihydrodipicolinic acid synthase is operably linked to a plant chloroplast transit sequence and to a seed-specific regulatory sequence; and (c) a third chimeric gene wherein a nucleic acid fragment encoding a lysine-rich protein having the amino acid sequence (MEEKLKA)$_6$(MEEKMKA)$_2$ (SEQ ID NO:108) is operably linked to a seed-specific regulatory sequence.

Also disclosed are plants comprising in their genome the nucleic acid fragments listed above, plants comprising in their genomes each of the chimeric genes discribed above and seeds obtained from such plants.

Also disclosed is a method for increasing the lysine content of the seeds of plants comprising:

(a) transforming plant cells with the nucleic acid fragment listed above;

(b) growing fertile mature plants from the transformed plant cells obtained from step (a) under conditions suitable to obtain seeds; and (c) selecting from the progeny seed of step (b) those seeds containing increased levels of lysine.

The invention also includes a novel transformed plant, preferably a rapeseed or soybean plant, wherein the seeds of the plant accumulate lysine at a level at least ten percent higher than do seeds of an untransformed plant (10% to 400% higher for soybean and 10% to 100% higher for rapeseed) than do seeds of an untransformed plant.

Further disclosed herein is a nucleic acid acid fragment wherein the seed-specific regulatory sequence is a monocot embyro-specific promoter, a monocot plant comprising in its genome such nucleic acid fragment and a seed obtained from that plant and comprising in its genome that nucleic acid fragment.

Disclosed is a method for increasing the lysine content of the seeds of monocot plants comprising:
(a) transforming plant cells with the nucleic acid fragment of Claim 33;
(b) growing fertile mature plants from the transformed plant cells obtained from step (a) under conditions suitable to obtain seeds; and
(c) selecting from the progeny seed of step (b) those seeds containing increased levels of lysine, and plants produced by such a method, wherein the plant is capable of transmitting said nucleic acid fragment to a progeny plant and wherein the progeny plant has the ability to produce levels of free lysine at least five times greater than free lysine levels of plants not containing the nucleic acid fragment.

Also disclosed is a transformed corn plant wherein the seeds of the plant accumulate lysine to a level between ten percent and one hundred thirty percent higher than do seeds of an untransformed plant and a method for increasing the lysine content and reducing the accumulation of lysine breakdown products of the seeds of plants.

Further disclosed is a method for increasing the lysine content and reducing the accumulation of lysine breakdown products of the seeds of plants comprising:
(a) transforming plant cells with the nucleic acid fragment described herein, then
(b) growing fertile mature plants from the transformed plant cells obtained from step (a) under conditions suitable to obtain seeds;
(c) selecting from the progeny seed of step (b) those seeds containing increased levels of lysine; and lysine breakdown products and
(d) introducing a mutation in the gene encoding lysine ketoglutarate reductase which reduces the enzyme activity and reduces accumulation of lysine breakdown products.

BRIEF DESCRIPTION OF THE DRAWINGS AND SEQUENCE DESCRIPTIONS

The invention can be more fully understood from the following detailed description and the accompanying drawings and the sequence descriptions which form a part of this application.

FIG. 1 shows an alpha helix from the side and top views.

FIG. 2 shows end (FIG. 2a) and side (FIG. 2b) views of an alpha helical coiled-coil structure.

FIG. 3 shows the chemical structure of leucine and methionine emphasizing their similar shapes.

FIG. 4 shows a schematic representation of gene expression cassettes.

Figure 7A:
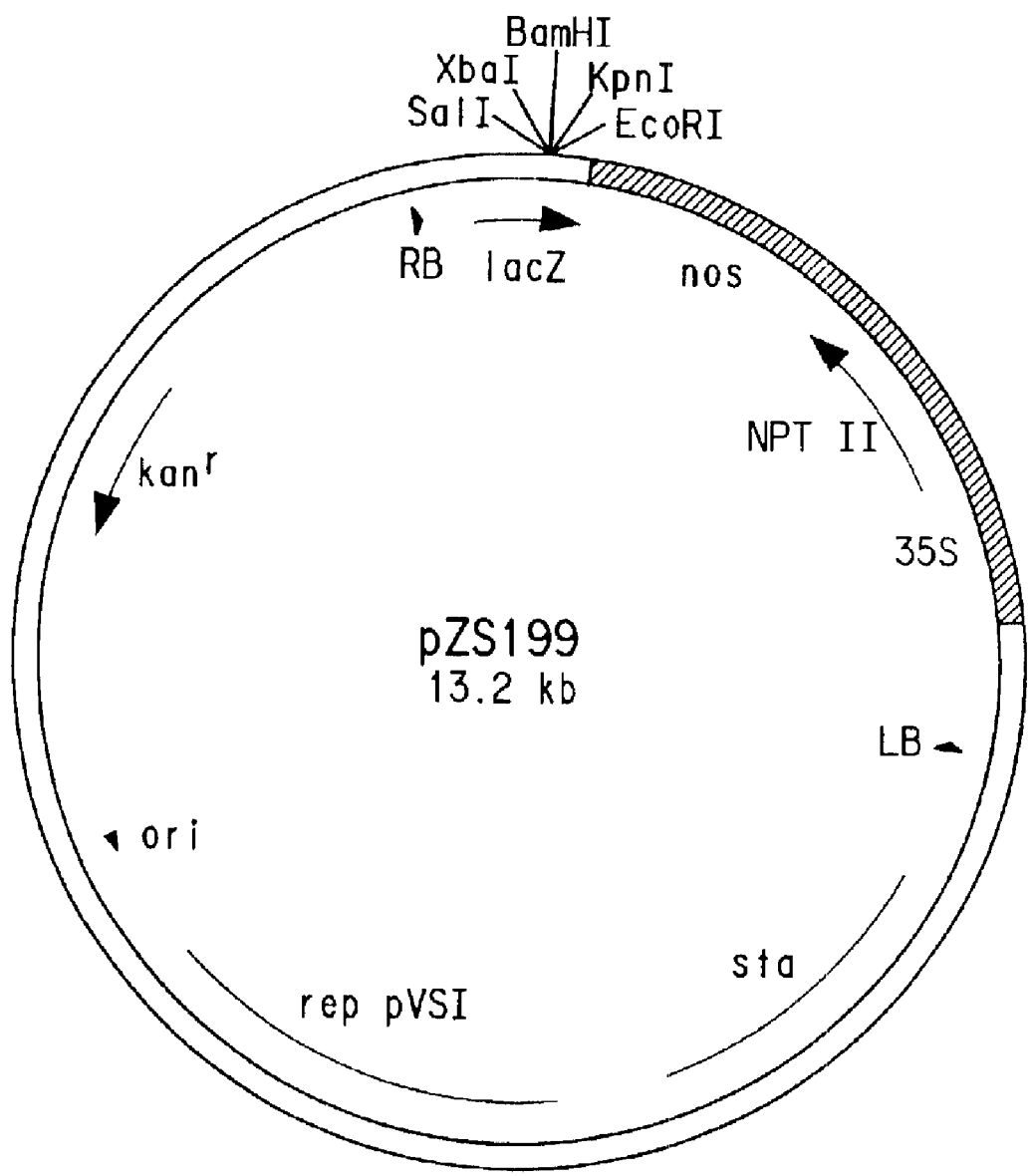
Figure 7B:
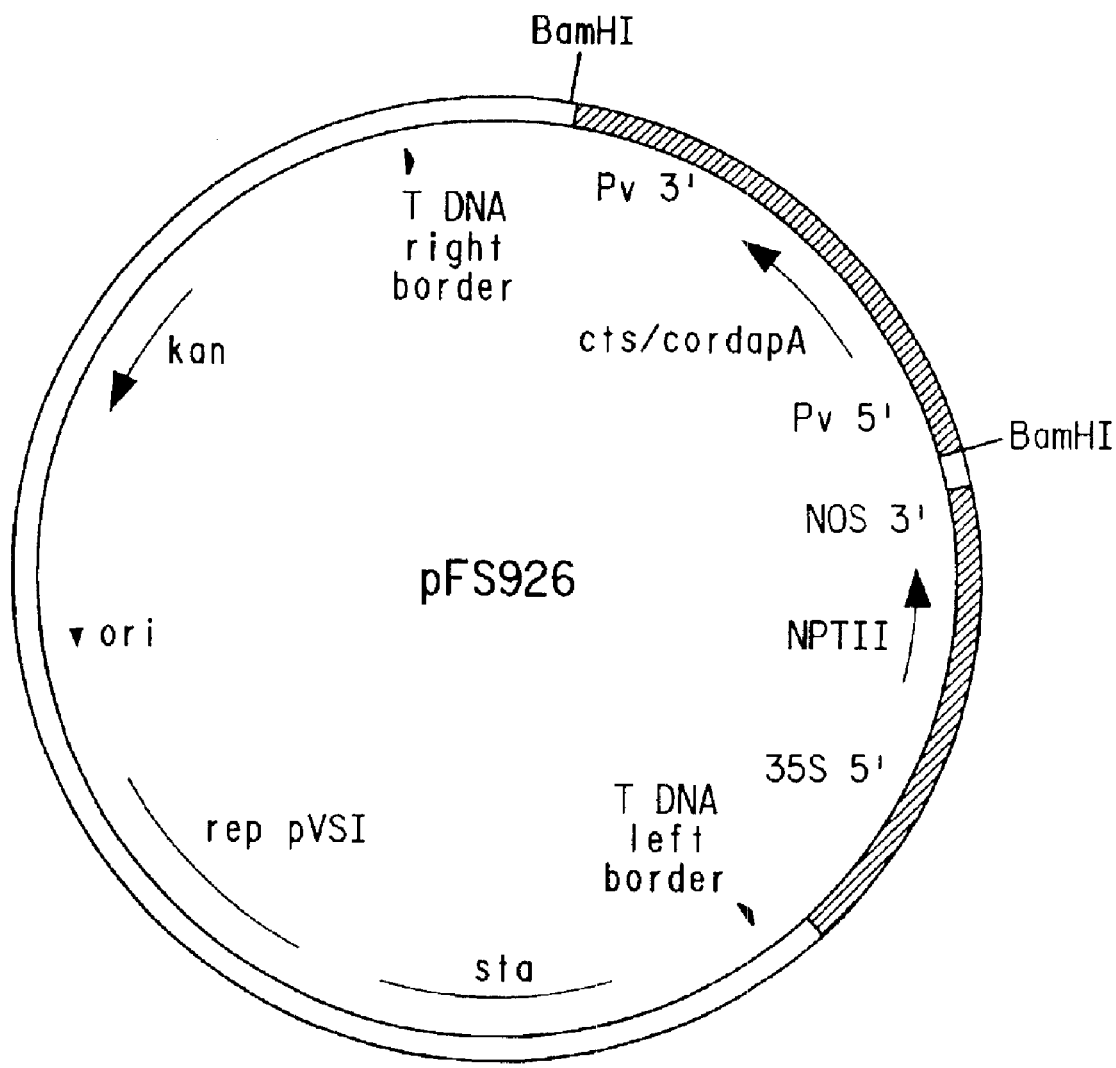
Figure 7C:
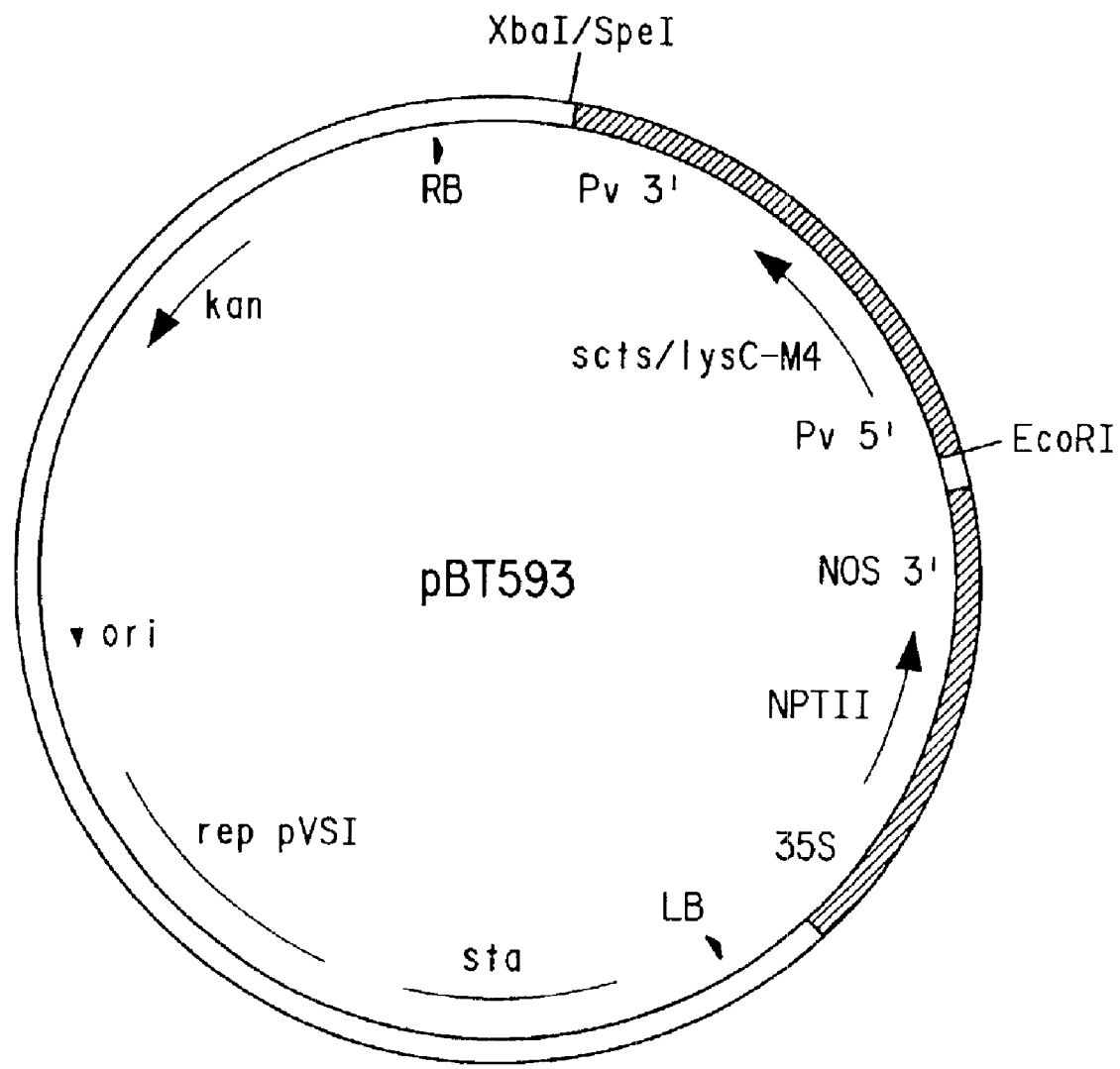
Figure 7D:
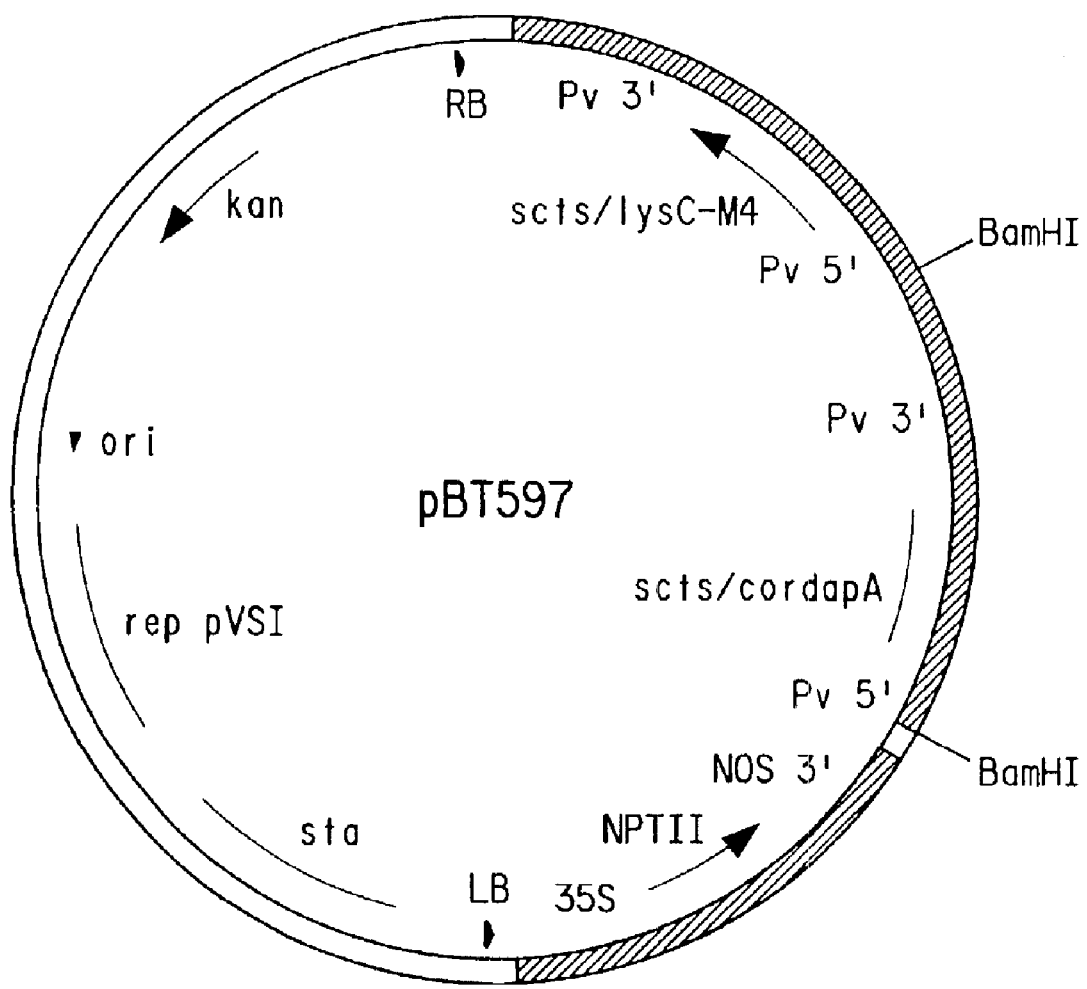

FIG. 7A shows a map of the binary plasmid vector pZS 199; FIG. 7B shows a map of the binary plasmid vector pFS926; FIG. 7C shows a map of the binary plasmid vector pBT593; FIG. 7D shows a map of the binary plasmid vector pBT597.

Figure 8A:
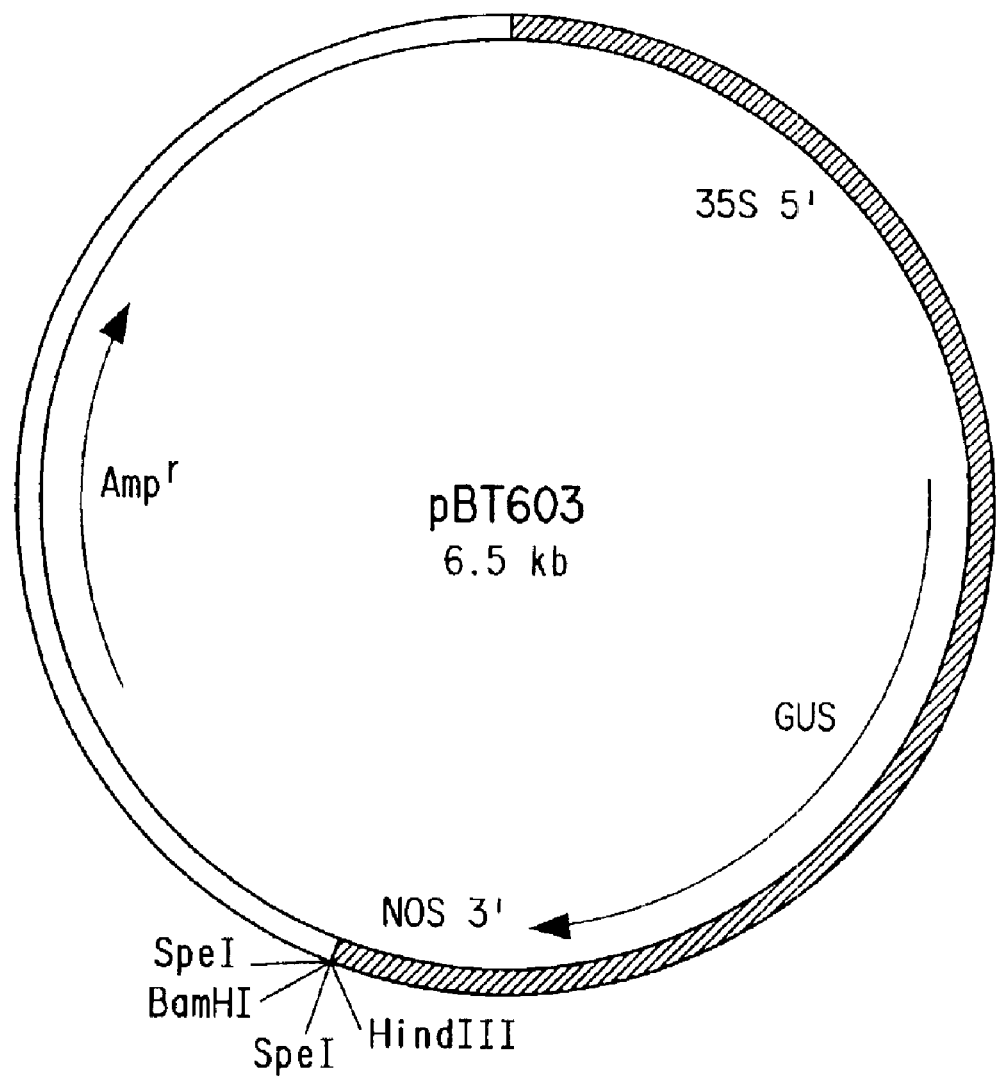
Figure 8B:
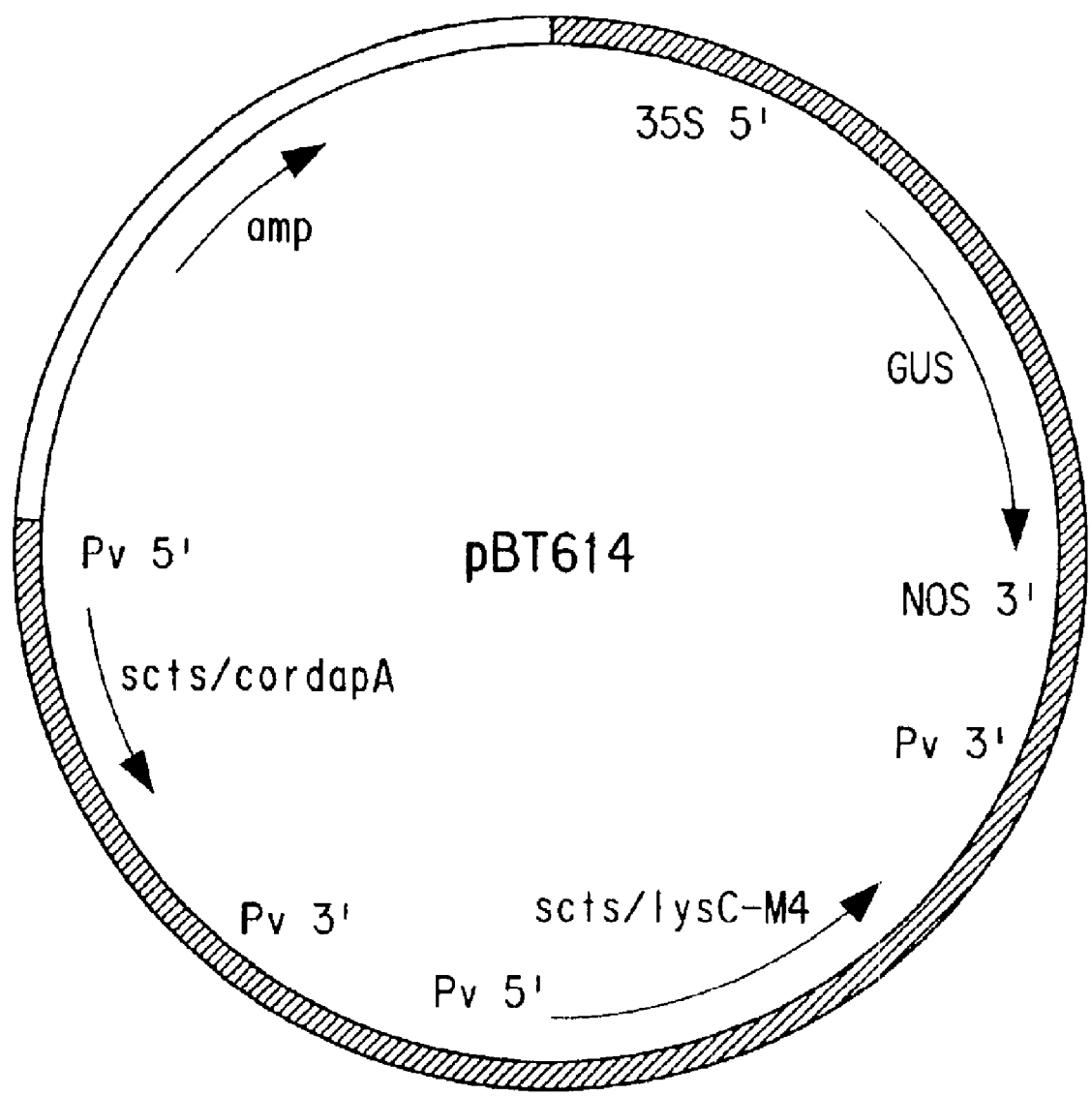

FIG. 8A shows a map of the plasmid vector pBT603; FIG. 8B shows a map of the plasmid vector pBT614.

FIG. 9 shows the amino acid sequence similarity between the polypeptides encoded by two plant cDNAs and fungal SDH (glutamate-forming).

Figure 10:
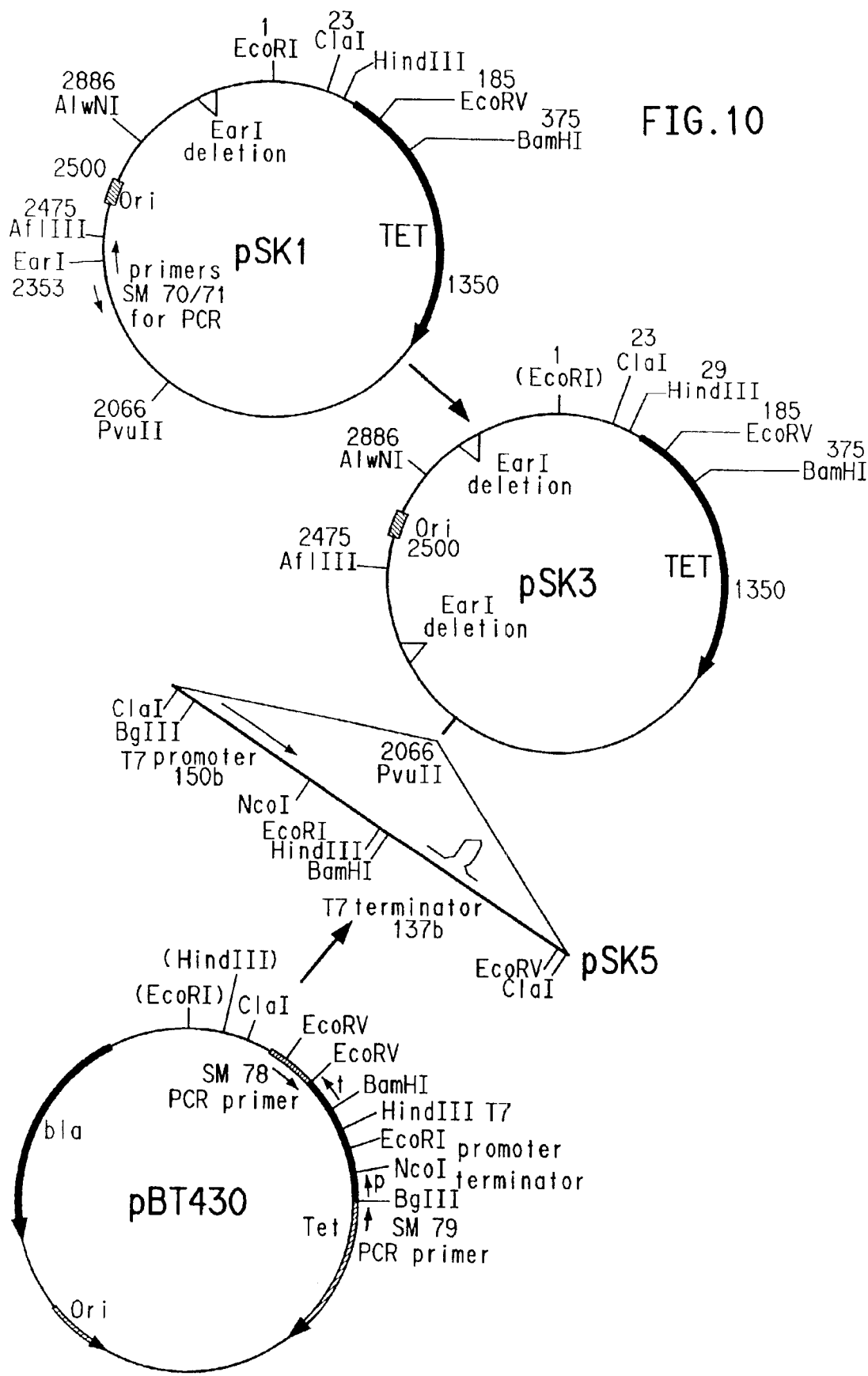

FIG. 10 depicts the strategy for creating a vector (pSK5) for use in construction and expression of the SSP gene sequences.

Figure 11:
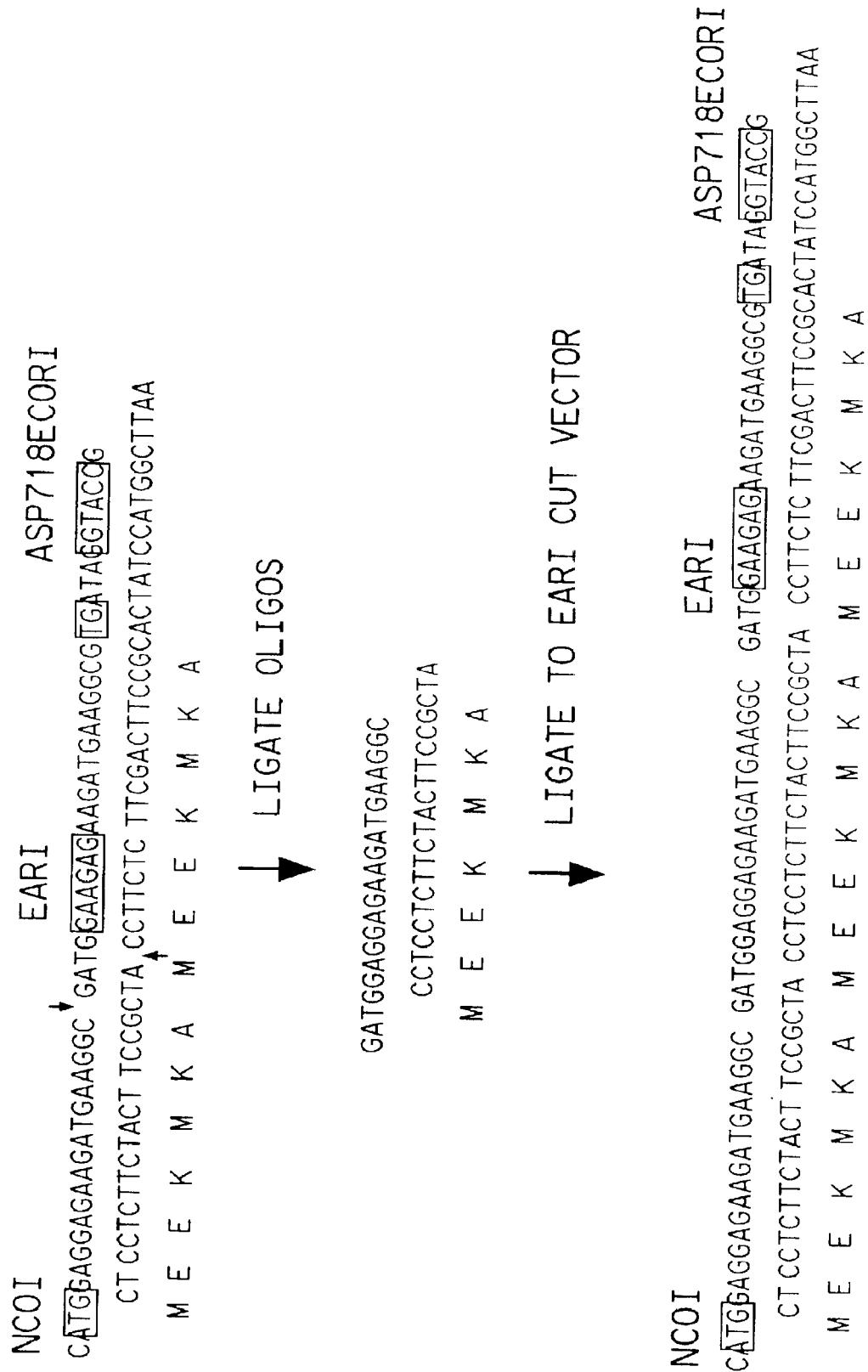

FIG. 11 shows the strategy for inserting oligonucleotide sequences into the unique Ear I site of the base gene sequence.

Figure 12:
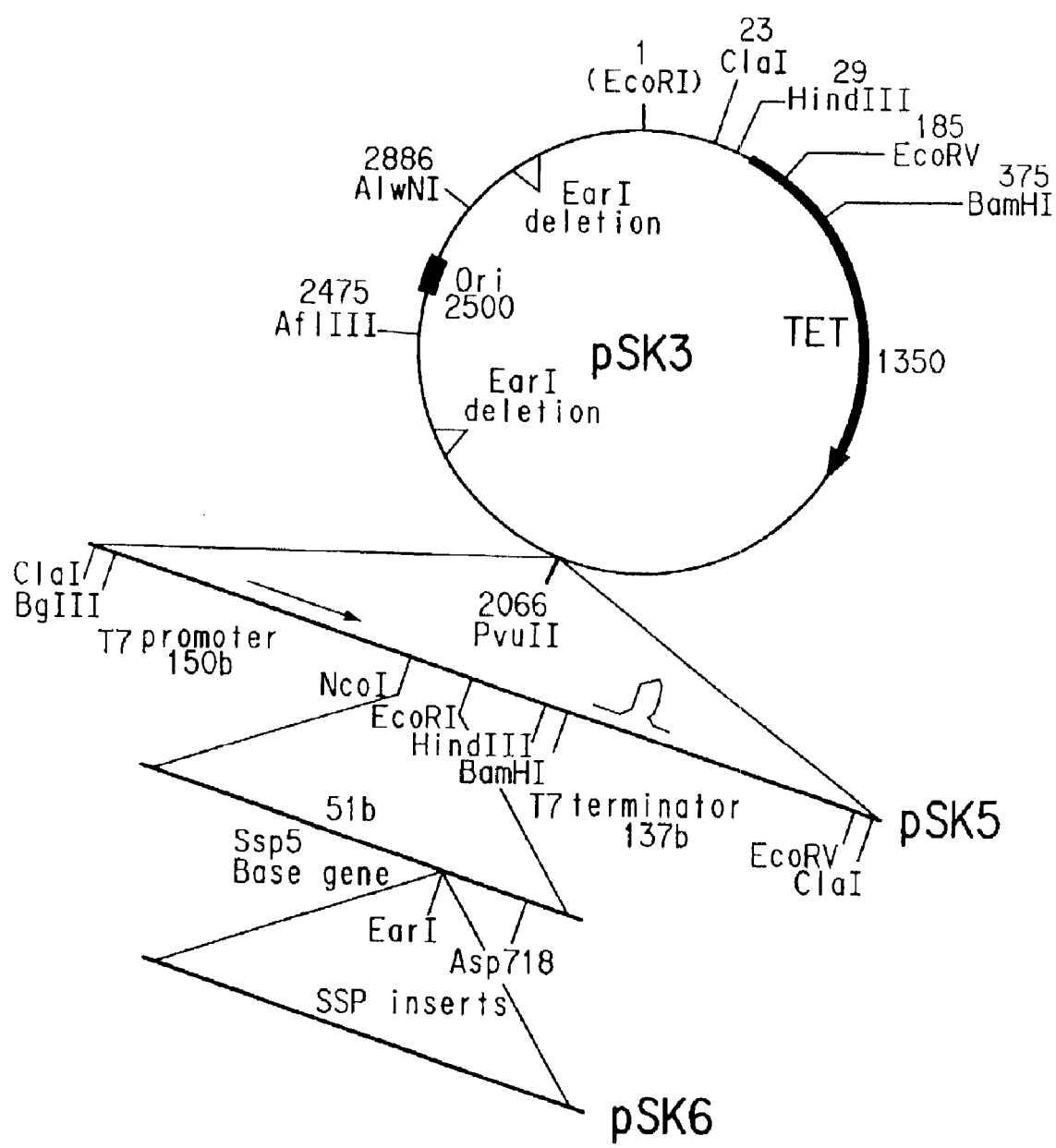

FIG. 12 shows the insertion of the base gene oligonucleotides into the Nco I/EcoR I sites of pSK5 to create the plasmid pSK6. This base gene sequence was used as in FIG. 8 to insert the various SSP coding regions at the unique Ear I site to create the cloned seqments listed.

FIG. 13 shows the insertion of the 63 bp "segment" oligonucleotides used to create non-repetitive gene sequences for use in the duplication scheme in FIG. 12.

Figure 14A:
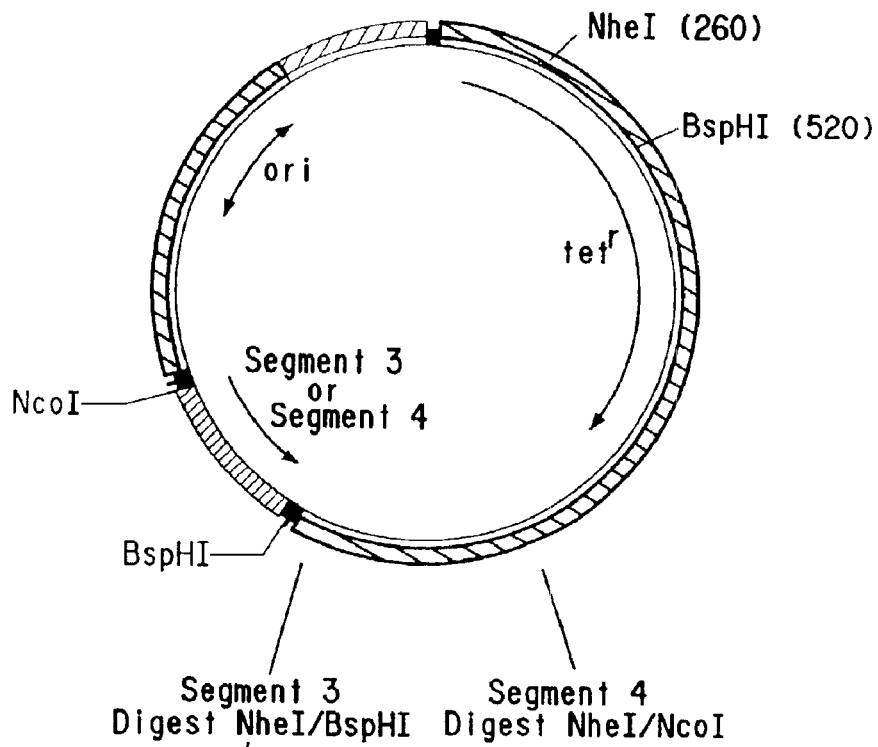
Figure 14B:
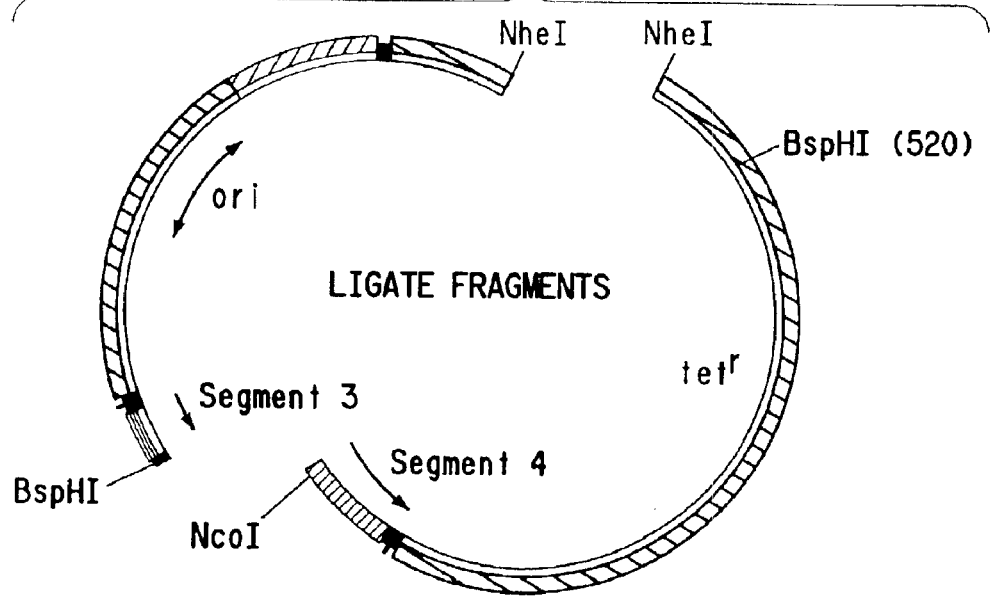

FIGS. 14(A and B) shows the strategy for multiplying non-repetitive gene "segments" utilizing in-frame fusions.

Figure 15:
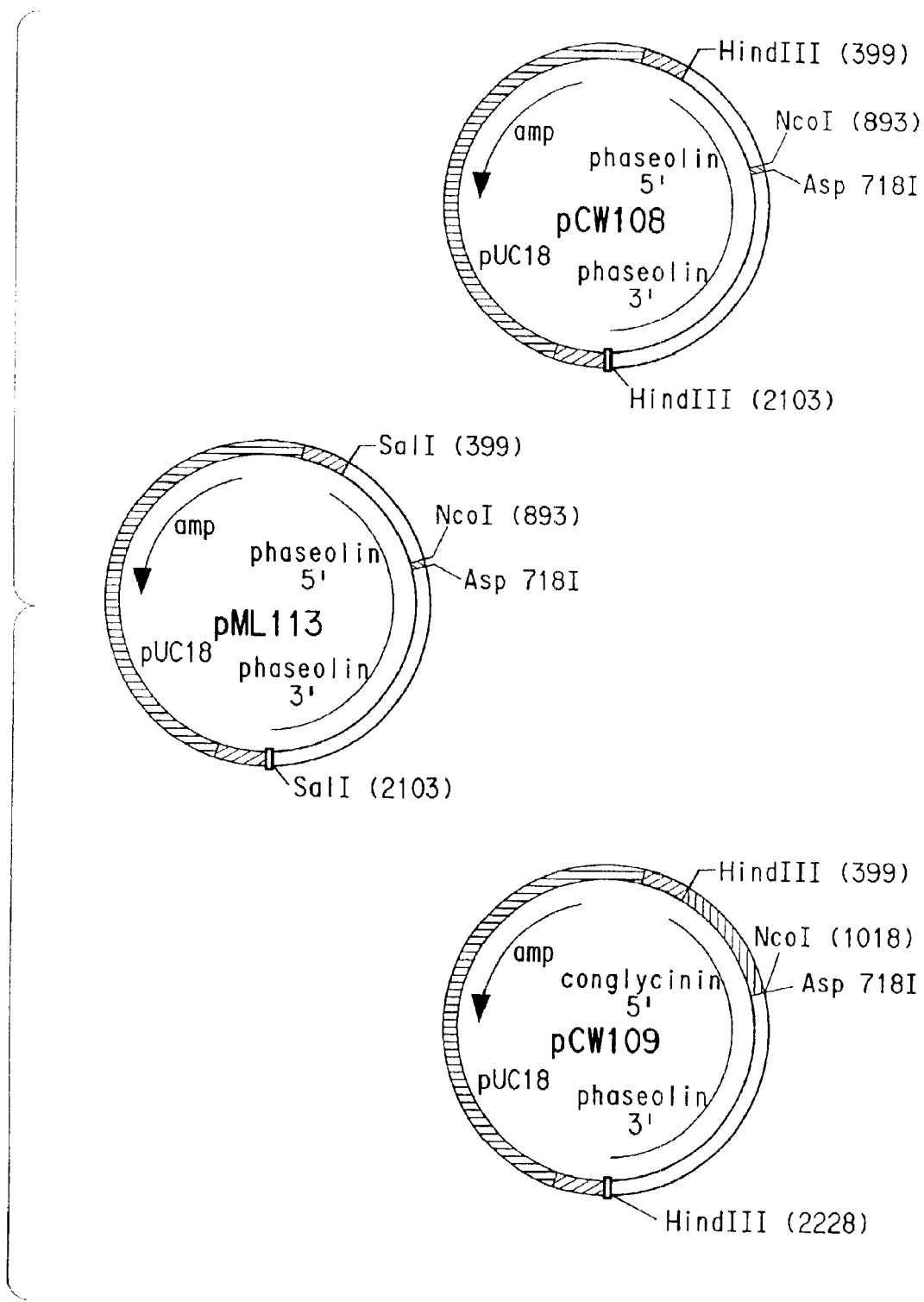

FIG. 15 shows the vectors containing seed specific promoter and 3' sequence cassettes. SSP sequences were inserted into these vectors using the Nco I and Asp718 sites.

Figure 16:
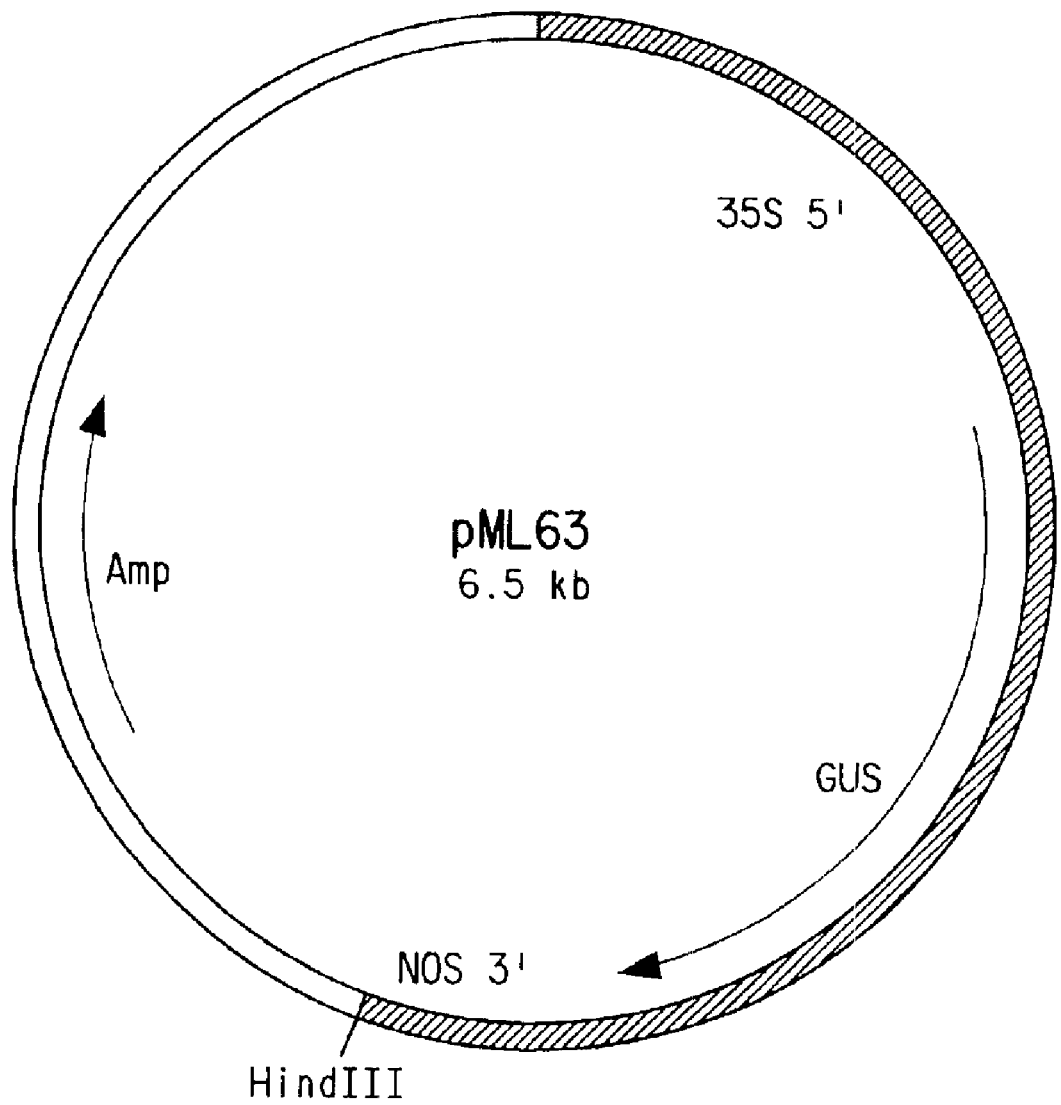

FIG. 16 shows a map of the plasmid vector pML63.

Figure 17:
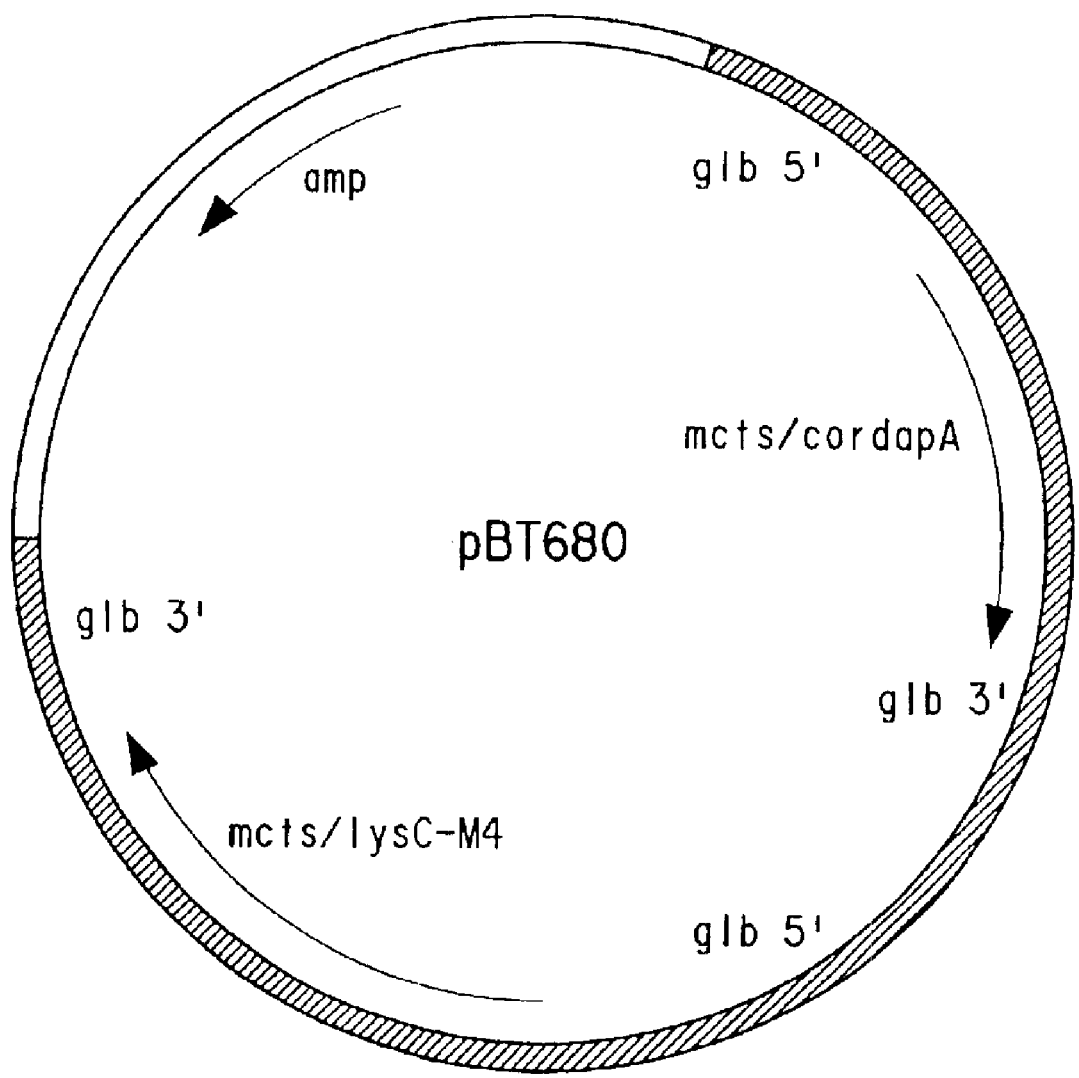

FIG. 17 shows a map of the plasmid vector pBT680.

Figure 18:
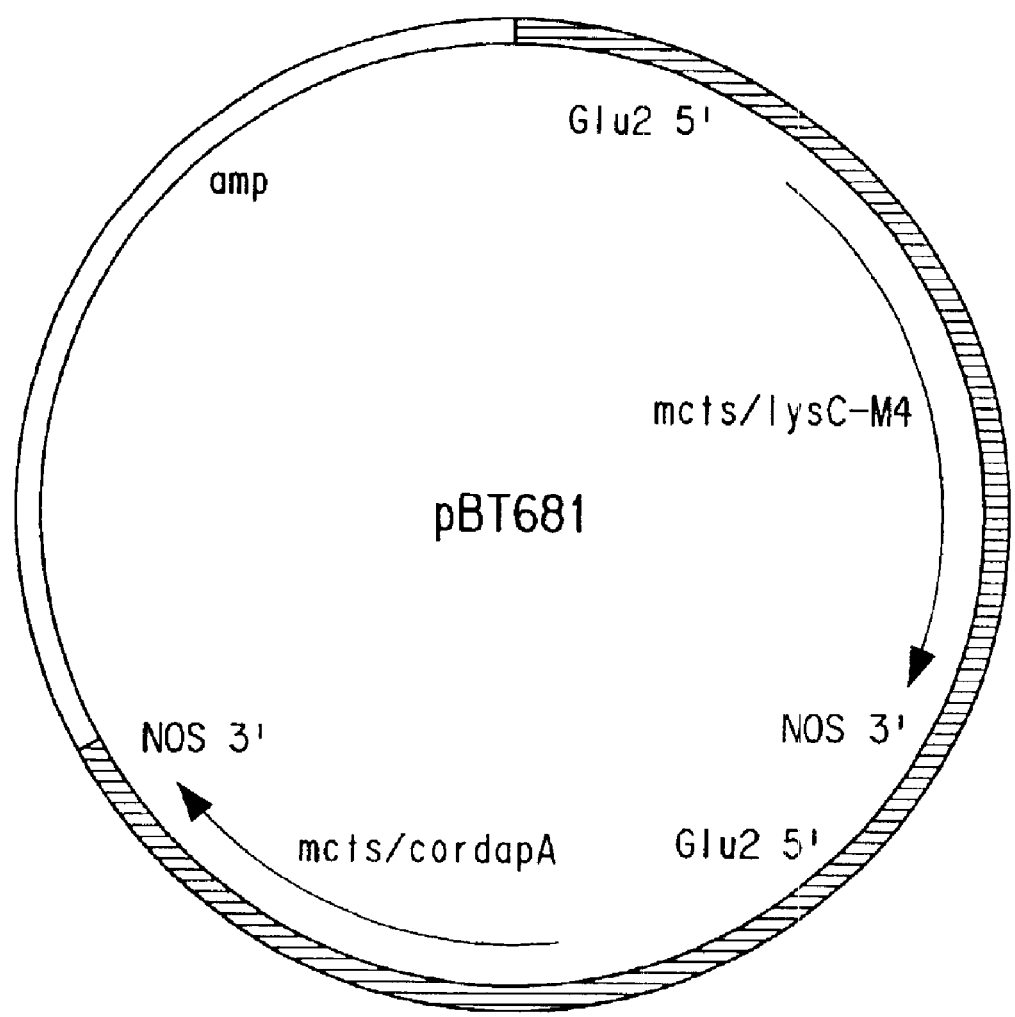

FIG. 18 shows a map of the plasmid vector pBT681.

Figure 19:
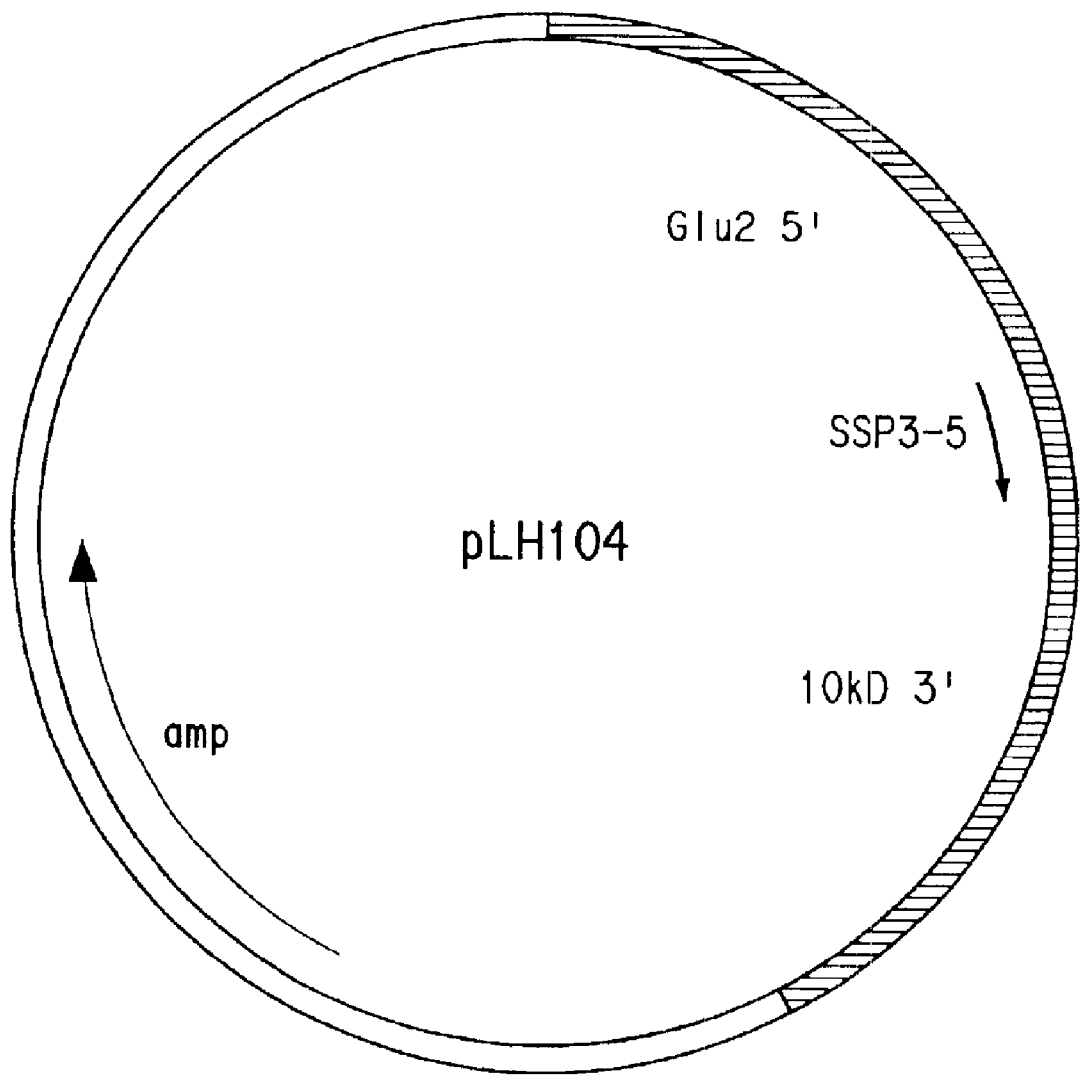

FIG. 19 shows a map of the plasmid vector pLH104.

Figure 20:
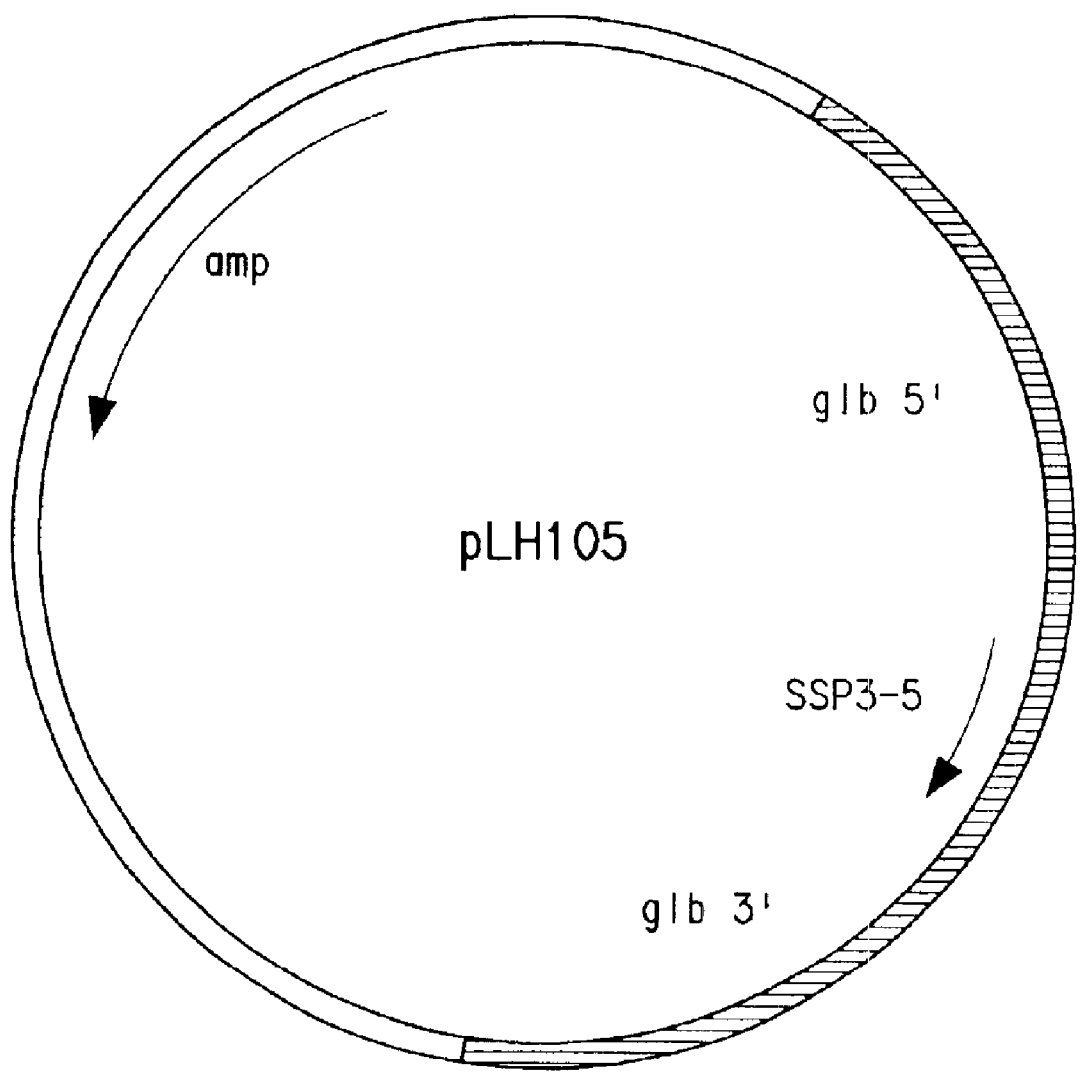

FIG. 20 shows a map of the plasmid vector pLH105.

Figure 21:
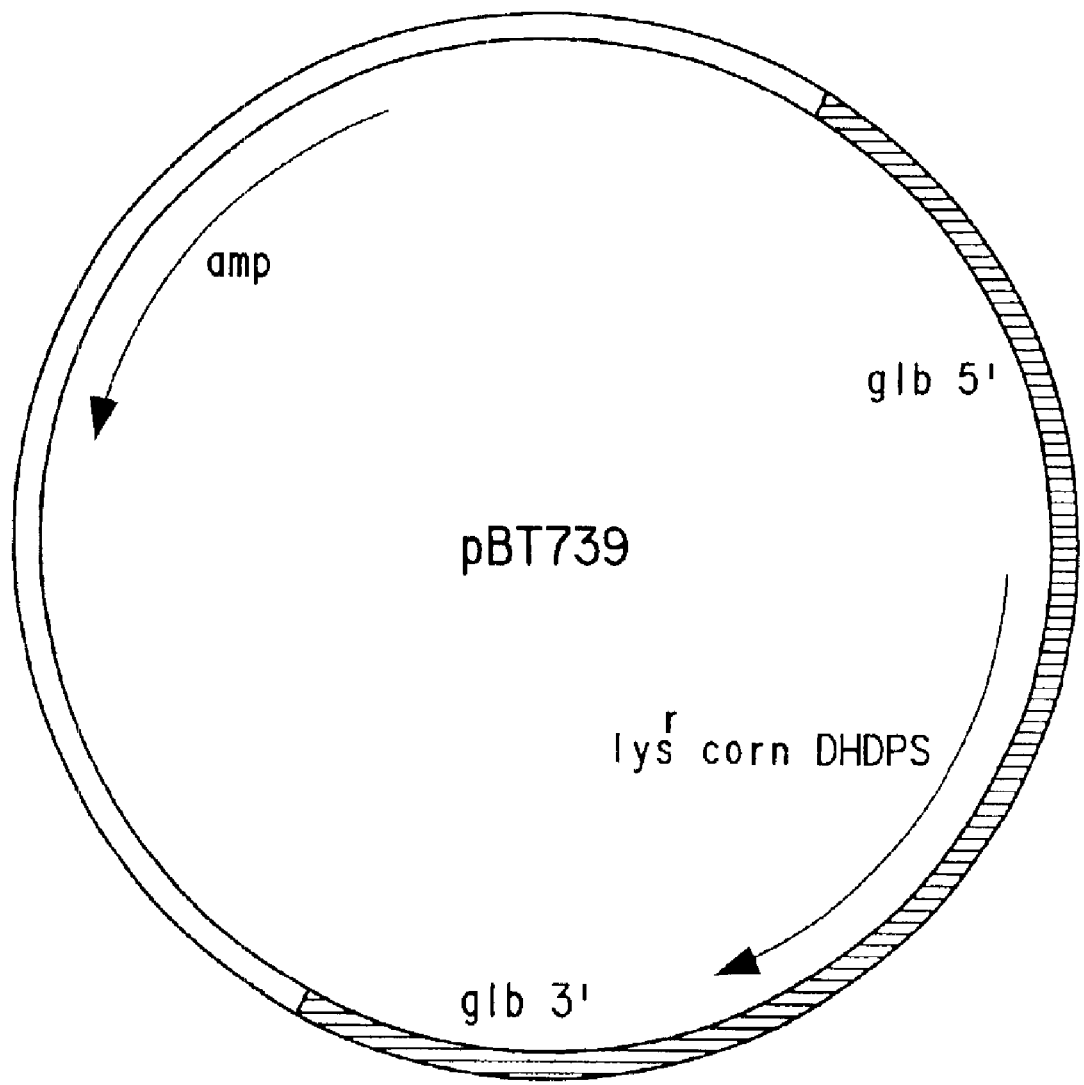

FIG. 21 shows a map of the plasmid vector pBT739.

Figure 22:
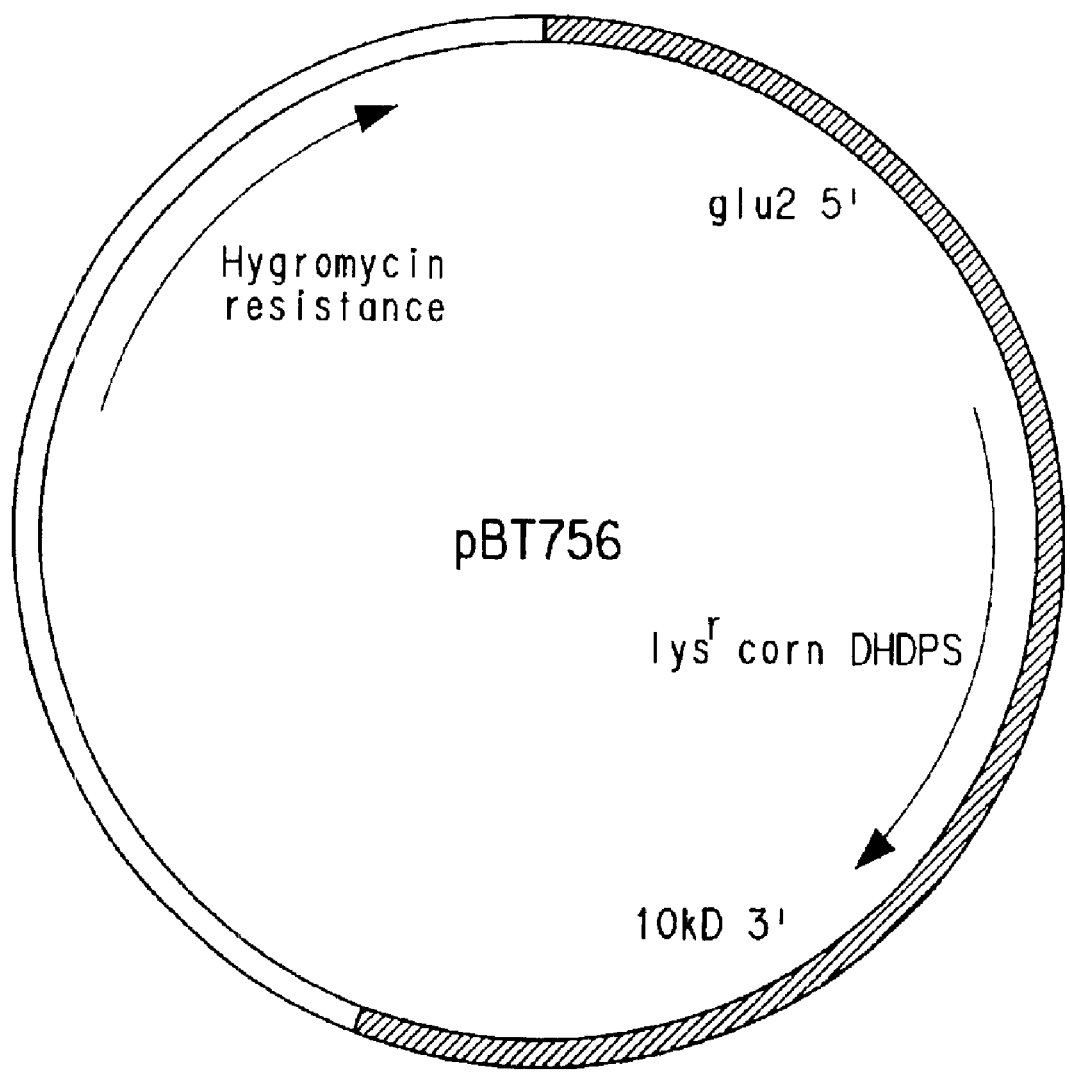

FIG. 22 shows a map of the plasmid vector pBT756.

SEQ ID NO:1 shows the nucleotide and amino acid sequence of the coding region of the wild type *E. coli* lysC gene, which encodes AKIII, described in Example 1.

SEQ ID NOS:2 and 3 were used in Example 2 to create an Nco I site at the translation start codon of the *E. coli* lysC gene.

SEQ ID NOS:4 and 5 were used in Example 3 as PCR primers for the isolation of the *Corynebacterium* dapA gene.

SEQ ID NO:6 shows the nucleotide and amino acid sequence of the coding region of the wild type *Corynebacterium* dapA gene, which encodes lysine-insensitive DHDPS, described in Example 3.

SEQ ID NO:7 was used in Example 4 to create an Nco I site at the translation start codon of the *E. coli* dapA gene.

SEQ ID NOS:8, 9, 10 and 11 were used in Example 6 to create a chloroplast transit sequence and link the sequence to the *E. coli* lysC, *E. coli* lysC-M4, *E. coli* dapA and Corynebacteria dapA genes.

SEQ ID NOS:12 and 13 were used in Example 6 to create a Kpn I site immediately following the translation stop codon of the *E. coli* dapA gene.

SEQ ID NOS:14 and 15 were used in Example 6 as PCR primers to create a chloroplast transit sequence and link the sequence to the *Corynebacterium* dapA gene.

SEQ ID NOS:16–92 represent nucleic acid fragments and the polypeptides they encode that are used to create chimeric genes for lysine-rich synthetic seed storage proteins suitable for expression in the seeds of plants.

SEQ ID NO:93 was used in Example 6 as a constitutive expression cassette for corn.

SEQ ID NOS:94–99 were used in Example 6 to create a corn chloroplast transit sequence and link the sequence to the *E. coli* lysC-M4 gene.

SEQ ID NOS:100 and 101 were used in Example 6 as PCR primers to create a corn chloroplast transit sequence and link the sequence to the *E. coli* dapA gene.

SEQ ID NOS:102 and 103 are cDNAs for plant lysine ketoglutarate reductase/saccharopine dehydrogenase from *Arabidopsis thaliana*.

SEQ ID NOS:104 and 105 are polypeptides homologous to fungal saccharopine dehydrogenase (glutamate-forming) encoded by SEQ ID NOS:102 and 103, respectively.

SEQ ID NOS:106 and 107 were used in Example 25 as PCR primers to add Nco I and Kpn I sites at the 5' and 3' ends of the corn DHDPS gene.

SEQ ID NO:108 is (MEEKLKA)$_6$(MEEKMKA)$_2$.

The Sequence Descriptions contain the one letter code for nucleotide sequence characters and the three letter codes for amino acids as defined in conformity with the IUPAC-IYUB standards described in Nucleic Acids Research 13:3021–3030(1985) and in the Biochemical Journal 219 (No. 2):345–373(1984) which are incorporated by reference herein.

DETAILED DESCRIPTION OF THE INVENTION

The teachings below describe nucleic acid fragments and procedures useful for increasing the accumulation of lysine in the seeds of transformed plants, as compared to levels of lysine in untransformed plants. In order to increase the accumulation of free lysine in the seeds of plants via genetic engineering, a determination was made of which enyzmes in this pathway controlled the pathway in the seeds of plants. In order to accomplish this, genes encoding enzymes in the pathway were isolated from bacteria. In some cases, mutations in the genes were obtained so that the enzyme encoded was made insensitive to end-product inhibition. Intracellular localization sequences and suitable regulatory sequences for expression in the seeds of plants were linked to create chimeric genes. The chimeric genes were then introduced into plants via transformation and assessed for their ability to elicit accumulation of the lysine in seeds.

Applicant has provided a unique first nucleic acid fragment comprised of two nucleic acid subfragments, one encoding AK which is substantially insensitive to inhibition by lysine and the other encoding DHDPS which is substantially insensitive to feedback inhibition by lysine. For the purposes of the present application the term substantially insensitive will mean at least 20-fold less sensitive to feedback inhibition by lysine than a typical plant enzyme catalyzing the same reaction. Applicant has found that a combination of subfragments successfully increases the lysine accumulated in seeds of transformed plants as compared to untransformed host plants.

It has been discovered that the full potential for accumulation of excess free lysine in seeds is reduced by lysine catabolism. Furthermore, it has been discovered that lysine catabolism results in the accumulation of lysine breakdown products such as saccharopine and α-amino adipic acid. Provided herein are two alternative routes to reduce the loss of excess lysine due to catabolism and to reduce the accumulation of lysine breakdown products. In the first approach, lysine catabolism is prevented through reduction in the activity of the enzyme lysine ketoglutarate reductase (LKR), which catalyzes the first step in lysine breakdown. This can be accomplished by introducing a mutation that reduces or eliminates enzyme function in the plant gene that encodes LKR. Such mutations can be identified in lysine over-producer lines by screening mutants for a failure to accumulate the lysine breakdown products, saccharopine and α-amino adipic acid. Alternatively, several procedures to isolate plant LKR genes are provided; nucleic acid fragments containing plant LKR cDNAs are also provided. Chimeric genes for expression of antisense LKR RNA or for cosuppression of LKR in the seeds of plants can then be created. The chimeric LKR gene is linked to chimeric genes encoding lysine insensitive AK and DHDPS and all are introduced into plants via transformation simultaneously, or the chimeric genes are brought together by crossing plants transformed independently with each of the chimeric genes.

In the second approach, excess free lysine is incorporated into a form that is insensitive to breakdown, e.g., by incorporating it into a di-, tri- or oligopeptide, or preferably a lysine-rich storage protein. The lysine-rich storage protein chosen should contain higher levels of lysine than average proteins. Ideally, these storage proteins should contain at least 15% lysine by weight. The design of a preferred class of polypeptides which can be expressed in vivo to serve as lysine-rich seed storage proteins is provided. Genes encoding the lysine-rich synthetic storage proteins (SSP) are synthesized and chimeric genes wherein the SSP genes are linked to suitable regulatory sequences for expression in the seeds of plants are created. The SSP chimeric gene is then linked to the chimeric DHDPS gene and both are introduced into plants via transformation simultaneously, or the genes are brought together by crossing plants transformed independently with each of the chimeric gens.

A method for transforming plants is taught herein wherein the resulting seeds of the plants have at least ten percent, preferably ten percent to four-fold greater, lysine than do the seeds of untransformed plants. Provided as examples herein are transformed rapeseed plants with seed lysine levels increased by 100% over untransformed plants and soybean plants with seed lysine levels increased by four-fold over lysine levels of untransformed plants.

In the context of this disclosure, a number of terms shall be utilized. As used herein, the term "nucleic acid" refers to a large molecule which can be single-stranded or double-stranded, composed of monomers (nucleotides) containing a sugar, phosphate and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers.

As used herein, the term "homologous to" refers to the complementarity between the nucleotide sequence of two nucleic acid molecules or between the amino acid sequences of two protein molecules. Quantitative estimates of homology are provided by either DNA-DNA or DNA-RNA hybridization under conditions of stringency as is well understood by those skilled in the art [as described in Hames and Higgins (eds.) Nucleic Acid Hybridisation, IRL Press, Oxford, U.K.]; or by the comparison of sequence similarity between two nucleic acids or proteins.

As used herein, "essentially similar" refers to DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alteration in the gene sequence which reflect the degeneracy of the genetic code, or which result in the production of a chemically equivalent amino acid at a given site, are contemplated; thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity of the encoded products. Moreover, the skilled artisan recognizes that "essentially similar" sequences encompassed by this invention are also defined by their ability to hybridize, under stringent conditions (0.1× SSC, 0.1% SDS, 65° C.), with the sequences exemplified herein.

"Gene" refers to a nucleic acid fragment that expresses a specific protein, including regulatory sequences preceding (5' non-coding) and following (3' non-coding) the coding region. "Native" gene refers to the gene as found in nature with its own regulatory sequences. "Chimeric" gene refers to a gene comprising heterogeneous regulatory and coding sequences. "Endogenous" gene refers to the native gene normally found in its natural location in the genome. A "foreign" gene refers to a gene not normally found in the host organism but that is introduced by gene transfer.

"Coding sequence" refers to a DNA sequence that codes for a specific protein and excludes the non-coding sequences.

"Initiation codon" and "termination codon" refer to a unit of three adjacent nucleotides in a coding sequence that specifies initiation and chain termination, respectively, of protein synthesis (mRNA translation). "Open reading frame" refers to the amino acid sequence encoded between translation initiation and termination codons of a coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript. "Messenger RNA (mRNA) refers to RNA that can be translated into protein by the cell. "cDNA" refers to a double-stranded DNA that is complementary to and derived from mRNA. "Sense" RNA refers to RNA transcript that includes the mRNA. "Antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases.

As used herein, suitable "regulatory sequences" refer to nucleotide sequences located upstream (5'), within, and/or downstream (3') to a coding sequence, which control the transcription and/or expression of the coding sequences, potentially in conjunction with the protein biosynthetic apparatus of the cell. These regulatory sequences include promoters, translation leader sequences, transcription termination sequences, and polyadenylation sequences.

"Promoter" refers to a DNA sequence in a gene, usually upstream (5') to its coding sequence, which controls the expression of the coding sequence by providing the recognition for RNA polymerase and other factors required for proper transcription. A promoter may also contain DNA sequences that are involved in the binding of protein factors which control the effectiveness of transcription initiation in response to physiological or developmental conditions. It may also contain enhancer elements.

An "enhancer" is a DNA sequence which can stimulate promoter activity. It may be an innate element of the promoter or a heterologous element inserted to enhance the level and/or tissue-specificity of a promoter. "Constitutive promoters" refers to those that direct gene expression in all tissues and at all times. "Organ-specific" or "development-specific" promoters as referred to herein are those that direct gene expression almost exclusively in specific organs, such as leaves or seeds, or at specific development stages in an organ, such as in early or late embryogenesis, respectively.

The term "operably linked" refers to nucleic acid sequences on a single nucleic acid molecule which are associated so that the function of one is affected by the other. For example, a promoter is operably linked with a structure gene (i.e., a gene encoding aspartokinase that is lysine-insensitive as given herein) when it is capable of affecting the expression of that structural gene (i.e., that the structural gene is under the transcriptional control of the promoter).

The term "expression", as used herein, is intended to mean the production of the protein product encoded by a gene. More particularly, "expression" refers to the transcription and stable accumulation of the sense (mRNA) or tha antisense RNA derived from the nucleic acid fragment(s) of the invention that, in conjuction with the protein apparatus of the cell, results in altered levels of protein product. "Antisense inhibition" refers to the production of antisense RNA transcripts capable of preventing the expression of the target protein. "Overexpression" refers to the production of a gene product in transgenic organisms that exceeds levels of production in normal or non-transformed organisms. "Cosuppression" refers to the expression of a foreign gene which has substantial homology to an endogenous gene resulting in the suppression of expression of both the foreign and the endogenous gene. "Altered levels" refers to the production of gene product(s) in transgenic organisms in amounts or proportions that differ from that of normal or non-transformed organisms.

The "3' non-coding sequences" refers to the DNA sequence portion of a gene that contains a polyadenylation signal and any other regulatory signal capable of affecting mRNA processing or gene expression. The polyadenylation signal is usually characterized by affecting the addition of polyadenylic acid tracts to the 3' end of the mRNA precursor.

The "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Mature" protein refers to a post-translationally processed polypeptide without its targeting signal. "Precursor" protein refers to the primary product of translation of mRNA. A "chloroplast targeting signal" is an amino acid sequence which is translated in conjunction with a protein and directs it to the chloroplast. "Chloroplast transit sequence" refers to a nucleotide sequence that encodes a chloroplast targeting signal.

"Transformation" herein refers to the transfer of a foreign gene into the genome of a host organism and its genetically stable inheritance. Examples of methods of plant transformation include Agrobacterium-mediated transformation and particle-accelerated or "gene gun" transformation technology.

"Amino acids" herein refer to the naturally occuring L amino acids (Alanine, Arginine, Aspartic acid, Asparagine, Cystine, Glutamic acid, Glutamine, Glycine, Histidine, Isoleucine, Leucine, Lysine, Methionine, Proline, Phenylalanine, Serine, Threonine, Tryptophan, Tyrosine, and Valine). "Essential amino acids" are those amino acids which cannot be synthesized by animals. A "polypeptide" or "protein" as used herein refers to a molecule composed of monomers (amino acids) linearly linked by amide bonds (also known as peptide bonds).

"Synthetic protein" herein refers to a protein consisting of amino acid sequences that are not known to occur in nature. The amino acid sequence may be derived from a consensus of naturally occuring proteins or may be entirely novel.

"Primary sequence" refers to the connectivity order of amino acids in a polypeptide chain without regard to the conformation of the molecule. Primary sequences are written from the amino terminus to the carboxy terminus of the polypeptide chain by convention.

"Secondary structure" herein refers to physico-chemically favored regular backbone arrangements of a polypeptide chain without regard to variations in side chain identities or conformations. "Alpha helices" as used herein refer to right-handed helices with approximately 3.6 residues residues per turn of the helix. An "amphipathic helix" refers herein to a polypeptide in a helical conformation where one side of the helix is predominantly hydrophobic and the other side is predominantly hydrophilic.

"Coiled-coil" herein refers to an aggregate of two parallel right-handed alpha helices which are wound around each other to form a left-handed superhelix.

"Salt bridges" as discussed here refer to acid-base pairs of charged amino acid side chains so arranged in space that an attractive electrostatic interaction is maintained between two parts of a polypeptide chain or between one chain and another.

"Host cell" means the cell that is transformed with the introduced genetic material.

Isolation of AK Genes

The E. coli lysC gene has been cloned, restriction endonuclease mapped and sequenced previously [Cassan et al. (1986) J. Biol. Chem. 261:1052–1057]. For the present invention the lysC gene was obtained on a bacteriphage lambda clone from an ordered library of 3400 overlapping segments of cloned E. coli DNA constructed by Kohara, Akiyama and Isono [Kohara et al. (1987) Cell 50:595–508]. The E. coli lysC gene encodes the enzyme AKIII, which is sensitive to lysine inhibition. Mutations were obtained in the lysC gene that cause the AKIII enzyme to be resistant to lysine.

To determine the molecular basis for lysine-resistance, the sequence of the wild type lysC gene and three mutant genes were determined. The sequence of the cloned wild type lysC gene, indicated in SEQ ID NO:1:, differed from the published lysC sequence in the coding region at 5 positions.

The sequences of the three mutant lysC genes that encoded lysine-insensitive aspartokinase each differed from the wild type sequnce by a single nucleotide, resulting in a single amino acid substitution in the protein. One mutant (M2) had an A substituted for a G at nucleotide 954 of SEQ ID NO:1: resulting in an isoleucine for methionine substitution in the amino acid sequence of AKIII and two mutants (M3 and M4) had identical T for C substitutions at nucleotide 1055 of SEQ ID NO:1 resulting in an isoleucine for threonine substitution.

Other mutations could be generated, either in vivo as described in Example 1 or in vitro by site-directed mutagenesis by methods known to those skilled in the art, that result in amino acid substitutions for the methionine or threonine residue present in the wild type AKIII at these positions. Such mutations would be expected to result in a lysine-insensitive enzyme. Furthermore, the method described in Example 1 could be used to easily isolate and characterize as many additional mutant lysC genes encoding lysine insensitive AKIII as desired.

A number of other AK genes have been isolated and sequenced. These include the thrA gene of E. coli (Katinka et al. (1980) Proc. Natl. Acad. Sci. USA 77:5730–5733], the metL gene of E. coli (Zakin et al. (1983) J. Biol. Chem. 258:3028–3031], the HOM3 gene of S. cerevisiae [Rafalski et al. (1988) J. Biol. Chem. 263:2146–2151]. The thrA gene of E. coli encodes a bifunctional protein, AKI-HDHI. The AK activity of this enzyme is insensitive to lysine, but sensitive to threonine. The metL gene of E. coli also encodes a bifunctional protein, AKII-HDHII, and the AK activity of this enzyme is also insensitive to lysine. The HOM3 gene of yeast encodes an AK which is insensitive to lysine, but sensitive to threonine.

In addition to these genes, several plant genes encoding lysine-insensitive AK are known. In barley lysine plus threonine-resistant mutants bearing mutations in two unlinked genes that result in two different lysine-insensitive AK isoenzymes have been described [Bright et al. (1982) Nature 299:278–279, Rognes et al. (1983) Planta 157:32–38, Arruda et al. (1984) Plant Phsiol. 76:442–446]. In corn, a lysine plus threonine-resistant cell line had AK activity that was less sensitive to lysine inhibition than its parent line [Hibberd et al. (1980) Planta 148:183–187]. A subsequently isolated lysine plus threonine-resistant corn mutant is altered at a different genetic locus and also produces lysine-insensitive AK [Diedrick et al. (1990) Theor. Appl. Genet. 79:209–215, Dotson et al. (1990) Planta 182:546–552]. In tobacco there are two AK enzymes in leaves, one lysine-sensitive and one threonine-sensitive. A lysine plus threonine-resistant tobacco mutant that expressed completely lysine-insensitive AK has been described [Frankard et al. (1991) Theor. Appl. Genet. 82:273–282]. These plant mutants could serve as sources of genes encoding lysine-insensitive AK and used, based on the teachings herein, to increase the accumulation of lysine and threonine in the seeds of transformed plants.

A partial amino acid sequence of AK from carrot has been reported [Wilson et al. (1991) Plant Physiol. 97:1323:1328]. Using this information a set of degenerate DNA oligonucleotides could be designed, synthesized and used as hybridization probes to permit the isolation of the carrot AK gene. Recently the carrot AK gene has been isolated and its nucleotide sequence has been determined [Matthews et al.

(1991) U.S. Ser. No. 07/746,705]. This gene can be used as a heterologous hybridization probe to isolate the genes encoding lysine-insensitive AK described above.

High Level Expression of Wild Type and Mutant lysC Genes in E. coli

To achieve high level expression of the lysC genes in E. coli, a bacterial expression vector which employs the bacteriophage T7 RNA polymerase/T7 promoter system [Rosenberg et al. (1987) Gene 56:125–135] was used. The expression vector and lysC gene were modified as described in Example 2 to construct a lysC expression vector. For expression of the mutant lysC genes (M2, M3 and M4), the wild type lysC gene was replaced with the mutant genes as described in Example 2.

For high level expression, each of the expression vectors was transformed into E. coli strain B121(DE3) [Studier et al. (1986) J. Mol. Biol. 189:113–130]. Cultures were grown, expression was induced, cells were collected, and extracts were prepared as described in Example 2. Supernatant and pellet fractions of extracts from uninduced and induces cultures were analyzed by SDS polyacrylamide gel electrophoresis and by AK enzyme assays as described in Example 2. The major protein visible by Coomassie blue staining in the supernatant and pellet fractions of induced cultures was AKIII. About 80% of the AKIII protein was in the supernatant and AKIII represented 10–20% of the total E. coli protein in the extract.

Approximately 80% of the AKIII enzyme activity was in the supernatant fraction. The specific activity of wild type and mutant crude extracts was 5–7 μmoles product per minute per milligram total protein. Wild type AKIII was sensitive to the presence of L-lysine in the assay. Fifty percent inhibition was found at a concentration of about 0.4 mM and 90 percent inhibition at about 0.1 mM. In contrast, mutants AKIII-M2, M3 and M4 were not inhibited at all by 15 mM L-lysine.

Wild type AKIII protein was purified from the supernatant of an induced culture as described in Example 2. Rabbit antibodies were raised against the purified AKIII protein.

Many other microbial expression vectors have been described in the literature. One skilled in the art could make use of any of these to construct lysC expression vectors. These lysC expression vectors could then be introduced into appropriate microorganisms via transformation to provide a system for high level expression of AKIII.

Isolation of DHDPS Genes

The E. coli dapA gene (ecodapA) has been cloned, restriction endonuclease mapped and sequenced previously [Richaud et al. (1986) J. Bacteriol. 166:297–300]. For the present invention the dapA gene was obtained on a bacteriophage lambda clone from an ordered library of 3400 overlapping segments of cloned E. coli. DNA constructed by Kohara, Akiyama and Isono [Kohara et al. (1987) Cell 50:595–508]. The ecodapA gene encodes a DHDPS enzyme that is sensitive to lysine inhibition. However, it is about 20-fold less sensitive to inhibition by lysine than a typical plant DHDPS, e.g., wheat germ DHDPS.

The Corynebacterium dapA gene (cordapA) was isolated from genomic DNA from ATCC strain 13032 using polymerase chain reaction (PCR). The nucleotide sequence of the Corynebacterium dapA gene has been published [Bonnassie et al. (1990) Nucleic Acids Res. 18:6421]. From the sequence it was possible to design oligonucleotide primers for polymerase chain reaction (PCR) that would allow amplification of a DNA fragment containing the gene, and at the same time add unique restriction endonuclease sites at the start codon and just past the stop codon of the gene to facilitate further constructions involving the gene. The details of the isolation of the cordapA gene are presented in Example 3. The cordapA gene encodes a DHDPS enzyme that is insensitive to lysine inhibiton.

In addition to introducing a restriction endonuclease site at the translation start codon, the PCR primers also changed the second codon of the cordapA gene from AGC coding for serine to GCT coding for alanine. Several cloned DNA fragments that expressed active, lysine-insensitive DHDPS were isolated, indicating that the second codon amino acid substitution did not affect enzyme activity.

The PCR-generated Corynebacterium dapA gene was subcloned into the phagemid vactor pGEM-9zf(-) from Promega, and single-stranded DNA was generated and sequenced (SEQ ID NO:6). Aside from the differenced in the second codon already mentioned, the sequence matched the published sequence except at two positions, nucleotides 798 and 799. In the published sequence these are TC, while in the gene shown in SEQ ID NO:6 they are CT. This change results in an amino acid substitution of leucine for serine. The reason for this difference is not known. The difference has no apparent effect on DHDPS enzyme activity.

The isolation of other genes encoding DHDPS has been described in the literature. A cDNA encoding DHDPS from wheat [Kaneko et al. (1990) J. Biol. Chem. 265:17451–17455], and a cDNA encoding DHDPS from corn [Frisch et al. (1991) Mol. Gen. Genet. 228:287–293] are two examples. These genes encode wild type lysine-sensitive DHDPS enzymes. However, Negrutui et al. [(1984) Theor. Appl. Genet. 68:11–20], obtained two AEC-resistant tobacco mutants in which DHDPS activity was less sensitive to lysine inhibition than the wild type enzyme. These genes could be isolated using the methods already described for isolating the wheat or corn genes or, alternatively, by using the wheat or corn genes as heterologous hybridization probes.

Still other genes encoding DHDPS could be isolated by one skilled in the art by using either the ecodapA gene, the cordapA gene, or either of the plant DHDPS genes as DNA hybridization probes. Alternatively, other genes encoding DHDPS could be isolated by functional complementation of an E. coli dapA mutant, as was done to isolate the cordapA gene [Yeh et al. (1988) Mol. Gen. Genet. 212:105–111] and the corn DHDPS gene.

High Level Expression of ecodapA and cordapA Genes in E. coli

To achieve high level expression of the ecodapA and cordapA genes in E. coli, a bacterial expression vector which employs the bacteriophage T7 RNA polymerase/T7 promoter system [Rosenberg et al. (1987) Gene 56:127–135] was used. The vector and dapA genes were modified as described below to construct ecodapA and cordapA expression vectors.

For high level expression each of the expression vectors was transformed into E. coli strain BL21(DE3) [Studier et al. (1986) J. Mol. Biol. 189:113–130]. Cultures were grown, expression was induced, cells were collected, and extracts were prepared as described in Example 4. Supernatant and pellet fractions of extracts from uninduced and induced cultures were analyzed by SDS polyacrylamide gel electrophoresis and by DHDPS enzyme assays as described in Example 4. The major protein visible by Coomassie blue staining in the supernatant and pellet fractions of both induced cultures had a molecular weight of 32–34 kd, the expected size for DHDPS. Even in the uninduced cultures this protein was the most prominent protein produced.

In the induced culture with the ecodapA gene about 80% of the DHDPS protein was in the supernatant and DHDPS represented 10–20% of the total protein in the extract. In the induced culture with the cordapA gene more than 50% of the DHDPS protein was in the pellet fraction. The pellet fractions in both cases were 90–95% pure DHDPS, with no other single protein present in significant amounts. Thus, these fractions were pure enough for use in the generation of rabbit antibodies.

The specific activity of E. coli DHDPS in the supernatant fraction of induced extracts was about 50 $OD_{540}$ units per milligram protein. E. coli DHDPS was sensitive to the presence of L-lysine in the assay. Fifty percent inhibition was found at a concentration of about 0.5 mM. For Corynebacterium DHDPS, enzyme activity was measured in the supernatant fraction of uninduced extracts, rather than induced extracts. Enzyme activity was about 4 $OD_{530}$ units per minute per milligram protein. In contrast to E. coli DHDPS, Corynebacterium DHDPS was not inhibited at all by L-lysine, even at a concentration of 70 mM.

Many other microbial expression vectors have been described in the literature. One skilled in the art could make use of any of these to construct ecodapA or cordapA expression vectors. These expression vectors could then be introduced into appropriate microorganisms via transformation to provide a system for high level expression of DHDPS.

Excretion of Amino Acids by E. coli Expressing High Levels of DHDPS and/or AKIII The E. coli expression cassettes were inserted into expression vectors and then transformed into E. coli strain BL21 (DE3) [Studier et al. (1986) J. Mol. Biol. 189:113–130] to induce E. coli to produce and excrete amino acids. Details of the procedures used and results are presented in Example 5.

Other microbial expression vectors known to those skilled in the art could be used to make and combine expression cassettes for the lysC and dapA genes. These expression vectors could then be introduced into appropriate microorganisms via transformation to provide alternative systems for production and excretion of lysine, theronine and methionine.

Construction of Chimeric Genes for Expression in Plants

A preferred class of heterologous hosts for the expression of the chimeric genes of this invention are eukaryotic hosts, particularly the cells of higher plants. Preferred among the higher plants and the seeds derived from them are soybean, rapeseed (Brassica napus, B. campestris), sunflower (Helianthus annus), cotton (Gossypium hirsutum), corn, tobacco (Nicotiana Tubacum), alfalfa (Medicago sativa), wheat (Triticum sp), barley (Hordeum vulgare), oats (Avena sativa, L), sorghum (Sorghum bicolor), rice (Oryza sativa), and forage grasses. Expression in plants will use regulatory sequences functional in such plants. The expression of foreign genes in plants is well-established [De Blaere et al. (1987) Meth. Enzymol. 143:277–291]. Proper level of expression of the different chimeric genes of this invention in plant cells may be achieved through the use of many different promoters. Such chimeric genes can be transferred into host plants either together in a single expression vector or sequentially using more than one vector.

The origin of promoter chosen to drive the expression of the coding sequence is not critical as long as it has sufficient transcriptional activity to accomplish the invention by expressing translatable mRNA or antisense RNA in the desired host tissue. Preferred promoters for expression in all plant organs, and especially for expression in leaves include those directing the 19S and 35S transcripts in Cauliflower mosaic virus [Odell et al.(1985) Nature 313:810–812; Hull et al. (1987) Virology 86:482–493], small subunit of ribulose 1,5-bisphosphate carboxylase [Morelli et al.(1985) Nature 315:200; Broglie et al. (1984) Science 224:838; Hererra-Estrella et al.(1984) Nature 310:115; Coruzzi et al.(1984) EMBO J. 3:1671; Faciotti et al.(1985) Bio/Technology 3:241], maize zein protein [Matzke et al.(1984) EMBO J. 3:1525], and chlorophyll a/b binding protein [Lampa et al. (1986) Nature 316:750–752].

Depending upon the application, it may be desirable to select promoters that are specific for expression in one or more organs of the plant. Examples include the light-inducible promoters of the small subunit of ribulose 1,5-bisphosphate carboxylase, if the expression is desired in photosynthetic organs, or promoters active specifically in seeds.

Preferred promoters are those that allow expression specifically in seeds. This may be especially useful, since seeds are the primary source of vegetable amino acids and also since seed-specific expression will avoid any potential deleterious effect in non-seed organs. Examples of seed-specific promoters include, but are not limited to, the promoters of seed storage proteins. The seed storage proteins are strictly regulated, being expressed almost exclusively in seeds in a highly organ-specific and stage-specific manner [Higgins et al.(1984) Ann. Rev. Plant Physiol. 35:191–221; Goldberg et al.(1989) Cell 56:149–160; Thompson et al. (1989) BioEssays 10: 108–113]. Moreover, different seed storage proteins may be expressed at different stages of seed development.

There are currently numerous examples for seed-specific expression of seed storage protein genes in transgenic dicotyledonous plants. These include genes from dicotyledonous plants for bean β-phaseolin [Sengupta-Goplalan et al. (1985) Proc. Natl. Acad. Sci. USA 82:3320–3324; Hoffman et al. (1988) Plant Mol. Biol. 11:717–729], bean lectin [Voelker et al. (1987) EMBO J. 6: 3571–3577], soybean lectin [Okamuro et al. (1986) Proc. Natl. Acad. Sci. USA 83:8240–8244], soybean kunitz trypsin inhibitor [Perez-Grau et al. (1989) Plant Cell 1:095–1109], soybean β-conglycinin [Beachy et al. (1985) EMBO J. 4:3047–3053; Barker et al. (1988) Proc. Natl. Acad. Sci. USA 85:458–462; Chen et al. (1988) EMBO J. 7:297–302; Chen et al. (1989) Dev. Genet. 10:112–122; Naito et al. (1988) Plant Mol. Biol. 11:109–123], pea vicilin [Higgins et al. (1988) Plant Mol. biol. 11:683–695], pea convicilin [Newbigin et al. (1990) Planta 180:461], pea legumin [Shirsat et al. (1989) Mol. Gen. Genetics 215:326]; rapeseed napin [Radke et al. (1988) Theor. Appl. Genet. 75:685–694] as well as genes from monocotyledonous plants such as for maize 15 kD zein [Hoffman et al. (1987)EMBO J. 6:3213–3221; Schernthaner et al. (1988) EMBO J. 7:1249–1253; Williamson et al. (1988) Plant Physiol. 88:1002–1007], barley β-hordein [Marris et al. (1988) Plant Mol. Biol. 10:359–366] and wheat glutenin [Colot et al. (1987) EMBO J. 6:3559–3564]. Moreover, promoters of seed-specific genes, operably linked to heterologous coding sequences in chimeric gene constructs, also maintain their temporal and spatial expression pattern in transgenic plants. Such examples include Arabidopsis thaliana 2S seed storage protein gene promoter to express enkephalin peptides in Arabidopsis and B. napus seeds [Vandekerckhove et al. (1989) Bio/Technology 7:929–932], bean lectin and bean β-phaseolin promoters to express luciferase [Riggs et al. (1989) Plant Sci. 63:47–57], and wheat glutenin promoters to express chloramphenicol acetyl transferase [Colot et al. (1987) EMBO J. 6:3559–3564].

Of particular use in the expression of the nucleic acid fragment of the invention will be the heterologous promoters from several extensively-characterized soybean seed storage protein genes such as those for the Kunitz trypsin inhibitor [Jofuku et al. (1989) Plant Cell 1:1079–1093; Perez-Grau et al. (1989) Plant Cell 1:1095–1109], glyceinin [Nielson et al. (1989) Plant Cell 1:313–328], β-conglycinin [Harada et al. (1989) Plant Cell 1:415–425]. Promoters of genes for α'- and β-subunits of soybean β-conglycinin storage protein will be particularly useful in expressing mRNAs or antisense RNAs in the cotyledons at mid- to late-stages of soybean seed development [Beachy et al. (1985) EMBO J. 4:3047–3053; Barker et al. (1988) Proc. Natl. Acad. Sci. USA 85:458–462; Chen et al. (1988) EMBO J. 7:297–302; Chen et al. (1989) Dev. Genet. 10:112–122; Naito et al. (1988) Plant Mol. biol. 11:109–123] in transgenic plants, since: a) there is very little position effect on their expression in transgenic seeds, and b) the two promoters show different temporal regulation: the promoter for the α'-subunit gene is expressed a few days before that for the β-subunit gene.

Also of particular use in the expression of the nucleic acid fragments of the invention will be the heterologous promoters from several extensively characterized corn seed storage protein genes such as endosperm-specific promoters from the 10 kD zein [Kirihara et al. (1988) Gene 71:359–370], the 27 kD zein [Prat et al. (1987) Gene 52:51–49; Gallardo et al. (1988) Plant Sci. 54:211–281], and the 19 kD zein [Marks et al. (1985) J. Biol. Chem. 260:16451–16459]. The relative transcriptional activities of these promoters in corn have been reported [Kodrzyck et al. (1989) Plant Cell 1:105–114] providing a basis for choosing a promoter for use in chimeric gene constructs for corn. For expression in corn embryos, the strong embryo-specific promoter from the GLB1 gene [Kriz (1989) Biochemical Genetics 27:239–251, Wallace et al. (1991) Plant Physiol. 95:973–975] can be used.

It is envisioned that the introduction of enhancers or enhancer-like elements into other promoter constructs will also provide increased levels of primary transcription to accomplish the invention. These would include viral enhancers such as that found in the 35S promoter [Odell et al. (1988) Plant Mol. Biol. 10:263–272], enhancers from the opine genes [Fromm et al. (1989) Plant Cell 1:977–984], or enhancers from any other source that result in increased transcription when placed into a promoter operably linked to the nucleic acid fragment of the invention.

Of particular importance is the DNA sequence element isolated from the gene for the α'-subunit of β-conglycinin that can confer 40-fold seed-specific enhancement to a constitutive promoter [Chen et al. (1988) EMBO J. 7:297–302; Chen et al. (1989) Dev. Genet. 10:112–122]. One skilled in the art can readily isolate this element and insert it within the promoter region of any gene in order to obtain seed-specific enhanced expression with the promoter in transgenic plants. Insertion of such an element in any seed-specific gene that is expressed at different times than the β-conglycinin gene will result in expression in transgenic plants for a longer period during seed development.

Any 3' non-coding region capable of providing a polyadenylation signal and other regulatory sequences that may be required for the proper expression can be used to accomplish the invention. This would include the 3' end from any storage protein such as the 3' end of the bean phaseolin gene, the 3' end of the soybean β-conglycinin gene, the 3' end from viral genes such as the 3' end of the 35S or the 19S cauliflower mosaic virus transcripts, the $_3$' end from the opine synthesis genes, the 3' ends of ribulose 1,5-bisphosphate carboxylase or chlorophyll a/b binding protein, or 3' end sequences from any source such that the sequence employed provides the necessary regulatory information within its nucleic acid sequence to result in the proper expression of the promoter/coding region combination to which it is operably linked. There are numerous examples in the art that teach the usefulness of different 3' non-coding regions [for example, see Ingelbrecht et al. (1989) Plant Cell 1:671–680].

DNA sequences coding for intracellular localization sequences may be added to the lysC and dapA coding sequence if required for the proper expression of the proteins to accomplish the invention. Plant amino acid biosynthetic enzymes are known to be localized in the chloroplasts and therefore are synthesized with a chloroplast targeting signal. Bacterial proteins such as DHDPS and AKIII have no such signal. A chloroplast transit sequence could, therefore, be fused to the dapA and lysC coding sequences. Preferred chloroplast transit sequences are those of the small subunit of ribulose 1,5-bisphosphate carboxylase, e.g. from soybean [Berry-Lowe et al. (1982) J. Mol. Appl. Genet. 1:483–498] for use in dicotyledonous plants and from corn [Lebrun et al. (1987) Nucleic Acids Res. 15:4360] for use in monocotyledonous plants.

Introduction of Chimeric Genes into Plants

Various methods of introducing a DNA sequence (i.e., of transforming) into eukaryotic cells of higher plants are available to those skilled in the art (see EPO publications 0 295 959 A2 and 0 138 341 A1). Such methods include those based on transformation vectors based on the Ti and Ri plasmids of Agrobacteruim spp. It is particularly preferred to use the binary type of these vectors. Ti-derived vectors transform a wide variety of higher plants, including monocotyledonous and dicotyledonous plants, such as soybean, cotton and rape [Pacciotti et al. (1985) Bio/Technology 3:241; Byrne et al. (1987) Plant Cell, Tissue and Organ Culture 8:3; Sukhapinda et al. (1987) Plant Mol. biol. 8:209–216; Lorz et al. (1985) Mol. Gen. Genet. 199:178; Potrykus (1985) Mol. Gen. Genet. 199:183].

For introduction into plants the chimeric genes of the invention can be inserted into binary vectors as described in Examples 7–12 and 14–16. The vectors are part of a binary Ti plasmid vector system [Bevan, (1984) Nucl. Acids. Res. 12:8711–8720] of Agrobacterium tumefaciens.

Other transformation methods are available to those skilled in the art, such as direct uptake of foreign DNA constructs [see EPO publication 0 295 959 A2], techniques of electroporation [see Fromm et al. (1986) Nature (London) 319:791] or high-velocity ballistic bombardment with metal particles coated with the nucleic acid constructs [see Kline et al. (1987) Nature (London) 327:70, and see U.S. Pat. No. 4,945,050]. Once transformed, the cells can be regenerated by those skilled in the art.

Of particular relevance are the recently described methods to transform foreign genes into commercially important crops, such as rapeseed [see De Block et al. (1989) Plant Physiol. 91:694–701], sunflower [Everett et al. (1987) Bio/Technology 5:1201], soybean [McCabe et al. (1988) Bio/

Technology 6:923; Hinchee et al. (1988) *Bio/Technology* 6:915; Chee et al. (1989) *Plant Physiol.* 91:1212–1218; Christou et al. (1989) Proc. Natl. Acad. Sci USA 86:7500–7504; EPO Publication 0 301 749 A2], and corn [Gordon-Kamm et al. (1990) Plant Cell 2:603–618; Fromm et al. (1990) Biotechnology 8:833–839].

For introduction into plants by high-velocity ballistic bombardment, the chimeric genes of the invention can be inserted into suitable vectors as described in Example 6. Transformed plants can be obtained as described in Examples 17–19.

Expression of lysC and dapA Chimeric Genes in Tobacco Plants

To assay for expression of the chimeric genes in leaves or seeds of the transformed plants, the AKIII or DHDPS proteins can be detected and quantitated enzymatically and/or immunologically by methods known to those skilled in the art. In this way lines producing high levels of expressed protein can be easily identified.

In order to measure the free amino acid composition of the leaves, free amino acids can be extracted by various methods including those as described in Example 7. To measure the free or total amino acid composition of seeds, extracts can be prepared by various methods including those as described in Example 8.

There was no significant effect of expression of AKIII or AKIII-M4 (with a chloroplast targeting signal) on the free lysine or threonine (or any other amino acid) levels in the leaves (see Table 2 in Example 7). Since AKIII-M4 is insensitive to feedback inhibition by any of the end-products of the pathway, this indicates that control must be exerted at other steps in the biosynthetic pathway in leaves.

In contrast, expression of the AKIII or AKIII-M4 (with a chloroplast targeting signal) in the seeds resulted in 2 to 4-fold or 4 to 23-fold increases, respectively, in the level of free threonine in the seeds compared to untransformed plants and 2 to 3-fold increases in the level of free lysine in some cases (Table 3, Example 8). There was a good correlation between transformants expressing higher levels of AKIII or AKIII-M4 protein and those having higher levels of free threonine, but this was not the case for lysine. The relatively small increases of free threonine or lysine achieved with the AKIII protein were not sufficient to yield detectable increases compared to untransformed plants, in the levels of total threonine or lysine in the seeds. The larger increases of free threonine achieved via expression of the AKIII-M4 protein were sufficient to yield detectable increases, compared to seeds from untransformed plants, in the levels of total threonine in the seeds. Sixteen to twenty-five percent increases in total threonine content of the seeds were observed. The lines that showed increased total threonine were the same ones the showed the highest levels of increase in free threonine and high expression of the AKIII-M4 protein.

The above teachings show that amino acid biosynthesis takes place in seeds and can be modulated by the expression of foreign genes encoding amino acid biosynthetic enzymes. Furthermore, they show that control of an amino acid biosynthetic pathway can differ markedly from one plant organ to another, e.g. seeds and leaves. The importance of this observation is emphasized upon considering the different effects of expressing a foreign DHDPS in leaves and seeds described below. It can be concluded that threonine biosynthesis in seeds is controlled primarily via end-product inhibition of AK. Therefore, threonine accumulation in the seeds of plants can be increased by expression of a gene, introduced via transformation, that encodes AK which is insensitive to lysine inhibition and which is localized in the chloroplast.

The above teachings also demonstrate that transformed plants which express higher levels of the introduced enzyme in seeds accumulate higher levels of free threonine in seeds. Furthermore, the teachings demonstrate that transformed plants which express a lysine-insensitive AK in seeds accumulate higher levels of free threonine in seeds than do transformed plants which express similar levels of a lysine-sensitive AK. To achieve commercially valuable increases in free threonine, a lysine-insensitive AK is preferred.

These teachings indicate that the level of free lysine in seeds controls the accumulation of another aspartate-derived amino acid, threonine, through end-product inhibition of AK. In order to accumulate high levels of free lysine itself, it will be necessary to bypass lysine inhibition of AK via expression of a lysine-insensitive AK.

Expression of active *E. coli* DHDPS enzyme was achieved in both young and mature leaves of the transformed tobacco plants (Table 4, Example 9). High levels of free lysine, 50 to 1 00-fold higher than normal tobacco plants, accumulated in the young leaves of the plants expressing the enzyme with a chloroplast targeting signal, but not without such a targeting signal. However, a much smaller accumulation of free lysine (2 to 8-fold) was seen in the larger leaves. Experiments that measure lysine in the phloem suggest that lysine is exported from the large leaves. This exported lysine may contribute to the accumulation of lysine in the small growing leaves, which are known to take up, rather than export nutrients. No effect on the free lysine levels in the seeds of these plants was observed even though *E. coli* DHDPS enzyme was expressed in the seeds as well as the leaves.

High level seed-specific expression of *E. coli* DHDPS enzyme, either with or without a chloroplast targeting signal, had no effect on the total, or free, lysine or threonine (or any other amino acid) composition of the seeds in any transformed line (Table 5, Example 10). These results demonstrate that expression in seeds of a DHDPS enzyme that is substantially insensitive to lysine inhibition is not sufficient to lead to increased production or accumulation of free lysine.

These teachings from transformants expressing the *E. coli* DHDPS enzyme indicate that lysine biosynthesis in leaves is controlled primarily via end-product inhibition of DHDPS, while in seeds there must be at least one additional point of control in the pathway. The teachings from transformants expressing the *E. coli* AKIII and AKIII-M4 enzymes indicate that the level of free lysine in seeds controls the accumulation of all aspartate-derived amino acids through end-product inhibition of AK. AK is therefore an additional control point.

To achieve simultaneous, high level expression of both *E. coli* DHDPS and AKIII-M4 in leaves and seeds, plants that express each of the genes could be crossed and hybrids that express both could be selected. Another method would be to construct vectors that contain both genes on the same DNA fragment and introduce the linked genes into plants via transformation. This is preferred because the genes would remain linked thoughout subsequent plant breeding efforts. Representative vectors carrying both genes on the same DNA fragment are described in Examples 11, 12, 15, 16, 18, 19, and 25.

Tobacco plants transformed with a vector carrying both *E. coli* DHDPS and AKIII-M4 genes linked to the 35S promoter are described in Example 11. In transformants that express little or no AKIII-M4, the level of expression of *E. coli* DHDPS determines the level of lysine accumulation in leaves (Example 11, Table 6). However, in transformants that express both AKIII-M4 and *E. coli* DHDPS, the level of expression of each protein plays a role in controlling the level of lysine accumulation. Transformed lines that express DHDPS at comparable levels accumulate more lysine when AKIII-M4 is also expressed (Table 6, compare lines 564-18A, 564-56A, 564-36E, 564-55B, and 564-47A). Thus, expression of a lysine-insensitive AK increases lysine accumulation in leaves when expressed in concert with a DHDPS enzyme that is 20-fold less sensitive to lysine than the endogenous plant enzyme.

These leaf results, taken together with the seed results derived from expressing *E. coli* AKIII-M4 and *E. coli* DHDPS separately in seeds, suggest that simultaneous expression of both *E. coli* AKIII-M4 and *E. coli* DHDPS in seeds would lead to increased accumulation of free lysine and would also lead to an increased accumulation of free threonine. Tobacco plants transformed with a vector carrying both *E. coli* DHDPS and AKIII-M4 genes linked to the phaseolin promoter are described in Example 12. There is an increased accumulation of free lysine and free threonine in these plants. The increased level of free threonine was 4-fold over normal seeds, rather than the 20-fold increase seen in seeds expressing AKIII-M4 alone. The reduction in accumulation of free threonine indicates that pathway intermediates are being diverted down the lysine branch of the biosynthetic pathway. The increased level of free lysine was 2-fold over normal seeds (or seeds expressing *E. coli* DHDPS alone). However, the lysine increase in seeds is not equivalent to the 100-fold increase seen in leaves.

The *E. coli* DHDPS enzyme is less sensitive to lysine inhibition than plant DHDPS, but is still inhibited by lysine. The above teachings on the AK proteins indicate that expression of a completely lysine-insensitive enzyme can lead to a much greater accumulation of the aspartate pathway end-product threonine than expression of an enzyme which, while less sensitive than the plant enzyme, is still inhibited by lysine. Therefore vectors carrying both *Corynebacterium* DHDPS and AKIII-M4 genes linked to the seed-specific promoters were constructed as described in Examples 15 and 19. Tobacco plants transformed with vectors carrying both *Corynebacterium* DHDPS and AKIII-M4 genes linked to seed-specific promoters are described in Example 15. As shown in Table 9, these plants did not show a greater accumulation of free lysine in seeds than previously described plants expressing the *E. coli* DHDPS enzyme in concert with the lysine-insensitive AK. In hindsight this result can be explained by the fact that lysine accumulation in seeds never reached a level high enough to inhibit the *E. coli* DHDPS, so replacement of this enzyme with lysine-insensitive *Corynebacterium* DHDPS had no effect.

In transformed lines expressing high levels of *E. coli* AKIII-M4 and *E. coli* DHDPS or *Corynebacterium* DHDPS, it was possible to detect substantial amounts of α-aminoadipic acid in seeds. This compound is thought to be an intermediate in the catabolism of lysine in cereal seeds, but is normally detected only via radioactive tracer experiments due to its low level of accumulation. The discovery of high levels of this intermediate, comparable to levels of free amino acids, indicates that a large amount of lysine is being produced in the seeds of these transformed lines and is entering the catabolic pathway. The build-up of α-aminoadipic acid was not observed in transformants expressing only *E. coli* DHDPS or only AKIII-M4 in seeds. These results show that it is necessary to express both enzymes simultaneously to produce high levels of free lysine in seeds. To accumulate high levels of free lysine it may also be necessary to prevent lysine catabolism. Alternatively, it may be desirable to convert the high levels of lysine produced into a form that is insensitive to breakdown, e.g. by incorporating it into a di-, tri- or oligopeptide, or a lysine-rich storage protein.

Expression of lysC and dapA Chimeric Genes in Rapeseed and Soybean Plants

To analyze for expression of the chimeric lysC and dapA genes in seeds of transformed rapeseed and soybean and to determine the consequences of expression on the amino acid content in the seeds, a seed meal can be prepared as described in Examples 16 or 19 or by any other suitable method. The seed meal can be partially or completely defatted, via hexane extraction for example, if desired. Protein extracts can be prepared from the meal and analyzed for AK and/or DHDPS enzyme activity. Alternatively the presence of the AK and/or DHDPS protein can be tested for immunologically by methods well-known to those skilled in the art. To measure free amino acid composition of the seeds, free amino acids can be extracted from the meal and analyzed by methods known to those skilled in the art (see Examples 8, 16 and 19 for suitable procedures).

All of the rapeseed transformants obtained from a vector carrying the cordapA gene expressed the *Corynebacterium* DHDPS protein, and six of eight transformants obtained from a vector carrying the lysC-M4 gene expressed the AKIII-M4 protein (Example 16, Table 12). Thus it is straightforward to express these proteins in oilseed rape seeds. Transformants expressing DHDPS protein showed a greater than 100-fold increase in free lysine level in their seeds. There was a good correlation between transformants expressing higher levels of DHDPS protein and those having higher levels of free lysine. One transformant that expressed AKIII-M4 in the absence of *Corynebacteria* DHDPS showed a 5-fold increase in the level of free threonine in the seeds. Concomitant expression of both enzymes resulted in accumulation of high levels of free lysine, but not threonine.

A high level of α-aminoadipic acid, indicative of lysine catabolism, was observed in many of the transformed lines, especially lines expressing the highest levels of DHDPS and AKIII protein. Thus, prevention of lysine catabolism by inactivation of lysine ketoglutarate reductase should further increase the accumulation of free lysine in the seeds. Alternatively, incorporation of lysine into a peptide or lysine-rich protein would prevent catabolism and lead to an increase in the accumulation of lysine in the seeds.

To measure the total amino acid composition of mature rapeseed seeds, defatted meal was analyzed as described in Example 16. Relative amino acid levels in the seeds were compared as percentages of lysine to total amino acids. Seeds with a 5–100% increase in the lysine level, compared to the untransformed control, were observed. The transfonnant with the highest lysine content expressed high levels of both *E. coli* AKIII-M4 and *Corynebacterium* DHDPS. In this transformant lysine makes up about 13% of the total seed amino acids, considerably higher than any previously known rapeseed seed.

Six of seven soybean transformants expressed the DHDPS protein. In the six transformants that expressed DHDPS, there was excellent correlation between expression of GUS and DHDPS in individual seeds. Therefore, the GUS and DHDPS genes are integrated at the same site in the soybean genome. Four of seven transformants expressed the AKIII protein, and again there was excellent correlation between expression of AKIII, GUS and DHDPS in individual seeds. Thus, in these four transformants the GUS, AKIII and DHDPS genes are integrated at the same site in the soybean genome.

Soybean transformants expressing *Corynebacteria* DHDPS alone and in concert with *E. coli* AKIII-M4 accumulated high levels of free lysine in their seeds. A high level of saccharopine, the first metabolic product of lysine catabolism, was also observed in seeds that contained high levels of lysine. Lesser amounts of α-amino adipic acid were also observed. Thus, prevention of lysine catabolism by inactivation of lysine ketoglutarate reductase should further increase the accumulation of free lysine in the soybean seeds. Alternatively, incorporation of lysine into a peptide or lysine-rich protein would prevent catabolism and lead to an increase in the accumulation of lysine in the soybean seeds.

Analyses of free lysine levels in individual seeds from transformants in which the transgenes segregated as a single locus revealed that the increase in free lysine level was significantly higher in about one-fourth of the seeds. Since one-fourth of the seeds are expected to be homozygous for the transgene, it is likely that the higher lysine seeds are the homozygotes. Furthermore, this indicates that the level of increase in free lysine is dependent upon the transgene copy number. Therefore, lysine levels could be further increased by making hybrids of two different transformants, and obtaining progeny that are homozygous at both transgene loci.

The soybean seeds expressing *Corynebacteria* DHDPS showed substantial increases in accumulation of total seed lysine. Seeds with a 5–35% increase in total lysine content, compared to the untransformed control, were observed. In these seeds lysine makes up 7.5–7.7% of the total seed amino acids.

Soybean seeds expressing *Corynebacteria* DHDPS in concert with *E. coli* AKIII-M4 showed much greater accumulation of total seed lysine than those expressing *Corynebacteria* DHDPS alone. Seeds with a more than four-fold increase in total lysine content were observed. In these seeds lysine makes up 20–25% of the total seed amino acids, considerably higher than any previously known soybean seed.

Expression of lysC and dapA Chimeric Genes in Corn Plants

Corn plants regenerated from transformed callus can be analyzed for the presence of the intact lysC and dapA transgenes via Southern blot or PCR. Plants carrying the genes are either selfed or outcrossed to an elite line to generate F1 seeds. Six to eight seeds are pooled and assayed for expression of the *Corynebacterium* DHDPS protein and the *E. coli* AKIII-M4 protein by western blot analysis. The free amino acid composition and total amino acid composition of the seeds are determined as described above.

Expression of the *Corynebacterium* DHDPS protein, and/ or the *E. coli* AKIII-M4 protein can be obtained in the embryo of the seed using regulatory sequences active in the embryo, preferably derived from the globulin 1 gene, or in the endosperm using regulatory sequences active in the endosperm, preferably derived from the glutelin 2 gene or the 10 kD zein gene (see Example 26 for details). Free lysine levels in the seeds is increased from about 1.4% of free amino acids in control seeds to 15–27% in seeds of transformants expressing *Corynebacterium* DHDPS alone from the globulin 1 promoter. The increased free lysine was localized to the embryo in seeds expressing *Corynebacterium* DHDPS from the globulin 1 promoter.

The large increases in free lysine result in significant increases in the total seed lysine content. Total lysine levels can be increased at least 130% in seeds expressing *Corynebacterium* DHDPS from the globulin 1 promoter. Greater increases in free lysine levels can be achieved by expressing *E. coli* AKIII-M4 protein from the globulin 1 promoter in concert with *Corynebacterium* DHDPS.

Lysine catabolism is expected to be much greater in the corn endosperm than the embryo. Thus, to achieve significant lysine increases in the endosperm it is preferable to express both *Corynebacterium* DHDPS and the *E. coli* AKIII-M4 in the endosperm and to reduce lysine catabolism by reducing the level of lysine ketoglutarate reductase as described below.

Isolation of a Plant Lysine Ketoglutarate Reductase Gene

It may be desirable to prevent lysine catabolism in order to accumulate higher levels of free lysine and to prevent accumulation of lysine breakdown products such as saccharopine and α-amino adipic acid. Evidence indicates that lysine is catabolized in plants via the saccharopine pathway. The first enzymatic evidence for the existence of this pathway was the detection of lysine ketoglutarate reductase (LKR) activity in immature endosperm of developing maize seeds [Arruda et al. (1982) *Plant Physiol.* 69:988–989]. LKR catalyzes the first step in lysine catabolism, the condensation of L-lysine with α-ketoglutarate into saccharopine using NADPH as a cofactor. LKR activity increases sharply from the onset of endosperm development in corn, reaches a peak level at about 20 days after pollination, and then declines [Arruda et al. (1983) *Phytochemistry* 22:2687–2689]. In order to prevent the catabolism of lysine it would be desirable to reduce or eliminate LKR expression or activity. This could be accomplished by cloning the LKR gene, preparing a chimeric gene for cosuppression of LKR or preparing a chimeric gene to express antisense RNA for LKR, and introducing the chimeric gene into plants via transformation. Alternatively, plant mutants could be obtained wherein LKR enzyme activity is absent.

Several methods to clone a plant LKR gene are available to one skilled in the art. The protein can be purified from corn endosperm, as described in Brochetto-Braga et al. [(1992) *Plant Physiol.* 98:1139–1147] and used to raise antibodies. The antibodies can then be used to screen an cDNA expression library for LKR clones. Alternatively the purified protein can be used to determine amino acid sequence at the amino-terminal of the protein or from protease derived internal peptide fragments. Degenerate oligonucleotide probes can be prepared based upon the amino acid sequence and used to screen a plant cDNA or genomic DNA library via hybridization.

Another method makes use of an *E. coli* strain that is unable to grow in a synthetic medium containing 20 μg/mL of L-lysine. Expression of LKR full-length cDNA in this strain will reverse the growth inhibition by reducing the lysine concentration. Construction of a suitable *E. coli* strain and its use to select clones from a plant cDNA library that lead to lysine-resistant growth is described in Example 20.

Yet another method relies upon homology between plant LKR and saccharopine dehydrogenase. Fungal saccharopine dehydrogenase (glutamate-forming) and saccharopine dehydrogenase (lysine-forming) catalyze the final two steps in the fungal lysine biosynthetic pathway. Plant LKR and fungal saccharopine dehydrogenase (lysine-forming) catalyze both forward and reverse reactions, use identical substrates and use similar co-factors. Similarly, plant saccharopine dehydrogenase (glutamate-forming), which catalyzes the second step in the lysine catabolic pathway, works in both forward and reverse reactions, uses identical substrates and uses similar co-factors as fungal saccharopine dehydrogenase (glutamate-forming). Several genes for fungal saccharopine dehydrogenases have been isolated and sequenced and are readily available to those skilled in the art [Xuan et al. (1990) *Mol. Cell. Biol.* 10:4795–4806, Feller et al. (1994) *Mol. Cell. Biol.* 14:6411–6418]. These genes could be used as heterologous hybridization probes to identify plant LKR and plant saccharopine dehydrogenase (glutamate-forming) nucleic acid fragments, or alternatively to identify homologous protein coding regions in plant cDNAs.

Biochemical and genetic evidence derived from human and bovine studies has demonstrated that mammalian LKR and saccharopine dehydrogenase (glutamate-forming) enzyme activities are present on a single protein with a monomer molecular weight of about 117,000. This contrasts with the fungal enzymes which are carried on separate proteins, saccharopine dehydrogenase (lysine-forming) with a molecular weight of about 44,000, and saccharopine dehydrogenase (glutamate-forming) with a molecular weight of about 51,000. Plant LKR has been reported to have a molecular weight of about 140,000 indicating that it is like the animal catabolic protein wherein both LKR and saccharopine dehydrogenase (glutamate-forming) enzyme activities are present on a single protein.

We provide two plant saccharopine dehydrogenase (glutamate-forming) nucleic acid fragments that contain cDNA derived from *Arabidopsis thaliana*. These were identified as cDNAs that encode proteins homologous to fungal saccharopine dehydrogenase (glutamate-forming). These nucleic acid fragments can be used as hybridization probes to identify and isolate genomic DNA fragments or cDNA fragments encoding both LKR and saccharopine dehydrogenase (glutamate-forming) enzyme activities from any plant desired.

In order to block expression of the LKR gene in transformed plants, a chimeric gene designed for cosuppression of LKR can be constructed by linking the LKR gene or gene fragment to any of the plant promoter sequences described above. (See U.S. Pat. No. 5,231,020 for methodology to block plant gene expression via cosuppression.) Alternatively, a chimeric gene designed to express antisense RNA for all or part of the LKR gene can be constructed by linking the LKR gene or gene fragment in reverse orientation to any of the plant promoter sequences described above. (See U.S. Pat. No. 5,107,065 for methodology to block plant gene expression via antisense RNA.) Either the cosuppression or antisense chimeric gene could be introduced into plants via transformation. Transformants wherein expression of the endogenous LKR gene is reduced or eliminated are then selected.

Preferred promoters for the chimeric genes would be seed-specific promoters. For soybean, rapeseed and other dicotyledonous plants, strong seed-specific promoters from a bean phaseolin gene, a soybean β-conglycinin gene, glycinin gene, Kunitz trypsin inhibitor gene, or rapeseed napin gene would be preferred. For corn and other monocotyledonous plants, a strong endosperm-specific promoter, e.g., the 10 kD or 27 kD zein promoter, would be preferred.

Transformed plants containing any of the chimeric LKR genes can be obtained by the methods described above. In order to obtain transformed plants that express a chimeric gene for cosuppression of LKR or antisense LKR, as well as a chimeric genes encoding substantially lysine-insensitive DHDPS and AK, the cosuppression or antisense LKR gene could be linked to the chimeric genes encoding substantially lysine-insensitive DHDPS and AK and the three genes could be introduced into plants via transformation. Alternatively, the chimeric gene for cosuppression of LKR or antisense LKR could be introduced into previously transformed plants that express substantially lysine-insensitive DHDPS and AK, or the cosuppression or antisense LKR gene could be introduced into normal plants and the transformants obtained could be crossed with plants that express substantially lysine-insensitive DHDPS and AK. As another alternative, plant mutants that express no LKR enzyme activity could be crossed with plants that express substantially lysine-insensitive DHDPS and AK.

Design of Lysine-Rich Polypeptides

It may be desirable to convert the high levels of lysine produced into a form that is insensitive to breakdown, e.g., by incorporating it into a di-, tri- or oligopeptide, or a lysine-rich storage protein. No natural lysine-rich proteins are known.

One aspect of this invention is the design of polypeptides which can be expressed in vivo to serve as lysine-rich seed storage proteins. Polypeptides are linear polymers of amino acids where the α-carboxyl group of one amino acid is covalently bound to the α-amino group of the next amino acid in the chain. Non-covalent interactions among the residues in the chain and with the surrounding solvent determine the final conformation of the molecule. Those skilled in the art must consider electrostatic forces, hydrogen bonds, Van der Waals forces, hydrophobic interactions, and conformational preferences of individual amino acid residues in the design of a stable folded polypeptide chain [see for example: Creighton, (1984) *Proteins, Structures and Molecular Properties*, W. H. Freeman and Company, New York, pp 133–197, or Schulz et al., (1979) *Principles of Protein Structure*, Springer Verlag, New York, pp 27–45]. The number of interactions and their complexity suggest that the design process may be aided by the use of natural protein models where possible.

The synthetic storage proteins (SSPs) embodied in this invention are chosen to be polypeptides with the potential to be enriched in lysine relative to average levels of proteins in plant seeds. Lysine is a charged amino acid at physiological pH and is therefore found most often on the surface of protein molecules [Chotia, (1976) *Journal of Molecular Biology* 105:1–14]. To maximize lysine content, Applicants chose a molecular shape with a high surface-to-volume ratio for the synthetic storage proteins embodied in this invention. The alternatives were either to stretch the common globular shape of most proteins to form a rod-like extended structure or to flatten the globular shape to a disk-like structure. Applicants chose the former configuration as there are several natural models for long rod-like proteins in the class of fibrous proteins [Creighton, (1984) *Proteins, Structures and Molecular Properties*, W. H. Freeman and Company, New York, p 191].

Coiled-coils constitute a well-studied subset of the class of fibrous proteins [see Cohen et al., (1986) *Trends Biochem. Sci.* 11:245–248]. Natural examples are found in α-keratins, paramyosin, light meromyosin and tropomyosin. These protein molecules consist of two parallel alpha helices twisted about each other in a left-handed supercoil. The repeat distance of this supercoil is 140 Å (compared to a repeat distance of 5.4 Å for one turn of the individual helices). The supercoil causes a slight skew (10°) between the axes of the two individual alpha helices.

In a coiled coil there are 3.5 residues per turn of the individual helices resulting in an exact 7 residue periodicity with respect to the superhelix axis (see FIG. 1). Every seventh amino acid in the polypeptide chain therefore occupies an equivalent position with respect to the helix axis. Applicants refer to the seven positions in this heptad unit of the invention as (d e f g a b c) as shown in FIGS. 1 and 2a. This conforms to the conventions used in the coiled-coil literature.

The a and d amino acids of the heptad follow a 4,3 repeat pattern in the primary sequence and fall on one side of an individual alpha helix (See FIG. 1). If the amino acids on one side of an alpha helix are all non-polar, that face of the helix is hydrophobic and will associate with other hydrophobic surfaces as, for example, the non-polar face of another similar helix. A coiled-coil structure results when two helices dimerize such that their hydrophobic faces are aligned with each other (See FIG. 2a).

The amino acids on the external faces of the component alpha helices (b, c, e, f, g) are usually polar in natural coiled-coils in accordance with the expected pattern of exposed and buried residue types in globular proteins [Schulz, et al., (1979) *Principles of Protein Structure*, Springer Verlag, New York, p 12; Talbot, et al , (1982) *Acc. Chem. Res.* 15:224–230; Hodges et al., (1981) *Journal of Biological Chemistry* 256:1214–1224]. Charged amino acids are sometimes found forming salt bridges between positions e and g' or positions g and e' on the opposing chain (see FIG. 2a).

Thus, two amphipathic helices like the one shown in FIG. 1 are held together by a combination of hydrophobic interactions between the a, a', d, and d' residues and by salt bridges between e and g' and/or g and e' residues. The packing of the hydrophobic residues in the supercoil maintains the chains "in register". For short polypeptides comprising only a few turns of the component alpha helical chains, the 10° skew between the helix axes can be ignored and the two chains treated as parallel (as shown in FIG. 2a).

A number of synthetic coiled-coils have been reported in the literature (Lau et al., (1984) *Journal of Biological Chemistry* 259:13253–13261; Hodges et al., (1988) *Peptide Research* 1:19–30; DeGrado et al., (1989) *Science* 243:622–628; O'Neil et al., (1990) *Science* 250:646–651]. Although these polypeptides vary in size, Lau et al. found that 29 amino acids were sufficient for dimerization to form the coiled-coil structure [Lau et al., (1984) *Journal of Biological Chemistry* 259:13253–13261]. Applicants constructed the polypeptides in this invention as 28-residue and larger chains for reasons of conformational stability.

The polypeptides of this invention are designed to dimerize with a coiled-coil motif in aqueous environments. Applicants have used a combination of hydrophobic interactions and electrostatic interactions to stabilize the coiled-coil conformation. Most nonpolar residues are restricted to the a and d positions which creates a hydrophobic stripe parallel to the axis of the helix. This is the dimerization face. Applicants avoided large, bulky amino acids along this face to minimize steric interference with dimerization and to facilitate formation of the stable coiled-coil structure.

Despite recent reports in the literature suggesting that methionine at positions a and d is destabilizing to coiled-coils in the leucine zipper subgroup [Landschulz et al., (1989) *Science* 243:1681–1688 and Hu et al., (1990) *Science* 250:1400–1403], Applicants chose to substitute methionine residues for leucine on the hydrophobic face of the SSP polypeptides. Methionine and leucine are similar in molecular shape (FIG. 3). Applicants demonstrated that any destabilization of the coiled-coil that may be caused by methionine in the hydrophobic core appears to be compensated in sequences where the formation of salt bridges (e–g' and g–e') occurs at all possible positions in the helix (i.e., twice per heptad).

To the extent that it is compatible with the goal of creating a polypeptide enriched in lysine, Applicants minimized the unbalanced charges in the polypeptide. This may help to prevent undesirable interactions between the synthetic storage proteins and other plant proteins when the polypeptides are expressed in vivo.

The polypeptides of this invention are designed to spontaneously fold into a defined, conformationally stable structure, the alpha helical coiled-coil, with minimal restrictions on the primary sequence. This allows synthetic storage proteins to be custom-tailored for specific end-user requirements. Any amino acid can be incorporated at a frequency of up to one in every seven residues using the b, c, and f positions in the heptad repeat unit. Applicants note that up to 43% of an essential amino acid from the group isoleucine, leucine, lysine, methionine, threonine, and valine can be incorporated and that up to 14% of the essential amino acids from the group phenylalanine, tryptophan, and tyrosine can be incorporated into the synthetic storage proteins of this invention.

In the SSPs only Met, Leu, Ile, Val or Thr are located in the hydrophobic core. Furthermore, the e, g, e', and g' positions in the SSPs are restricted such that an attractive electrostatic interaction always occurs at these positions between the two polypeptide chains in an SSP dimer. This makes the SSP polypeptides more stable as dimers.

Thus, the novel synthetic storage proteins described in this invention represent a particular subset of possible coiled-coil polypeptides. Not all polypeptides which adopt an amphipathic alpha helical conformation in aqueous solution are suitable for the applications described here.

The following rules derived from Applicants' work define the SSP polypeptides that Applicants use in their invention:

The synthetic polypeptide comprises n heptad units (d e f g a b c), each heptad being either the same or different, wherein:

n is at least 4;

a and d are independently selected from the group consisting of Met, Leu, Val, Ile and Thr;

e and g are independently selected from the group consisting of the acid/base pairs Glu/Lys, Lys/Glu, Arg/Glu, Arg/Asp, Lys/Asp, Glu/Arg, Asp//Arg and Asp/Lys; and b, c and f are independently any amino acids except Gly or Pro and at least two amino acids of b, c and f in each heptad are selected from the group consisting of Glu, Lys, Asp, Arg, His, Thr, Ser, Asn, Gln, Cys and Ala.

Chimeric Genes Encoding Lysine-Rich Polypeptides

DNA sequences which encode the polypeptides described above can be designed based upon the genetic code. Where multiple codons exist for particular amino acids, codons should be chosen from those preferable for translation in plants. Oligonucleotides corresponding to these DNA sequences can be synthesized using an ABI DNA synthesizer, annealed with oligonucleotides corresponding to the complementary strand and inserted into a plasmid vector by methods known to those skilled in the art. The encoded polypeptide sequences can be lengthened by inserting additional annealed oligonucleotides at restriction endonuclease sites engineered into the synthetic gene. Some representative strategies for constructing genes encoding lysine-rich polypeptides of the invention, as well as DNA and amino acid sequences of preferred embodiments are provided in Example 21.

A chimeric gene designed to express RNA for a synthetic storage protein gene encoding a lysine-rich polypeptide can be constructed by linking the gene to any of the plant promoter sequences described above. Preferred promoters would be seed-specific promoters. For soybean, rapeseed and other dicotyledonous plants strong seed-specific promoters from a bean phaseolin gene, a soybean β-conglycinin gene, glycinin gene, Kunitz trypsin inhibitor gene, or rapeseed napin gene would be preferred. For corn or other monocotyledonous plants, a strong endosperm-specific promoter, e.g., the 10 kD or 27 kD zein promoter, or a strong embryo-specific promoter, e.g., the corn globulin 1 promoter, would be preferred.

In order to obtain plants that express a chimeric gene for a synthetic storage protein gene encoding a lysine-rich polypeptide, plants can be transformed by any of the methods described above. In order to obtain plants that express both a chimeric SSP gene and chimeric genes encoding substantially lysine-insensitive DHDPS and AK, the SSP gene could be linked to the chimeric genes encoding substantially lysine-insensitive DHDPS and AK and the three genes could be introduced into plants via transformation. Alternatively, the chimeric SSP gene could be introduced into previously transformed plants that express substantially lysine-insensitive DHDPS and AK, or the SSP gene could be introduced into normal plants and the transformants obtained could be crossed with plants that express substantially lysine-insensitive DHDPS and AK.

Results from genetic crosses of transformed plants containing lysine biosynthesis genes with transformed plants containing lysine-rich protein genes (see Example 23) demonstrate that the total lysine levels in seeds can be increased by the coordinate expression of these genes. This result was especially striking because the gene copy number of all of the transgenes was reduced in the hybrid. It is expected that the lysine level would be further increased if the biosynthesis genes and the lysine-rich protein genes were all homozygous.

Use of the cts/lysC-M4 Chimeric Gene as a Selectable Marker for Plant Transformation Growth of cell cultures and seedlings of many plants is inhibited by high concentrations of lysine plus threonine. Growth is restored by addition of methionine (or homoserine which is converted to methionine in vivo). Lysine plus threonine inhibition is thought to result from feedback inhibition of endogenous AK, which reduces flux through the pathway leading to starvation for methionine. In tobacco there are two AK enzymes in leaves, one lysine-sensitive and one threonine sensitive.[Negrutui et al. (1984) *Theor. Appl. Genet.* 68:11–20]. High concentrations of lysine plus threonine inhibit growth of shoots from tobacco leaf disks and inhibition is reversed by addition of low concentrations of methionine. Thus, growth inhibition is presumably due to inhibition of the two AK isozymes.

Expression of active lysine and threonine insensitive AKIII-M4 also reverses lysine plus threonine growth inhibition (Table 2, Example 7). There is a good correlation between the level of AKIII-M4 protein expressed and the resistance to lysine plus threonine. Expression of lysine-sensitive wild type AKIII does not have a similar effect. Since expression of the AKIII-M4 protein permits growth under normally inhibitory conditions, a chimeric gene that causes expression of AKIII-M4 in plants can be used as a selectable genetic marker for transformation as illustrated in Examples 13 and 17.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Isolation of the *E. coli* lysC Gene and Mutations in lysC Resulting in Lysine-insensitive AKIII The *E. coli* lysC gene has been cloned, restriction endonuclease mapped and sequenced previously [Cassan et al. (1986) *J. Biol. Chem.* 261:1052–1057]. For the present invention the lysC gene was obtained on a bacteriophage lambda clone from an ordered library of 3400 overlapping segments of cloned *E. coli* DNA constructed by Kohara, Akiyama and Isono [Kohara et al. (1987) *Cell* 50:595–508]. This library provides a physical map of the whole *E. coli* chromosome and ties the physical map to the genetic map. From the knowledge of the map position of lysC at 90 min on the *E. coli* genetic map [Theze et al. (1974) *J. Bacteriol.* 11 7:133–143], the restriction endonuclease map of the cloned gene [Cassan et al. (1986) *J. Biol. Chem.* 261:1052–1057], and the restriction endonuclease map of the cloned DNA fragments in the *E. coli* library [Kohara et al. (1987) *Cell* 50:595–508], it was possible to choose lambda phages 4E5 and 7A4 [Kohara et al. (1987) *Cell* 50:595–508] as likely candidates for carrying the lysC gene. The phages were grown in liquid culture from single plaques as described [see *Current Protocols in Molecular Biology* (1987) Ausubel et al. Eds. John Wiley & Sons New York] using LE392 as host [see Sambrook et al. (1989) *Molecular Cloning, A Laboratory Manual,* Cold Spring Harbor Laboratory Press]. Phage DNA was prepared by phenol extraction as described [see *Current Protocols in Molecular Biology* (1987) Ausubel et al. eds. John Wiley & Sons New York].

From the sequence of the gene several restriction endonuclease fragments diagnostic for the lysC gene were predicted, including an 1860 bp EcoR I-Nhe I fragment, a 2140 bp EcoR I-Xmn I fragment and a 1600 bp EcoR I-BamH I fragment. Each of these fragments was detected in both of the phage DNAs confirming that these carried the lysC gene. The EcoR I-Nhe I fragment was isolated and subcloned in plasmid pBR322 digested with the same enzymes, yielding an ampicillin-resistant, tetracycline-sensitive *E. coli* transformant. The plasmid was designated pBT436.

To establish that the cloned lysC gene was functional, pBT436 was transformed into *E. coli* strain Gif106M1 (*E. coli* Genetic Stock Center strain CGSC-5074) which has mutations in each of the three *E. coli* AK genes [Theze et al. (1974) *J. Bacteriol.* 117:133–143]. This strain lacks all AK activity and therefore requires diaminopimelate (a precursor to lysine which is also essential for cell wall biosynthesis), threonine and methionine. In the transformed strain all these nutritional requirements were relieved demonstrating that the cloned lysC gene encoded functional AKIII.

Addition of lysine (or diaminopimelate which is readily converted to lysine in vivo) at a concentration of approximately 0.2 mM to the growth medium inhibits the growth of Gif106M1 transformed with pBT436. M9 media [see Sambrook et al. (1989) *Molecular Cloning, A Laboratory Manual,* Cold Spring Harbor Laboratory Press] supplemented with the arginine and isoleucine, required for Gif106M1 growth, and ampicillin, to maintain selection for the pBT436 plasmid, was used. This inhibition is reversed by addition of threonine plus methionine to the growth media. These results indicated that AKIII could be inhibited by exogenously added lysine leading to starvation for the other amino acids derived from aspartate. This property of pBT436-transformed Gif106M1 was used to select for mutations in lysC that encoded lysine-insensitive AKIII.

Single colonies of Gif106M1 transformed with pBT436 were picked and resuspended in 200 µL of a mixture of 100 µL 1% lysine plus 100 µL of M9 media. The entire cell suspension containing $10^7$–$10^8$ cells was spread on a petri dish containing M9 media supplemented with the arginine, isoleucine, and ampicillin. Sixteen petri dishes were thus prepared. From 1 to 20 colonies appeared on 11 of the 16 petri dishes. One or two (if available) colonies were picked and retested for lysine resistance and from this nine lysine-resistant clones were obtained. Plasmid DNA was prepared from eight of these and re-transformed into Gif106M 1 to determine whether the lysine resistance determinant was plasmid-borne. Six of the eight plasmid DNAs yielded lysine-resistant colonies. Three of these six carried lysC genes encoding AKIII that was uninhibited by 15 mM lysine, whereas wild type AKIII is 50% inhibited by 0.3–0.4 mM lysine and >90% inhibited by 1 mM lysine (see Example 2 for details).

To determine the molecular basis for lysine-resistance the sequences of the wild type lysC gene and three mutant genes were determined. A method for "Using mini-prep plasmid DNA for sequencing double stranded templates with sequenase™" [Kraft et al. (1988) *BioTechniques* 6:544–545] was used. Oligonucleotide primers, based on the published lysC sequence and spaced approximately every 200 bp, were synthesized to facilitate the sequencing. The sequence of the wild type lysC gene cloned in pBT436 (SEQ ID NO:1) differed from the published lysC sequence in the coding region at 5 positions. Four of these nucleotide differences were at the third position in a codon and would not result in a change in the amino acid sequence of the AKIII protein. One of the differences would result in a cysteine to glycine substitution at amino acid 58 of AKIII. These differences are probably due to the different strains from which the lysC genes were cloned.

The sequences of the three mutant lysC genes that encoded lysine-insensitive AK each differed from the wild type sequence by a single nucleotide, resulting in a single amino acid substitution in the protein. Mutant M2 had an A substituted for a G at nucleotide 954 of SEQ ID NO:1 resulting in an isoleucine for methionine substitution at amino acid 318 and mutants M3 and M4 had identical T for C substitutions at nucleotide 1055 of SEQ ID NO:1 resulting in an isoleucine for threonine substitution at amino acid 352. Thus, either of these single amino acid substitutions is sufficient to render the AKIII enzyme insensitive to lysine inhibition.

Example 2

High Level Expression of Wild Type and Mutant lysC Genes in *E. coli*

An Nco I (CCATGG) site was inserted at the translation initiation codon of the lysC gene using the following oligonucleotides:

```
SEQ ID NO:2:
GATCCATGGC TGAAATTGTT GTCTCCAAAT TTGGCG

SEQ ID NO:3:
GTACCGCCAA ATTTGGAGAC AACAATTTCA GCCATG
```

When annealled these oligonucleotides have BamH I and Asp718 "sticky" ends. The plasmid pBT436 was digested with BamH I, which cuts upstream of the lysC coding sequence and Asp718 which cuts 31 nucleotides downstream of the initiation codon. The annealled oligonucleotides were ligated to the plasmid vector and *E. coli* transformants were obtained. Plasmid DNA was prepared and screened for insertion of the oligonucleotides based on the presence of an Nco I site. A plasmid containing the site was sequenced to assure that the insertion was correct, and was designated pBT457. In addition to creating an Nco I site at the initiation codon of lysC, this oligonucleotide insertion changed the second codon from TCT, coding for serine, to GCT, coding for alanine. This amino acid substitution has no apparent effect on the AKIII enzyme activity.

To achieve high level expression of the lysC genes in *E. coli*, the bacterial expression vector pBT430 was used. This vector is a derivative of pET-3a [Rosenberg et al. (1987) *Gene* 56:125–135] which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

The lysC gene was cut out of plasmid pBT457 as a 1560 bp Nco I-EcOR I fragment and inserted into the expression vector pBT430 digested with the same enzymes, yielding plasmid pBT461. For expression of the mutant lysC genes (M2, M3 and M4) pBT461 was digested with Kpn I-EcoR I, which removes the wild type lysC gene from about 30 nucleotides downstream from the translation start codon, and inserting the homologous Kpn I-EcoR I fragments from the mutant genes yielding plasmids pBT490, pBT491 and pBT492, respectively.

For high level expression each of the plasmids was transformed into *E. coli* strain BL21(DE3) [Studier et al. (1986) *J. Mol. Biol.* 189:113–130]. Cultures were grown in LB medium containing ampicillin (100 mg/L) at 25° C. At an optical density at 600 nm of approximately 1, IPTG (isopropylthio-β-galactoside, the inducer) was added to a final concentration of 0.4 mM and incubation was continued for 3 h at 25° C. The cells were collected by centrifugation and resuspended in ¹⁄₂₀th (or ¹⁄₁₀₀th) the original culture volume in 50 mM NaCl; 50 mM Tris-Cl, pH 7.5; 1 mM EDTA, and frozen at −20° C. Frozen aliquots of 1 mL were thawed at 37° C. and sonicated, in an ice-water bath, to lyse the cells. The lysate was centrifuged at 4° C. for 5 min at 15,000 rpm. The supernatant was removed and the pellet was resuspended in 1 mL of the above buffer.

The supernatant and pellet fractions of uninduced and IPTG-induced cultures of BL21(DE3)/pBT461 were analyzed by SDS polyacrylamide gel electrophoresis. The major protein visible by Coomassie blue staining in the supernatant of the induced culture had a molecular weight of about 48 kd, the expected size for AKIII. About 80% of the AKIII protein was in the supernatant and AKIII represented 10–20% of the total E. coli protein in the extract.

AK activity was assayed as shown below:
Assay mix (for 12 assay tubes):
4.5 mL H$_2$O
1.0 mL 8M KOH
1.0 mL 8M NH$_2$OH-HCl
1.0 mL IM Tris-HCl pH 8.0
0.5 mL 0.2M ATP (121 mg/mL in 0.2M NaOH)
50 µL 1M MgSO$_4$
Each 1.5 mL eppendorf assay tube contained:
0.64 mL assay mix
0.04 mL 0.2 M L-aspartic acid or 0.04 mL H$_2$O
0.0005–0.12 mL extract
H$_2$O to total volume 0.8 mL Assay tubes were incubated at 30° C. for desired time (10–60 min). Then 0.4 mL FeCl$_3$ reagent (10% w/v FeCl$_3$, 3.3% trichloroacetic acid, 0.7 M HCl) was added and the material centrifuged for 2 min in an eppendorf centrifuge. The supernatant was decanted. The OD was read at 540 nm and compared to the aspartyl-hydroxamate standard.

Approximately 80% of the AKIII activity was in the supernatant fraction. The specific activity of wild type and mutant crude extracts was 5–7 µM product per min per milligram total protein. Wild type AKIII was sensitive to the presence of L-lysine in the assay. Fifty percent inhibition was found at a concentration of about 0.4 mM and 90% inhibition at about 1.0 mM. In contrast, mutants AKIII-M2, M3 and M4 (see Example 1) were not inhibited at all by 15 mM L-lysine.

Wild type AKIII protein was purified from the supernatant of the IPTG-induced culture as follows. To 1 mL of extract, 0.25 mL of 10% streptomycin sulfate was added and kept at 4° C. overnight. The mixture was centrifuged at 4° C. for 15 min at 15,000 rpm. The supernatant was collected and desalted using a Sephadex G-25 M column (Column PD-10, Pharmacia). It was then run on a Mono-Q HPLC column and eluted with a 0–1M NaCl gradient. The two 1 mL fractions containing most of the AKIII activity were pooled, concentrated, desalted and run on an HPLC sizing column (TSK G3000SW). Fractions were eluted in 20 mM KPO$_4$ buffer, pH7.2, 2 mM MgSO$_4$, 10 mM β-mercaptoethanol, 0,15M KCl, 0.5 mM L-lysine and were found to be >95% pure by SDS polyacrylamide gel electrophoresis. Purified AKIII protein was sent to Hazelton Research Facility (310 Swampridge Road, Denver, Pa. 17517) to have rabbit antibodies raised against the protein.

Example 3

Isolation of the E. coli and Corynebacterium glutamicum dapA Genes

The E. coli dapA gene (ecodapA) has been cloned, restriction endonuclease mapped and sequenced previously [Richaud et al. (1986) J. Bacteriol. 166:297–300]. For the present invention the dapA gene was obtained on a bacteriophage lambda clone from an ordered library of 3400 overlapping segments of cloned E. coli DNA constructed by Kohara, Akiyama and Isono [Kohara et al. (1987) Cell 50:595–508, see Example 1]. From the knowledge of the map position of dapA at 53 min on the E. coli genetic map [Bachman (1983) Microbiol. Rev. 47:180–230], the restriction endonuclease map of the cloned gene [Richaud et al. (1986) J. Bacteriol. 166:297–300], and the restriction endonuclease map of the cloned DNA fragments in the E. coli library [Kohara et al. (1987) Cell 50:595–508], it was possible to choose lambda phages 4C11 and 5A8 [Kohara et al. (1987) Cell 50:595–508] as likely candidates for carrying the dapA gene. The phages were grown in liquid culture from single plaques as described [see Current Protocols in Molecular Biology (1987) Ausubel et al. eds., John Wiley & Sons New York] using LE392 as host [see Sambrook et al. (1989) Molecular Cloning, A Laboratory Manual, Cold Spring Harbor Laboratory Press]. Phage DNA was prepared by phenol extraction as described [see Current Protocols in Molecular Biology (1987) Ausubel et al. eds., John Wiley & Sons New York]. Both phages contained an approximately 2.8 kb Pst I DNA fragment expected for the dapA gene [Richaud et al. (1986) J. Bacteriol. 166:297–300]. The fragment was isolated from the digest of phage 5A8 and inserted into Pst I digested vector pBR322 yielding plasmid pBT427.

The Corynebacterium dapA gene (cordapA) was isolated from genomic DNA from ATCC strain 13032 using polymerase chain reaction (PCR). The nucleotide sequence of the Corynebacterium dapA gene has been published [Bonnassie et al. (1990) Nucleic Acids Res. 18:6421]. From the sequence it was possible to design oligonucleotide primers for PCR that would allow amplification of a DNA fragment containing the gene, and at the same time add unique restriction endonuclease sites at the start codon (Nco I) and just past the stop codon (EcoR 1) of the gene. The oligonucleotide primers used were:

```
SEQ ID NO:4:
CCCGGGCCAT GGCTACAGGT TTAACAGCTA AGACCGGAGT
AGAGCACT

SEQ ID NO:5:
GATATCGAAT TCTCATTATA GAACTCCAGC TTTTTTC
```

PCR was performed using a Perkin-Elmer Cetus kit according to the instructions of the vendor on a thermocycler manufactured by the same company. The reaction product, when run on an agarose gel and stained with ethidium bromide, showed a strong DNA band of the size expected for the Corynebacterium dapA gene, about 900 bp. The PCR-generated fragment was digested with restriction endonucleases Nco I and EcoR I and inserted into expression vector pBT430 (see Example 2) digested with the same enzymes. In addition to introducing an Nco I site at the translation start codon, the PCR primers also resulted in a change of the second codon from AGC coding for serine to GCT coding for alanine. Several clones that expressed active, lysine-insensitive DHDPS (see Example 4) were isolated, indicating that the second codon amino acid substitution did not affect activity; one clone was designated FS766.

The Nco I to EcoR I fragment carrying the PCR-generated Corynebacterium dapA gene was subcloned into the phagemid vector pGEM-9Zf(−) from Promega, single-stranded DNA was prepared and sequenced. This sequence is shown in SEQ ID NO:6.

Aside from the differences in the second codon already mentioned, the sequence matched the published sequence except at two positions, nucleotides 798 and 799. In the published sequence these are TC, while in the gene shown in SEQ ID NO:6 they are CT. This change results in an amino acid substitution of leucine for serine. The reason for this difference is not known. It may be due to an error in the published sequence, the difference in strains used to isolate the gene, or a PCR-generated error. The latter seems unlikely since the same change was observed in at least 3 independently isolated PCR-generated dapA genes. The difference has no apparent effect on DHDPS enzyme activity (see Example 4).

Example 4

High Level Expression of the *E. coli* and *Corynebacterium glutamicum* dapA Genes in *E. coli*

An Nco I (CCATGG) site was inserted at the translation initiation codon of the *E. coli* dapA gene using oligonucleotide-directed mutagenesis. The 2.8 kb Pst I DNA fragment carrying the dapA gene in plasmid pBT427 (see Example 3) was inserted into the Pst I site of phagemid vector pTZ18R (Pharmacia) yielding pBT431. The orientation of the dapA gene was such that the coding strand would be present on the single-stranded phagemid DNA. Oligonucleotide-directed mutagenesis was carried out using a Muta-Gene kit from Bio-Rad according to the manufacturer's protocol with the mutagenic primer shown below: SEQ ID NO:7:
CTTCCCGTGA CCATGGGCCA TC Putative mutants were screened for the presence of an Nco I site and a plasmid, designated pBT437, was shown to have the the proper sequence in the vicinity of the mutation by DNA sequencing. The addition of an Nco I site at the translation start codon also resulted in a change of the second codon from TTC coding for phenylalanine to GTC coding for valine.

To achieve high level expression of the dapA genes in *E. coli* the bacterial expression vector pBT430 (see Example 2) was used. The *E. coli* dapA gene was cut out of plasmid pBT437 as an 1150 bp Nco I-Hind III fragment and inserted into the expression vector pBT430 digested with the same enzymes, yielding plasmid pBT442. For expression of the *Corynebacterium* dapA gene, the 910 bp Nco I to EcoR I fragment of SEQ ID NO:6 inserted in pBT430 (pFS766, see Example 3) was used.

For high level expression each of the plasmids was transformed into *E. coli* strain BL21(DE3) [Studier et al. (1986) *J. Mol. Biol.* 189:113–130]. Cultures were grown in LB medium containing ampicillin (100 mg/L) at 25° C. At an optical density at 600 nm of approximately 1, IPTG (isopropylthio-β-galactoside, the inducer) was added to a final concentration of 0.4 mM and incubation was continued for 3 h at 25° C. The cells were collected by centrifugation and resuspended in 1/20th (or 1/100th) the original culture volume in 50 mM NaCl; 50 mM Tris-Cl, pH 7.5; 1 mM EDTA, and frozen at −20° C. Frozen aliquots of 1 mL were thawed at 37° C. and sonicated, in an ice-water bath, to lyse the cells. The lysate was centrifuged at 4° C. for 5 min at 15,000 rpm. The supernatant was removed and the pellet was resuspended in 1 mL of the above buffer.

The supernatant and pellet fractions of uninduced and IPTG-induced cultures of BL21(DE3)/pBT442 or BL21 (DE3)/pFS766 were analyzed by SDS polyacrylamide gel electrophoresis. The major protein visible by Coomassie blue staining in the supernatant and pellet fractions of both induced cultures had a molecular weight of 32–34 kd, the expected size for DHDPS. Even in the uninduced cultures this protein was the most prominent protein produced.

In the BL21(DE3)/pBT442 IPTG-induced culture about 80% of the DHDPS protein was in the supernatant and DHDPS represented 10–20% of the total protein in the extract. In the BL21(DE3)/pFS766 IPTG-induced culture more than 50% of the DHDPS protein was in the pellet fraction. The pellet fractions in both cases were 90–95% pure DHDPS, with no other single protein present in significant amounts. Thus, these fractions were pure enough for use in the generation of antibodies. The pellet fractions containing 2–4 mg of either *E. coli* DHDPS or *Corynebacterium* DHDPS were solubilized in 50 mM NaCl; 50 mM Tris-Cl, pH 7.5; 1 mM EDTA, 0.2 mM dithiothreitol, 0.2% SDS and sent to Hazelton Research Facility (310 Swampridge Road, Denver, Pa. 17517) to have rabbit antibodies raised against the proteins.

DHDPS enzyme activity was assayed as follows: Assay mix (for 10×1.0 mL assay tubes or 40×0.25 mL for microtiter dish); made fresh, just before use:

| 2.5 mL | $H_2O$ |
| 0.5 mL | 1.0M Tris-HCl pH 8.0 |
| 0.5 mL | 0.1M Na Pyruvate |
| 0.5 mL | o-Aminobenzaldehyde (10 mg/mL in ethanol) |
| 25 μL | 1.0M DL-Aspartic-β-semialdehyde (ASA) in 1.0 N HCl |

| | Assay (1.0 mL): | MicroAssay (0.25 mL): |
| --- | --- | --- |
| DHDPS assay mix | 0.40 mL | 0.10 mL |
| enzyme extract + $H_2O$; | 0.10 mL | .025 mL |
| 10 mM L-lysine | 5 μL or 20 μL | 1 μL or 5 μL |
| 1.0N HCl | 0.50 mL | 0.125 mL |

Color allowed to develop for 30–60 min. Precipitate spun down in eppendorf centrifuge. $OD_{540}$ vs 0 min read as blank. For MicroAssay, aliquot 0.2 mL into microtiter well and read at $OD_{530}$.

The specific activity of *E. coli* DHDPS in the supernatant fraction of induced extracts was about 50 $OD_{540}$ units per minute per milligram protein in a 1.0 mL assay. *E. coli* DHDPS was sensitive to the presence of L-lysine in the assay. Fifty percent inhibition was found at a concentration of about 0.5 mM. For *Corynebacterium* DHDPS, the activity was measured in the supernatant fraction of uninduced extracts, rather than induced extracts. Enzyme activity was about 4 $OD_{530}$ units per min per milligram protein in a 0.25 mL assay. In contrast to *E. coli* DHDPS, *Corynebacterium* DHDPS was not inhibited at all by L-lysine, even at a concentration of 70 mM.

Example 5

Excretion of Amino Acids by *E. coli* Expressing High Levels of DHDPS and/or AKIII The *E. coli* expression cassette with the *E. coli* dapA gene linked to the T7 RNA polymerase promoter was isolated by digesting pBT442 (see Example 4) with Bgl II and BamH I separating the digestion products via agarose gel electrophoresis and eluting the approximately 1250 bp fragment from the gel. This fragment was inserted into the BamH I site of plasmids pBT461 (containing the T7 promoter/lysC gene) and pBT492 (containing the T7 promoter/lysC-M4 gene). Inserts where transcription of both genes would be in the same direction were identified by restriction endonuclease analysis yielding plasmids pBT517 (T7/dapA+T7/lysC-M4) and pBT519 (T7/dapA+T7/lysC).

In order to induce *E. coli* to produce and excrete amino acids, these plasmids, as well as plasmids pBT442, pBT461 and pBT492 (and pBR322 as a control) were transformed into *E. coli* strain BL21(DE3) [Studier et al. (1986) *J. Mol. Biol.* 189:113–130]. All of these plasmids, but especially pBT517 and pBT519, are somewhat unstable in this host strain, necessitating careful maintenance of selection for ampicillin resistance during growth.

All strains were grown in minimal salts M9 media [see Sambrook et al. (1989) Molecular Cloning, *A Laboratory Manual*, Cold Spring Harbor Laboratory Press] supplemented with ampicillin to maintain selection for the plasmids overnight at 37° C. Cultures were collected when they reached an $OD_{600}$ of 1. Cells were removed by centrifugation and the supernatants (3 mL) were passed through 0.2 micron filters to remove remaining cells and large molecules. Five microliter aliquots of the supernatant fractions were analyzed for amino acid composition with a Beckman Model 6300 amino acid analyzer using post-column ninhydrin detection. Results are shown in Table 1.

TABLE 1

Amino Acid Concentration in Culture Supernatants [mM]

| Plasmid | Lys | Thr | Met | Ala | Val | Asp | Glu |
|---|---|---|---|---|---|---|---|
| pBR322 | 0 | 0 | 0 | 0.05 | 0.1 | 0 | 0 |
| pBT442 | 0.48 | 0 | 0 | 0.04 | 0.06 | 0 | 0 |
| pBT461 | 0.14 | 0.05 | 0 | 0.02 | 0.03 | 0 | 0 |
| pBT492 | 0.16 | 0.07 | 0 | 0.02 | 0.03 | 0 | 0 |
| pBT517 | 0.18 | 0 | 0.01 | 0 | 0 | 0.02 | 0.02 |
| pBT519 | 0.14 | 0 | 0.01 | 0 | 0 | 0.01 | 0 |

All of the plasmids, except the pBR322 control, lead to the excretion of lysine into the culture medium. Expression of the lysC or the lysC-M4 gene lead to both lysine and threonine excretion. Expression of lysC-M4+dapA lead to excretion of lysine, methionine, aspartic acid and glutamic acid, but not threonine. In addition, alanine and valine were not detected in the culture supernatant. Similar results were obtained with lysC+dapA, except that no glutamic acid was excreted.

Example 6

Construction of Chimeric dapA, lysC and lysC-M4 Genes for Expression in Plants

Several gene expression cassettes were used for construction of chimeric genes for expression of ecodapA, cordapA, lysC and lysC-M4 in plants. A leaf expression cassette (FIG. 4*a*) is composed of the 35S promoter of cauliflower mosaic virus [Odell et al.(1985) *Nature* 313:810–812; Hull et al. (1987) *Virology* 86:482–493], the translation leader from the chlorophyll a/b binding protein (Cab) gene, [Dunsmuir (1985) *Nucleic Acids Res.* 13:2503–2518] and 3' transcription termination region from the nopaline synthase (Nos) gene [Depicker et al. (1982) *J. Mol. Appl. Genet.* 1:561–570]. Between the 5' and 3' regions are the restriction endonuclease sites Nco I (which includes the ATG translation initiation codon), EcoR I, Sma I and Kpn I. The entire cassette is flanked by Sal I sites; there is also a BamH I site upstream of the cassette.

A seed-specific expression cassette (FIG. 4*b*) is composed of the promoter and transcription terminator from the gene encoding the β subunit of the seed storage protein phaseolin from the bean *Phaseolus vulgaris* [Doyle et al. (1986) *J. Biol. Chem.* 261:9228–9238]. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

A second seed expression cassette was used for the cordapA gene. This was composed of the promoter and transcription terminator from the soybean Kunitz trysin inhibitor 3 (KTI3) gene [Jofuku et al. (1989) *Plant Cell* 1:427–435]. The KTI3 cassette includes about 2000 nucleotides upstream (5') from the translation initiation codon and about 240 nucleotides downstream (3') from the translation stop codon of phaseolin. Between the 5' and 3' regions are the unique restriction endonuclease sites Nco I (which includes the ATG translation initiation codon), Xba I, Kpn I and Sma I. The entire cassette is flanked by BamH I sites.

A constitutive expression cassette for corn was used for expression of the lysC-M4 gene and the ecodapA gene. It was composed of a chimeric promoter derived from pieces of two corn promoters and modified by in vitro site-specific mutagenesis to yield a high level constitutive promoter and a 3' region from a corn gene of unknown function. Between the 5' and 3' regions are the unique restriction endonuclease sites Nco I (which includes the ATG translation initiation codon), Sma I and Bgl II. The nucleotide sequence of the constitutive corn expression cassette is shown in SEQ ID NO:93.

Plant amino acid biosynthetic enzymes are known to be localized in the chloroplasts and therefore are synthesized with a chloroplast targeting signal. Bacterial proteins such as DHDPS and AKIII have no such signal. A chloroplast transit sequence (cts) was therefore fused to the ecodapA, cordapA, lysC, and lysC-M4 coding sequence in some chimeric genes. The cts used was based on the the cts of the small subunit of ribulose 1,5-bisphosphate carboxylase from soybean [Berry-Lowe et al. (1982) *J. Mol. Appl. Genet.* 1:483–498]. The oligonucleotides SEQ ID NOS:8–11 were synthesized and used as described below. For corn the cts used was based on the the cts of the small subunit of ribulose 1,5-bisphosphate carboxylase from corn [Lebrun et al. (1987) *Nucleic Acids Res.* 15:4360] and is designated mcts to distinguish it from the soybean cts. The oligonucleotides SEQ ID NOS:17–22 were synthesized and used as described below.

Fourteen chimeric genes were created:
No. 1) 35S promoter/Cab leader/lysC/Nos 3'
No. 2) 35S promoter/Cab leader/cts/lysC/Nos 3'
No. 3) 35S promoter/Cab leader/cts/lysC-M4/Nos 3'
No. 4) phaseolin 5' region/cts/lysC/phaseolin 3' region
No. 5) phaseolin 5' region/cts/lysC-M4/phaseolin 3' region
No. 6) 35S promoter/Cab leader/ecodapA/Nos 3'
No. 7) 35S promoter/Cab leader/cts/ecodapA/Nos 3
No. 8) phaseolin 5' region/ecodapA/phaseolin 3' region
No. 9) phaseolin 5' region/cts/ecodapA/phaseolin 3' region
No. 10) 35S promoter/Cab leader/cts/cordapA/Nos 3
No. 11) phaseolin 5' region/cts/cordapA/phaseolin 3' region No. 12) KTI3 5' region/cts/cordapA/KTI3 3' region
No. 13) HH534 5' region/mcts/lysC-M4/HH2-1 3' region
No. 14) HH534 5' region/mcts/ecodapA/HH2-1 3' region A 1440 bp Nco I-Hpa I fragment containing the entire lysC coding region plus about 90 bp of 3' non-coding sequence was isolated from an agarose gel following electrophoresis and inserted into the leaf expression cassette digested with Nco I and Sma I (chimeric gene No. 1), yielding plasmid pBT483.

Oligonucleotides SEQ ID NO:8 and SEQ ID NO:9, which encode the carboxy terminal part of the chloroplast targeting signal, were annealed, resulting in Nco I compatible ends, purified via polyacrylamide gel electrophoresis, and inserted into Nco I digested pBT461. The insertion of the correct sequence in the correct orientation was verified by DNA sequencing yielding pBT496. Oligonucleotides SEQ ID NO:10 and SEQ ID NO:11, which encode the amino terminal part of the chloroplast targeting signal, were annealed, resulting in Nco I compatible ends, purified via polyacrylamide gel electrophoresis, and inserted into Nco I digested pBT496. The insertion of the correct sequence in the correct orientation was verified by DNA sequencing yielding pBT521. Thus the cts was fused to the lysC gene.

To fuse the cts to the lysC-M4 gene, pBT521 was digested with Sal I, and an approximately 900 bp DNA fragment that included the cts and the amino terminal coding region of lysC was isolated. This fragment was inserted into Sal I digested pBT492, effectively replacing the amino terminal coding region of lysC-M4 with the fused cts and the amino terminal coding region of lysC. Since the mutation that resulted in lysine-insensitivity was not in the replaced fragment, the new plasmid, pBT523, carried the cts fused to lysC-M4.

The 1600 bp Nco I-Hpa I fragment containing the cts fused to lysC plus about 90 bp of 3' non-coding sequence was isolated and inserted into the leaf expression cassette digested with Nco I and Sma I (chimeric gene No. 2), yielding plasmid pBT541 and the seed-specific expression cassette digested with Nco I and Sma I (chimeric gene No. 4), yielding plasmid pBT543.

Similarly, the 1600 bp Nco I-Hpa I fragment containing the cts fused to lysC-M4 plus about 90 bp of 3' non-coding sequence was isolated and inserted into the leaf expression cassette digested with Nco I and Sma I (chimeric gene No. 3), yielding plasmid pBT540 and the seed-specific expression cassette digested with Nco I and Sma I (chimeric gene No. 5), yielding plasmid pBT544.

Before insertion into the expression cassettes, the ecodapA gene was modified to insert a restriction endonuclease site, Kpn I, just after the translation stop codon. The oligonucleotides SEQ ID NOS:12–13 were synthesized for this purpose:

```
SEQ ID NO:12:
CCGGTTTGCT GTAATAGGTA CCA

SEQ ID NO:13:
AGCTTGGTAC CTATTACAGC AAACCGGCAT G
```

Oligonucleotides SEQ ID NO:12 and SEQ ID NO:13 were annealed, resulting in an Sph I compatible end on one end and a Hind III compatible end on the other and inserted into Sph I plus Hind III digested pBT437. The insertion of the correct sequence was verified by DNA sequencing yielding pBT443.

An 880 bp Nco I-Kpn I fragment from pBT443 containing the entire ecodapA coding region was isolated from an agarose gel following electrophoresis and inserted into the leaf expression cassette digested with Nco I and Kpn I (chimeric gene No. 6), yielding plasmid pBT450 and into the seed-specific expression cassette digested with Nco I and Kpn I (chimeric gene No. 8), yielding plasmid pBT494.

Oligonucleotides SEQ ID NO:8 and SEQ ID NO:9, which encode the carboxy terminal part of the chloroplast targeting signal, were annealed resulting in Nco I compatible ends, purified via polyacrylamide gel electrophoresis, and inserted into Nco I digested pBT450. The insertion of the correct sequence in the correct orientation was verified by DNA sequencing yielding pBT45 1. A 950 bp Nco I-Kpn I fragment from pBT451 encoding the carboxy terminal part of the chloroplast targeting signal fused to the entire ecodapA coding region was isolated from an agarose gel following electrophoresis and inserted into the seed-specific expression cassette digested with Nco I and Kpn I, yielding plasmid pBT495. Oligonucleotides SEQ ID NO:10: and SEQ ID NO:11:, which encode the amino terminal part of the chloroplast targeting signal, were annealed resulting in Nco I compatible ends, purified via polyacrylamide gel electrophoresis, and inserted into Nco I digested pBT451 and pBT495. Insertion of the correct sequence in the correct orientation was verified by DNA sequencing yielding pBT455 and pBT520, respectively. Thus the cts was fused to the ecodapA gene in the leaf expression cassette (chimeric gene No. 7) and the seed-specific expression cassette (chimeric gene No. 9).

An 870 bp Nco I-EcoR I fragment from pFS766 containing the entire cordapA coding region was isolated from an agarose gel following electrophoresis and inserted into the leaf expression cassette digested with Nco I and EcoR I, yielding plasmid pFS789. To attach the cts to the cordapA gene, a DNA fragment containing the entire cts was prepared using PCR. The template DNA was pBT540 and the oligonucleotide primers used were:

```
SEQ ID NO:14:
GCTTCCTCAA TGATCTCCTC CCCAGCT

SEQ ID NO:15:
CATTGTACTC TTCCACCGTT GCTAGCAA
```

PCR was performed using a Perkin-Elmer Cetus kit according to the instructions of the vendor on a thermocycler manufactured by the same company. The PCR-generated 160 bp fragment was treated with T4 DNA polymerase in the presence of the 4 deoxyribonucleotide triphosphates to obtain a blunt-ended fragment. The cts fragment was inserted into pFS789 which had been digested with Nco I and treated with the Klenow fragment of DNA polymerase to fill in the 5' overhangs. The inserted fragment and the vector/insert junctions were determined to be correct by DNA sequencing, yielding pFS846 containing chimeric gene No. 10.

A 1030 bp Nco I-Kpn I fragment from pFS846 containing the cts attached to the cordapA coding region was isolated from an agarose gel following electro-phoresis and inserted into the phaseolin seed expression cassette digested with Nco I and Kpn I, yielding plasmid pFS889 containing chimeric gene No. 11. Similarly, the 1030 bp Nco I-Kpn I fragment from pFS846 was inserted into the KTI3 seed expression cassette digested with Nco I and Kpn I, yielding plasmid pFS862 containing chimeric gene No. 12.

Oligonucleotides SEQ ID NO:94 and SEQ ID NO:95, which encode the carboxy terminal part of the corn chloroplast targeting signal, were annealed, resulting in Xba I and Nco I compatible ends, purified via polyacrylamide gel electrophoresis, and inserted into Xba I plus Nco I digested pBT492 (see Example 2). The insertion of the correct sequence was verified by DNA sequencing yielding pBT556. Oligonucleotides SEQ ID NO:96 and SEQ ID NO:97, which encode the middle part of the chloroplast targeting signal, were annealed, resulting in Bgl II and Xba I compatible ends, purified via polyacrylamide gel electrophoresis, and inserted into Bgl II and Xba I digested pBT556. The insertion of the correct sequence was verified by DNA sequencing yielding pBT557. Oligonucleotides SEQ ID NO:98 and SEQ ID NO:99, which encode the amino terminal part of the chloroplast targeting signal, were annealed, resulting in Nco I and Afl II compatible ends, purified via polyacrylamide gel electrophoresis, and inserted into Nco I and Afl II digested pBT557. The insertion of the correct sequence was verified by DNA sequencing yielding pBT558. Thus the mcts was fused to the lysC-M4 gene.

A 1.6 kb Nco I-Hpa I fragment from pBT558 containing the mcts attached to the lysC-M4 gene was isolated from an agarose gel following electrophoresis and inserted into the constitutive corn expression cassette digested with Nco I and Sma I, yielding plasmid pBT573 containing chimeric gene No. 13.

To attach the mcts to the ecodapA gene a DNA fragment containing the entire mcts was prepared using PCR as described above. The template DNA was pBT558 and the oligonucleotide primers used were:

SEQ ID NO:100:
GCGCCCACCG TGATGA

SEQ ID NO:101:
CACCGGATTC TTCCGC

The mcts fragment was inserted into pBT450 (above) which had been digested with Nco I and treated with the Klenow fragment of DNA polymerase to fill in the 5' overhangs. The inserted fragment and the vector/insert junctions were determined to be correct by DNA sequencing, yielding pBT576. Plasmid pBT576 was digested with Asp718, treated with the Klenow fragment of DNA polymerase to yield a blunt-ended fragment, and then digested with Nco I. The resulting 1030 bp Nco I-blunt-ended fragment containing the ecodapA gene attached to the mcts was isolated from an agarose gel following electrophoresis. This fragment was inserted into the constitutive corn expression cassette digested with Bgl II, treated with the Klenow fragment of DNA polymerase to yield a blunt-ended fragment, and then digested with Nco I, yielding plasmid pBT583 containing chimeric gene No. 14.

Example 7

Transformation of Tobacco with the 35S Promoter/lysC Chimeric Genes

Transformation of tobacco with the 35S promoter/lysC chimeric genes was effected according to the following:

The 35S promoter/Cab leader/lysC/Nos 3', 35S promoter/Cab leader/cts/lysC/Nos 3', and 35S promoter/Cab leader/cts/lysC-M4/Nos 3' chimeric genes were isolated as 3.5–3.6 kb BamH I-EcoR I fragments and inserted into BamH I-EcoR I digested vector pZS97K (FIG. 5), yielding plasmids pBT497, pBT545 and pBT542, respectively. The vector is part of a binary Ti plasmid vector system [Bevan, (1984) *Nucl. Acids. Res.* 12:8711–8720] of *Agrobacterium tumefaciens*. The vector contains: (1) the chimeric gene nopaline synthase promoter/neomycin phosphotransferase coding region (nos:NPT II) as a selectable marker for transformed plant cells [Bevan et al. (1983) *Nature* 304:184–186]; (2) the left and right borders of the T-DNA of the Ti plasmid [Bevan (1984) *Nucl. Acids. Res.* 12:8711–8720]; (3) the *E. coli* lacZ α-complementing segment [Vieria and Messing (1982) *Gene* 19:259–267] with unique restriction endonuclease sites for EcoR I, Kpn I, BamH I and Sal I; (4) the bacterial replication origin from the Pseudomonas plasmid pVS1 [Itoh et al. (1984) *Plasmid* 11:206–220]; and (5) the bacterial neomycin phosphotransferase gene from Tn5 [Berg et al. (1975) *Proc. Natl. Acad Sci. U.S.A.* 72:3628–3632] as a selectable marker for transformed *A. tumefaciens*.

The 35S promoter/Cab leader/cts/lysC/Nos 3', and 35S promoter/Cab leader/cts/lysC-M4/Nos 3' chimeric genes were also inserted into the binary vector pBT456, yielding pBT547 and pBT546, respectively. This vector is pZS97K, into which the chimeric gene 35S promoter/Cab leader/cts/dapA/Nos 3' had previously been inserted as a BamH I-Sal I fragment (see Example 9). In the cloning process large deletions of the dapA chimeric gene occurred. As a consequence these plasmids are equivalent to pBT545 and pBT542, in that the only transgene expressed in plants (other than the selectable marker gene, NPT II) was 35S promoter/Cab leader/cts/lysC/Nos 3' or 35S promoter/Cab leader/cts/lysC-M4/Nos 3'.

The binary vectors containing the chimeric lysC genes were transferred by tri-parental matings [Ruvkin et al. (1981) *Nature* 289:85–88] to *Agrobacterium* strain LBA4404/pAL4404 [Hockema et al (1983), *Nature* 303:179–180]. The *Agrobacteruim* transformants were used to inoculate tobacco leaf disks [Horsch et al. (1985) *Science* 227:1229–1231]. Transgenic plants were regenerated in selective medium containing kanamycin.

To assay for expression of the chimeric genes in leaves of the transformed plants, protein was extracted as follows. Approximately 2.5 g of young plant leaves, with the midrib removed, were placed in a dounce homogenizer with 0.2 g of polyvinyl polypyrrolidone and 11 mL of 50 mM Tris-HCl pH8.0, 50 mM NaCl, 1 mM EDTA (TNE) and ground thoroughly. The suspension was further homogenized by a 20 sec treatment with a Brinkman Polytron Homogenizer operated at setting 7. The resultant suspensions were centrifuged at 16,000 rpm for 20 min at 4° C. in a Dupont-Sorvall superspeed centrifuge using an SS34 rotor to remove particulates. The supernatant was decanted, the volume was adjusted to be 10 mL by addition of TNE if necessary, and 8 mL of cold, saturated ammonium sulfate was added. The mixture was set on ice for 30 min and centrifuged as described above. The supernatant was decanted and the pellet, which contained the AKIII protein, was resuspended in 1 mL of TNE and desalted by passage over a Sephadex G-25 M column (Column PD-10, Pharmacia).

For immunological characterization, three volumes of extract were mixed with 1 volume of 4×SDS-gel sample buffer (0.17M Tris-HCl pH6.8, 6.7% SDS, 16.7% β-mercaptoethanol, 33% glycerol) and 3 µL from each extract were run per lane on an SDS polyacrylamide gel, with bacterially produced AKIII serving as a size standard and protein extracted from untransformed tobacco leaves serving as a negative control. The proteins were then electrophoretically blotted onto a nitrocellulose membrane (Western Blot). The membranes were exposed to the AKIII antibodies prepared as described in Example 2 at a 1:5000 dilution of the rabbit serum using standard protocol provided by BioRad with their Immun-Blot Kit. Following rinsing to remove unbound primary antibody, the membranes were exposed to the secondary antibody, donkey anti-rabbit Ig conjugated to horseradish peroxidase (Amersham) at a 1:3000 dilution. Following rinsing to remove unbound secondary antibody, the membranes were exposed to Amersham chemiluminescence reagent and X-ray film.

Seven of thirteen transformants containing the chimeric gene, 35S promoter/Cab leader/cts/lysC-M4/Nos 3', and thirteen of seventeen transformants containing the chimeric gene, 35S promoter/Cab leader/cts/lysC/Nos 3', produced AKIII protein (Table 2). In all cases protein which reacted with the AKIII antibody was of several sizes. Approximately equal quantities of proteins equal in size to AKIII produced in *E. coli*, and a protein about 6 kd larger were evident in all samples, suggesting that the chloroplast targeting signal had been removed from about half of the protein synthesized. This further suggests that about half of the the protein entered the chloroplast. In addition, a considerable amount of protein of higher molecular weight was observed. The origin of this protein is unclear; the total amount present was equal or slightly greater than the amounts of the mature and putative AKIII precursor proteins combined.

The leaf extracts were assayed for AK activity as described in Example 2. AKIII could be distinguished from endogenous AK activity, if it were present, by its increased resistance to lysine plus threonine. Unfortunately, however, this assay was not sensitive enough to reliably detect AKIII activity in these extracts. Zero of four transformants containing the chimeric gene, 35S promoter/Cab leader/lysC/Nos 3', showed AKIII activity. Only one extract, from a transformant containing the 35S promoter/Cab leader/cts/lysC-M4/Nos 3' gene, produced a convincing level of enzyme activity. This came from transformant 546–49A, and was also the extract that showed the highest level of AKIII-M4 protein via Western blot.

An alternative method to detect the expression of active AKIII enzyme was to evaluate the sensitivity or resistance of leaf tissue to high concentrations of lysine plus threonine. Growth of cell cultures and seedlings of many plants is inhibited by high concentrations of lysine plus threonine; this is reversed by addition of methionine (or homoserine which is converted to methionine in vivo). Lysine plus threonine inhibition is thought to result from feedback inhibition of endogenous AK, which reduces flux through the pathway leading to starvation for methionine. In tobacco there are two AK enzymes in leaves, one lysine-sensitive and one threonine sensitive [Negrutui et al. (1984) Theor. Appl. Genet. 68:11–20]. High concentrations of lysine plus threonine inhibit growth of shoots from tobacco leaf disks and inhibition is reversed by addition of low concentrations of methionine. Thus, growth inhibition is presumably due to inhibition of the two AK isozymes.

Expression of active lysine and threonine insensitive AKIII-M4 would be predicted to reverse the growth inhibition. As can be seen in Table 2, this was observed. There is, in fact, a good correlation between the level of AKIII-M4 protein expressed and the resistance to lysine plus threonine inhibition. Expression of lysine-sensitive wild type AKIII does not have a similar effect. Only the highest expressing transformant showed any resistance to lysine plus threonine inhibition, and this was much less dramatic than that observed with AKIII-M4.

To measure free amino acid composition of the leaves, free amino acids were extracted as follows. Approximately 30–40 mg of young leaf tissue was chopped with a razor and dropped into 0.6 mL of methanol/chloroform/water mixed in ratio of 12v/5v/3v (MCW) on dry ice. After 10–30 min the suspensions were brought to room temperature and homogenized with an Omni 1000 Handheld Rechargeable Homogenizer and then centrifuged in an eppendorf microcentrifuge for 3 min. Approximately 0.6 mL of supernatant was decanted and an additional 0.2 mL of MCW was added to the pellet which was then vortexed and centrifuged as above. The second supernatant, about 0.2 mL, was added to the first. To this, 0.2 mL of chloroform was added followed by 0.3 mL of water. The mixture was vortexed and the centrifuged in an eppendorf microcentrifuge for about 3 min, the upper aqueous phase, approximately 1.0 mL, was removed, and was dried down in a Savant Speed Vac Concentrator. One-tenth of the sample was run on a Beckman Model 6300 amino acid analyzer using post-column ninhydrin detection. Relative free amino acid levels in the leaves were compared as ratios of lysine or threonine to leucine, thus using leucine as an internal standard. There was no consistent effect of expression of AKIII or AKIII-M4 on the lysine or threonine (or any other amino acid) levels in the leaves (Table 2).

TABLE 2

BT542 transformants: 35S promoter/Cab leader/cts/<u>lysC</u>-M4/Nos 3'
BT545 transformants: 35S promoter/Cab leader/cts/<u>lysC</u>/Nos 3'
BT546 transformants: 35S promoter/Cab leader/cts/<u>lysC</u>-M4/Nos 3'
BT547 transformants: 35S promoter/Cab leader/cts/<u>lysC</u>/Nos 3'

| LINE | FREE AMINO ACIDS/ LEAF K/L | T/L | AKIII ACTIVITY U/MG/HR | WESTERN BLOT | RESISTANCE TO Lys 3 mM + Thr 3 mM |
|---|---|---|---|---|---|
| 542-5B | 0.5 | 3.5 | 0 | – | – |
| 542-26A | 0.5 | 3.3 | 0 | – | – |
| 542-27B | 0.5 | 3.4 | 0 | ++ | +++ |
| 542-35A | 0.5 | 4.3 | 0.01 | – | – |
| 542-54A | 0.5 | 2.8 | 0 | – | – |
| 542-57B | 0.5 | 3.4 | 0 | – | + |
| 545-5A | n.d. | n.d. | 0.02 | ++ | |
| 545-7B | 0.5 | 3.4 | 0 | + | |
| 545-17B | 0.6 | 2.5 | 0.01 | + | |
| 545-27A | 0.6 | 3.5 | 0 | ++ | |
| 545-50E | 0.6 | 3.6 | 0.03 | ++ | |
| 545-52A | 0.5 | 3.6 | 0.02 | – | |
| 546-4A | 0.4 | 4.5 | 0 | + | + |
| 546-24B | 0.6 | 4.9 | 0.04 | ++ | ++ |
| 546-44A | 0.5 | 6.0 | 0.03 | + | ++ |
| 546-49A | 0.7 | 7.0 | 0.10 | +++ | +++ |
| 546-54A | 0.5 | 6.4 | 0 | + | + |
| 546-56B | 0.5 | 4.4 | 0.01 | – | – |
| 546-58B | 0.6 | 8.0 | 0 | + | ++ |
| 547-3D | 0.4 | 5.4 | 0 | ++ | – |
| 547-8B | 0.6 | 5.0 | 0.02 | – | |
| 547-9A | 0.5 | 4.3 | 0.03 | +++ | |
| 547-12A | 0.7 | 3.9 | 0 | +++ | + |
| 547-15B | 0.6 | 4.5 | 0 | + | – |
| 547-16A | 0.5 | 3.6 | 0 | ++ | |
| 547-18A | 0.5 | 4.0 | | +++ | – |
| 547-22A | 0.8 | 4.4 | | – | |
| 547-25C | 0.5 | 4.3 | | + | – |
| 547-28C | 0.6 | 5.6 | | – | |
| 547-29C | 0.5 | 3.8 | | +++ | + |

Example 8

Transformation of Tobacco with the Phaseolin Promoter/lysC Chimeric Genes

The phaseolin promoter/lysC chimeric gene cassettes, phaseolin 5' region/cts/lysC/phaseolin 3' region, and phaseolin 5' region/cts/lysC-M4/phaseolin 3' region (Example 6) were isolated as approximately 3.3 kb Hind III fragments. These fragments were inserted into the unique Hind III site of the binary vector pZS97 (FIG. 6) yielding pBT548 and pBT549, respectively. This vector is similar to pZS97K described in Example 7 except for the presence of two additional unique cloning sites, Sma I and Hind III, and the bacterial β-lactamase gene (causing ampicillin resistance) as a selectable marker for transformed *A. tumefaciens* instead of the bacterial neomycin phosphotransferase gene.

The binary vectors containing the chimeric lysC genes were transferred by tri-parental matings to *Agrobacteruim* strain LBA4404/pAL4404, the *Agrobacteruim* transformants were used to inoculate tobacco leaf disks and transgenic plants regenerated by the methods set out in Example 7.

To assay for expression of the chimeric genes in the seeds of the transformed plants, the plants were allowed to flower, self-pollinate and go to seed. Total proteins were extracted from mature seeds as follows. Approximately 30–40 mg of seeds were put into a 1.5 mL disposable plastic microfuge tube and ground in 0.25 mL of 50 mM Tris-HCl pH6.8, 2 mM EDTA, 1% SDS, 1% β-mercaptoethanol. The grinding was done using a motorized grinder with disposable plastic shafts designed to fit into the microfuge tube. The resultant suspensions were centrifuged for 5 min at room temperature in a microfuge to remove particulates. Three volumes of extract was mixed with 1 volume of 4×SDS-gel sample buffer (0.17M Tris-HCl pH6.8, 6.7% SDS, 16.7% β-mercaptoethanol, 33% glycerol) and 5 μL from each extract were run per lane on an SDS polyacrylamide gel, with bacterially produced AKIII serving as a size standard and protein extracted from untransformed tobacco seeds serving as a negative control. The proteins were then electrophoretically blotted onto a nitrocellulose membrane. The membranes were exposed to the AKIII antibodies (prepared as described in Example 2) at a 1:5000 dilution of the rabbit serum using standard protocol provided by BioRad with their Immun-Blot Kit. Following rinsing to remove unbound primary antibody the membranes were exposed to the secondary antibody, donkey anti-rabbit Ig conjugated to horseradish peroxidase (Amersham) at a 1:3000 dilution. Following rinsing to remove unbound secondary antibody, the membranes were exposed to Amersham chemiluminescence reagent and X-ray film.

Ten of eleven transformants containing the chimeric gene, phaseolin 5' region/cts/lysC/phaseolin 3' region, and ten of eleven transformants containing the chimeric gene, phaseolin 5' region/cts/lysC-M4/phaseolin 3' region, produced AKIII protein (Table 3). In all cases protein which reacted with the AKIII antibody was of several sizes. Approximately equal quantities of proteins equal in size to AKIII produced in *E. coli*, and about 6 kd larger were evident in all samples, suggesting that the chloroplast targeting signal had been removed from about half of the protein synthesized. This further suggests that about half of the the protein entered the chloroplast. In addition, some proteins of lower molecular weight were observed, probably representing breakdown products of the AKIII polypeptide.

To measure free amino acid composition of the seeds, free amino acids were extracted from mature seeds as follows. Approximately 30–40 mg of seeds and an approximately equal amount of sterilized sand were put into a 1.5 mL disposable plastic microfuge tube along with 0.2 mL of methanol/chloroform/water mixed in ratio of 12v/5v/3v (MCW) at room temperature. The seeds were ground using a motorized grinder with disposable plastic shafts designed to fit into the microfuge tube. After grinding an additional 0.5 mL of MCW was added, the mixture was vortexed and then centrifuged in an eppendorf microcentrifuge for about 3 min. Approximately 0.6 mL of supernatant was decanted and an additional 0.2 mL of MCW was added to the pellet which was then vortexed and centrifuged as above. The second supernatant, about 0.2 mL, was added to the first. To this, 0.2 mL of chloroform was added followed by 0.3 mL of water. The mixture was vortexed and then centrifuged in an eppendorf microcentrifuge for about 3 min, the upper aqueous phase, approximately 1.0 mL, was removed, and was dried down in a Savant Speed Vac Concentrator. The samples were hydrolyzed in 6N hydrochloric acid, 0.4% β-mercaptoethanol under nitrogen for 24 h at 110–120° C.; ¼ of the sample was run on a Beckman Model 6300 amino acid analyzer using post-column ninhydrin detection. Relative free amino acid levels in the seeds were compared as ratios of lysine, methionine, threonine or isoleucine to leucine, thus using leucine as an internal standard.

To measure the total amino acid composition of the seeds, 6 seeds were hydrolyzed in 6N hydrochloric acid, 0.4% β-mercaptoethanol under nitrogen for 24 h at 110–120° C.; ⅒ of the sample was run on a Beckman Model 6300 amino acid analyzer using post-column ninhydrin detection. Relative amino acid levels in the seeds were compared as ratios of lysine, methionine, threonine or isoleucine to leucine, thus using leucine as an internal standard. Because the transgene was segregating in these self-pollinated progeny of the primary transformant and only six seeds were analyzed, there was expected to be some sampling error. Therefore, the measurement was repeated multiple times for some of the lines (Table 3).

Expression of the cts/lysC gene in the seeds resulted in a 2 to 4-fold increase in the level of free threonine in the seeds and a 2 to 3-fold increase in the level of free lysine in some cases. There was a good correlation between transformants expressing higher levels of AKIII protein and those having higher levels of free threonine, but this was not the case for lysine. These relatively small increases of free threonine or lysine were not sufficient to yield detectable increases in the levels of total threonine or lysine in the seeds. Expression of the cts/lysC-M4 gene in the seeds resulted in a 4 to 23-fold increase in the level of free threonine in the seeds and a 2 to 3-fold increase in the level of free lysine in some cases. There was a good correlation between transformants expressing higher levels of AKIII protein and those having higher levels of free threonine, but this was again not the case for lysine. The larger increases of free threonine were sufficient to yield detectable increases in the levels of total threonine in the seeds. Sixteen to twenty-five percent increases in total threonine content of the seeds were observed in three lines which were sampled multiple times. (Isoleucine to leucine ratios are shown for comparison.) The lines that showed increased total threonine were the same ones the showed the highest levels of increase in free threonine and high expression of the AKIII-M4 protein. From these results it can be estimated that free threonine represents about 1% of the total threonine present in a normal tobacco seed, but about 18% of the total threonine present in seeds expressing high levels of AKIII-M4.

TABLE 3

BT548 Transformants: phaseolin 5' region/cts/<u>lysC</u>/phaseolin 3'
BT549 Transformants: phaseolin 5' region/cts/<u>lysC</u>-M4/phaseolin 3'

| LINE | SEED FREE AMINO ACID | | | SEED TOTAL AMINO ACID | | | WESTERN |
|---|---|---|---|---|---|---|---|
| | K/L | T/L | I/L | K/L | T/L | I/L | |
| NORMAL | 0.49 | 1.34 | 0.68 | 0.35 | 0.68 | 0.63 | – |
| 548-2A | 1.15 | 2.3 | 0.78 | 0.43 | 0.71 | 0.67 | + |

TABLE 3-continued

BT548 Transformants: phaseolin 5' region/cts/lysC/phaseolin 3'
BT549 Transformants: phaseolin 5' region/cts/lysC-M4/phaseolin 3'

| LINE | SEED FREE AMINO ACID | | | SEED TOTAL AMINO ACID | | | WESTERN |
|---|---|---|---|---|---|---|---|
| | K/L | T/L | I/L | K/L | T/L | I/L | |
| 548-4D | 0.69 | 5.3 | 0.80 | 0.35 | 0.69 | 0.65 | +++ |
| 548-6A | 0.39 | 3.5 | 0.85 | 0.35 | 0.69 | 0.64 | + |
| 548-7A | 0.82 | 4.2 | 0.83 | 0.36 | 0.68 | 0.65 | ++ |
| 548-14A | 0.41 | 3.1 | 0.82 | 0.32 | 0.67 | 0.65 | + |
| 548-18A | 0.51 | 1.5 | 0.69 | 0.37 | 0.67 | 0.63 | − |
| 548-22A | 1.41 | 2.9 | 0.75 | 0.47 | 0.74 | 0.65 | +++ |
| 548-24A | 0.73 | 3.7 | 0.81 | 0.38 | 0.68 | 0.65 | ++ |
| 548-41A | 0.40 | 2.8 | 0.77 | 0.37 | 0.68 | 0.65 | + |
| 548-50A | 0.46 | 4.0 | 0.81 | 0.33 | 0.68 | 0.65 | + |
| 548-57A | 0.50 | 3.8 | 0.80 | 0.33 | 0.67 | 0.65 | ++ |
| 549-5A | 0.63 | 5.9 | 0.69 | 0.32 | 0.65 | 0.65 | + |
| 549-7A | 0.51 | 8.3 | 0.78 | 0.33 | 0.67 | 0.63 | ++ |
| 549-20A | 0.67 | 30 | 0.88 | 0.38* | 0.82* | 0.65* | ++++ |
| 549-34A | 0.43 | 1.3 | 0.69 | 0.32 | 0.64 | 0.63 | − |
| 549-39D | 0.83 | 16 | 0.83 | 0.35 | 0.71 | 0.63 | +++ |
| 549-40A | 0.80 | 4.9 | 0.74 | 0.33 | 0.63 | 0.64 | + |
| 549-41C | 0.99 | 13 | 0.80 | 0.38* | 0.79* | 0.65* | +++ |
| 549-46A | 0.48 | 7.7 | 0.84 | 0.34 | 0.70 | 0.64 | + |
| 549-52A | 0.81 | 9.2 | 0.80 | 0.39 | 0.70 | 0.65 | ++ |
| 549-57A | 0.60 | 15 | 0.77 | 0.35* | 0.85* | 0.64* | +++ |
| 549-60D | 0.85 | 11 | 0.79 | 0.37 | 0.73 | 0.65 | ++ |

Normal was calculated as the average of 6 samples for free amino acid and 23 samples for total amino acids.
*Indicates average of at least 5 samples Seeds derived from self-pollination of two plants transformed with the phaseolin 5' region/cts/lysC-M4/phaseolin 3' region, plants 549–5A and 549–40A, showed 3 kanamycin resistant to 1 kanamycin sensitive seedlings, indicative of a single site of insertion of the transgene. Progeny plants were grown, self-pollinated and seed was analyzed for segregation of the kanamycin marker gene. Progeny plants that were homozygous for the transgene insert, thus containing two copies of the gene cassette, accumulated approximately 2 times as much threonine in their seed as their sibling heterozygous progeny with one copy of the gene cassette and about 8 times as much as seed without the gene. This demonstrates that the level of expression of the *E. coli* enzyme controls the accumulation of free threonine.

Example 9

Transformation of Tobacco with the 35S Promoter/ecodapA Chimeric Genes

The 35S promoter/Cab leader/ecodapA/Nos 3' and 35S promoter/Cab leader/cts/ecodapA/Nos 3', chimeric genes were isolated as 3.1, and 3.3 kb BamH I-Sal I fragments, respectively and inserted into BamH I-Sal I digested binary vector pZS97K (FIG. 5), yielding plasmids pBT462 and pBT463, respectively. The binary vector is described in Example 7.

The binary vectors containing the chimeric ecodapA genes were transferred by tri-parental matings to *Agrobacteruim* strain LBA4404/pAL4404, the *Agrobacteruim* transformants used to inoculate tobacco leaf disks and the resulting transgenic plants regenerated by the methods set out in Example 7.

To assay for expression of the chimeric genes in leaves of the transformed plants, protein was extracted as described in Example 7, with the following modifications. The supernatant from the first ammonium sulfate precipitation, approximately 18 mL, was mixed with an additional 12 mL of cold, saturated ammonium sulfate. The mixture was set on ice for 30 min and centrifuged as described in Example 7. The supernatant was decanted and the pellet, which contained the DHDPS protein, was resuspended in 1 mL of TNE and desalted by passage over a Sephadex G-25 M column (Column PD-10, Pharmacia).

The leaf extracts were assayed for DHDPS activity as described in Example 4. *E. coli* DHDPS could be distinguished from tobacco DHDPS activity by its increased resistance to lysine; *E. coli* DHDPS retained 80–90% of its activity at 0.1 mM lysine, while tobacco DHDPS was completely inhibited at that concentration of lysine. One of ten transformants containing the chimeric gene, 35S promoter/Cab leader/ecodapA/Nos 3', showed *E. coli* DHDPS expression, while five of ten transformants containing the chimeric gene, 35S promoter/Cab leader/cts/ecodapA/Nos 3' showed *E. coli* DHDPS expression.

Free amino acids were extracted from leaves as described in Example 7. Expression of the chimeric gene, 35S promoter/Cab leader/cts/ecodapA/Nos 3', but not 35S promoter/Cab leader/ecodapA/Nos 3' resulted in substantial increases in the level of free lysine in the leaves. Free lysine levels from two to 90-fold higher than untransformed tobacco were observed.

The transformed plants were allowed to flower, self-pollinate and go to seed. Seeds from several lines transformed with the 35S promoter/Cab leader/cts/ecodapA/Nos 3' gene were surface sterilized and germinated on agar plates in the presence of kanamycin. Lines that showed 3 kanamycin resistant to 1 kanamycin sensitive seedlings, indicative of a single site of insertion of the transgenes, were identified. Progeny that were homozygous for the transgene insert were obtained from these lines using standard genetic analysis. The homozygous progeny were then characterized for expression of *E. coli* DHDPS in young and mature leaves and for the levels of free amino acids accumulated in young and mature leaves and in mature seeds.

Expression of active *E. coli* DHDPS enzyme was clearly evident in both young and mature leaves of the homozygous progeny of the transformants (Table 4). High levels of free lysine, 50 to 100-fold higher than normal tobacco plants, accumulated in the young leaves of the plants, but a much smaller accumulation of free lysine (2 to 8-fold) was seen in the larger leaves. Experiments that measure lysine in the phloem suggest that lysine is exported from the large leaves. This exported lysine may contribute to the accumulation of lysine in the small growing leaves, which are known to take up, rather than export nutrients. Since the larger leaves make up the major portion of the biomass of the plant, the total increased accumulation of lysine in the plant is more influenced by the level of lysine in the larger leaves. No effect on the free lysine levels in the seeds of these plants was observed (Table 4).

TABLE 4

Progeny of BT463 transformants homozygous for
35S promoter/Cab leader/cts/ecodapA/Nos 3'

| LINE | LEAF SIZE | LEAF FREE AMINO ACID | | E. COLI DHDPS | SEED FREE AMINO ACID |
|---|---|---|---|---|---|
| | | K/L | K/TOT | OD/60'/mg | K/L |
| NORMAL | 3 in. | 0.5 | 0.006 | 0 | 0.5 |
| 463-18C-2 | 3 in. | 47 | 0.41 | 7.6 | 0.4 |
| 463-18C-2 | 12 in. | 1 | 0.02 | 5.5 | — |
| 463-25A-4 | 3 in. | 58 | 0.42 | 6.6 | 0.4 |
| 463-25A-4 | 12 in. | 4 | 0.02 | 12.2 | — |

TABLE 4-continued

Progeny of BT463 transformants homozygous for
35S promoter/Cab leader/cts/ecodapA/Nos 3'

| LINE | LEAF SIZE | LEAF FREE AMINO ACID K/L | LEAF FREE AMINO ACID K/TOT | E. COLI DHDPS OD/60'/mg | SEED FREE AMINO ACID K/L |
|---|---|---|---|---|---|
| 463-38C-3 | 3 in. | 28 | 0.28 | 6.1 | 0.5 |
| 463-38C-3 | 12 in. | 2 | 0.04 | 8.3 | — |

Example 10

Transformation of Tobacco with the Phaseolin Promoter/ecodapA Chimeric Genes

The chimeric gene cassettes, phaseolin 5' region/ecodapA/phaseolin 3' region, and phaseolin 5' region/cts/ecodapA/phaseolin 3' region (Example 6) were isolated as approximately 2.6 and 2.8 kb Hind III fragments, respectively. These fragments were inserted into the unique Hind III site of the binary vector pZS97 (FIG. 6), yielding pBT506 and pBT534, respectively. This vector is described in Example 8.

The binary vectors containing the chimeric ecodapA genes were transferred by tri-parental matings to Agrobacteruim strain LBA4404/pAL4404, the Agrobacteruim transformants used to inoculate tobacco leaf disks and the resulting transgenic plants were regeneratedby the methods set out in Example 7.

To assay for expression of the chimeric genes, the transformed plants were allowed to flower, self-pollinate and go to seed. Total seed proteins were extracted as described in Example 8 and immunologically analyzed as described in Example 7, with the following modification. The Western blot membranes were exposed to the DHDPS antibodies prepared in Example 4 at a 1:5000 dilution of the rabbit serum using standard protocol provided by BioRad with their Immun-Blot Kit.

Thirteen of fourteen transformants containing the chimeric gene, phaseolin 5' region/ecodapA/phaseolin 3' region and nine of thirteen transformants containing the chimeric gene, phaseolin 5' region/cts/ecodapA/phaseolin 3' region, produced DHDPS protein detectable via Western blotting (Table 3). Protein which reacted with the DHDPS antibody was of several sizes. Most of the protein was equal in size to DHDPS produced in E. coli, whether or not the chimeric gene included the chloroplast transit sequence. This indicated that the chloroplast targeting signal had been efficiently removed from the precursor protein synthesized. This further suggests the majority of the protein entered the chloroplast. In addition, some proteins of lower molecular weight were observed, probably representing breakdown products of the DHDPS polypeptide.

To measure free amino acid composition and total amino acid composition of the seeds, free amino acids and total amino acids were extracted from mature seeds and analyzed as described in Example 8. Expression of either the ecodapA gene or cts/ecodapA had no effect on the total lysine or threonine composition of the seeds in any of the transformed lines (Table 5). Several of the lines that were transformed with the phaseolin 5' region/cts/ecodapA/phaseolin 3' chimeric gene were also tested for any effect on the free amino acid composition. Again, not even a modest effect on the lysine or threonine composition of the seeds was observed in lines expressing high levels of E. coli DHDPS protein (Table 5). This was a surprising result, given the dramatic effect (described in Example 9) that expression of this protein has on the free lysine levels in leaves.

One possible explanation for this was that the DHDPS protein observed via Western blot was not functional. To test this hypothesis, total protein extracts were prepared from mature seeds and assayed for DHDPS activity. Approximately 30–40 mg of seeds were put into a 1.5 mL disposable plastic microfuge tube and ground in 0.25 mL of 50 mM Tris-HCl, 50 mM NaCl, 1 mM EDTA (TNE). The grinding was done using a motorized grinder with disposable plastic shafts designed to fit into the microfuge tube. The resultant suspensions were centrifuged for 5 min at room temperature in a microfuge to remove particulates. Approximately 0.1 mL of aqueous supernatant was removed between the pelleted material and the upper oil phase. The seed extracts were assayed for DHDPS activity as described in Example 4. E. coli DHDPS could be distinguished from tobacco DHDPS activity by its increased resistance to lysine; E. coli DHDPS retained about 50% of its activity at 0.4 mM lysine, while tobacco DHDPS was completely inhibited at that concentration of lysine. High levels of E. coli DHDPS activity were seen in all four seed extracts tested eliminating this explanation.

The presence of the cts sequence in the chimeric ecodapA gene was essential for eliciting accumulation of high levels of lysine in leaves. Thus another possible explanation was that the cts sequence had somehow been lost during the insertion of the chimeric phaseolin 5' region/cts/ecodapA/phaseolin 3' gene into the binary vector. PCR analysis of several of the transformed lines demonstrated the presence of the cts sequence, however, ruling out this possibility.

A third explanation was that amino acids are not normally synthesized in seeds, and therefore the other enzymes in the pathway were not present in the seeds. The results of experiments presented in Example 8, wherein expression of phaseolin 5' region/cts/lysC-M4/phaseolin 3' gene resulted in accumulation of high levels of free threonine in seeds, indicate that this is not the case.

Taken together these results and the results presented in Example 9, demonstrate that expression of a lysine-insensitive DHDPS in either seeds or leaves is not sufficient to achieve accumulation of increased free lysine in seeds.

TABLE 5

BT506 Transformants: phaseolin 5' region/ecodapA/phaseolm 3'
BT534 Transformants: phaseolin 5' region/cts/ecodapA/phaseolin 3'

| LINE | SEED: FREE AMINO ACIDS K/L | SEED: FREE AMINO ACIDS T/L | SEED: TOTAL AMINO ACIDS K/L | SEED: TOTAL AMINO ACIDS T/L | E. COLI DHDPS 0D/60'/MG | WESTERN |
|---|---|---|---|---|---|---|
| NORMAL | 0.49 | 1.34 | 0.35 | 0.68 | | |
| 506-2B | | | 0.34 | 0.66 | | + |
| 506-4B | | | 0.33 | 0.67 | | + |
| 506-16A | | | 0.34 | 0.67 | | + |
| 506-17A | | | 0.36 | 0.55 | 7.7 | +++ |
| 506-19A | | | 0.37 | 0.45 | | ++ |
| 506-22A | | | 0.34 | 0.67 | | ++ |
| 506-23B | | | 0.35 | 0.67 | | ++ |
| 506-33B | | | 0.34 | 0.67 | | ++ |
| 506-38B | | | 0.36 | 0.69 | 8.7 | +++ |
| 506-39A | | | 0.37 | 0.70 | | ++ |
| 506-40A | | | 0.36 | 0.68 | | − |
| 506-47A | | | 0.32 | 0.68 | | +++ |
| 506-48A | | | 0.33 | 0.69 | | +++ |

TABLE 5-continued

BT506 Transformants: phaseolin 5' region/ecodapA/phaseolm 3'
BT534 Transformants: phaseolin 5' region/cts/ecodapA/phaseolin 3'

| LINE | SEED: FREE AMINO ACIDS K/L | SEED: FREE AMINO ACIDS T/L | SEED: TOTAL AMINO ACIDS K/L | SEED: TOTAL AMINO ACIDS T/L | E. COLI DHDPS 0D/60'/MG | WESTERN |
|---|---|---|---|---|---|---|
| 506-49A | | | 0.33 | 0.69 | | +++ |
| 534-8A | | | 0.34 | 0.66 | | − |
| 534-9A | | | 0.36 | 0.67 | | ++ |
| 534-22B | 0.43 | 1.32 | 0.39 | 0.51 | 4.9 | +++ |
| 534-31A | | | 0.34 | 0.66 | | − |
| 534-38A | 0.35 | 1.49 | 0.42 | 0.33 | | +++ |
| 534-39A | | | 0.38 | 0.69 | | + |
| 534-7A | | | 0.34 | 0.67 | | +++ |
| 534-25B | | | 0.35 | 0.67 | | +++ |
| 534-34B | 0.80 | 1.13 | 0.42 | 0.70 | | − |
| 534-35A | 0.43 | 1.18 | 0.33 | 0.67 | | +++ |
| 534-37B | 0.42 | 1.58 | 0.37 | 0.68 | | − |
| 534-43A | | | 0.35 | 0.68 | | +++ |
| 534-48A | 0.46 | 1.24 | 0.35 | 0.68 | 6.2 | +++ |

Example 11

Figure 5:
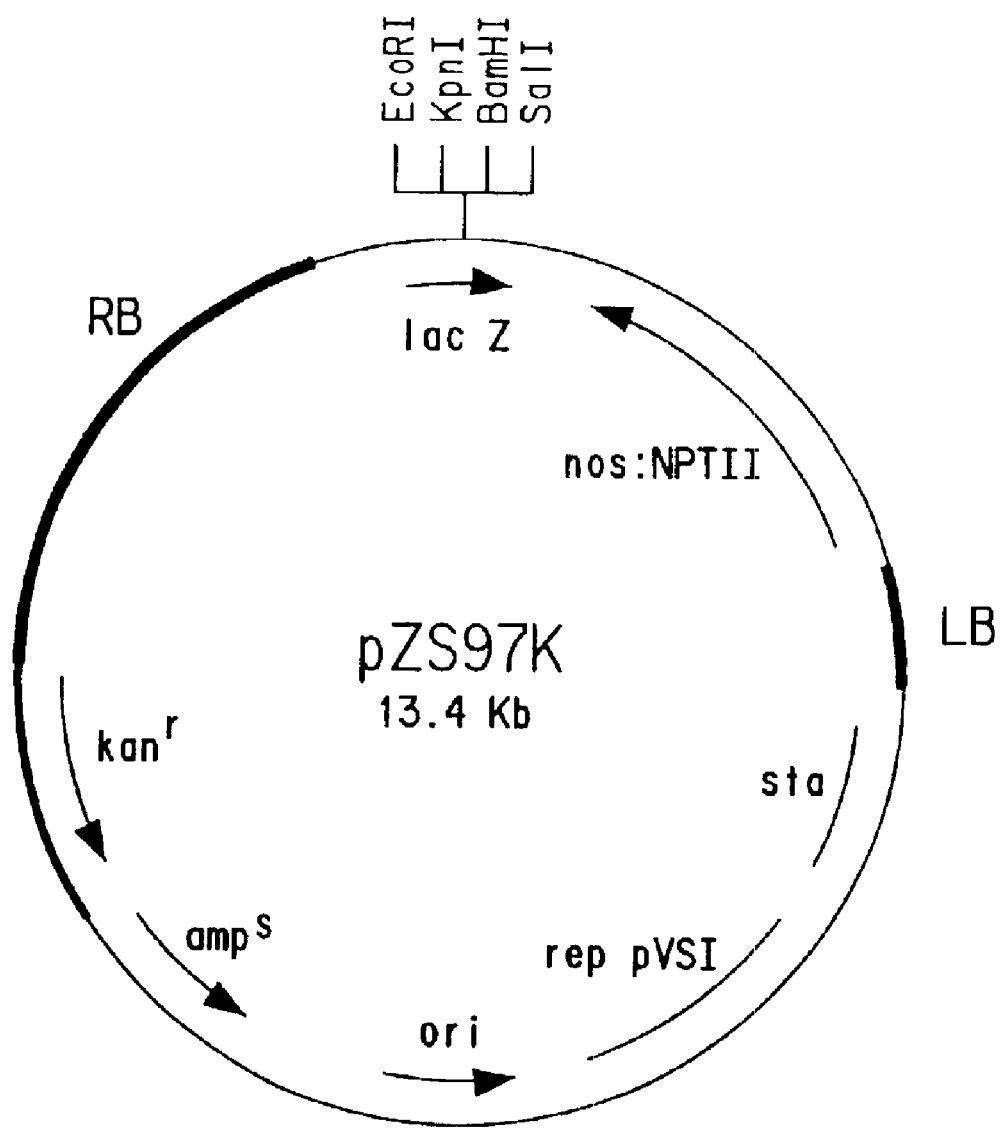
FIG. 5 shows a map of the binary plasmid vector pZS97K.

Transformation of Tobacco with the 35S Promoter/cts/dapA Plus 35S Promoter/cts/lysC-M4 Chimeric Genes The 35S promoter/Cab leader/cts/ecodapAJNos 3', and 35S promoter/Cab leader/cts/lysC-M4/Nos 3' chimeric genes were combined in the binary vector pZS97K (FIG. 5). The binary vector is described in Example 7. An oligonucleotide adaptor was synthesized to convert the BamH I site at the 5' end of the 35S promoter/Cab leader/cts/lysC-M4/Nos 3' chimeric gene (see FIG. 4) to an EcoR I site. The 35S promoter/Cab leader/cts/lysC-M4/Nos 3' chimeric gene was then isolated as a 3.6 kb EcoR I fragment from plasmid pBT540 (Example 6) and inserted into pBT463 (Example 9) digested with EcoR I, yielding plasmid pBT564. This vector has both the 35S promoter/Cab leader/cts/ecodapA/Nos 3', and 35S promoter/Cab leader/cts/lysC-M4/Nos 3' chimeric genes inserted in the same orientation.

The binary vector containing the chimeric ecodapA and lysC-M4 genes was transferred by tri-parental matings to Agrobacteruim strain LBA4404/pAL4404, the Agrobacteruim transformants used to inoculate tobacco leaf disks and the resulting transgenic plants regenerated by the methods set out in Example 7.

To assay for expression of the chimeric genes in leaves of the transformed plants, protein was extracted as described in Example 7 for AKIII, and as described in Example 9 for DHDPS. The leaf extracts were assayed for DHDPS activity as described in Examples 4 and 9. E. coli DHDPS could be distinguished from tobacco DHDPS activity by its increased resistance to lysine; E. coli DHDPS retained 80–90% of its activity at 0.1 mM lysine, while tobacco DHDPS was completely inhibited at that concentration of lysine. Extracts were characterized immunologically for expression of AKIII and DHDPS proteins via Western blots as described in Examples 7 and 10.

Ten of twelve transformants expressed E. coli DHDPS enzyme activity (Table 6). There was a good correlation between the level of enzyme activity and the amount of DHDPS protein detected immunologically. As described in Example 7, the AK assay was not sensitive enough to detect enzyme activity in these extracts. However, AKIII-M4 protein was detected immunologically in eight of the twelve extracts. In some transformants, 564-21A and 47A, there was a large disparity between the level of expression of DHDPS and AKIII-M4, but in 10 of 12 lines there was a good correlation.

Free amino acids were extracted from leaves and analyzed for amino acid composition as described in Example 7. In the absence of significant AKIII-M4, the level of expression of the chimeric gene, 35S promoter/Cab leader/cts/ecodapA/Nos 3' determined the level of lysine accumulation (Table 6). Compare lines 564-21A, 47A and 39C, none of which expresses significant AKIII-M4. Line 564-21A accumulates about 10-fold higher levels of lysine than line 564-47A which expresses a lower level of E. coli DHDPS and 40-fold higher levels of lysine than 564-39C which expresses no E. coli DHDPS. However, in transformants that all expressed similar amounts of E. coli DHDPS (564-18A, 56A, 36E, 55B, 47A), the level of expression of the chimeric gene, 35S promoter/Cab leader/cts/lysC-M4/Nos 3', controlled the level of lysine accumulation. Thus it is clear that although expression of 35S promoter/Cab leader/cts/lysC-M4/Nos 3' has no effect on the free amino acid levels of leaves when expressed alone (see Example 7), it can increase lysine accumulation when expressed in concert with the 35S promoter/Cab leader/cts/ecodapA/Nos 3' chimeric gene. Expression of these genes together did not effect the level of any other free amino acid in the leaves.

TABLE 6

BT564 Transformants: 35S promoter/Cab leader/cts/ecodapA/Nos 3'
35S promoter/Cab leader/cts/lusC-M4/Nos 3'

| LINE | FREE AA LEAF nmol/4 mg TOT | FREE AA LEAF K | FREE AA LEAF K/L | FREE AA LEAF K/TOT | E. COLI DHDPS U/MG/HR | WESTERN DHDPS | WESTERN AK-III |
|---|---|---|---|---|---|---|---|
| 564-21A | 117 | 57 | 52 | 0.49 | 2.4 | +++ | +/− |
| 564-18A | 99 | 56 | 69 | 0.57 | 1.1 | ++ | ++ |
| 564-56A | 104 | 58 | 58 | 0.56 | 1.5 | ++ | ++ |
| 564-36E | 85 | 17 | 17 | 0.20 | 1.5 | ++ | +++ |
| 564-55B | 54 | 5 | 9.1 | 0.10 | 1.0 | ++ | + |
| 564-47A | 18 | 1 | 4.8 | 0.06 | 0.8 | ++ | − |
| 564-35A | 37 | 7 | 13 | 0.18 | 0.3 | + | ++ |
| 564-60D | 61 | 3 | 4.5 | 0.06 | 0.2 | + | ++ |
| 564-45A | 46 | 4 | 8.1 | 0.09 | 0.4 | + | + |
| 564-44B | 50 | 1 | 1.7 | 0.02 | 0.1 | +/− | − |

TABLE 6-continued

BT564 Transformants: 35S promoter/Cab leader/cts/ecodapA/Nos 3'
35S promoter/Cab leader/cts/lysC-M4/Nos 3'

| LINE | FREE AA LEAF nmol/4 mg TOT | K | FREE AA LEAF K/L | K/TOT | E. COLI DHDPS U/MG/HR | WESTERN DHDPS | WESTERN AK-III |
|---|---|---|---|---|---|---|---|
| 564-49A | 53 | 1 | 1.0 | 0.02 | 0 | +/− | − |
| 564-39C | 62 | 1 | 1.4 | 0.02 | 0 | − | − |

Free amino acids were extracted from mature seeds derived from self-pollinated plants and quantitated as described in Example 8. There was no significant difference in the free amino acid content of seeds from untransformed plants compared to that from the plants showing the highest free lysine accumulation in leaves, i.e. plants 564-18A, 564-21A, 564-36E, 564-56A.

Example 12

Figure 6:
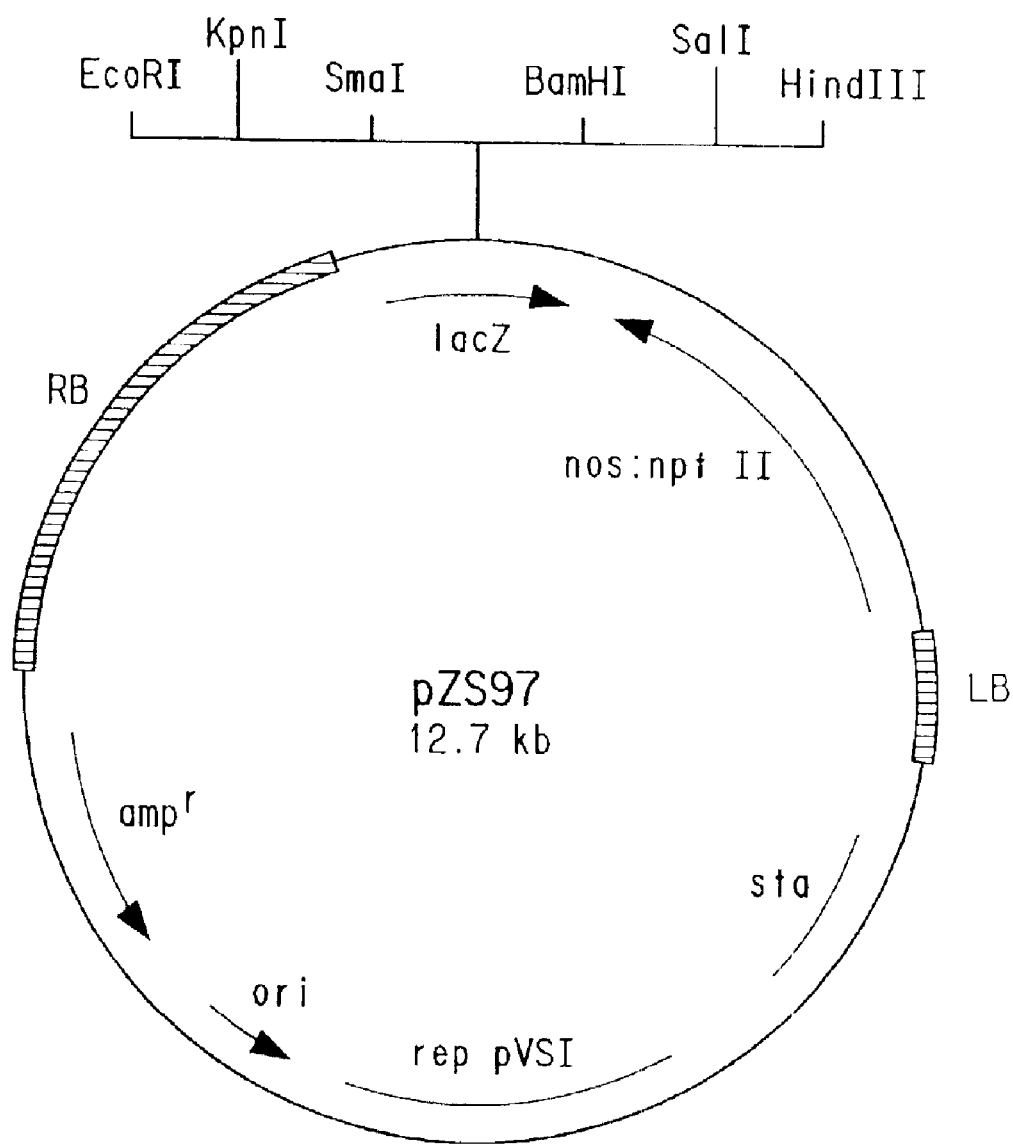
FIG. 6 shows a map of the binary plasmid vector pZS97.

Transformation of Tobacco with the Phaseolin Promoter/cts/ecodapA Plus Phaseolin Promoter/cts/lysC-M4 Chimeric Genes The chimeric gene cassettes, phaseolin 5' region/cts/ecodapA/phaseolin 3' region and phaseolin 5' region/cts/lysC-M4/phaseolin 3' (Example 6) were combined in the binary vector pZS97 (FIG. 6). The binary vector is described in Example 8. To accomplish this the phaseolin 5' region/cts/ecodapA/phaseolin 3' chimeric gene was isolated as a 2.7 kb Hind III fragment and inserted into the Hind III site of vector pUC1318 [Kay et al (1987) Nucleic Acids Res. 6:2778], yielding pBT568. It was then possible to digest pBT568 with BamH I and isolate the chimeric gene on a 2.7 kb BamH I fragment. This fragment was inserted into BamH I digested pBT549 (Example 8), yielding pBT570. This binary vector has both chimeric genes, phaseolin 5' region/cts/ecodapA/phaseolin 3' gene and phaseolin 5' region/cts/lysC-M4/phaseolin 3' inserted in the same orientation.

The binary vector pBT570 was transferred by tri-parental mating to Agrobacteruim strain LBA4404/pAL4404, the Agrobacteruim transformants used to inoculate tobacco leaf disks and the resulting transgenic plants regenerated by the methods set out in Example 7.

To assay for expression of the chimeric genes in the seeds of the transformed plants, the plants were allowed to flower, self-pollinate and go to seed. Total proteins were extracted from mature seeds and analyzed via western blots as described in Example 8.

Twenty-one of twenty-five transformants expressed the DHDPS protein and nineteen of these also expressed the AKIII protein (Table 7). The amounts of the proteins expressed were related to the number of gene copies present in the transformants; the highest expressing lines, 570-4B, 570-12C, 570-59B and 570-23B, all had two or more sites of insertion of the gene cassette based on segregation of the kanamycin marker gene. Enzymatically active E. coli DHDPS was observed in mature seeds of all the lines tested wherein the protein was detected.

To measure free amino acid composition of the seeds, free amino acids were extracted from mature seeds and analyzed as described in Example 8. There was a good correlation between transformants expressing higher levels of both DHDPS and AKIII protein and those having higher levels of free lysine and threonine. The highest expressing lines (marked by asterisk in Table 7) showed up to a 2-fold increase in free lysine levels and up to a 4-fold increase in the level of free threonine in the seeds.

In the highest expressing lines it was possible to detect a high level of α-aminoadipic acid. This compound is known to be an intermediate in the catabolism of lysine in cereal seeds, but is normally detected only via radioactive tracer experiments due to its low level of accumulation. The build-up of high levels of this intermediate indicates that a large amount of lysine is being produced in the seeds of these transformed lines and is passing through the catabolic pathway. The build-up of α-aminoadipic acid was not observed in transformants expressing only E. coli DHDPS or only AKIII-M4 in seeds. These results show that it is necessary to express both enzymes simultaneously to produce high levels of free lysine.

TABLE 7

BT570 Transformants: phaseolin 5' region/cts/lysC-M4/phaseolin 3' region
phaseolin 5' region/cts/ecodapA/phaseolin 3' region

| LINE | FREE AMINO ACIDS/ SEED K/L | T/L | FREE AMINO ACIDS/ SEED K/L | T/L | WESTERN E. COLI DHDPS | WESTERN E. COLI AKIII | E. COLI DHDPS U/MG/HR | Progeny Kan$^r$:Kan$^s$ |
|---|---|---|---|---|---|---|---|---|
| NORMAL | 0.49 | 1.3 | 0.35 | 0.68 | − | − | | |
| 570-4B | 0.31 | 2.6 | 0.34 | 0.64 | +++ | ++ | | 15:1 |
| 570-7C | 0.39 | 2.3 | 0.34 | 0.64 | ++ | + | | |
| 570-8B | 0.29 | 2.1 | 0.34 | 0.63 | + | − | | |
| 570-12C* | 0.64 | 5.1 | 0.36 | 0.68 | ++++ | ++++ | >4.3 | >15:1 |
| 570-18A | 0.33 | 3.0 | 0.35 | 0.65 | ++ | ++ | | 15:1 |
| 570-24A | 0.33 | 2.0 | 0.34 | 0.65 | ++ | − | | |
| 570-37A | 0.33 | 2.1 | 0.34 | 0.64 | +/− | +/− | | |

TABLE 7-continued

BT570 Transformants: phaseolin 5' region/cts/lysC-M4/phaseolin 3' region
phaseolin 5' region/cts/ecodapA/phaseolin 3' region

| LINE | FREE AMINO ACIDS/ SEED | | FREE AMINO ACIDS/ SEED | | WESTERN E. COLI DHDPS | WESTERN E. COLI AKIII | E. COLI DHDPS U/MG/HR | Progeny Kan$^r$:Kan$^s$ |
|---|---|---|---|---|---|---|---|---|
| | K/L | T/L | K/L | T/L | | | | |
| 570-44A | 0.29 | 2.1 | 0.34 | 0.64 | ++ | + | | |
| 570-46B | 0.41 | 2.1 | 0.35 | 0.65 | ++ | + | | |
| 570-51B | 0.33 | 1.5 | 0.33 | 0.64 | − | − | 0 | |
| 570-59B* | 0.46 | 3.0 | 0.35 | 0.65 | +++ | +++ | 2.6 | >15:1 |
| 570-80A | 0.31 | 2.2 | 0.34 | 0.64 | ++ | + | | |
| 570-11A | 0.28 | 2.3 | 0.34 | 0.67 | ++ | ++ | | 3:1 |
| 570-17B | 0.27 | 1.6 | 0.34 | 0.65 | − | − | | |
| 570-20A | 0.41 | 2.3 | 0.35 | 0.67 | ++ | + | | |
| 570-21B | 0.26 | 2.4 | 0.34 | 0.68 | ++ | + | | |
| 570-23B* | 0.40 | 3.6 | 0.34 | 0.68 | +++ | +++ | 3.1 | 63:1 |
| 570-25D | 0.30 | 2.3 | 0.35 | 0.66 | ++ | +/− | | |
| 570-26A | 0.28 | 1.5 | 0.34 | 0.64 | − | − | | |
| 570-32A | 0.25 | 2.5 | 0.34 | 0.67 | ++ | + | | |
| 570-35A | 0.25 | 2.5 | 0.34 | 0.63 | ++ | ++ | | 3:1 |
| 570-38A-1 | 0.25 | 2.6 | 0.34 | 0.64 | ++ | ++ | | 3:1 |
| 570-38A-3 | 0.33 | 1.6 | 0.35 | 0.63 | − | − | | |
| 570-42A | 0.27 | 2.5 | 0.34 | 0.62 | ++ | ++ | | 3:1 |
| 570-45A | 0.60 | 3.4 | 0.39 | 0.64 | ++ | ++ | | 3:1 |

*indicates free amino acid sample has α-aminoadipic acid

Example 13

Use of the cts/lysC-M4 Chimeric Gene as a Selectable Marker for Tobacco Transformation The 35S promoter/Cab leader/cts/lysC-M4/Nos 3' chimeric gene in the binary vector pZS97K (pBT542, see Example 7) was used as a selectable genetic marker for transformation of tobacco. High concentrations of lysine plus threonine inhibit growth of shoots from tobacco leaf disks. Expression of active lysine and threonine insensitive AKIII-M4 reverses this growth inhibition (see Example 7).

The binary vector pBT542 was transferred by tri-parental mating to Agrobacteruim strain LBA4404/pAL4404, the Agrobacteruim transformants used to inoculate tobacco leaf disks and the resulting transformed shoots were selected on shooting medium containing 3 mM lysine plus 3 mM threonine. Shoots were transferred to rooting media containing 3 mM lysine plus 3 mM threonine. Plants were grown from the rooted shoots. Leaf disks from the plants were placed on shooting medium containing 3 mM lysine plus 3 mM threonine. Transformed plants were identified by the shoot proliferation which occurred around the leaf disks on this medium.

Example 14

Transformation of Tobacco with the 35S Promoter/ cts/cordapA Chimeric Gene

The 35S promoter/Cab leader/cts/cordapA/Nos 3' chimeric gene was isolated as a 3.0 kb BamH I-Sal I fragment and inserted into BamH I-Sal I digested binary vector pZS97K (FIG. 5), yielding plasmid pFS852. The binary vector is described in Example 7.

The binary vector containing the chimeric cordapA gene was transferred by tri-parental mating to Agrobacteruim strain LBA4404/pAL4404, the Agrobacteruim transformant was used to inoculate tobacco leaf disks and the resulting transgenic plants were regenerated by the methods set out in Example 7.

To assay for expression of the chimeric gene in leaves of the transformed plants, protein was extracted as described in Example 7, with the following modifications. The supernatant from the first ammonium sulfate precipitation, approximately 18 mL, was mixed with an additional 12 mL of cold, saturated ammonium sulfate. The mixture was set on ice for 30 min and centrifuged as described in Example 7. The supernatant was decanted and the pellet, which contained the DHDPS protein, was resuspended in 1 mL of TNE and desalted by passage over a Sephadex G-25 M column (Column PD-10, Pharmacia).

The leaf extracts were assayed for DHDPS protein and enzyme activity as described in Example 4. Corynebacteria DHDPS enzyme activity could be distinguished from tobacco DHDPS activity by its insensitivity to lysine inhibition. Eight of eleven transformants showed Corynebacteria DHDPS expression, both as protein detected via western blot and as active enzyme.

Free amino acids were extracted from leaves as described in Example 7. Expression of Corynebacteria DHDPS resulted in large increases in the level of free lysine in the leaves (Table 8). However, there was not a good correlation between the level of expression of DHDPS and the amount of free lysine accumulated. Free lysine levels from 2 to 50-fold higher than untransformed tobacco were observed. There was also a 2 to 2.5-fold increase in the level of total leaf lysine in the lines that showed high levels of free lysine.

TABLE 8

FS586 transformants: 35S promoter/Cab leader/cts/cordapA/Nos 3'

| LINE | FREE AMINO ACIDS/LEAF K/L | TOTAL AMINO ACIDS/LEAF K/L | WESTERN CORYNE. DHDPS | CORYNE. DHDPS U/MG/HR |
|---|---|---|---|---|
| NORMAL | 0.5 | 0.8 | − | — |
| FS586-2A | 1.0 | 0.8 | − | — |
| FS586-4A | 0.9 | 0.8 | + | 6.1 |
| FS586-11B | 3.6 | 0.8 | + | 3.4 |
| FS586-11D | 26 | 2.0 | + | 3.5 |
| FS586-13A | 2.4 | 0.8 | + | 3.5 |
| FS586-19C | 5.1 | 0.8 | + | 3.1 |
| FS586-22B | >15 | 1.5 | + | 2.3 |
| FS586-30B |  | 0.8 | − | − |
| FS586-38B | 18 | 1.5 | ++ | 3.9 |
| FS586-51A | 1.3 | 0.8 | − | — |
| FS586-58C | 1.2 | 0.8 | + | 5.1 |

The plants were allowed to flower, self-pollinate and go to seed. Mature seed was harvested and assayed for free amino acid composition as described in Example 8. There was no difference in the free lysine content of the transformants compared to untransformed tobacco seed.

Example 15

Transformation of Tobacco with the KTI3 Promoter/cts/cordapA or Phaseolin Promoter/cts/cordapA Plus Phaseolin Promoter/cts/lysC-M4 Chimeric Genes The chimeric gene cassettes, KTI3 5' region/cts/cordapA/KTI3 3' region and phaseolin 5' region/cts/lysC-M4/phaseolin 3' as well as phaseolin 5' region/cts/cordapA/phaseolin 3' region and phaseolin 5' region/cts/lysC-M4/phaseolin 3' (Example 6) were combined in the binary vector pZS97 (FIG. 6). The binary vector is described in Example 8.

To accomplish this the KTI3 5' region/cts/cordapA/KTI3 3' region chimeric gene cassette was isolated as a 3.3 kb BamH I fragment and inserted into BamH I digested pBT549 (Example 8), yielding pFS883. This binary vector has the chimeric genes, KTI3 5' region/cts/cordapA/KTI3 3' region and phaseolin 5' region/cts/lysC-M4/phaseolin 3' region inserted in opposite orientations.

The phaseolin 5' region/cts/cordapA/phaseolin 3' region chimeric gene cassette was modified using oligonucleotide adaptors to convert the Hind III sites at each end to BamH I sites. The gene cassette was then isolated as a 2.7 kb BamH I fragment and inserted into BamH I digested pBT549 (Example 8), yielding pFS903. This binary vector has both chimeric genes, phaseolin 5' region/cts/cordapA/phaseolin 3' region and phaseolin 5' region/cts/lysC-M4/phaseolin 3' region inserted in the same orientation.

The binary vectors pFS883 and pFS903 were transferred by tri-parental mating to Agrobacteruim strain LBA4404/pAL4404, the Agrobacterium transformants were used to inoculate tobacco leaf disks and the resulting transgenic plants were regenerated by the methods set out in Example 7.

To assay for expression of the chimeric genes in the seeds of the transformed plants, the plants were allowed to flower, self-pollinate and go to seed. Total proteins were extracted from mature seeds and analyzed via western blots as described in Example 8.

Twenty-one of twenty-two transformants tested expressed the DHDPS protein and eighteen of these also expressed the AKIII protein (Table 8). Enzymatically active *Corynebacteria* DHDPS was observed in mature seeds of all the lines tested wherein the protein was detected except one.

To measure free amino acid composition of the seeds, free amino acids were extracted from mature seeds and analyzed as described in Example 8. There was a good correlation between transformants expressing higher levels of both DHDPS and AKIII protein and those having higher levels of free lysine and threonine. The highest expressing lines showed up to a 3-fold increase in free lysine levels and up to a 8-fold increase in the level of free threonine in the seeds. As was described in Example 12, a high level of α-aminoadipic acid, indicative of lysine catabolism, was observed in many of the transformed lines (indicated by asterisk in Table 9). There was no major difference in the free amino acid composition or level of protein expression between the transformants which had the KTI3 or Phaseolin regulatory sequences driving expression of the Corynebacteria DHDPS gene.

TABLE 9

FS883 Transformants: phaseolin 5' region/cts/lysC-M4/phaseolin 3'
KTI3 5' region/cts/cordapA/KTI3 3'
FS903 Transformants: phaseolin 5' region/cts/lysC-M4/phaseolin 3'
phaseolin 5' region/cts/cordapA/phaseolin 3'

| LINE | FREE AMINO ACIDS/SEED K/L | T/L | WESTERN CORYNE. DHDPS | WESTERN E. COLI AKIII | CORYNE DHDPS U/MG/HR | Progeny Kan$^r$:Kan$^s$ |
|---|---|---|---|---|---|---|
| NORMAL | 0.5 | 1.3 | − | − |  |  |
| FS883-4A | 0.9 | 4.0 | + | + |  | >15:1 |
| FS883-11A | 1.0 | 3.5 | ++ | ++ | 3.1 | 3:1 |

TABLE 9-continued

FS883 Transformants: phaseolin 5' region/cts/lysC-M4/phaseolin 3'
KTI3 5' region/cts/cordapA/KTI3 3'
FS903 Transformants: phaseolin 5' region/cts/lysC-M4/phaseolin 3'
phaseolin 5' region/cts/cordapA/phaseolin 3'

| LINE | FREE AMINO ACIDS/ SEED K/L | T/L | WESTERN CORYNE. DHDPS | WESTERN E. COLI AKIII | CORYNE DHDPS U/MG/HR | Progeny Kan$^r$:Kan$^s$ |
|---|---|---|---|---|---|---|
| FS883-14B | 0.5 | 2.5 | ++ | ++ | | |
| FS883-16A* | 0.7 | 10.5 | + | +++ | 0 | |
| FS883-17A* | 1.0 | 5.0 | +++ | +++ | 7.0 | |
| FS883-18C* | 1.2 | 3.5 | ++ | + | 5.8 | 3:1 |
| FS883-21A | 0.5 | 1.5 | + | +/− | | |
| FS883-26B* | 1.1 | 3.6 | ++ | ++ | 2.4 | |
| FS883-29B | 0.5 | 1.5 | + | − | 0.4 | |
| FS883-32B | 0.7 | 2.4 | ++ | + | 1.5 | 3:1 |
| FS883-38B* | 1.1 | 11.3 | + | ++ | 2.0 | |
| FS883-59C* | 1.4 | 6.1 | + | + | 0.5 | 15:1 |
| FS903-3C | 0.5 | 1.8 | + | +++ | | |
| FS903-8A* | 0.8 | 2.1 | +++ | ++++ | | |
| FS903-9B | 0.6 | 1.8 | ++ | ++ | 4.3 | |
| FS903-10A | 0.5 | 1.5 | − | − | | |
| FS903-22F | 0.5 | 1.8 | ++ | ++ | 0.9 | |
| FS903-35B* | 0.8 | 2.1 | ++ | ++ | | |
| FS903-36B | 0.7 | 1.5 | + | − | | |
| FS903-40A | 0.6 | 1.8 | + | + | | |
| FS903-41A* | 1.2 | 2.0 | ++ | +++ | | |
| FS903-42A | 0.7 | 2.2 | ++ | +++ | 5.4 | |
| FS903-44C | 0.5 | 1.9 | | | | |
| FS903-53B | 0.6 | 1.9 | | | | |

*indicates free amino acid sample has α-aminoadipic acid

Free amino acid composition and expression of bacterial DHDPS and AKIII proteins was also analyzed in developing seeds of two lines that segregated as single gene cassette insertions (see Table 10). Expression of the DHDPS protein under control of the KTI3 promoter was detected at earlier times than that of the AKIII protein under control of the Phaseolin promoter, as expected. At 14 days after flowering both proteins were expressed at a high level and there was about an 8-fold increase in the level of free lysine compared to normal seeds. These results confirm that simultaneous expression of lysine insensitive DHDPS and lysine-insensitive AK results in the production of high levels of free lysine in seeds. Free lysine does not continue to accumulate to even higher levels, however. In mature seeds free lysine is at a level 2 to 3-fold higher than in normal mature seeds, and the lysine breakdown product α-aminoadipic acid accumulates. These results provide further evidence that lysine catabolism occurs in seeds and prevents accumulation of the high levels of free lysine produced in transformants expressing lysine insensitive DHDPS and lysine insensitive AK.

TABLE 10

Developing seeds of FS883 Transformants:
phaseolin 5' region/cts/lysC-M4/phaseolin 3' region
KTI3 5' region/cts/cordapA/KTI3 3' region

| LINE | DAYS AFTER FLOWERING | FREE AMINO ACIDS/ SEED K/L | T/L | WESTERN CORYNE DHDPS | WESTERN E. COLI AKIII |
|---|---|---|---|---|---|
| FS883-18C | 9 | 1.1 | 2.1 | − | − |
| FS883-18C | 10 | 1.4 | 3.3 | +/− | − |
| FS883-18C | 11 | 1.4 | 2.5 | + | − |
| FS883-18C | 14 | 4.3 | 1.0 | ++ | ++ |
| FS883-18C* | MATURE | 1.2 | 3.5 | +++ | ++ |
| FS883-32B | 9 | 1.3 | 2.9 | + | − |
| FS883-32B | 10 | 1.6 | 2.7 | + | − |
| FS883-32B | 11 | 1.4 | 2.3 | + | − |
| FS883-32B* | 14 | 3.9 | 1.3 | ++ | ++ |
| FS883-32B* | MATURE | 0.7 | 2.4 | +++ | ++ |

*indicates free amino acid sample has α-aminoadipic acid

Example 16

Transformation of Oilseed Rape with the Phaseolin Promoter/cts/cordapA and Phaseolin Promoter/cts/lysC-M4 Chimeric Genes The chimeric gene cassettes, phaseolin 5' region/cts/cordapA/phaseolin 3' region, phaseolin 5' region/cts/lysC-M4/phaseolin 3', and phaseolin 5' region/cts/cordapA/phaseolin 3' region plus phaseolin 5' region/cts/lysC-M4/phaseolin 3' (Example 6) were inserted into the binary vector pZS 199 (FIG. 7A), which is similar to pSZ97K described in Example 8. In pZS199 the 35S promoter from Cauliflower Mosaic Virus replaced the nos promoter driving expression of the NPT II to provide better expression of the marker gene, and the orientation of the polylinker containing the multiple restriction endonuclease sites was reversed.

To insert the phaseolin 5' region/cts/cordapA/phaseolin 3' region 3', the gene cassette was isolated as a 2.7 kb BamH I fragment (as described in Example 15) and inserted into BamH I digested pZS199, yielding plasmid pFS926 (FIG. 7B). This binary vector has the chimeric gene, phaseolin 5' region/cts/cordapA/phaseolin 3' region inserted in the same orientation as the 35S/NPT II/nos 3' marker gene.

To insert the phaseolin 5' region/cts/lysC-M4/phaseolin 3' region, the gene cassette was isolated as a 3.3 kb EcoR I to Spe I fragment and inserted into EcoR I plus Xba I digested pZS199, yielding plasmid pBT593 (FIG. 7C). This binary vector has the chimeric gene, phaseolin 5' region/cts/lysC-M4/phaseolin 3' region inserted in the same orientation as the 35S/NPT II/nos 3' marker gene.

To combine the two cassettes, the EcoR I site of pBT593 was converted to a BamH I site using oligonucleotide adaptors, the resulting vector was cut with BamH I and the phaseolin 5' region/cts/cordapA/phaseolin 3' region gene cassette was isolated as a 2.7 kb BamH I fragment and inserted, yielding pBT597 (FIG. 7D). This binary vector has both chimeric genes, phaseolin 5' region/cts/cordapA/phaseolin 3' region and phaseolin 5' region/cts/lysC-M4/phaseolin 3' region inserted in the same orientation as the 35S/NPT II/nos 3' marker gene.

*Brassica napus* cultivar "Westar" was transformed by co-cultivation of seedling pieces with disarmed *Agrobacterium tumefaciens* strain LBA4404 carrying the the appropriate binary vector.

*B. napus* seeds were sterilized by stirring in 10% Chlorox, 0.1% SDS for thirty min, and then rinsed thoroughly with sterile distilled water. The seeds were germinated on sterile medium containing 30 mM CaCl2 and 1.5% agar, and grown for 6 d in the dark at 24° C.

Liquid cultures of *Agrobacteruim* for plant transformation were grown overnight at 28° C. in Minimal A medium containing 100 mg/L kanamycin. The bacterial cells were pelleted by centrifugation and resuspended at a concentration of $10^8$ cells/mL in liquid Murashige and Skoog Minimal Organic medium containing 100 uM acetosyringone.

*B. napus* seedling hypocotyls were cut into 5 mm segments which were immediately placed into the bacterial suspension. After 30 min, the hypocotyl pieces were removed from the bacterial suspension and placed onto BC-35 callus medium containing 100 uM acetosyringone. The plant tissue and Agrobacteria were co-cultivated for 3 d at 24° C. in dim light.

The co-cultivation was terminated by transferring the hypocotyl pieces to BC-35 callus medium containing 200 mg/L carbenicillin to kill the Agrobacteria, and 25 mg/L kanamycin to select for transformed plant cell growth. The seedling pieces were incubated on this medium for three weeks at 24° C. under continuous light.

After three weeks, the segments were transferred to BS-48 regeneration medium containing 200 mg/L carbenicillin and 25 mg/L kanamycin. Plant tissue was subcultured every two weeks onto fresh selective regeneration medium, under the same culture conditions described for the callus medium. Putatively transformed calli grew rapidly on regeneration medium; as calli reached a diameter of about 2 mm, they were removed from the hypocotyl pieces and placed on the same medium lacking kanamycin Shoots began to appear within several weeks after transfer to BS-48 regeneration medium. As soon as the shoots formed discernable stems, they were excised from the calli, transferred to MSV-1A elongation medium, and moved to a 16:8-h photoperiod at 24° C.

Once shoots had elongated several internodes, they were cut above the agar surface and the cut ends were dipped in Rootone. Treated shoots were planted directly into wet Metro-Mix 350 soiless potting medium. The pots were covered with plastic bags which were removed when the plants were clearly growing, after about 10 days. Results of the transformation are shown in Table 11. Transformed plants were obtained with each of the binary vectors.

| Minimal A Bacterial Growth Medium Dissolve in distilled water: | |
|---|---|
| 10.5 | g potassium phosphate, dibasic |
| 4.5 | g potassium phosphate, monobasic |
| 1.0 | g ammonium sulfate |
| 0.5 | g sodium citrate, dihydrate |

Make up to 979 mL with distilled water

Autoclave

Add 20 mL filter-sterilized 10% sucrose

Add 1 mL filter-sterilized 1 M MgSO4

*Brassica* Callus Medium BC-35

Per liter:

Murashige and Skoog Minimal Organic Medium (MS salts, 100 mg/L i-inositol, 0.4 mg/L thiamine; GIBCO #510-3118)

30 g sucrose 18 g mannitol 0.5 mg/L 2,4-D 0.3 mg/L kinetin 0.6% agarose pH 5.8

*Brassica* Regeneration Medium BS-48

Murashige and Skoog Minimal Organic Medium

Gamborg B5 Vitamins (SIGMA #1019)

10 g glucose 250 mg xylose 600 mg MES 0.4% agarose pH 5.7

Filter-sterilize and add after autoclaving:

2.0 mg/L zeatin 0.1 mg/L IAA

*Brassica* Shoot Elongation Medium MSV-1A

Murashige and Skoog Minimal Organic Medium

Gamborg B5 Vitamins 10 g sucrose 0.6% agarose pH 5.8

TABLE 11

Canola transformants

| BINARY VECTOR | NUMBER OF CUT ENDS | NUMBER OF KAN^R CALLI | NUMBER OF SHOOTING CALLI | NUMBER OF PLANTS |
|---|---|---|---|---|
| pZS199 | 120 | 41 | 5 | 2 |
| pFS926 | 600 | 278 | 52 | 28 |
| pBT593 | 600 | 70 | 10 | 3 |
| pBT597 | 600 | 223 | 40 | 23 |

Plants were grown under a 16:8-h photoperiod, with a daytime temperature of 23° C. and a nightime temperature of 17° C. When the primary flowering stem began to elongate, it was covered with a mesh pollen-containment bag to prevent outcrossing. Self-pollination was facilitated by shaking the plants several times each day. Mature seeds derived from self-pollinations were harvested about three months after planting.

A partially defatted seed meal was prepared as follows: 40 mg of mature dry seed was ground with a mortar and pestle under liquid nitrogen to a fine powder. One milliliter of hexane was added and the mixture was shaken at room temperature for 15 min. The meal was pelleted in an eppendorf centrifuge, the hexane was removed and the hexane extraction was repeated. Then the meal was dried at 65° for 10 min until the hexane was completely evaporated leaving a dry powder. Total proteins were extracted from mature seeds as follows. Approximately 30–40 mg of seeds were put into a 1.5 mL disposable plastic microfuge tube and ground in 0.25 mL of 50 mM Tris-HCl pH 6.8, 2 mM EDTA, 1% SDS, 1% β-mercaptoethanol. The grinding was done using a motorized grinder with disposable plastic shafts designed to fit into the microfuge tube. The resultant suspensions were centrifuged for 5 min at room temperature in a microfuge to remove particulates. Three volumes of extract was mixed with 1 volume of 4×SDS-gel sample buffer (0.17M Tris-HCl pH6.8, 6.7% SDS, 16.7% β-mercaptoethanol, 33% glycerol) and 5 µL from each extract were run per lane on an SDS polyacrylamide gel, with bacterially produced DHDPS or AKIII serving as a size standard and protein extracted from untransformed tobacco seeds serving as a negative control. The proteins were then electrophoretically blotted onto a nitrocellulose membrane. The membranes were exposed to the DHDPS or AKIII antibodies at a 1:5000 dilution of the rabbit serum using standard protocol provided by BioRad with their Immun-Blot Kit. Following rinsing to remove unbound primary antibody the membranes were exposed to the secondary antibody, donkey anti-rabbit Ig conjugated to horseradish peroxidase (Amersham) at a 1:3000 dilution. Following rinsing to remove unbound secondary antibody, the membranes were exposed to Amersham chemiluminescence reagent and X-ray film.

Eight of eight FS926 transformants and seven of seven BT597 transformants expressed the DHDPS protein. The single BT593 transformant and five of seven BT597 transformants expressed the AKIII-M4 protein (Table 12). Thus it is straightforward to express these proteins in oilseed rape seeds.

To measure free amino acid composition of the seeds, free amino acids were extracted from 40 mg of the defatted meal in 0.6 mL of methanol/chloroform/water mixed in ratio of 12v/5v/3v (MCW) at room temperature. The mixture was vortexed and then centrifuged in an eppendorf microcentrifuge for about 3 min. Approximately 0.6 mL of supernatant was decanted and an additional 0.2 mL of MCW was added to the pellet which was then vortexed and centrifuged as above. The second supernatant, about 0.2 mL, was added to the first. To this, 0.2 mL of chloroform was added followed by 0.3 mL of water. The mixture was vortexed and then centrifuged in an eppendorf microcentrifuge for about 3 min, the upper aqueous phase, approximately 1.0 mL, was removed, and was dried down in a Savant Speed Vac Concentrator. The samples were hydrolyzed in 6N hydrochloric acid, 0.4% β-mercaptoethanol under nitrogen for 24 h at 110–120° C.; ¼ of the sample was run on a Beckman Model 6300 amino acid analyzer using post-column ninhydrin detection. Relative free amino acid levels in the seeds were compared as ratios of lysine or threonine to leucine, thus using leucine as an internal standard.

In contrast to tobacco seeds, expression of *Corynebacterium* DHDPS lead to large increases in accumulation of free lysine in rapeseed transform ants. The highest expressing lines showed a greater than 100-fold increase in free lysine level in the seeds. The transformant that expressed AKIII-M4 in the absence of Corynebacteria DHDPS showed a 5-fold increase in the level of free threonine in the seeds. Concomitant expression of both enzymes resulted in accumulation of high levels of free lysine, but not threonine.

A high level of α-aminoadipic acid, indicative of lysine catabolism, was observed in many of the transformed lines. Thus, prevention of lysine catabolism by inactivation of lysine ketoglutarate reductase should further increase the accumulation of free lysine in the seeds. Alternatively, incorporation of lysine into a peptide or lysine-rich protein would prevent catabolism and lead to an increase in the accumulation of lysine in the seeds.

To measure the total amino acid composition of mature seeds, 2 mg of the defatted meal were hydrolyzed in 6N hydrochloric acid, 0.4% β-mercaptoethanol under nitrogen for 24 h at 110–120° C.; ¹/₁₀₀ of the sample was run on a Beckman Model 6300 amino acid analyzer using post-column ninhydrin detection. Relative amino acid levels in the seeds were compared as percentages of lysine, threonine or α-aminoadipic acid to total amino acids.

There was a good correlation between expression of DHDPS protein and accumulation of high levels of lysine in the seeds of transformants. Seeds with a 5–100% increase in the lysine level, compared to the untransformed control, were observed. In the transformant with the highest level, lysine makes up about 13% of the total seed amino acids, considerably higher than any previously known rapeseed seed. This transformant expresses high levels of both *E. coli* AKIII-M4 and *Corynebacterium* DHDPS.

TABLE 12

FS926 Transformants: phaseolin 5' region/cts/cordapA/phaseolin 3'
BT593 Transformants: phaseolin 5' region/cts/lysC-M4/phaseolin 3'
BT597 Transformants: phaseolin 5' region/cts/lysC-M4/phaseolin 3'
phaseolin 5' region/cts/cordapA/phaseolin 3'

| | FREE AMINO ACIDS | | | WESTERN CORYNE. | WESTERN E. COLI | % TOTAL AMINO ACIDS | | |
|---|---|---|---|---|---|---|---|---|
| LINE | K/L | T/L | AA/L | DHDPS | AKIII-M4 | K | T | AA |
| WESTAR | 0.8 | 2.0 | 0 | – | – | 6.5 | 5.6 | 0 |
| ZS199 | 1.3 | 3.2 | 0 | – | – | 6.3 | 5.4 | 0 |
| FS926-3 | 140 | 2.0 | 16 | ++++ | – | 12 | 5.1 | 1.0 |
| FS926-9 | 110 | 1.7 | 12 | ++++ | – | 11 | 5.0 | 0.8 |
| FS926-11 | 7.9 | 2.0 | 5.2 | ++ | – | 7.7 | 5.2 | 0 |
| FS926-6 | 14 | 1.8 | 4.6 | +++ | – | 8.2 | 5.9 | 0 |
| FS926-22 | 3.1 | 1.3 | 0.3 | + | – | 6.9 | 5.7 | 0 |
| FS926-27 | 4.2 | 1.9 | 1.1 | ++ | – | 7.1 | 5.6 | 0 |
| FS926-29 | 38 | 1.8 | 4.7 | ++++ | – | 12 | 5.2 | 1.6 |
| FS926-68 | 4.2 | 1.8 | 0.9 | ++ | – | 8.3 | 5.5 | 0 |
| BT593-42 | 1.4 | 11 | 0 | – | ++ | 6.3 | 6.0 | 0 |
| BT597-14 | 6.0 | 2.6 | 4.3 | ++ | +/– | 7.0 | 5.3 | 0 |
| BT597-145 | 1.3 | 2.9 | 0 | + | – | | | |
| BT597-4 | 38 | 3.7 | 4.5 | ++++ | ++++ | 13 | 5.6 | 1.6 |
| BT597-68 | 4.7 | 2.7 | 1.5 | ++ | + | 6.9 | 5.8 | 0 |
| BT597-100 | 9.1 | 1.9 | 1.7 | +++ | + | 6.6 | 5.7 | 0 |
| BT597-148 | 7.6 | 2.3 | 0.9 | +++ | + | 7.3 | 5.7 | 0 |
| BT597-169 | 5.6 | 2.6 | 1.7 | +++ | +++ | 6.6 | 5.7 | 0 |

AA is α-amino adipic acid

Example 17

Transformation of Maize Using a Chimeric lysC-M4 Gene as a Selectable Marker

Embryogenic callus cultures were initiated from immature embryos (about 1.0 to 1.5 mm) dissected from kernels of a corn line bred for giving a "type II callus" tissue culture response. The embryos were dissected 10 to 12 d after pollination and were placed with the axis-side down and in contact with agarose-solidified N6 medium [Chu et al. (1974) Sci Sin 18:659–668] supplemented with 0.5 mg/L 2,4-D (N6-0.5). The embryos were kept in the dark at 27° C. Friable embryogenic callus consisting of undifferentiated masses of cells with somatic proembryos and somatic embryos borne on suspensor structures proliferated from the scutellum of the immature embryos. Clonal embryogenic calli isolated from individual embryos were identified and sub-cultured on N6-0.5 medium every 2 to 3 weeks.

The particle bombardment method was used to transfer genes to the callus culture cells. A Biolistic™ PDS-1000/He (BioRAD Laboratories, Hercules, Calif.) was used for these experiments.

The plasmid pBT573, containing the chimeric gene HH534 5' region/mcts/lysC-M4/HH2-1 3' region (see Example 6) designed for constitutive gene expression in corn, was precipitated onto the surface of gold particles. To accomplish this 2.5 μg of pBT573 (in water at a concentration of about 1 mg/mL) was added to 25 mL of gold particles (average diameter of 1.5 μm) suspended in water (60 mg of gold per mL). Calcium chloride (25 mL of a 2.5 M solution) and spermidine (10 mL of a 1.0 M solution) were then added to the gold-DNA suspension as the tube was vortexing. The gold particles were centrifuged in a microfuge for 10 s and the supernatant removed. The gold particles were then resuspended in 200 mL of absolute ethanol, were centrifuged again and the supernatant removed. Finally, the gold particles were resuspended in 25 mL of absolute ethanol and sonicated twice for one sec. Five μL of the DNA-coated gold particles were then loaded on each macro carrier disk and the ethanol was allowed to evaporate away leaving the DNA-covered gold particles dried onto the disk.

Embryogenic callus (from the callus line designated #132.2.2) was arranged in a circular area of about 6 cm in diameter in the center of a 100×20 mm petri dish containing N6-0.5 medium supplemented with 0.25M sorbitol and 0.25M mannitol. The tissue was placed on this medium for 2 h prior to bombardment as a pretreatment and remained on the medium during the bombardment procedure. At the end of the 2 h pretreatment period, the petri dish containing the tissue was placed in the chamber of the PDS-1000/He. The air in the chamber was then evacuated to a vacuum of 28 inch of Hg. The mcacrocarrier was accelerated with a helium shock wave using a rupture membrane that bursts when the He pressure in the shock tube reaches 1100 psi. The tissue was placed approximately 8 cm from the stopping screen. Four plates of tissue were bombarded with the DNA-coated gold particles. Immediately following bombardment, the callus tissue was transferred to N6-0.5 medium without supplemental sorbitol or mannitol.

Seven d after bombardment small (2–4 mM diameter) clumps of callus tissue were transferred to N6-0.5 medium lacking casein or proline, but supplemented with 2 mM each of lysine and threonine (LT). The tissue continued to grow slowly on this medium and was transferred to fresh N6-0.5 medium supplemented with LT every 2 weeks. After 12 weeks two clones of actively growing callus was identified on two separate plates containing LT-supplemented medium. These clones continued to grow when sub-cultured on the selective medium. The presence of the lysC-M4 gene in the selected clones was confirmed by PCR analysis. Callus was transferred to medium that promotes plant regeneration.

Example 18

Transformation of Corn with the Constitutive Corn Promoter/cts/ecodapA and Constitutive Corn Promoter/cts/lysC-M4

The chimeric gene cassettes, HH534 5' region/mcts/ecodapA/HH2-1 3' region plus HH534 5' region/mcts/lysC- M4/HH2-1 3' region, (Example 6) were inserted into the vector pGem9z to generate a corn transformation vector. Plasmid pBT583 (Example 6) was digested with Sal I and an 1850 bp fragment containing the HH534 5' region/mcts/ecodapA/HH2-1 3' region gene cassette was isolated. This DNA fragment was inserted into pBT573 (Example 6), which carries the HH534 5' region/mcts/lysC-M4/HH2-1 3' region, digested with Xho I. The resulting vector with both chimeric genes in the same orientation was designated pBT586.

Vector pBT586 was introduced into embryogenic corn callus tissue using the particle bombardment method. The establishment of the embryogenic callus cultures and the parameters for particle bombardment were as described in Example 17.

Either one of two plasmid vectors containing selectable markers were used in the transformations. One plasmid, pALSLUC [Fromm et al. (1990) *Biotechnology* 8:833–839], contained a cDNA of the maize acetolactate synthase (ALS) gene. The ALS cDNA had been mutated in vitro so that the enzyme coded by the gene would be resistant to chlorsulfuron. This plasmid also contains a gene that uses the 35S promoter from Cauliflower Mosaic Virus and the 3' region of the nopaline synthase gene to express a firefly luciferase coding region [de Wet et al. (1987) *Molec. Cell Biol.* 7:725–737]. The other plasmid, pDETRIC, contained the bar gene from *Streptomyces hygroscopicus* that confers resistance to the herbicide glufosinate [Thompson et al. (1987 The *EMBO Journal* 6:2519–2523]. The bacterial gene had its translation codon changed from GTG to ATG for proper translation initiation in plants [De Block et al. (1987) The *EMBO Journal* 6:2513–2518]. The bar gene was driven by the 35S promoter from Cauliflower Mosaic Virus and uses the termination and polyadenylation signal from the octopine synthase gene from *Agrobacterium tumefaciens*.

For bombardment, 2.5 μg of each plasmid, pBT586 and one of the two selectable marker plasmids, was co-precipitated onto the surface of gold particles as described in Example 17. Bombardment of the embryogenic tissue cultures was also as described in Example 17.

Seven days after bombardment the tissue was transferred to selective medium. The tissue bombarded with the selectable marker pALSLUC was transferred to N6-0.5 medium that contained chlorsulfuron (30 ng/L) and lacked casein or proline. The tissue bombarded with the selectable marker, pDETRIC, was transferred to N6-0.5 medium that contained 2 mg/L glufosinate and lacked casein or proline. The tissue continued to grow slowly on these selective media. After an additional 2 weeks the tissue was transferred to fresh N6-0.5 medium containing the selective agents.

Chlorsulfuron- and glufosinate-resistance callus clones could be identified after an additional 6–8 weeks. These clones continued to grow when transferred to the selective media.

The presence of pBT586 in the transformed clones has been confirmed by PCR analysis. Functionality of the introduced AK enzyme was tested by plating out transformed clones on N6-0.5 media containing 2 mM each of lysine and threonine (LT selection; see Example 13). All of the clones were capable of growing on LT medium indicating that the *E. coli* aspartate kinase was expressed and was functioning properly. To test that the *E. coli* DHDPS enzyme was functional, transformed callus was plated on N6-0.5 media containing 2 μg 2-aminoethylcysteine (AEC), a lysine analog and potent inhibitor of plant DHDPS. The transformed callus tissue was resistant to AEC indicating that the introduced DHDPS, which is about 16-fold less sensitive to AEC than the plant enzyme, was being produced and was functional. Plants have been regenerated from several transformed clones and are being grown to maturity.

Example 19

Transformation of Soybean with the Phaseolin Promoter/cts/cordapA and Phaseolin Promoter/cts/lysC-M4 Chimeric Genes The chimeric gene cassettes, phaseolin 5' region/cts/cordapA/phaseolin 3' region plus phaseolin 5' region/cts/lysC-M4/phaseolin 3', (Example 6) were inserted into the soybean transformation vector pBT603 (FIG. 8A). This vector has a soybean transformation marker gene consisting of the 35S promoter from Cauliflower Mosaic Virus driving expression of the *E. coli* β-glucuronidase gene [Jefferson et al. (1986) *Proc. Natl. Acad. Sci. USA* 83:8447–8451] with the Nos 3' region in a modified pGEM9Z plasmid.

To insert the phaseolin 5' region/cts/lysC-M4/phaseolin 3' region, the gene cassette was isolated as a 3.3 kb Hind III fragment and inserted into Hind III digested pBT603, yielding plasmid pBT609. This binary vector has the chimeric gene, phaseolin 5' region/cts/lysC-M4/phaseolin 3' region inserted in the opposite orientation from the 35S/GUS/Nos 3' marker gene.

To insert the phaseolin 5' region/cts/cordapA/phaseolin 3' region 3', the gene cassette was isolated as a 2.7 kb BamH I fragment (as described in Example 15) and inserted into BamH I digested pBT609, yielding plasmid pBT614 (FIG. 8B). This vector has both chimeric genes, phaseolin 5' region/cts/lysC-M4/phaseolin 3' region and phaseolin 5' region/cts/cordapA/phaseolin 3' region inserted in the same orientation, and both are in the opposite orientation from the 35S/GUS/Nos 3' marker gene.

Soybean was transformed with plasmid pBT614 according to the procedure described in U.S. Pat. No. 5,015,580. Soybean transformation was performed by Agracetus Company (Middleton, Wis.). Seeds from five transformed lines were obtained and analyzed.

It was expected that the transgenes would be segregating in the R1 seeds of the transformed plants. To identify seeds that carried the transformation marker gene, a small chip of the seed was cut off with a razor and put into a well in a disposable plastic microtiter plate. A GUS assay mix consisting of 100 mM $NaH_2PO_4$, 10 mM EDTA, 0.5 mM $K_4Fe(CN)_6$, 0.1% Triton X-100, 0.5 mg/mL 5-Bromo-4-chloro-3-indolyl β-D-glucuronic acid was prepared and 0.15 mL was added to each microtiter well. The microtiter plate was incubated at 37° for 45 min. The development of blue color indicated the expression of GUS in the seed.

Five of seven transformed lines showed approximately 3:1 segregation for GUS expression indicating that the GUS gene was inserted at a single site in the soybean genome. The other transformants showed 9:1 and 15:1 segregation, suggesting that the GUS gene was inserted at two sites.

A meal was prepared from a fragment of individual seeds by grinding into a fine powder. Total proteins were extracted from the meal by adding 1 mg to 0.1 mL of 43 mM Tris-HCl pH 6.8, 1.7% SDS, 4.2% β-mercaptoethanol, 8% glycerol, vortexing the suspension, boiling for 2–3 min and vortexing again. The resultant suspensions were centrifuged for 5 min at room temperature in a microfuge to remove particulates and 10 μL from each extract were run per lane on an SDS polyacrylamide gel, with bacterially produced DHDPS or AKIII serving as a size standard. The proteins were then electrophoretically blotted onto a nitrocellulose membrane. The membranes were exposed to the DHDPS or AKIII antibodies, at a 1:5000 or 1:1000 dilution, respectively, of the rabbit serum using standard protocol provided by Bio-Rad with their Immun-Blot Kit. Following rinsing to remove unbound primary antibody the membranes were exposed to the secondary antibody, donkey anti-rabbit Ig conjugated to horseradish peroxidase (Amersham) at a 1:3000 dilution. Following rinsing to remove unbound secondary antibody, the membranes were exposed to Amersham chemiluminescence reagent and X-ray film.

Six of seven transformants expressed the DHDPS protein. In the six transformants that expressed DHDPS, there was excellent correlation between expression of GUS and DHDPS in individual seeds (Table 13). Therefore, the GUS and DHDPS genes are integrated at the same site in the soybean genome. Four of seven transformants expressed the AKIII protein, and again there was excellent correlation between expression of AKIII, GUS and DHDPS in individual seeds (Table 13). Thus, in these four transformants the GUS, AKIII and DHDPS genes are integrated at the same site in the soybean genome. One transformant expressed only GUS in its seeds.

To measure free amino acid composition of the seeds, free amino acids were extracted from 8–10 milligrams of the meal in 1.0 mL of methanol/chloro-form/water mixed in ratio of 12v/5v/3v (MCW) at room temperature. The mixture was vortexed and then centrifuged in an eppendorf microcentrifuge for about 3 min; approximately 0.8 mL of supernatant was decanted. To this supernatant, 0.2 mL of chloroform was added followed by 0.3 mL of water. The mixture was vortexed and then centrifuged in an eppendorf microcentrifuge for about 3 min, the upper aqueous phase, approximately 1.0 mL, was removed, and was dried down in a Savant Speed Vac Concentrator. The samples were hydrolyzed in 6N hydrochloric acid, 0.4% β-mercaptoethanol under nitrogen for 24 h at 110–120° C.; 1/10 of the sample was run on a Beckman Model 6300 amino acid analyzer using post-column ninhydrin detection. Relative free amino acid levels in the seeds were compared as ratios of lysine to leucine, thus using leucine as an internal standard.

Soybean transformants expressing Corynebacteria DHDPS alone and in concert with E. coli AKIII-M4 accumulated high levels of free lysine in their seeds. From 20 fold to 120-fold increases in free lysine levels were observed (Table 13). A high level of saccharopine, indicative of lysine catabolism, was also observed in seeds that contained high levels of lysine. Thus, prevention of lysine catabolism by inactivation of lysine ketoglutarate reductase should further increase the accumulation of free lysine in the seeds. Alternatively, incorporation of lysine into a peptide or lysine-rich protein would prevent catabolism and lead to an increase in the accumulation of lysine in the seeds.

To measure the total amino acid composition of mature seeds, 1–1.4 milligrams of the seed meal was hydrolyzed in 6N hydrochloric acid, 0.4% β-mercaptoethanol under nitrogen for 24 h at 110–120° C.; 1/50 of the sample was run on a Beckman Model 6300 amino acid analyzer using post-column ninhydrin detection. Lysine (and other amino acid) levels in the seeds were compared as percentages of the total amino acids.

The soybean seeds expressing Corynebacteria DHDPS showed substantial increases in accumulation of total seed lysine. Seeds with a 5–35% increase in total lysine content, compared to the untransformed control, were observed. In these seeds lysine makes up 7.5–7.7% of the total seed amino acids.

Soybean seeds expressing Corynebacteria DHDPS in concert with E. coli AKIII-M4 showed much greater accumulation of total seed lysine than those expressing Corynebacteria DHDPS alone. Seeds with a more than four-fold increase in total lysine content were observed. In these seeds lysine makes up 20–25% of the total seed amino acids, considerably higher than any previously known soybean seed.

TABLE 13

| LINE-SEED | GUS | Free LYS/LEU | DHDPS | AKIII | % TOTAL SEED LYS |
|---|---|---|---|---|---|
| A2396-145-4 | − | 0.9 | − | − | 5.8 |
| A2396-145-8 | − | 1.0 | − | − | |
| A2396-145-5 | − | 0.8 | | | 5.9 |
| A2396-145-3 | − | 1.0 | | | |
| A2396-145-9 | + | 2.0 | | | |
| A2396-145-6 | + | 4.6 | | | |
| A2396-145-1 | + | 8.7 | | | |
| A2396-145-10 | + | 18.4 | | | 7.5 |
| A2396-145-7 | + | 21.7 | + | − | 6.7 |
| A2396-145-2 | + | 45.5 | + | − | 7.2 |
| A5403-175-9 | − | 1.3 | | | |
| A5403-175-4 | − | 1.2 | − | − | 6.0 |
| A5403-175-3 | − | 1.0 | − | − | 6.0 |
| A5403-175-7 | + | 1.5 | | | |
| A5403-175-5 | + | 1.8 | | | |
| A5403-175-1 | + | 6.2 | | | |
| A5403-175-2 | + | 6.5 | | | 6.3 |
| A5403-175-6 | + | 14.4 | | | |
| A5403-175-8 | + | 47.8 | + | − | 7.7 |
| A5403-175-10 | + | 124.3 | + | − | 7.5 |
| A5403-181-9 | + | 1.4 | | | |
| A5403-181-10 | + | 1.4 | − | − | 5.7 |
| A5403-181-8 | + | 0.9 | | | |
| A5403-181-6 | + | 1.5 | | | |
| A5403-181-4 | − | 0.7 | − | − | 5.9 |
| A5403-181-5 | + | 1.1 | | | |
| A5403-181-2 | − | 1.8 | − | − | 5.6 |
| A5403-181-3 | + | 2.7 | − | − | 5.5 |
| A5403-181-7 | + | 1.9 | | | |
| A5403-181-1 | − | 2.3 | | | |
| A5403-183-9 | − | 0.8 | | | |
| A5403-183-6 | − | 0.7 | | | 6.0 |
| A5403-183-8 | − | 1.3 | | | |
| A5403-183-4 | − | 1.3 | − | − | 6.0 |
| A5403-183-5 | + | 0.9 | | | |
| A5403-183-3 | + | 3.1 | | | |
| A5403-183-1 | + | 3.3 | | | |
| A5403-183-7 | + | 9.9 | | | |
| A5403-183-10 | + | 22.3 | + | + | 6.7 |
| A5403-183-2 | + | 23.1 | + | + | 7.3 |
| A5403-196-8 | − | 0.9 | − | − | 5.9 |
| A5403-196-6 | + | 8.3 | | | |
| A5403-196-1 | + | 16.1 | + | + | 6.8 |
| A5403-196-7 | + | 27.9 | | | |
| A5403-196-3 | + | 52.8 | | | |
| A5403-196-5 | + | 26 | | | |
| A5403-196-2 | + | 16.2 | + | + | |
| A5403-196-10 | + | 29 | + | + | 7.5 |
| A5403-196-4 | + | 58.2 | + | + | 7.6 |
| A5403-196-9 | + | 47.1 | | | |
| A2396-233-1 | + | | + | + | 25 |
| A2396-233-2 | + | | | | 18 |
| A2396-233-3 | + | | | | 23 |
| A2396-233-4 | + | | | | 20 |
| A2396-233-5 | − | | +/− | − | 6.0 |
| A2396-233-6 | + | | | | 16 |
| A2396-233-13 | + | | + | + | 18 |
| A2396-234-1 | + | | + | + | 8.3 |
| A2396-234-2 | + | | + | + | 13 |
| A2396-234-3 | + | | | | 10 |
| A2396-234-4 | + | | | | 19 |
| A2396-234-9 | + | | | | 15 |
| A2396-234-16 | − | | − | − | 5.9 |
| wild type control | − | 0.9 | − | − | 5.6 |

Example 20

Isolation of a Plant Lysine Ketoglutarate Reductase Gene

Lysine Ketoglutarate Reductase (LKR) enzyme activity has been observed in immature endosperm of developing maize seeds [Arruda et al. (1982) *Plant Physiol.* 69:988–989]. LKR activity increases sharply from the onset of endosperm development, reaches a peak level at about 20 d after pollination, and then declines [Arruda et al. (1983) *Phytochemistry* 22:2687–2689].

In order to clone the corn LKR gene, RNA was isolated from developing seeds 19 days after pollination. This RNA was sent to Clontech Laboratories, Inc., (Palo Alto, Calif.) for the custom synthesis of a cDNA library in the vector Lambda Zap II. The conversion of the Lambda Zap II library into a phagemid library, then into a plasmid library was accomplished following the protocol provided by Clontech. Once converted into a plasmid library the ampicillin-resistant clones obtained carry the cDNA insert in the vector pBluescript SK(−). Expression of the cDNA is under control of the lacZ promoter on the vector.

Two phagemid libraries were generated using the mixtures of the Lambda Zap II phage and the filamentous helper phage of 100 μL to 1 μL. Two additional libraries were generated using mixtures of 100 μL Lambda Zap II to 10 μL helper phage and 20 μL Lambda Zap II to 10 μL helper phage. The titers of the phagemid preparations were similar regardless of the mixture used and were about $2\times10^3$ ampicillin-resistant-transfectants per mL with *E. coli* strain XLI-Blue as the host and about $1\times10^3$ with DE126 (see below) as host.

To select clones that carried the LKR gene a specially designed *E. coli* host, DE126 was constructed. Construction of DE126 occurred in several stages. (1) A generalized transducing stock of coliphage P1 vir was produced by infection of a culture of TST1 [F$^-$ $^{araD}$139, delta(argF-lac) 205, flb5301, ptsF25, relA1, rpsL150, malE52::Tn10, deoC1, $\lambda^-$] (*E. coli* Genetic Stock Center #6137) using a standard method (for Methods see J. Miller, Experiments in Molecular Genetics).

(2) This phage stock was used as a donor in a transductional cross (for Method see J. Miller, Experiments in Molecular Genetics) with strain GIF106M1 [F$^-$, arg-, ilvA296, lysC1001, thrA1101, metL1000, $\lambda^-$, rpsL9, malT1, xyl-7, mtl-2, thi1(?), supE44(?)] (*E. coli* Genetic Stock Center #5074) as the recipient.

Recombinants were selected on rich medium [L supplemented with DAP] containing the antibiotic tetracycline. The transposon Tn10, conferring tetracycline resistance, is inserted in the malE gene of strain TST1. Tetracycline-resistant transductants derived from this cross are likely to contain up to 2 min of the *E. coli* chromosome in the vicinity of malE. The genes malE and lysC are separated by less than 0.5 minutes, well within cotransduction distance.

(3) 200 tetracycline-resistant transductants were thoroughly phenotyped; appropriate fermentation and nutritional traits were scored. The recipient strain GIF106M1 is completely devoid of aspartokinase isozymes due to mutations in thrA, metL and lysC, and therefore requires the presence of threonine, methionine, lysine and meso-diaminopimelic acid (DAP) for growth. Transductants that had inherited lysC$^+$ with malE::Tn10 from TST1 would be expected to grow on a minimal medium that contains vitamin B 1, L-arginine, L-isoleucine and L-valine in addition to glucose which serves as a carbon and energy source. Moreover strains having the genetic constitution of lysC$^+$, metL- and thrA- will only express the lysine sensitive aspartokinase. Hence addition of lysine to the minimal medium should prevent the growth of the lysC$^+$ recombinant by leading to starvation for threonine, methionine and DAP. Of the 200 tetracycline resistant transductants examined, 49 grew on the minimal medium devoid of threonine, methionine and DAP. Moreover, all 49 were inhibited by the addition of L-lysine to the minimal medium. One of these transductants was designated DE125.

DE125 has the phenotype of tetracycline resistance, growth requirements for arginine, isoleucine and valine, and sensitivity to lysine. The genotype of this strain is F$^-$ $^{malE}$52::Tn10 arg-ilvA296 thrA1101 metL1000 lambda-rpsL9 malT1 xyl-7 mtl-2 thi1 (?) supE44(?).

(4) This step involves production of a male derivative of strain DE125. Strain DE125 was mated with the male strain AB1528 [F'16/delta(gpt-proA)62, lacY1 or lacZ4, glnV44, galK2 rac$^-$(?), hisG4, rfbd1, mgl-51, kdgK51(?), ilvC7, argE3, thi-1] (*E. coli* Genetic Stock Center #1528) by the method of conjugation. F'16 carries the ilvGMEDAYC gene cluster. The two strains were cross streaked on rich medium permissive for the growth of each strain. After incubation, the plate was replica plated to a synthetic medium containing tetracycline, arginine, vitamin B1 and glucose. DE125 cannot grow on this medium because it cannot synthesize isoleucine. Growth of AB1528 is prevented by the inclusion of the antibiotic tetracycline and the omission of proline and histidine from the synthetic medium. A patch of cells grew on this selective medium. These recombinant cells underwent single colony isolation on the same medium. The phenotype of one clone was determined to be Ilv$^+$, Arg$^-$, TetR, Lysine-sensitive, male specific phage (MS2)-sensitive, consistent with the simple transfer of F'16 from AB1528 to DE125. This clone was designated DE126 and has the genotype F'16/malE52::Tn10, arg$^-$, ilvA296, thrA1101, metL100, lysC$^+$, $\lambda^-$, rpsL9, malT1, xyl-7, mtl-2, thi-1?, supE44?. It is inhibited by 20 μg/mL of L-lysine in a synthetic medium.

To select for clones from the corn cDNA library that carried the LKR gene, 100 μL of the phagemid library was mixed with 100 μL of an overnight culture of DE126 grown in L broth and the cells were plated on synthetic media containing vitamin B 1, L-arginine, glucose as a carbon and energy source, 100 μg/mL ampicillin and L-lysine at 20, 30 or 40 μg/mL. Four plates at each of the three different lysine concentrations were prepared. The amount of phagemid and DE126 cells was expected to yield about $1\times10^5$ ampicillin-resistant transfectants per plate. Ten to thirty lysine-resistant colonies grew per plate (about 1 lysine-resistant per 5000 ampicillin-resistant colonies).

Plasmid DNA was isolated from 10 independent clones and retransformed into DE126. Seven of the ten DNAs yielded lysine-resistant clones demonstrating that the lysine-resistance trait was carried on the plasmid. Several of the cloned DNAs were sequenced and biochemically characterized. The inserted DNA fragments were found to be derived from the *E. coli* genome, rather than a corn cDNA indicating that the cDNA library provided by Clontech was contaminated.

Another method was used to identify plant cDNAs that encode LKR. This method was based upon expected homology between plant LKR and fungal genes encoding saccharopine dehydrogenase. Fungal saccharopine dehydrogenase (glutamate-forming) and saccharopine dehydrogenase (lysine-forming) catalyze the final two steps in the fungal lysine biosynthetic pathway. Plant LKR and fungal saccharopine dehydrogenase (lysine-forming) catalyze both forward and reverse reactions, use identical substrates and use similar co-factors. Similarly, plant saccharopine dehydrogenase (glutamate-forming), which catalyzes the second step in the lysine catabolic pathway, works in both forward and reverse reactions, uses identical substrates and uses similar co-factors as fungal saccharopine dehydrogenase (glutamate-forming).

Biochemical and genetic evidence derived from human and bovine studies has demonstrated that mammalian LKR and saccharopine dehydrogenase (glutamate-forming) enzyme activities are present on a single protein with a monomer molecular weight of about 117,000. This contrasts with the fungal enzymes which are carried on separate proteins, saccharopine dehydrogenase (lysine-forming) with a molecular weight of about 44,000 and saccharopine dehydrogenase (glutamate-forming) with a molecular weight of about 51,000. Plant LKR has been reported to have a molecular weight of about 140,000 indicating that it is like the animal catabolic protein wherein both LKR and saccharopine dehydrogenase (glutamate-forming) enzyme activities are present on a single protein.

Several genes for fungal saccharopine dehydrogenases have been isolated and sequenced [Xuan et al. (1990) Mol. Cell. Biol. 10:4795–4806, Feller et al. (1994) *Mol. Cell. Biol.* 14:6411–6418]. The fungal protein sequences, deduced from these gene sequences, were used to search plant cDNA databases for DNA fragments that encoded plant proteins homologous to the fungal saccharopine dehydrogenases. We discovered two plant cDNA fragments from *Arabidopsis thaliana*, SEQ ID NO:102: and SEQ ID NO:103:, that encoded polypeptides SEQ ID NO:104: and SEQ ID NO:105:, respectively, that are homologous to fungal saccharopine dehydrogenase (glutamate-forming). The sequence similarity between the fungal and plant polypeptides (see FIG. 9) demonstrate that these cDNAs encode *Arabidopsis* saccharopine dehydrogenase. Full length cDNAs encoding plant LKR plus saccharopine dehydrogenase or genomic DNAs containing the entire LKR/saccharopine dehydrogenase gene can be readily identified by hybridization to labelled cDNA fragments of SEQ ID NO:102: or SEQ ID NO:103: and thus isolated.

In order to block expression of the LKR gene in transformed plants, a chimeric gene designed for cosuppression of LKR can be constructed by linking the LKR gene or gene fragment to any of the plant promoter sequences described above. (See U.S. Pat. No. 5,231,020 for methodology to block plant gene expression via cosuppression.) Alternatively, a chimeric gene designed to express antisense RNA for all or part of the LKR gene can be constructed by linking the LKR gene or gene fragment in reverse orientation to any of the plant promoter sequences described above. (See U.S. Pat. No. 5,107,065 for methodology to block plant gene expression via antisense RNA.) Either the cosuppression or antisense chimeric gene could be introduced into plants via transformation. Transformants wherein expression of the endogenous LKR gene is reduced or eliminated are selected.

Example 21

Construction of Synthetic Genes in Expression Vector pSK5

To facilitate the construction and expression of the synthetic genes described below, it was necessary to construct a plasmid vector with the following attributes:

1. No Ear I restriction endonuclease sites such that insertion of sequences would produce a unique site.
2. Containing a tetracycline resistance gene to avoid loss of plasmid during growth and expression of toxic proteins.
3. Containing approximately 290 bp from plasmid pBT430 including the T7 promoter and terminator seqment for expression of inserted sequences in *E. coli*.
4. Containing unique EcoR I and Nco I restriction endonuclease recognition sites in proper location behind the T7 promoter to allow insertion of the oligonucleotide sequences.

To obtain attributes 1 and 2 Applicants used plasmid pSK1 which was a spontaneous mutant of pBR322 where the ampicillin gene and the Ear I site near that gene had been deleted. Plasmid pSK1 retained the tetracycline resistance gene, the unique EcoR I restriction sites at base 1 and a single Ear I site at base 2353. To remove the Ear I site at base 2353 of pSK1 a polymerase chain reaction (PCR) was performed using pSK1 as the template. Approximately 10 femtomoles of pSK1 were mixed with 1 µg each of oligonucleotides SM70 and SM71 which had been synthesized on an ABI1306B DNA synthesizer using the manufacturer's procedures.

SM70   5'-CTGACTCGCTGCGCTCGGTC 3'      SEQ ID NO:16

SM71   5'-TATTTTCTCCTTACGCATCTGTGC-3'  SEQ ID NO:17

The priming sites of these oligonucleotides on the pSK1 template are depicted in FIG. 10. The PCR was performed using a Perkin-Elmer Cetus kit (Emeryville, Calif.) according to the instructions of the vendor on a thermocycler manufactured by the same company. The 25 cycles were 1 min at 95°, 2 min at 42° and 12 min at 72°. The oligonucleotides were designed to prime replication of the entire pSK1 plasmid excluding a 30 b fragment around the Ear I site (see FIG. 10). Ten microliters of the 100 µL reaction product were run on a 1% agarose gel and stained with ethidium bromide to reveal a band of about 3.0 kb corresponding to the predicted size of the replicated plasmid.

The remainder of the PCR reaction mix (90 µL) was mixed with 20 µL of 2.5 mM deoxynucleotide triphosphates (dATP, dTTP, dGTP, and dCTP), 30 units of Klenow enzyme added and the mixture incubated at 37° for 30 min followed by 65° for 10 min. The Klenow enzyme was used to fill in ragged ends generated by the PCR. The DNA was ethanol precipitated, washed with 70% ethanol, dried under vacuum and resuspended in water. The DNA was then treated with T4 DNA kinase in the presence of 1 mM ATP in kinase buffer. This mixture was incubated for 30 min at 37° followed by 10 min at 65°. To 10 µL of the kinased preparation, 2 µL of 5×ligation buffer and 10 units of T4 DNA ligase were added. The ligation was carried out at 15° for 16 h. Following ligation, the DNA was divided in half and one half digested with Ear I enzyme. The Klenow, kinase, ligation and restriction endonuclease reactions were performed as described in Sambrook et al., [*Molecular Cloning, A Laboratory Manual,* 2nd ed. (1989) Cold Spring Harbor Laboratory Press]. Klenow, kinase, ligase and most restriction endonucleases were purchased from BRL. Some restriction endonucleases were purchased from NEN Biolabs (Beverly, Mass.) or Boehringer Mannheim (Indianapolis, Ind.). Both the ligated DNA samples were transformed separately into competent JM103 [supE thi del (lac-proAB) F' [traD36 porAB, lacIq lacZ del M15] restriction minus] cells using the CaCl$_2$ method as described in Sambrook et al., [*Molecular Cloning, A Laboratory Manual*, 2nd ed. (1989) Cold Spring Harbor Laboratory Press] and plated onto media containing 12.5 ug/mL tetracycline. With or without Ear I digestion the same number of transformants were recovered suggesting that the Ear I site had been removed from these constructs. Clones were screened by preparing DNA by the alkaline lysis miniprep procedure as described in Sambrook et al., [*Molecular Cloning, A Laboratory Manual*, 2nd ed. (1989) Cold Spring Harbor Laboratory Press] followed by restriction endonuclease digest analysis. A single clone was chosen which was tetracycline-resistant and did not contain any Ear I sites. This vector was designated pSK2. The remaining EcoR I site of pSK2 was destroyed by digesting the plasmid with EcoR I to completion, filling in the ends with Klenow and ligating. A clone which did not contain an EcoR I site was designated pSK3.

To obtain attributes 3 and 4 above, the bacteriophage T7 RNA polymerase promoter/terminator segment from plasmid pBT430 (see Example 2) was amplified by PCR. Oligonucleotide primers SM78 (SEQ ID NO:18) and SM79 (SEQ ID NO: 19) were designed to prime a 300b fragment from pBT430 spanning the T7 promoter/terminator sequences (see FIG. 10).

```
SM78
5'-TTCATCGATAGGCGACCACACCCGTCC-3'      SEQ ID NO:18

SM79
5'-AATATCGATGCCACGATGCGTCCGGCG-3'      SEQ ID NO:19
```

The PCR reaction was carried out as described previously using pBT430 as the template and a 300 bp fragment was generated. The ends of the fragment were filled in using Klenow enzyme and kinased as described above. DNA from plasmid pSK3 was digested to completion with PvuII enzyme and then treated with calf intestinal alkaline phophatase (Boehringer Mannheim) to remove the 5' phosphate. The procedure was as described in Sambrook et al., [*Molecular Cloning, A Laboratory Manual*, 2nd ed. (1989) Cold Spring Harbor Laboratory Press]. The cut and phosphatased pSK3 DNA was purified by ethanol precipitation and a portion used in a ligation reaction with the PCR generated fragment containing the T7 promoter sequence. The ligation mix was transformed JM103 [supE thi del (lac-proAB) F' [traD36 porAB, lacIq lacZ del M15] restriction minus] and tetracycline-resistant colonies were screened. Plasmid DNA was prepared via the alkaline lysis mini prep method and restriction endonuclease analysis was performed to detect insertion and orientation of the PCR product. Two clones were chosen for sequence analysis: Plasmid pSK5 had the fragment in the orientation shown in FIG. 10. Sequence analysis performed on alkaline denatured double-stranded DNA using Sequenase® T7 DNA polymerase (US Biochemical Corp) and manufacturer's suggested protocol revealed that pSK5 had no PCR replication errors within the T7 promoter/terminator sequence.

The strategy for the construction of repeated synthetic gene sequences based on the Ear I site is depicted in FIG. 11. The first step was the insertion of an oligonucleotide sequence encoding a base gene of 14 amino acids. This oligonucleotide insert contained a unique Ear I restriction site for subsequent insertion of oligonucleotides encoding one or more heptad repeats and added an unique Asp 718 restriction site for use in transfer of gene sequences to plant vectors. The overhanging ends of the oligonucleotide set allowed insertion into the unique Nco I and EcoR I sites of vector pSK5.

```
              M   E   E   K   M   K   A   M   E   E   K        (SEQ ID NO:22)
SM81    5'-CATGGAGGAGAAGATGAAGGCGATGGAAGAGAAG          (SEQ ID NO:20)
SM80    3'-CTCCTCTTCTACTTCCGCTACCTTCTCTTC              (SEQ ID NO:21)
        NCO I                          EAR I

M   K   A
SM81    ATGAAGGCGTGATAGGTACCG-3'
SM80    TACTTCCGCACTATCCATGGCTTAA-5'
                      ASP718 ECOR I
```

DNA from plasmid pSK5 was digested to completion with Nco I and EcoR I restriction endonucleases and purified by agarose gel electrophoresis. Purified DNA (0.1 ug) was mixed with 1 μg of each oligonucleotide SM80 (SEQ ID NO:14) and SM81 (SEQ ID NO:13) and ligated. The ligation mixture was transformed into *E. coli* strain JM103 [supE thi del (lac-proAB) F' [traD36 porAB, lacIq lacZ del M15] restriction minus] and tetracycline resistant transformants screened by rapid plasmid DNA preps followed by restriction digest analysis. A clone was chosen which had one each of Ear I, Nco I, Asp 718 and EcoR I sites indicating proper insertion of the oligonucleotides. This clone was designated pSK6 (FIG. 12). Sequencing of the region of DNA following the T7 promoter confirmed insertion of oligonucleotides of the expected sequence.

Repetitive heptad coding sequences were added to the base gene construct of described above by generating oligonucleotide pairs which could be directly ligated into the unique Ear I site of the base gene. Oligonucleotides SM84 (SEQ ID NO:23) and SM85 (SEQ ID NO:24) code for repeats of the SSP5 heptad. Oligonucleotides SM82 (SEQ ID NO:25) and SM83 (SEQ ID NO:26) code for repeats of the SSP7 heptad.

```
SSP5            M   E   E   K   M   K   A         (SEQ ID NO:28)
SM84    5'-GATGGAGGAGAAGATGAAGGC-3'                (SEQ ID NO:23)
SM85    3'-CCTCCTCTTCTACTTCCGCTA-5'                (SEQ ID NO:24)

SSP7            M   E   E   K   L   K   A         (SEQ ID NO:27)
SM82    5'-GATGGAGGAGAAGCTGAAGGC-3'                (SEQ ID NO:25)
SM83    3'-CCTCCTCTTCGACTTCCGCTA-5'                (SEQ ID NO:26)
```

Oligonucleotide sets were ligated and purified to obtain DNA fragments encoding multiple heptad repeats for insertion into the expression vector. Oligonucleo-tides from each set totalling about 2 μg were kinased, and ligated for 2 h at room temperature. The ligated multimers of the oligonucleotide sets were separated on an 18% non-denaturing 20×20× 0.015 cm polyacrylamide gel (Acrylamide: bis-acrylamide= 19:1). Multimeric forms which separated on the gel as 168 bp (8n) or larger were purified by cutting a small piece of polyacrylamide containing the band into fine pieces, adding 1.0 mL of 0.5 M ammonium acetate, 1 mM EDTA (pH 7.5) and rotating the tube at 37° overnight. The polyacrylamide was spun down by centrifugation, 1 µg of tRNA was added to the supernatant,the DNA fragments were precipitated with 2 volumes of ethanol at −70°, washed with 70% ethanol, dried, and resuspended in 10 µL of water.

Ten micrograms of pSK6 DNA were digested to completion with Ear I enzyme and treated with calf intestinal alkaline phosphatase. The cut and phosphatased vector DNA was isolated following electrophoresis in a low melting point agarose gel by cutting out the banded DNA, liquifying the agarose at 55°, and purifying over NACS PREPAC__ columns (BRL) following manufacturer's suggested procedures. Approximately 0.1 µg of purified Ear I digested and phosphatase treated pSK6 DNA was mixed with 5 µL of the gel purified multimeric oligonucleotide sets and ligated. The ligated mixture was transformed into E. coli strain JM103 [supE thi del (lac-proAB) F' [traD36 porAB, lacIq lacZ del M15] restriction minus] and tetracycline-resistant colonies selected. Clones were screened by restriction digests of rapid plasmid prep DNA to determine the length of the inserted DNA. Restriction endonuclease analyses were usually carried out by digesting the plasmid DNAs with Asp 718 and Bgl II, followed by separation of fragments on 18% non-denaturing polyacrylamide gels. Visualization of fragments with ethidium bromide, showed that a 150 bp fragment was generated when only the base gene segment was present. Inserts of the oligonucleotide fragments increased this size by multiples of 21 bases. From this screening several clones were chosen for DNA sequence analysis and expression of coded sequences in E. coli.

TABLE 14

| Clone # | SEQ ID NO: | Sequence by Heptad Amino Acid Repeat (SSP) | SEQ ID NO: |
|---|---|---|---|
| C15 | 29 | 5.<u>7.7.7.7.7</u>.5 | 30 |
| C20 | 31 | 5.<u>7.7.7.7</u>.5 | 32 |
| C30 | 33 | 5.<u>7.7.7</u>.5 | 34 |
| D16 | 35 | 5.<u>5.5</u>.5 | 36 |
| D20 | 37 | 5.<u>5.5.5</u>.5 | 38 |
| D33 | 39 | 5.<u>5.5</u>.5 | 40 |

The first and last SSP5 heptads flanking the sequence of each construct are from the base gene described above. Inserts are designated by underlining.

Because the gel purification of the oligomeric forms of the oligonucleotides did not give the expected enrichment of longer (i.e., >8n) inserts, Applicants used a different procedure for a subsequent round of insertion constructions. For this series of constructs four more sets of oligonucleotides were generated which code for SSP 8, 9, 10 and 11 amino acid sequences respectively:

```
SSP8        M  E  E  K  L  K  K          (SEQ ID NO:49)
SM86   5'-GATGGAGGAGAAGCTGAAGAA-3'       (SEQ ID NO:41)
SM87   3'-CCTCCTCTTCGACTTCTTCTA-5'       (SEQ ID NO:42)

SSP9        M  E  E  K  L  K  W          (SEQ ID NO:50)
SM88   5'-GATGGAGGAGAAGCTGAAGTG-3'       (SEQ ID NO:43)
SM89   3'-CCTCCTCTTCGACTTCACCTA-5'       (SEQ ID NO:44)

SSP10       M  E  E  K  M  K  K          (SEQ ID NO:51)
SM90   5'-GATGGAGGAGAAGATGAAGAA-3'       (SEQ ID NO:45)
SM91   3'-CCTCCTCTTCTACTTCTTCTA-5'       (SEQ ID NO:46)

SSP11       M  E  E  K  M  K  W          (SEQ ID NO:52)
SM92   5'-GATGGAGGAGAAGATGAAGTG-3'       (SEQ ID NO:47)
SM93   3'-CCTCCTCTTCTACTTCACCTA-5'       (SEQ ID NO:48)
```

The following HPLC procedure was used to purify multimeric forms of the oligonucleotide sets after kinasing and ligating the oligonucleotides as described above. Chromatography was performed on a Hewlett Packard Liquid Chromatograph instrument, Model 1090M. Effluent absorbance was monitored at 260 nm. Ligated oligonucleotides were centrifuged at 12,000×g for 5 min and injected onto a 2.5µ TSK DEAE-NPR ion exchange column (35 cm×4.6 mm I.D.) fitted with a 0.5µ in-line filter (Supelco). The oligonucleotides were separated on the basis of length using a gradient elution and a two buffer mobile phase [Buffer A: 25 mM Tris-Cl, pH 9.0, and Buffer B: Buffer A+1 M NaCl]. Both Buffers A and B were passed through 0.2µ filters before use. The following gradient program was used with a flow rate of 1 mL per min at 30°:

| Time | % A | % B |
|---|---|---|
| initial | 75 | 25 |
| 0.5 min | 55 | 45 |
| 5 min | 50 | 50 |
| 20 min | 38 | 62 |
| 23 min | 0 | 100 |
| 30 min | 0 | 100 |
| 31 min | 75 | 25 |

Fractions (500 µL) were collected between 3 min and 9 min. Fractions corresponding to lengths between 120 bp and 2000 bp were pooled as determined from control separations of restriction digests of plasmid DNAs.

The 4.5 mL of pooled fractions for each oligonucleotide set were precipitated by adding 10 µg of tRNA and 9.0 mL of ethanol, rinsed twice with 70% ethanol and resuspended in 50 µL of water. Ten µL of the resuspended HPLC purified oligonucleotides were added to 0.1 µg of the Ear I cut, phosphatased pSK6 DNA described above and ligated overnight at 15°. All six oligonucleotide sets described above which had been kinased and self-ligated but not purified by gel or HPLC were also used in separate ligation reactions with the pSK6 vector. The ligation mixtures were transformed into E. coli strain DH5α [supE44 del lacU169 (phi 80 lacZ del M15) hsdR17 recA1 endA1 gyr196 thi1 relA1] and tetracycline-resistant colonies selected. Applicants chose to use the DH5α [supE44 del lacU169 (phi 80 lacZ del M15) hsdR17 recA1 endA1 gyr196 thi1 relA1] strain for all subsequent work because this strain has a very high transformation rate and is recA-. The recA-phenotype eliminates concerns that these repetitive DNA structures may be substrates for homologous recombination leading to deletion of multimeric sequences.

Clones were screened as described above. Several clones were chosen to represent insertions of each of the six oligonucleotide sets.

TABLE 15

| Clone # | SEQ ID NO: | Sequence by Heptad Amino Acid Repeat (SSP) | SEQ ID NO: |
|---|---|---|---|
| 82-4 | 53 | <u>7.7.7.7.7.7</u>.5 | 54 |
| 84-H3 | 55 | 5.<u>5.5</u>.5 | 56 |

TABLE 15-continued

| Clone # | SEQ ID NO: | Sequence by Heptad Amino Acid Repeat (SSP) | SEQ ID NO: |
|---------|------------|---------------------------------------------|------------|
| 86-H23  | 57         | 5.8.8.5                                     | 58         |
| 88-2    | 59         | 5.9.9.9.5                                   | 60         |
| 90-H8   | 61         | 5.10.10.10.5                                | 62         |
| 92-2    | 63         | 5.11.11.5                                   | 64         |

The first and last SSP5 heptads flanking the sequence represent the base gene sequence. Insert sequences are underlined. Clone numbers including the letter "H" designate HPLC-purified oligonucleotides. The loss of the first base gene repeat in clone 82–4 may have resulted from homologous recombination between the base gene repeats 5.5 before the vector pSK6 was transferred to the recA- strain. The HPLC procedure did not enhance insertion of longer multimeric forms of the oligonucleotide sets into the base gene but did serve as an efficient purification of the ligated oligonucleotides.

Oligonucleotides were designed which coded for mixtures of the SSP sequences and which varied codon usage as much as possible. This was done to reduce the possibility of deletion of repetitive inserts by recombination once the synthetic genes were transformed into plants and to extend the length of the constructed gene segments. These oligonucleotides encode four repeats of heptad coding units (28 amino acid residues) and can be inserted at the unique Ear I site in any of the previously constructed clones. SM96 and SM97 code for SSP(5)$_4$, SM98 and SM99 code for SSP(7)$_4$ and SM100 plus SM101 code for SSP8.9.8.9.

TABLE 16

| Clone # | SEQ ID NO: | Sequence by Heptad Amino Acid Repeat (SSP) | SEQ ID NO: |
|---------|------------|---------------------------------------------|------------|
| 2-9     | 74         | 7.7.7.7.7.7.8.9.8.9.5                       | 75         |
| 3-5     | 78         | 7.7.7.7.7.7.5.5                             | 79         |
| 5-1     | 76         | 5.5.5.7.7.7.7.5                             | 77         |

Inserted oligonucleotide segments are underlined

Clone 2-9 was derived from oligonucleotides SM100 (SEQ ID NO:71) and SM101 (SEQ ID NO:72) ligated into the Ear I site of clone 82-4 (see above). Clone 3-5 (SEQ ID NO:78) was derived from the insertion of the first 22 bases of the oligonucleotide set SM96 (SEQ ID NO:65) and SM97 (SEQ ID NO:66) into the Ear I site of clone 82-4 (SEQ ID NO:53). This partial insertion may reflect improper annealing of these highly repetitive oligos. Clone 5-1 (SEQ ID NO:76) was derived from oligonucleotides SM98 (SEQ ID NO:68) and SM99 (SEQ ID NO:69) ligated into the Ear I site of clone 84-H3 (SEQ ID NO:55).

Strategy II

A second strategy for construction of synthetic gene sequences was implemented to allow more flexibility in both DNA and amino acid sequence. This strategy is depicted in FIG. 13 and FIG. 14. The first step was the insertion of an

```
          M  E  E  K  M  K  A  M  E  E  K  M  K                    (SEQ ID NO:67)
SM96  5'-GATGGAGGAAAAGATGAAGGCGATGGAGGAGAAAATGAAA                   (SEQ ID NO:65)
SM97  3'    CCTCCTTTTCTACTTCCGCTACCTCCTCTTTTACTTT                   (SEQ ID NO:66)

A  M  E  E  K  M  K  A  M  E  E  K  M  K  A
      GCTATGGAGGAAAAGATGAAAGCGATGGAGGAGAAAATGAAGGC-3'
      CGATACCTCCTTTTCTACTTTCGCTACCTCCTCTTTTACTTCCGCTA-5'

M  E  E  K  L  K  A  M  E  E  K  L  K                    (SEQ ID NO:70)
SM98  5'-GATGGAGGAAAAGCTGAAAGCGATGGAGGAGAAACTCAAG                   (SEQ ID NO:68)
SM99  3'    CCTCCTTTTCGACTTTCGCTACCTCCTCTTTGAGTTC                   (SEQ ID NO:69)

A  M  E  E  K  L  K  A  M  E  E  K  L  K  A
      GCTATGGAAGAAAAGCTTAAAGCGATGGAGGAGAAACTGAAGGC-3'
      CGATACCTTCTTTTCGAATTTCGCATCCTCCTCTTTGACTTCCGCTA-5'

M  E  E  K  L  K  K  M  E  E  K  L  K                    (SEQ ID NO:73)
SM100 5'-GATGGAGGAAAAGCTTAAGAAGATGGAAGAAAAGCTGAAA                   (SEQ ID NO:71)
SM101 3'    CCTCCTTTTCGAATTCTTCTACCTTCTTTTCGACTTT                   (SEQ ID NO:72)

W  M  E  E  K  L  K  K  M  E  E  K  L  K  W
      TGGATGGAGGAGAAACTCAAAAAGATGGAGGAAAAGCTTAAATG-3'
      ACCTACCTCCTCTTTGAGTTTTTCATCCTCCTTTTCGAATTTACCTA-5'
```

DNA from clones 82–4 and 84-H3 were digested to completion with Ear I enzyme, treated with phosphatase and gel purified. About 0.2 μg of this DNA were mixed with 1.0 μg of each of the oligonucleotide sets SM96 and SM97, SM98 and SM99 or SM100 and SM101 which had been previously kinased. The DNA and oligonucleotides were ligated overnight and then the ligation mixes transformed into *E. coli* strain DH5α. Tetracycline-resistant colonies were screened as described above for the presence of the oligonucleotide inserts. Clones were chosen for sequence analysis based on their restriction endonuclease digestion patterns.

oligonucleotide sequence encoding a base gene of 16 amino acids into the original vector pSK5. This oligonucleotide insert contained an unique Ear I site as in the previous base gene construct for use in subsequent insertion of oligonucleotides encoding one or more heptad repeats. The base gene also included a BspH I site at the 3' terminus. The overhanging ends of this cleavage site are designed to allow "in frame" protein fusions using Nco I overhanging ends. Therefore, gene segments can be multiplied using the duplication scheme described in FIG. 14. The overhanging ends of the oligonucleotide set allowed insertion into the unique Nco I and EcoR I sites of vector pSK5.

```
              M   E   E   K   M   K   K   L   E   E   K     (SEQ ID NO:82)
SM107   5'-CATGGAGGAGAAGATGAAAAAGCTCGAAGAGAAG               (SEQ ID NO:80)
SM106        3'-CTCCTCTTCTACTTTTTCGAGCTTCTCTTC              (SEQ ID NO:81)
              NCO I                      EAR I

M   K   V   M   K
         ATGAAGGTCATGAAGTGATAGGTACCG-3'
         TACTTCCAGTACTTCACTATCCATGGCTTAA-5'
              BSPH I         ASP 718
```

The oligonucleotide set was inserted into pSK5 vector as described in Strategy I above. The resultant plasmid was designated pSK34.

Oligonucleotide sets encoding 35 amino acid "segments" were ligated into the unique Ear I site of the pSK34 base gene using procedures as described above. In this case, the oligonucleotides were not gel or HPLC purified but simply annealed and used in the ligation reactions. The following oligonucleotide sets were used:

```
SEG3        L   E   E   K   M   K   A   M   E   D   K   M   K   W     (SEQ ID NO:85)
                                                                       (amino acids 8-28)
SM110   5'-GCTGGAAGAAAAGATGAAGGCTATGGAGGACAAGATGAAATGG                 (SEQ ID NO:83)
SM111   3'-CCTTCTTTTCTACTTCCGATACCTCCTGTTCTACTTTACC                    (SEQ ID NO:84)

L   E   E   K   M   K
            CTTGAGGAAAAGATGAAGAA-3'
         GAACTCCTTTTCTACTTCTTCGA-5'

SEG4        L   E   E   K   M   K   A   M   E   D   K   M   K   W     (SEQ ID NO:86)
                                                                       (amino acids 8-28)
SM112   5'-GCTCGAAGAAAGATGAAGGCAATGGAAGACAAAATGAAGTGG                  (SEQ ID NO:87)
SM113     3'-GCTTCTTTCTACTTCCGTTACCTTCTGTTTTACTTCACC                   (SEQ ID NO:88)

L   E   E   K   M   K
            CTTGAGGAGAAAATGAAGAA-3'
         GAACTCCTCTTTTACTTCTTCGA-5'

SEG 5       L   K   E   E   M   A   K   M   K   D   E   M   W   K     (SEQ ID NO:89)
                                                                       (amino acids 8-28)
SM114   5'-GCTCAAGGAGGAAATGGCTAAGATGAAAGACGAAATGTGGAAA                 (SEQ ID NO:90)
SM115     3'-GTTCCTCCTTTACCGATTCTACTTTCTGCTTTACACCTTT                  (SEQ ID NO:91)

L   K   E   E   M   K   K
            CTGAAAGAGGAAATGAAGAA
         GACTTTCTCCTTTACTTCTTCGA
```

Clones were screened for the presence of the inserted segments by restriction digestion followed by separation of fragments on 6% acrylamide gels. Correct insertion of oligonucleotides was confirmed by DNA sequence analyses. Clones containing segments 3, 4 and 5 respectively were designated pSKseg3, pSKseg4, and pSKseg5.

These "segment" clones were used in a duplication scheme as shown in FIG. 14. Ten μg of plasmid pSKseg3 were digested to completion with Nhe I and BspH I and the 1503 bp fragment isolated from an agarose gel using the Whatmann paper technique. Ten μg of plasmid pSKseg4 were digested to completion with Nhe I and Nco I and the 2109 bp band gel isolated. Equal amounts of these fragments were ligated and recombinants selected on tetracycline. Clones were screened by restriction digestions and their sequences confirmed. The resultant plasmid was designated pSKseg34.

pSKseg34 and pSKseg5 plasmid DNAs were digested, fragments isolated and ligated in a similar manner as above to create a plasmid containing DNA sequences encoding segment 5 fused to segments 3 and 4. This construct was designated pSKseg534 and encodes the following amino acid sequence:

SSP534 NH2-MEEKMKKLKEEMAKMKDEMWKLKEE (SEQ ID NO:92)

MKKLEEKMKVMEEKMKKLEEKMKAMEDKM

KWLEEKMKKLEEKMKVMEEKMKKLEEKMK

AMEDKMKWLEEKMKKLEEKMKVMK-COOH

Example 22
Construction of SSP Chimeric Genes for Expression in the Seeds of Plants To express the synthetic gene products described in Example 21 in plant seeds, the sequences were transferred to the seed promoter vectors CW108, CW109 or ML113 (FIG. 15). The vectors CW108 and ML113 contain the bean phaseolin promoter (from base +1 to base −494),and 1191 bases of the 3' sequences from bean phaseolin gene. CW109 contains the soybean β-conglycinin promoter (from base +1 to base −619) and the same 1191 bases of 3' sequences from the bean phaseolin gene. These vectors were designed to allow direct cloning of coding sequences into unique Nco I and Asp 718 sites. These vectors also provide sites (Hind III or Sal I) at the 5' and 3' ends to allow transfer of the promoter/coding region/3' sequences directly to appropriate binary vectors.

To insert the synthetic storage protein gene sequences, 10 μg of vector DNA were digested to completion with Asp 718 and Nco I restriction endonucleases. The linearized vector was purified via electrophoresis on a 1.0% agarose gel overnight electrophoresis at 15 volts. The fragment was collected by cutting the agarose in front of the band, inserting a 10×5 mm piece of Whatman 3 MM paper into the agarose and electrophoresing the fragment into the paper [Errington, (1990) Nucleic Acids Research, 18:17]. The fragment and buffer were spun out of the paper by centrifugation and the DNA in the ~100 μL was precipitated by adding 10 mg of tRNA, 10 μL of 3 M sodium acetate and 200 μL of ethanol. The precipitated DNA was washed twice with 70% ethanol and dried under vacuum. The fragment DNA was resuspended in 20 μL of water and a portion diluted 10-fold for use in ligation reactions.

Plasmid DNA (10 mg) from clone 3-5 (carrying the SSP3-5 coding sequence) and pSK534 (carrying the SSP534 coding sequence) was digested to completion with Asp 718 and Nco I restriction endonucleases. The digestion products were separated on an 18% polyacrylamide non-denaturing gel. Gel slices containing the desired fragments were cut from the gel and purified by inserting the gel slices into a 1% agarose gel and electrophoresing for 20 min at 100 volts. DNA fragments were collected on 10×5 mm pieces of Whatman 3 MM paper, the buffer and fragments spun out by centrifugation and the DNA precipitated with ethanol. The fragments were resuspended in 6 μL water. One microliter of the diluted vector fragment described above, 2 μL of 5×ligation buffer and 1 μL of T4 DNA ligase were added. The mixture was ligated overnight at 15°.

The ligation mixes were transformed into *E. coli* strain DH5α [supE44 del lacU169 (phi 80 lacZ del M15) hsdR17 recA1 endA1 gyr196 thi1 relA1] and ampicillin-resistant colonies selected. The clones were screened by restriction endonuclease digestion analyses of rapid plasmid DNAs and by DNA sequencing.

Example 23
Tobacco Plants Containing the Chimeric Genes Phaseolin Promoter/cts/lysC-M4 and β-conglycinin Promoter/SSP3-5

The binary vector pZS97 was used to transfer the chimeric SSP3-5 gene of Example 22 and the chimeric *E. coli* dapA and lysC-M4 genes of Example 4 to tobacco plants. Binary vector pZS97 (FIG. 6) is part of a binary Ti plasmid vector system [Bevan, (1984) *Nucl. Acids. Res.* 12:8711–8720] of *Agrobacterium tumefaciens*. The vector contains: (1) the chimeric gene nopaline synthase::neomycin phosphotransferase (nos::NPTII) as a selectable marker for transformed plant cells [Bevan et al., (1983) *Nature* 304:184–186], (2) the left and right borders of the T-DNA of the Ti plasmid [Bevan, (1984) Nucl. Acids. Res. 12:8711–8720], (3) the *E. coli* lacZ a-complementing segment [Viering et al., (1982) *Gene* 19:259–267] with a unique Sal I site(pSK97K) or unique Hind III site (pZS97) in the polylinker region, (4) the bacterial replication origin from the Pseudomonas plasmid pVS1 [Itoh et al., (1984) *Plasmid* 11:206–220], and (5) the bacterial β-lactamase gene as a selectable marker for transformed *A. tumefaciens*.

Plasmid pZS97 DNA was digested to completion with Hind III enzyme and the digested plasmid was gel purified. The Hind III digested pZS97 DNA was mixed with the Hind III digested and gel isolated chimeric SSP3-5 gene of Example 22, ligated, transformed and colonies selected on ampicillin.

The binary vector containing the chimeric gene was transferred by tri-parental mating [Ruvkin et al., (1981) *Nature* 289:85–88] to *Agrobacteruim* strain LBA4404/ pAL4404 [Hockema et al., (1983), *Nature* 303:179–180] selecting for carbenicillin resistance. Cultures of *Agrobacteruim* containing the binary vector was used to transform tobacco leaf disks [Horsch et al., (1985) *Science* 227:1229–1231]. Transgenic plants were regenerated in selective medium containing kanamycin.

Transformed tobacco plants containing the chimeric gene, β-conglycinin promoter/SSP3-5/phaseolin 3' region, were thus obtained. Two transformed lines, pSK44-3A and pSK44-9A, which carried a single site insertion of the SSP3-5 gene were identified based upon 3:1 segregation of the marker gene for kanamycin resistance. Progeny of the primary transformants, which were homozygous for the transgene, pSK44-3A-6 and pSK44-9A-5, were then identified based upon 4:0 segregation of the kanamycin resistance in seeds of these plants.

Similarly, transformed tobacco plants with the chimeric genes phaseolin 5' region/cts/lysC-M4/phaseolin 3' region and phaseolin 5' region/cts/ecodapA/phaseolin 3' region were obtained as described in Example 12. A transformed line, BT570-45A, which carried a single site insertion of the DHDPS and AK genes was identified based upon 3:1 segregation of the marker gene for kanamycin resistance. Progeny from the primary transformant which were homozygous for the transgene, BT570-45A-3 and BT570-45A-4, were then identified based upon 4:0 segregation of the kanamycin resistance in seeds of these plants.

To generate plants carrying all three chimeric genes genetic crosses were performed using the homozygous parents. Plants were grown to maturity in greenhouse conditions. Flowers to be used as male and female were selected one day before opening and older flowers on the inflorescence removed. For crossing, female flowers were chosen at the point just before opening when the anthers were not dehiscent. The corolla was opened on one side and the anthers removed. Male flowers were chosen as flowers which had opened on the same day and had dehiscent anthers shedding mature pollen. The anthers were removed and used to pollinate the pistils of the anther-stripped female flowers. The pistils were then covered with plastic tubing to prevent further pollination. The seed pods were allowed to develop and dry for 4–6 weeks and harvested. Two to three separate pods were recovered from each cross. The following crosses were performed:

| Male | X | Female |
|---|---|---|
| BT570-45A-3 | | pSK44-3A-6 |
| BT570-45A-4 | | pSK44-3A-6 |
| pSK44-3A-6 | | BT570-45A-4 |
| BT570-45A-5 | | pSK44-9A-5 |
| pSk44-9A-5 | | BT570-45A-5 |

Dried seed pods were broken open and seeds collected and pooled from each cross. Thirty seeds were counted out for each cross and for controls seeds from selfed flowers of each parent were used. Duplicate seed samples were hydrolyzed and assayed for total amino acid content as described in Example 8. The amount of increase in lysine as a percent of total seeds amino acids over wild type seeds, which contain 2.56% lysine, is presented in Table 16 along the copy number of each gene in the endosperm of the seed.

TABLE 17

| male | X | female | copy number AK & DHDPS genes | copy number SSP gene | lysine increase |
|---|---|---|---|---|---|
| BT570-45A | X | BT570-45A | 1* | 0 | 0 |
| pSK44-9A | X | pSK44-9A | 0 | 1* | 0.12 |
| pSK44-9A-5 | X | pSK44-9A-5 | 0 | 2 | 0.29 |
| pSK44-9A-5 | X | BT570-45A-5 | 1 | 1 | 0.6 |
| BT570-45A-5 | X | pSK44-9A-5 | 1 | 1 | 0.29 |
| pSK44-3A | X | pSK44-3A | 0 | 1* | 0.28 |
| pSK44-3A-6 | X | pSK44-3A-6 | 0 | 2 | 0.5 |
| pSK44-3A-6 | X | BT570-45A-4 | 1 | 1 | 0.62 |
| BT570-45A-3 | X | pSK44-3A-6 | 1 | 1 | 0.27 |
| BT570-45A-4 | X | pSK44-3A-6 | 1 | 1 | 0.29 |

*copy number is average in population of seeds

The results of these crosses demonstrate that the total lysine levels in seeds can be increased by the coordinate expression of the lysine biosynthesis genes and the high lysine protein SSP3-5. In seeds derived from hybrid tobacco plants, this synergism is strongest when the biosynthesis genes are derived from the female parent. It is expected that the lysine level would be further increased if the biosynthesis genes and the lysine-rich protein genes were all homozygous.

Example 24

Soybean Plants Containing the Chimeric Genes Phaseolin Promoter/cts/cordapA, Phaseolin Promoter/cts/lysC-M4 and Phaseolin Promoter/ SSP3-5

Transformed soybean plants that express the chimeric gene, phaseolin promoter/cts/cordapA/phaseolin 3' region and phaseolin promoter/cts/lysC-M4/phaseolin 3' region have been described in Example 19. Transformed soybean plants that express the chimeric gene, phaseolin promoter/ SSP3-5/phaseolin 3' region, were obtained by inserting the chimeric gene as an isolated Hind III fragment into an equivalent soybean transformation vector plasmid pML63 (FIG. 16) and carrying out transformation as described in Example 19.

Seeds from primary transformants were sampled by cutting small chips from the sides of the seeds away from the embryonic axis. The chips were assayed for GUS activity as described in Example 19 to determine which of the segregating seeds carried the transgenes. Half seeds were ground to meal and assayed for expression of SSP3-5 protein by Enzyme Linked ImmunoSorbent Assay (ELISA). Elisa was performed as follows:

A fusion protein of glutathione-S-transferase and the SSP3-5 gene product was generated through the use of the Pharmacia__pGEX GST Gene Fusion System (*Current Protocols in Molecular Biology*, Vol. 2, pp 16.7.1–8, (1989) John Wiley and Sons). The fusion protein was purified by affinity chromatography on glutathione agarose (Sigma) or glutathione sepharose (Pharmacia) beads, concentrated using Centricon 10__(Amicon) filters, and then subjected to SDS polyacrylamide electrophoresis (15% Acrylamide, 19:1 Acrylamide:Bis-acrylamide) for further purification. The gel was stained with Coomassie Blue for 30 min, destained in 50% Methanol, 10% Acetic Acid and the protein bands electroeluted using an Amicon__Centiluter Microelectroeluter (Paul T. Matsudaira ed., *A Practical Guide to Protein and Peptide Purification for Microsequencing*, Academic Press, Inc. New York, 1989). A second gel prepared and run in the same manner was stained in a non acetic acid containing stain [9 parts 0.1% Coomassie Blue G250 (Bio-Rad) in 50% methanol and 1 part Serva Blue (Serva, Westbury, N.Y.) in distilled water] for 1–2 h. The gel was briefly destained in 20% methanol, 3% glycerol for 0.5–1 h until the GST-SSP3-5 band was just barely visible. This band was excised from the gel and sent with the electroeluted material to Hazelton Laboratories for use as an antigen in immunizing a New Zealand Rabbit. A total of 1 mg of antigen was used (0.8 mg in gel, 0.2 mg in solution). Test bleeds were provided by Hazelton Laboratories every three weeks. The approximate titer was tested by western blotting of *E. coli* extracts from cells containing the SSP-3-5 gene under the control of the T7 promoter at different dilutions of protein and of serum.

IgG was isolated from the serum using a Protein A sepharose column. The IgG was coated onto microtiter plates at 5 µg per well. A separate portion of the IgG was biotinylated.

Aqueous extracts from transgenic plants were diluted and loaded into the wells usually starting with a sample containing 1 µg of total protein. The sample was diluted several more times to insure that at least one of the dilutions gave a result that was within the range of a standard curve generated on the same plate. The standard curve was generated using chemically synthesized SSP3-5 protein. The samples were incubated for 1 h at 37° and the plates washed. The biotinylated IgG was then added to the wells. The plate was incubated at 37° for 1 h and washed. Alkaline phosphatase conjugated to streptavidin was added to the wells, incubated at 37° for 1 h and washed. A substrate consisting of 1 mg/mL p nitrophenylphosphate in 1 M diethanolamine was added to the wells and the plates incubated at 37° for 1 h. A 5% EDTA stop solution was added to the wells and the absorbance read at 405 nm minus 650 nm reading. Transgenic soybean seeds contained 0.5 to 2.0% of water extractable protein as SSP3-5.

The remaining half seeds positive for GUS and SSP3-5 protein were planted and grown to maturity in greenhouse conditions. To determine homozygotes for the GUS phenotype, seed from these R1 plants were screened for segregation of GUS activity as above. Plants homozygous for the phaseolin/SSP3-5 gene are then crossed with homozygous transgenic soybeans expressing the *Corynebacterium* dapA gene product or expressing the *Corynebacterium* dapA gene product plus the *E. coli* lysC-M4 gene product.

As an preferred alternative to bringing the chimeric SSP gene and chimeric cordapA gene plus the *E. coli* lysC-M4 gene together via genetic crossing, a single soybean tranformation vector carrying all the genes can be constructed from the gene fragments described above and transformed into soybean as described in Example 19.

Example 25

Construction of Chimeric Genes for Expression of *Corynebacterium* DHDPS, lys$^r$-Corn DHDPS, *E. coli* AKIII-M4 and SSP3-5 Proteins in the Embryo and Endosperm of Transformed Corn The following chimeric genes were made for transformation into corn:

globulin 1 promoter/mcts/lysC-M4/NOS 3' region
globulin 1 promoter/mcts/cordapA/NOS 3 region
glutelin 2 promoter/mcts/lysC-M4/NOS 3' region
glutelin 2 promoter/mcts/cordapA/NOS 3' region
globulin 1 promoter/SSP3-5/globulin 1 3' region
glutelin 2 promoter/SSP3-5/10 kD 3' region
globulin 1 promoter/corn lys$^r$-mutant DHDPS gene/globulin 1 3' region
glutelin 2 promoter/corn lys$^r$-mutant DHDPS gene/10 kD 3' region The glutelin 2 promoter was cloned from corn genomic DNA using PCR with primers based on the published sequence [Reina et al. (1990) *Nucleic Acids Res.* 18:6426–64261]. The promoter fragment includes 1020 nucleotides upstream from the ATG translation start codon. An Nco I site was introduced via PCR at the ATG start site to allow for direct translational fusions. A BamH I site was introduced on the 5' end of the promoter. The 1.02 kb BamH I to Nco I promoter fragment was cloned into the BamH I to Nco I sites of the plant expression vector pML63 (see Example 24) replacing the 35S promoter to create vector pML90. This vector contains the glutelin 2 promoter linked to the GUS coding region and the NOS 3'.

The 10 kD zein 3' region was derived from a 10 kD zein gene clone generated by PCR from genomic DNA using oligonucleotide primers based on the published sequence [Kirihara et al. (1988) *Gene* 71:359–370]. The 3' region extends 940 nucleotides from the stop codon. Restriction endonuclease sites for Kpn I, Sma I and Xba I sites were added immediately following the TAG stop codon by oligonucleotide insertion to facilitate cloning. A Sma I to Hind III segment containing the 10 kD 3' region was isolated and ligated into Sma I and Hind III digested pML90 to replace the NOS 3' sequence with the 10 kD 3' region, thus creating plasmid pML103. pML103 contains the glutelin 2 promoter, an Nco I site at the ATG start codon of the GUS gene, Sma I and Xba I sites after the stop codon, and 940 nucleotides of the 10 kD zein 3' sequence.

The globulin 1 promoter and 3' sequences were isolated from a Clontech corn genomic DNA library using oligonucleotide probes based on the published sequence of the globulin 1 gene [Kriz et al. (1989) *Plant Physiol.* 91:636]. The cloned segment includes the promoter fragment extending 1078 nucleotides upstream from the ATG translation start codon, the entire globulin coding sequence including introns and the 3' sequence extending 803 bases from the translational stop. To allow replacement of the globulin 1 coding sequence with other coding sequences an Nco I site was introduced at the ATG start codon, and Kpn I and Xba I sites were introduced following the translational stop codon via PCR to create vector pCC50. There is a second Nco I site within the globulin 1 promoter fragment. The globulin 1 gene cassette is flanked by Hind III sites.

The plant amino acid biosynthetic enzymes are known to be localized in the chloroplasts and therefore are synthesized with a chloroplast targeting signal. Bacterial proteins such as DHDPS and AKIII have no such signal. A chloroplast transit sequence (cts) was therefore fused to the cordapA and lysC-M4 coding sequence in the chimeric genes described below. For corn the cts used was based on the the cts of the small subunit of ribulose 1,5-bisphosphate carboxylase from corn [Lebrun et al. (1987) *Nucleic Acids Res.* 15:4360] and is designated mcts to distinguish it from the soybean cts. The oligonucleotides SEQ ID NOS:94–99 were synthesized and used as described in Example 6.

To construct the chimeric gene:
globulin 1 promoter/mcts/lysC-M4/NOS 3' region an Nco I to Hpa I fragment containing the mcts/lysC-M4 coding sequence was isolated from plasmid pBT558 (see Example 6) and inserted into Nco I plus Sma I digested pCC50 creating plasmid pBT663.

To construct the chimeric gene:
globulin 1 promoter/mcts/cordapA/NOS 3 region an Nco I to Kpn I fragment containing the mcts/ecodapA coding sequence was isolated from plasmid pBT576 (see Example 6) and inserted into Nco I plus Kpn I digested pCC50 creating plasmid pBT662. Then the ecodapA coding sequence was replaced with the cordapA coding sequence as follows. An Afl II to Kpn I fragment containing the distal two thirds of the mcts fused to the cordapA coding sequence was inserted into Afl II to Kpn I digested pBT662 creating plasmid pBT677.

To construct the chimeric gene:
glutelin 2 promoter/mcts/lysC-M4/NOS 3' region an Nco I to Hpa I fragment containing the mcts/lysC-M4 coding sequence was isolated from plasmid pBT558 (see Example 6) and inserted into Nco I plus Sma I digested pML90 creating plasmid pBT580.

To construct the chimeric gene:
glutelin 2 promoter/mcts/cordapA/NOS 3' region an Nco I to Kpn I fragment containing the mcts/cordapA coding sequence was isolated from plasmid pBT677 and inserted into Nco I to Kpn I digested pML90, creating plasmid pBT679.

The chimeric genes:
globulin 1 promoter/mcts/lysC-M4/NOS 3' region and
globulin 1 promoter/mcts/cordapA/NOS 3 region were linked on one plasmid as follows. pBT677 was partially digested with Hind III and full-length linearized plasmid DNA was isolated. A Hind III fragment carrying the globulin 1 promoter/mcts/lysC-M4/NOS 3' region was isolated from pBT663 and ligated to the linearized pBT677 plasmid creating pBT680 (FIG. 17).

The chimeric genes:
glutelin 2 promoter/mcts/lysC-M4/NOS 3' region and
glutelin 2 promoter/mcts/cordapA/NOS 3' region were linked on one plasmid as follows. pBT580 was partially digested with Sal I and full-length linearized plasmid DNA was isolated. A Sal I fragment carrying the glutelin 2 promoter/mcts/cordapA/NOS 3' region was isolated from pBT679 and ligated to the linearized pBT580 plasmid creating pBT681 (FIG. 18).

To construct the chimeric gene:
glutelin 2 promoter/SSP3-5/10 kD 3' region the plasmid pML103 (above) containing the glutelin 2 promoter and 10 kD zein 3' region was cleaved at the Nco I and Sma I sites. The SSP3-5 coding region (Example 22) was isolated as an Nco I to blunt end fragment by cleaving with Xba I followed by filling in the sticky end using Klenow fragment of DNA polymerase, then cleaving with Nco I. The 193 base pair Nco I to blunt end fragment was ligated into the Nco I and Sma I cut pML103 to create pLH104 (FIG. 19).

To construct the chimeric gene:
globulin 1 promoter/SSP3-5/globulin 1 3' region the 193 base pair Nco I and Xba I fragment containing the SSP3-5 coding region (Example 22) was inserted into plasmid pCC50 (above) between the globulin 1 5' and 3' regions creating pLH105 (FIG. 20).

The corn DHDPS cDNA gene was cloned and sequenced previously [Frisch et al. (1991) *Mol Gen Genet* 228:287–293]. A mutation that rendered the protein insensitive to feedback inhibition by lysine was introduced into the gene. This mutation is a single nucleotide change that results in a single amino acid substitution in the protein; ala166 is changed to val. The lys$^r$ corn DHDPS gene was obtained from Dr. Burle Gengenbach at the University of Minnesota. An Nco I site was introduced at the translation start codon of the gene and a Kpn I site was introduced immediately following the translation stop codon of the gene via PCR using the following primers:

SEQ ID NO:106: 5'-ATTCCCCATG GTTTCGCCGA CGAAT

SEQ ID NO:107: 5'-CTCTCGGTAC CTAGTACCTA CTGATCAAC

To construct the chimeric gene:
globulin 1 promoter/lys$^r$ corn DHDPS gene/globulin 1 3' region the 1144 base pair Nco I and Kpn I fragment containing the lys$^r$ corn DHDPS gene was inserted into plasmid pCC50 (above) between the globulin 1 5' and 3' regions creating pBT739 (FIG. 21).

To construct the chimeric gene:
glutelin 2 promoter/lys$^r$ corn DHDPS gene/10 kD 3' region the 1144 base pair Nco I and Kpn I fragment containing the lys$^r$ corn DHDPS gene was inserted into a plasmid containing the glutelin 2 promoter and 10 kD zein 3' region creating plasmid pBT756 (FIG. 22).

Corn transformations were done as described in Examples 17 and 18 with the following exceptions:

1) Embryogenic cell culture development was as described in Example 17 except the exact culture used for bombardment was designated LH132.5.X, or LH132.6.X.

2) The selectable marker used for these experiments was either the 35S/bar gene from pDETRIC as described in Example 18 or 35S/Ac, a synthetic phosphinothricin-N-acetyltransferase (pat) gene under the control of the 35S promoter and 3' terminator/polyadenylation signal from Cauliflower Mosiac Virus [Eckes et.al., (1989) *J Cell Biochem Suppl* 13 D]

3) The bombardment parameters were as described for Example 17 and 18 except that the bombardments were performed as "tribombardments" by co-precipitating 1.5 μg of each of the DNAs (35S/bar or 35S/Ac, pBT681 and pLH104 or 35S/Ac, pbt680 and pLH105) onto the gold particles.

4) Selection of transgenic cell lines was as described for glufosinate selection as in Example 18 except that the tissue was placed on the selection media within 24 h after bombardment.

Example 26

Corn Plants Containing Chimeric Genes for Expression of *Corynebacterium* DHDPS and *E. coli* AKIII-M4 or lys$^r$-Corn DHDPS in the Embryo and Endosperm Corn was transformed as described in Example 25 with the chimeric genes:

globulin 1 promoter/mcts/cordapA/NOS 3 region along with or without globulin 1 promoter/mcts/lysC-M4/NOS 3' region; or glutelin 2 promoter/mcts/cordapA/NOS 3' region along with or without glutelin 2 promoter/mcts/lysC-M4/NOS 3' region.

Plants regenerated from transformed callus were analyzed for the presence of the intact transgenes via Southern blot or PCR. The plants were either selfed or outcrossed to an elite line to generate F1 seeds. Six to eight seeds were pooled and assayed for expression of the *Corynebacterium* DHDPS protein and the *E. coli* AKIII-M4 protein by western blot analysis. The free amino acid composition and total amino acid composition of the seeds were determined as described in previous examples.

Expression of the *Corynebacterium* DHDPS protein, driven by either the globulin 1 or glutelin 2 promoter, was observed in the corn seeds (Table 12). Expression of the *E. coli* AKIII-M4 protein, driven by the glutelin promoter was also observed in the corn seeds. Free lysine levels in the seeds increased from about 1.4% of free amino acids in control seeds to 15–27% in seeds of three different transformants expressing *Corynebacterium* DHDPS from the globulin 1 promoter. The increased free lysine, and a high level of saccharopine, indicative of lysine catabolism, were both localized to the embryo in seeds expressing *Corynebacterium* DHDPS from the globulin 1 promoter. No increase in free lysine was observed in seeds expressing *Corynebacterium* DHDPS from the glutelin 2 promoter with or without *E. coli* AKIII-M4. Lysine catabolism is expected to be much greater in the endosperm than the embryo and this probably prevents the accumulation of increased levels of lysine in seeds expressing *Corynebacterium* DHDPS plus *E. coli* AKIII-M4 from the glutelin 2 promoter.

Lysine normally represents about 2.3% of the seed amino acid content. It is therefore apparent from Table 12 that a 130% increase in lysine as a percent of total seed amino acids was found in seeds expressing *Corynebacterium* DHDPS from the globulin 1 promoter.

TABLE 12

| TRANSGENIC LINE | PROMOTER | WESTERN CORYNE. DHDPS | WESTERN E. COLI AKIII-M4 | % LYS OF FREE SEED AMINO ACIDS | % LYS OF TOTAL SEED AMINO ACIDS |
|---|---|---|---|---|---|
| 1088.1.2 x elite | globulin 1 | + | − | 15 | 3.6 |
| 1089.4.2 x elite | globulin 1 | + | − | 21 | 5.1 |
| 1099.2.1 x self | globulin 1 | + | − | 27 | 5.3 |
| 1090.2.1 x elite | glutelin 2 | + | − | 1.2 | 1.7 |
| 1092.2.1 x elite | glutelin 2 | + | + | 1.1 | 2.2 |

What is claimed is:

1. A plant comprising in its genome two foreign nucleotide sequences which cause seeds obtained from said plant to accumulate lysine at a level of at least ten percent higher than do seeds of a plant which do not comprise said foreign nucleotide sequences in its genome wherein the foreign nucleotide sequences each comprise a nucleic acid fragment, said fragments being different from each other, and said fragments each being operably linked to a plant seed specific promoter and said fragments are (a) a nucleic acid fragment encoding an aspartokinase which is substantially insensitive to lysine inhibition and further wherein said fragment is operably linked to a plant chloroplast transit sequence, and (b) a nucleic acid fragment encoding a dihydrodipicolinic acid synthase which is substantially insensitive to lysine inhibition and further wherein said fragment is operably linked to a plant chloroplast transit sequence.

2. The plant of claim 1 wherein said plant is selected from the group consisting of rapeseed, soybean, and corn.

3. Progeny plants from the plant of claim 1 wherein said progeny plants comprise in their genome the two foreign nucleotide sequences of the plant of claim 1.

4. Seeds obtained from the plants of claim 1 wherein said seeds comprise in their genome the two foreign nucleotide sequences of the plant of claim 1.

5. Seeds obtained from the progeny plants of claim 3.

6. The progeny plants of claim 3 wherein said plants are selected from the group consisting of rapeseed, soybean, and corn.

7. The seeds of claim 4 wherein wherein said plants are selected from the group consisting of rapeseed, soybean, and corn.

8. The seeds of claim 5 wherein said plants are selected from the group consisting of rapeseed, soybean, and corn.

* * * * *

SEQUENCE LISTING (1) GENERAL INFORMATION:

(iii) NUMBER OF SEQUENCES: 108

(2) INFORMATION FOR SEQ ID NO: 1:

(i) SEQUENCE CHARACTERISTICS:
      (A) LENGTH: 1350 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..1350

(xi) SEQUENCE DESCRIPTION: SEQ ID NO: 1:

```
ATG GCT GAA ATT GTT GTC TCC AAA TTT GGC GGT ACC AGC GTA GCT GAT        48
Met Ala Glu Ile Val Val Ser Lys Phe Gly Gly Thr Ser Val Ala Asp
 1               5                  10                  15

TTT GAC GCC ATG AAC CGC AGC GCT GAT ATT GTG CTT TCT GAT GCC AAC        96
Phe Asp Ala Met Asn Arg Ser Ala Asp Ile Val Leu Ser Asp Ala Asn
                20                  25                  30

GTG CGT TTA GTT GTC CTC TCG GCT TCT GCT GGT ATC ACT AAT CTG CTG       144
Val Arg Leu Val Val Leu Ser Ala Ser Ala Gly Ile Thr Asn Leu Leu
         35                  40                  45

GTC GCT TTA GCT GAA GGA CTG GAA CCT GGC GAG CGA TTC GAA AAA CTC       192
Val Ala Leu Ala Glu Gly Leu Glu Pro Gly Glu Arg Phe Glu Lys Leu
 50                  55                  60

GAC GCT ATC CGC AAC ATC CAG TTT GCC ATT CTG GAA CGT CTG CGT TAC       240
Asp Ala Ile Arg Asn Ile Gln Phe Ala Ile Leu Glu Arg Leu Arg Tyr
 65                  70                  75                  80

CCG AAC GTT ATC CGT GAA GAG ATT GAA CGT CTG CTG GAG AAC ATT ACT       288
Pro Asn Val Ile Arg Glu Glu Ile Glu Arg Leu Leu Glu Asn Ile Thr
                 85                  90                  95

GTT CTG GCA GAA GCG GCG GCG CTG GCA ACG TCT CCG GCG CTG ACA GAT       336
Val Leu Ala Glu Ala Ala Ala Leu Ala Thr Ser Pro Ala Leu Thr Asp
                100                 105                 110

GAG CTG GTC AGC CAC GGC GAG CTG ATG TCG ACC CTG CTG TTT GTT GAG       384
Glu Leu Val Ser His Gly Glu Leu Met Ser Thr Leu Leu Phe Val Glu
            115                 120                 125

ATC CTG CGC GAA CGC GAT GTT CAG GCA CAG TGG TTT GAT GTA CGT AAA       432
Ile Leu Arg Glu Arg Asp Val Gln Ala Gln Trp Phe Asp Val Arg Lys
        130                 135                 140

GTG ATG CGT ACC AAC GAC CGA TTT GGT CGT GCA GAG CCA GAT ATA GCC       480
Val Met Arg Thr Asn Asp Arg Phe Gly Arg Ala Glu Pro Asp Ile Ala
145                 150                 155                 160
```

```
GCG CTG GCG GAA CTG GCC GCG CTG CAG CTG CTC CCA CGT CTC AAT GAA       528
Ala Leu Ala Glu Leu Ala Ala Leu Gln Leu Leu Pro Arg Leu Asn Glu
            165                 170                 175

GGC TTA GTG ATC ACC CAG GGA TTT ATC GGT AGC GAA AAT AAA GGT CGT       576
Gly Leu Val Ile Thr Gln Gly Phe Ile Gly Ser Glu Asn Lys Gly Arg
        180                 185                 190

ACA ACG ACG CTT GGC CGT GGA GGC AGC GAT TAT ACG GCA GCC TTG CTG       624
Thr Thr Thr Leu Gly Arg Gly Gly Ser Asp Tyr Thr Ala Ala Leu Leu
        195                 200                 205

GCG GAG GCT TTA CAC GCA TCT CGT GTT GAT ATC TGG ACC GAC GTC CCG       672
Ala Glu Ala Leu His Ala Ser Arg Val Asp Ile Trp Thr Asp Val Pro
    210                 215                 220

GGC ATC TAC ACC ACC GAT CCA CGC GTA GTT TCC GCA GCA AAA CGC ATT       720
Gly Ile Tyr Thr Thr Asp Pro Arg Val Val Ser Ala Ala Lys Arg Ile
225                 230                 235                 240

GAT GAA ATC GCG TTT GCC GAA GCG GCA GAG ATG GCA ACT TTT GGT GCA       768
Asp Glu Ile Ala Phe Ala Glu Ala Ala Glu Met Ala Thr Phe Gly Ala
                245                 250                 255

AAA GTA CTG CAT CCG GCA ACG TTG CTA CCC GCA GTA CGC AGC GAT ATC       816
Lys Val Leu His Pro Ala Thr Leu Leu Pro Ala Val Arg Ser Asp Ile
            260                 265                 270

CCG GTC TTT GTC GGC TCC AGC AAA GAC CCA CGC GCA GGT GGT ACG CTG       864
Pro Val Phe Val Gly Ser Ser Lys Asp Pro Arg Ala Gly Gly Thr Leu
        275                 280                 285

GTG TGC AAT AAA ACT GAA AAT CCG CCG CTG TTC CGC GCT CTG GCG CTT       912
Val Cys Asn Lys Thr Glu Asn Pro Pro Leu Phe Arg Ala Leu Ala Leu
        290                 295                 300

CGT CGC AAT CAG ACT CTG CTC ACT TTG CAC AGC CTG AAT ATG CTG CAT       960
Arg Arg Asn Gln Thr Leu Leu Thr Leu His Ser Leu Asn Met Leu His
305                 310                 315                 320

TCT CGC GGT TTC CTC GCG GAA GTT TTC GGC ATC CTC GCG CGG CAT AAT      1008
Ser Arg Gly Phe Leu Ala Glu Val Phe Gly Ile Leu Ala Arg His Asn
                325                 330                 335

ATT TCG GTA GAC TTA ATC ACC ACG TCA GAA GTG AGC GTG GCA TTA ACC      1056
Ile Ser Val Asp Leu Ile Thr Thr Ser Glu Val Ser Val Ala Leu Thr
            340                 345                 350

CTT GAT ACC ACC GGT TCA ACC TCC ACT GGC GAT ACG TTG CTG ACG CAA      1104
Leu Asp Thr Thr Gly Ser Thr Ser Thr Gly Asp Thr Leu Leu Thr Gln
        355                 360                 365

TCT CTG CTG ATG GAG CTT TCC GCA CTG TGT CGG GTG GAG GTG GAA GAA      1152
Ser Leu Leu Met Glu Leu Ser Ala Leu Cys Arg Val Glu Val Glu Glu
        370                 375                 380

GGT CTG GCG CTG GTC GCG TTG ATT GGC AAT GAC CTG TCA AAA GCC TGC      1200
Gly Leu Ala Leu Val Ala Leu Ile Gly Asn Asp Leu Ser Lys Ala Cys
385                 390                 395                 400

GCC GTT GGC AAA GAG GTA TTC GGC GTA CTG GAA CCG TTC AAC ATT CGC      1248
Ala Val Gly Lys Glu Val Phe Gly Val Leu Glu Pro Phe Asn Ile Arg
                405                 410                 415

ATG ATT TGT TAT GGC GCA TCC AGC CAT AAC CTG TGC TTC CTG GTG CCC      1296
Met Ile Cys Tyr Gly Ala Ser Ser His Asn Leu Cys Phe Leu Val Pro
            420                 425                 430

GGC GAA GAT GCC GAG CAG GTG GTG CAA AAA CTG CAT AGT AAT TTG TTT      1344
Gly Glu Asp Ala Glu Gln Val Val Gln Lys Leu His Ser Asn Leu Phe
        435                 440                 445

GAG TAA                                                              1350
Glu  *
    450

(2) INFORMATION FOR SEQ ID NO: 2:
```

```
    (i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 2:

GATCCATGGC TGAAATTGTT GTCTCCAAAT TTGGCG                                 36

(2) INFORMATION FOR SEQ ID NO: 3:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

GTACCGCCAA ATTTGGAGAC AACAATTTCA GCCATG                                 36

(2) INFORMATION FOR SEQ ID NO: 4:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

CCCGGGCCAT GGCTACAGGT TTAACAGCTA AGACCGGAGT AGAGCACT                    48

(2) INFORMATION FOR SEQ ID NO: 5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

GATATCGAAT TCTCATTATA GAACTCCAGC TTTTTTC                                37

(2) INFORMATION FOR SEQ ID NO: 6:

(i) SEQUENCE CHARACTERISTICS:
        (A) LENGTH: 917 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY:  CDS
        (B) LOCATION:  3..911

(xi) SEQUENCE DESCRIPTION: SEQ ID NO: 6:

CC ATG GCT ACA GGT TTA ACA GCT AAG ACC GGA GTA GAG CAC TTC GGC          47
   Met Ala Thr Gly Leu Thr Ala Lys Thr Gly Val Glu His Phe Gly
   1               5                   10                  15

ACC GTT GGA GTA GCA ATG GTT ACT CCA TTC ACG GAA TCC GGA GAC ATC         95
```

```
Thr Val Gly Val Ala Met Val Thr Pro Phe Thr Glu Ser Gly Asp Ile
            20                  25                  30

GAT ATC GCT GCT GGC CGC GAA GTC GCG GCT TAT TTG GTT GAT AAG GGC    143
Asp Ile Ala Ala Gly Arg Glu Val Ala Ala Tyr Leu Val Asp Lys Gly
            35                  40                  45

TTG GAT TCT TTG GTT CTC GCG GGC ACC ACT GGT GAA TCC CCA ACG ACA    191
Leu Asp Ser Leu Val Leu Ala Gly Thr Thr Gly Glu Ser Pro Thr Thr
            50                  55                  60

ACC GCC GCT GAA AAA CTA GAA CTG CTC AAG GCC GTT CGT GAG GAA GTT    239
Thr Ala Ala Glu Lys Leu Glu Leu Leu Lys Ala Val Arg Glu Glu Val
65                  70                  75

GGG GAT CGG GCG AAG CTC ATC GCC GGT GTC GGA ACC AAC AAC ACG CGG    287
Gly Asp Arg Ala Lys Leu Ile Ala Gly Val Gly Thr Asn Asn Thr Arg
80                  85                  90                  95

ACA TCT GTG GAA CTT GCG GAA GCT GCT GCT TCT GCT GGC GCA GAC GGC    335
Thr Ser Val Glu Leu Ala Glu Ala Ala Ala Ser Ala Gly Ala Asp Gly
                    100                 105                 110

CTT TTA GTT GTA ACT CCT TAT TAC TCC AAG CCG AGC CAA GAG GGA TTG    383
Leu Leu Val Val Thr Pro Tyr Tyr Ser Lys Pro Ser Gln Glu Gly Leu
            115                 120                 125

CTG GCG CAC TTC GGT GCA ATT GCT GCA GCA ACA GAG GTT CCA ATT TGT    431
Leu Ala His Phe Gly Ala Ile Ala Ala Ala Thr Glu Val Pro Ile Cys
            130                 135                 140

CTC TAT GAC ATT CCT GGT CGG TCA GGT ATT CCA ATT GAG TCT GAT ACC    479
Leu Tyr Asp Ile Pro Gly Arg Ser Gly Ile Pro Ile Glu Ser Asp Thr
            145                 150                 155

ATG AGA CGC CTG AGT GAA TTA CCT ACG ATT TTG GCG GTC AAG GAC GCC    527
Met Arg Arg Leu Ser Glu Leu Pro Thr Ile Leu Ala Val Lys Asp Ala
160                 165                 170                 175

AAG GGT GAC CTC GTT GCA GCC ACG TCA TTG ATC AAA GAA ACG GGA CTT    575
Lys Gly Asp Leu Val Ala Ala Thr Ser Leu Ile Lys Glu Thr Gly Leu
            180                 185                 190

GCC TGG TAT TCA GGC GAT GAC CCA CTA AAC CTT GTT TGG CTT GCT TTG    623
Ala Trp Tyr Ser Gly Asp Asp Pro Leu Asn Leu Val Trp Leu Ala Leu
            195                 200                 205

GGC GGA TCA GGT TTC ATT TCC GTA ATT GGA CAT GCA GCC CCC ACA GCA    671
Gly Gly Ser Gly Phe Ile Ser Val Ile Gly His Ala Ala Pro Thr Ala
            210                 215                 220

TTA CGT GAG TTG TAC ACA AGC TTC GAG GAA GGC GAC CTC GTC CGT GCG    719
Leu Arg Glu Leu Tyr Thr Ser Phe Glu Glu Gly Asp Leu Val Arg Ala
            225                 230                 235

CGG GAA ATC AAC GCC AAA CTA TCA CCG CTG GTA GCT GCC CAA GGT CGC    767
Arg Glu Ile Asn Ala Lys Leu Ser Pro Leu Val Ala Ala Gln Gly Arg
240                 245                 250                 255

TTG GGT GGA GTC AGC TTG GCA AAA GCT GCT CTG CGT CTG CAG GGC ATC    815
Leu Gly Gly Val Ser Leu Ala Lys Ala Ala Leu Arg Leu Gln Gly Ile
            260                 265                 270

AAC GTA GGA GAT CCT CGA CTT CCA ATT ATG GCT CCA AAT GAG CAG GAA    863
Asn Val Gly Asp Pro Arg Leu Pro Ile Met Ala Pro Asn Glu Gln Glu
            275                 280                 285

CTT GAG GCT CTC CGA GAA GAC ATG AAA AAA GCT GGA GTT CTA TAA TGAG   917
Leu Glu Ala Leu Arg Glu Asp Met Lys Lys Ala Gly Val Leu  *
            290                 295                 300
```

(2) INFORMATION FOR SEQ ID NO: 7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 7:

CTTCCCGTGA CCATGGGCCA TC                                               22

(2) INFORMATION FOR SEQ ID NO: 8:

(i) SEQUENCE CHARACTERISTICS:
            (A) LENGTH: 75 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 8:

CATGGCTGGC TTCCCCACGA GGAAGACCAA CAATGACATT ACCTCCATTG CTAGCAACGG       60

TGGAAGAGTA CAATG                                                       75

(2) INFORMATION FOR SEQ ID NO: 9:

(i) SEQUENCE CHARACTERISTICS:
            (A) LENGTH: 75 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 9:

CATGCATTGT ACTCTTCCAC CGTTGCTAGC AATGGAGGTA ATGTCATTGT TGGTCTTCCT       60

CGTGGGGAAG CCAGC                                                       75

(2) INFORMATION FOR SEQ ID NO: 10:

(i) SEQUENCE CHARACTERISTICS:
            (A) LENGTH: 90 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 10:

CATGGCTTCC TCAATGATCT CCTCCCCAGC TGTTACCACC GTCAACCGTG CCGGTGCCGG       60

CATGGTTGCT CCATTCACCG GCCTCAAAAG                                       90

(2) INFORMATION FOR SEQ ID NO: 11:

(i) SEQUENCE CHARACTERISTICS:
            (A) LENGTH: 90 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 11:

CATGCTTTTG AGGCCGGTGA ATGGAGCAAC CATGCCGGCA CCGGCACGGT TGACGGTGGT       60

AACAGCTGGG GAGGAGATCA TTGAGGAAGC                                       90

(2) INFORMATION FOR SEQ ID NO: 12:

(i) SEQUENCE CHARACTERISTICS:

```
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

CCGGTTTGCT GTAATAGGTA CCA                                         23

(2) INFORMATION FOR SEQ ID NO: 13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

AGCTTGGTAC CTATTACAGC AAACCGGCAT G                                31

(2) INFORMATION FOR SEQ ID NO: 14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

GCTTCCTCAA TGATCTCCTC CCCAGCT                                     27

(2) INFORMATION FOR SEQ ID NO: 15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

CATTGTACTC TTCCACCGTT GCTAGCAA                                    28

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..20
        (D) OTHER INFORMATION: /product= "synthetic
            oligonucleotide"
            /standard_name= "SM
            70"

(xi) SEQUENCE DESCRIPTION: SEQ ID NO: 16:

CTGACTCGCT GCGCTCGGTC                                             20
```

(2) INFORMATION FOR SEQ ID NO: 17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..24
        (D) OTHER INFORMATION: /product= "synthetic
            oligonucleotide"
            /standard_name= "SM
            71"

(xi) SEQUENCE DESCRIPTION: SEQ ID NO: 17:

TATTTTCTCC TTACGCATCT GTGC                                    24

(2) INFORMATION FOR SEQ ID NO: 18:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..27
        (D) OTHER INFORMATION: /product= "synthetic
            oligonucleotide"
            /standard_name= "SM
            78"

(xi) SEQUENCE DESCRIPTION: SEQ ID NO: 18:

TTCATCGATA GGCGACCACA CCCGTCC                                27

(2) INFORMATION FOR SEQ ID NO: 19:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..27
        (D) OTHER INFORMATION: /product= "synthetic
            oligonucleotide"
            /standard_name= "SM
            79"

(xi) SEQUENCE DESCRIPTION: SEQ ID NO: 19:

AATATCGATG CCACGATGCG TCCGGCG                                27

(2) INFORMATION FOR SEQ ID NO: 20:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

```
        (ix) FEATURE:
              (A) NAME/KEY:  misc_feature
              (B) LOCATION:  1..55
              (D) OTHER INFORMATION:  /product= "synthetic
                    oligonucleotide"
                    /standard_name= "SM
                    81"

(xi) SEQUENCE DESCRIPTION: SEQ ID NO: 20:

CATGGAGGAG AAGATGAAGG CGATGGAAGA GAAGATGAAG GCGTGATAGG TACCG            55

(2) INFORMATION FOR SEQ ID NO: 21:

(i) SEQUENCE CHARACTERISTICS:
              (A) LENGTH: 55 base pairs
              (B) TYPE: nucleic acid
              (C) STRANDEDNESS: single
              (D) TOPOLOGY: linear (ii) MOLECULE TYPE: DNA (genomic)

(ix) FEATURE:
              (A) NAME/KEY:  misc_feature
              (B) LOCATION:  1..55
              (D) OTHER INFORMATION:  /product= "synthetic
                    oligonucleotide"
                    /standard_name= "SM
                    80"

(xi) SEQUENCE DESCRIPTION: SEQ ID NO: 21:

AATTCGGTAC CTATCACGCC TTCATCTTCT CTTCCATCGC CTTCATCTTC TCCTC            55

(2) INFORMATION FOR SEQ ID NO: 22:

(i) SEQUENCE CHARACTERISTICS:
              (A) LENGTH: 14 amino acids
              (B) TYPE: amino acid
              (C) STRANDEDNESS: unknown
              (D) TOPOLOGY: unknown (ii) MOLECULE TYPE: protein (ix) FEATURE:
              (A) NAME/KEY:  Protein
              (B) LOCATION:  1..14
              (D) OTHER INFORMATION:   /label= name
                    /note= "base gene
                    [(SSP5)2]"

(xi) SEQUENCE DESCRIPTION: SEQ ID NO: 22:

Met Glu Glu Lys Met Lys Ala Met Glu Glu Lys Met Lys Ala
1               5                   10

(2) INFORMATION FOR SEQ ID NO: 23:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: DNA (genomic)

(ix) FEATURE:
              (A) NAME/KEY:  misc_feature
              (B) LOCATION:  1..21
              (D) OTHER INFORMATION:  /product=
                    "synthetic
                    oligonucleotide"
                    /standard_name= "SM
                    84"
```

```
    (xi) SEQUENCE DESCRIPTION: SEQ ID NO: 23:

GATGGAGGAG AAGATGAAGG C                                              21

(2) INFORMATION FOR SEQ ID NO: 24:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY:  misc_feature
        (B) LOCATION:  1..21
        (D) OTHER INFORMATION:   /product= "synthetic
            oligonucleotide"
            /standard_name= "SM
            85"

(xi) SEQUENCE DESCRIPTION: SEQ ID NO: 24:

ATCGCCTTCA TCTTCTCCTC C                                              21

(2) INFORMATION FOR SEQ ID NO: 25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY:  misc_feature
        (B) LOCATION:  1..21
        (D) OTHER INFORMATION:   /product= "synthetic
            oligonucleotide"
            /standard_name= "SM
            82"

(xi) SEQUENCE DESCRIPTION: SEQ ID NO: 25:

GATGGAGGAG AAGCTGAAGG C                                              21

(2) INFORMATION FOR SEQ ID NO: 26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY:  misc_feature
        (B) LOCATION:  1..21
        (D) OTHER INFORMATION:   /product= "synthetic
            oligonucleotide"
            /standard_name= "SM
            83"

(xi) SEQUENCE DESCRIPTION: SEQ ID NO: 26:

ATCGCCTTCA GCTTCTCCTC C                                              21

(2) INFORMATION FOR SEQ ID NO: 27:

(i) SEQUENCE CHARACTERISTICS:
        (A) LENGTH: 7 amino acids
        (B) TYPE: amino acid
```

```
        (C) STRANDEDNESS: unknown
        (D) TOPOLOGY: unknown (ii) MOLECULE TYPE: protein (xi) SEQUENCE DESCRIPTION: SEQ ID NO: 27:

Met Glu Glu Lys Leu Lys Ala
1               5

(2) INFORMATION FOR SEQ ID NO: 28:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 28:

Met Glu Glu Lys Met Lys Ala
1               5

(2) INFORMATION FOR SEQ ID NO: 29:

(i) SEQUENCE CHARACTERISTICS:
        (A) LENGTH: 160 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: E. coli
        (G) CELL TYPE: DH5 alpha (vii) IMMEDIATE SOURCE:
        (B) CLONE: C15

(ix) FEATURE:
        (A) NAME/KEY:  CDS
        (B) LOCATION:  2..151
        (D) OTHER INFORMATION:   /function= "synthetic
            storage protein"
            /product= "protein"
            /gene= "ssp"
            /standard_name=
            "5.7.7.7.7.7.5"

(xi) SEQUENCE DESCRIPTION: SEQ ID NO: 29:

C ATG GAG GAG AAG ATG AAG GCG ATG GAG GAG AAG CTG AAG GCG ATG          46
  Met Glu Glu Lys Met Lys Ala Met Glu Glu Lys Leu Lys Ala Met
  1               5                  10                  15

GAG GAG AAG CTG AAG GCG ATG GAG GAG AAG CTG AAG GCG ATG GAG GAG        94
Glu Glu Lys Leu Lys Ala Met Glu Glu Lys Leu Lys Ala Met Glu Glu
                20                  25                  30

AAG CTG AAG GCG ATG GAG GAG AAG CTG AAG GCG ATG GAA GAG AAG ATG       142
Lys Leu Lys Ala Met Glu Glu Lys Leu Lys Ala Met Glu Glu Lys Met
            35                  40                  45

AAG GCG TGATAGGTAC CG                                                 160
Lys Ala
        50

(2) INFORMATION FOR SEQ ID NO: 30:

(i) SEQUENCE CHARACTERISTICS:
        (A) LENGTH: 49 amino acids
        (B) TYPE: amino acid
        (D) TOPOLOGY: linear
```

(ii) MOLECULE TYPE: protein (xi) SEQUENCE DESCRIPTION: SEQ ID NO: 30:

```
Met Glu Glu Lys Met Lys Ala Met Glu Glu Lys Leu Lys Ala Met Glu
 1               5                  10                  15

Glu Lys Leu Lys Ala Met Glu Glu Lys Leu Lys Ala Met Glu Glu Lys
                20                  25                  30

Leu Lys Ala Met Glu Glu Lys Leu Lys Ala Met Glu Glu Lys Met Lys
            35                  40                  45

Ala
```

(2) INFORMATION FOR SEQ ID NO: 31:

(i) SEQUENCE CHARACTERISTICS:
        (A) LENGTH: 160 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: E. coli
        (G) CELL TYPE: DH5 alpha (vii) IMMEDIATE SOURCE:
        (B) CLONE: C20

(ix) FEATURE:
        (A) NAME/KEY: CDS
        (B) LOCATION: 2..151
        (D) OTHER INFORMATION: /function= "synthetic
            storage protein"
            /product= "protein"
            /gene= "ssp"
            /standard_name=
            "5.7.7.7.7.7.5"

(xi) SEQUENCE DESCRIPTION: SEQ ID NO: 31:

```
C ATG GAG GAG AAG ATG AAG GCG ATG GAG GAG AAG CTG AAG GCG ATG        46
  Met Glu Glu Lys Met Lys Ala Met Glu Glu Lys Leu Lys Ala Met
   1               5                  10                  15

GAG GAG AAG CTG AAG GCG ATG GAG GAG AAG CTG AAG GCG ATG GAG GAG       94
Glu Glu Lys Leu Lys Ala Met Glu Glu Lys Leu Lys Ala Met Glu Glu
                20                  25                  30

AAG CTG AAG GCG ATG GAG GAG AAG CTG AAG GCG ATG GAA GAG AAG ATG      142
Lys Leu Lys Ala Met Glu Glu Lys Leu Lys Ala Met Glu Glu Lys Met
            35                  40                  45

AAG GCG TGATAGGTAC CG                                                 160
Lys Ala
        50
```

(2) INFORMATION FOR SEQ ID NO: 32:

(i) SEQUENCE CHARACTERISTICS:
        (A) LENGTH: 49 amino acids
        (B) TYPE: amino acid
        (D) TOPOLOGY: linear (ii) MOLECULE TYPE: protein (xi) SEQUENCE DESCRIPTION: SEQ ID NO: 32:

```
Met Glu Glu Lys Met Lys Ala Met Glu Glu Lys Leu Lys Ala Met Glu
 1               5                  10                  15

Glu Lys Leu Lys Ala Met Glu Glu Lys Leu Lys Ala Met Glu Glu Lys
                20                  25                  30
```

```
Leu Lys Ala Met Glu Glu Lys Leu Lys Ala Met Glu Glu Lys Met Lys
        35                  40                  45
Ala
```

(2) INFORMATION FOR SEQ ID NO: 33:

(i) SEQUENCE CHARACTERISTICS:
        (A) LENGTH: 139 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: E. coli
        (G) CELL TYPE: DH5 alpha (vii) IMMEDIATE SOURCE:
        (B) CLONE: C30

(ix) FEATURE:
        (A) NAME/KEY: CDS
        (B) LOCATION: 2..130
        (D) OTHER INFORMATION: /function= "synthetic
            storage protein"
            /product= "protein"
            /gene= "ssp"
            /standard_name=
            "5.7.7.7.7.5"

(xi) SEQUENCE DESCRIPTION: SEQ ID NO: 33:

```
C ATG GAG GAG AAG ATG AAG GCG ATG GAG GAG AAG CTG AAG GCG ATG          46
  Met Glu Glu Lys Met Lys Ala Met Glu Glu Lys Leu Lys Ala Met
   1               5                  10                  15

GAG GAG AAG CTG AAG GCG ATG GAG GAG AAG CTG AAG GCG ATG GAG GAG        94
Glu Glu Lys Leu Lys Ala Met Glu Glu Lys Leu Lys Ala Met Glu Glu
                20                  25                  30

AAG CTG AAG GCG ATG GAA GAG AAG ATG AAG GCG TGATAGGTAC CG             139
Lys Leu Lys Ala Met Glu Glu Lys Met Lys Ala
                35                  40
```

(2) INFORMATION FOR SEQ ID NO: 34:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO: 34:

```
Met Glu Glu Lys Met Lys Ala Met Glu Glu Lys Leu Lys Ala Met Glu
 1               5                  10                  15

Glu Lys Leu Lys Ala Met Glu Glu Lys Leu Lys Ala Met Glu Glu Lys
                20                  25                  30

Leu Lys Ala Met Glu Glu Lys Met Lys Ala
                35                  40
```

(2) INFORMATION FOR SEQ ID NO: 35:

(i) SEQUENCE CHARACTERISTICS:
        (A) LENGTH: 97 base pairs
        (B) TYPE: nucleic acid
        (C) STRANDEDNESS: double
        (D) TOPOLOGY: linear (ii) MOLECULE TYPE: DNA (genomic)

```
    (vi) ORIGINAL SOURCE:
         (B) STRAIN: E. coli
         (G) CELL TYPE: DH5 alpha (vii) IMMEDIATE SOURCE:
         (B) CLONE: D16

(ix) FEATURE:
         (A) NAME/KEY: CDS
         (B) LOCATION: 2..88
         (D) OTHER INFORMATION: /function= "synthetic
             storage protein"
             /product= "protein"
             /gene= "ssp"
             /standard_name=
             "5.5.5.5"

(xi) SEQUENCE DESCRIPTION: SEQ ID NO: 35:

C ATG GAG GAG AAG ATG AAG GCG ATG GAG GAG AAG ATG AAG GCG ATG             46
  Met Glu Glu Lys Met Lys Ala Met Glu Glu Lys Met Lys Ala Met
  1               5                  10                 15

GAG GAG AAG ATG AAG GCG ATG GAA GAG AAG ATG AAG GCG TGATAGGTAC            95
Glu Glu Lys Met Lys Ala Met Glu Glu Lys Met Lys Ala
                20                  25

CG                                                                        97

(2) INFORMATION FOR SEQ ID NO: 36:

(i) SEQUENCE CHARACTERISTICS:
         (A) LENGTH: 28 amino acids
         (B) TYPE: amino acid
         (D) TOPOLOGY: linear (ii) MOLECULE TYPE: protein (xi) SEQUENCE DESCRIPTION: SEQ ID NO: 36:

Met Glu Glu Lys Met Lys Ala Met Glu Glu Lys Met Lys Ala Met Glu
1               5                  10                  15

Glu Lys Met Lys Ala Met Glu Glu Lys Met Lys Ala
            20                  25

(2) INFORMATION FOR SEQ ID NO: 37:

(i) SEQUENCE CHARACTERISTICS:
         (A) LENGTH: 118 base pairs
         (B) TYPE: nucleic acid
         (C) STRANDEDNESS: double
         (D) TOPOLOGY: linear (ii) MOLECULE TYPE: DNA (genomic)

(vi) ORIGINAL SOURCE:
         (B) STRAIN: E. coli
         (G) CELL TYPE: DH5 alpha (vii) IMMEDIATE SOURCE:
         (B) CLONE: D20

(ix) FEATURE:
         (A) NAME/KEY: CDS
         (B) LOCATION: 2..109
         (D) OTHER INFORMATION: /function= "synthetic
             storage protein"
             /product= "protein"
             /gene= "ssp"
             /standard_name=
             "5.5.5.5"

(xi) SEQUENCE DESCRIPTION: SEQ ID NO: 37:

C ATG GAG GAG AAG ATG AAG GCG ATG GAG GAG AAG ATG AAG GCG ATG             46
```

```
    Met Glu Glu Lys Met Lys Ala Met Glu Glu Lys Met Lys Ala Met
    1               5                  10                  15

GAG GAG AAG ATG AAG GCG ATG GAG GAG AAG ATG AAG GCG ATG GAA GAG        94
Glu Glu Lys Met Lys Ala Met Glu Glu Lys Met Lys Ala Met Glu Glu
                20                  25                  30

AAG ATG AAG GCG TGATAGGTAC CG                                         118
Lys Met Lys Ala
            35

(2) INFORMATION FOR SEQ ID NO: 38:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO: 38:

Met Glu Glu Lys Met Lys Ala Met Glu Glu Lys Met Lys Ala Met Glu
1               5                  10                  15

Glu Lys Met Lys Ala Met Glu Glu Lys Met Lys Ala Met Glu Glu Lys
            20                  25                  30

Met Lys Ala
        35

(2) INFORMATION FOR SEQ ID NO: 39:

(i) SEQUENCE CHARACTERISTICS:
        (A) LENGTH: 97 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: E. coli
        (G) CELL TYPE: DH5 alpha (vii) IMMEDIATE SOURCE:
        (B) CLONE: D33

(ix) FEATURE:
        (A) NAME/KEY: CDS
        (B) LOCATION: 2..88
        (D) OTHER INFORMATION: /function= "synthetic
            storage protein"
            /product= "protein"
            /gene= "ssp"
            /standard_name=
            "5.5.5.5"

(xi) SEQUENCE DESCRIPTION: SEQ ID NO: 39:

C ATG GAG GAG AAG ATG AAG GCG ATG GAG GAG AAG ATG AAG GCG ATG         46
  Met Glu Glu Lys Met Lys Ala Met Glu Glu Lys Met Lys Ala Met
  1               5                  10                  15

GAG GAG AAG ATG AAG GCG ATG GAA GAG AAG ATG AAG GCG TGATAGGTAC        95
Glu Glu Lys Met Lys Ala Met Glu Glu Lys Met Lys Ala
                20                  25

CG                                                                    97

(2) INFORMATION FOR SEQ ID NO: 40:

(i) SEQUENCE CHARACTERISTICS:
        (A) LENGTH: 28 amino acids
        (B) TYPE: amino acid
        (D) TOPOLOGY: linear
```

(ii) MOLECULE TYPE: protein (xi) SEQUENCE DESCRIPTION: SEQ ID NO: 40:

Met Glu Glu Lys Met Lys Ala Met Glu Glu Lys Met Lys Ala Met Glu
1               5                   10                  15

Glu Lys Met Lys Ala Met Glu Glu Lys Met Lys Ala
            20                  25

(2) INFORMATION FOR SEQ ID NO: 41:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..21
        (D) OTHER INFORMATION: /product= "synthetic
            oligonucleotide"
            /standard_name= "SM
        86"

(xi) SEQUENCE DESCRIPTION: SEQ ID NO: 41:

GATGGAGGAG AAGCTGAAGA A                                            21

(2) INFORMATION FOR SEQ ID NO: 42:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..21
        (D) OTHER INFORMATION: /product= "synthetic
            oligonucleotide"
            /standard_name= "SM
        87"

(xi) SEQUENCE DESCRIPTION: SEQ ID NO: 42:

ATCTTCTTCA GCTTCTCCTC C                                            21

(2) INFORMATION FOR SEQ ID NO: 43:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..21
        (D) OTHER INFORMATION: /product= "synthetic
            oligonucleotide"
            /standard_name= "SM
        88"

(xi) SEQUENCE DESCRIPTION: SEQ ID NO: 43:

GATGGAGGAG AAGCTGAAGT G                                            21

(2) INFORMATION FOR SEQ ID NO: 44:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..21
        (D) OTHER INFORMATION: /product= "synthetic
            oligonucleotide"
            /standard_name= "SM
            89"

(xi) SEQUENCE DESCRIPTION: SEQ ID NO: 44:

ATCCACTTCA GCTTCTCCTC C                                              21

(2) INFORMATION FOR SEQ ID NO: 45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..21
        (D) OTHER INFORMATION: /product= "synthetic
            oligonucleotide"
            /standard_name= "SM
            90"

(xi) SEQUENCE DESCRIPTION: SEQ ID NO: 45:

GATGGAGGAG AAGATGAAGA A                                              21

(2) INFORMATION FOR SEQ ID NO: 46:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..21
        (D) OTHER INFORMATION: /product= "synthetic
            oligonucleotide"
            /standard_name= "SM
            91"

(xi) SEQUENCE DESCRIPTION: SEQ ID NO: 46:

ATCTTCTTCA TCTTCTCCTC C                                              21

(2) INFORMATION FOR SEQ ID NO: 47:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
            (A) NAME/KEY: misc_feature
            (B) LOCATION: 1..21
            (D) OTHER INFORMATION: /product= "synthetic
                oligonucleotide"
                /standard_name= "SM
                92"

(xi) SEQUENCE DESCRIPTION: SEQ ID NO: 47:

GATGGAGGAG AAGATGAAGT G                                          21

(2) INFORMATION FOR SEQ ID NO: 48:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..21
        (D) OTHER INFORMATION: /product= "synthetic
            oligonucleotide"
            /standard_name= "SM
            93"

(xi) SEQUENCE DESCRIPTION: SEQ ID NO: 48:

ATCCACTTCA TCTTCTCCTC C                                          21

(2) INFORMATION FOR SEQ ID NO: 49:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 49:

Met Glu Glu Lys Leu Lys Lys
1               5

(2) INFORMATION FOR SEQ ID NO: 50:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 50:

Met Glu Glu Lys Leu Lys Trp
1               5

(2) INFORMATION FOR SEQ ID NO: 51:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 51:

Met Glu Glu Lys Met Lys Lys
1               5

(2) INFORMATION FOR SEQ ID NO: 52:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 52:

Met Glu Glu Lys Met Lys Trp
1               5

(2) INFORMATION FOR SEQ ID NO: 53:

(i) SEQUENCE CHARACTERISTICS:
        (A) LENGTH: 160 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: E. coli
        (G) CELL TYPE: DH5 alpha (vii) IMMEDIATE SOURCE:
        (B) CLONE: 82-4

(ix) FEATURE:
        (A) NAME/KEY:  CDS
        (B) LOCATION:  2..151
        (D) OTHER INFORMATION:   /function= "synthetic
            storage protein
            /product= "protein"
            /gene= "ssp"
            /standard_name=
            "7.7.7.7.7.7.5"

(xi) SEQUENCE DESCRIPTION: SEQ ID NO: 53:

C ATG GAG GAG AAG CTG AAG GCG ATG GAG GAG AAG CTG AAG GCG ATG       46
  Met Glu Glu Lys Leu Lys Ala Met Glu Glu Lys Leu Lys Ala Met
  1               5                  10                  15

GAG GAG AAG CTG AAG GCG ATG GAG GAG AAG CTG AAG GCG ATG GAG GAG     94
Glu Glu Lys Leu Lys Ala Met Glu Glu Lys Leu Lys Ala Met Glu Glu
                20                  25                  30

AAG CTG AAG GCG ATG GAG GAG AAG CTG AAG GCG ATG GAA GAG AAG ATG    142
Lys Leu Lys Ala Met Glu Glu Lys Leu Lys Ala Met Glu Glu Lys Met
            35                  40                  45

AAG GCG TGATAGGTAC CG                                               160
Lys Ala
        50

(2) INFORMATION FOR SEQ ID NO: 54:

(i) SEQUENCE CHARACTERISTICS:
        (A) LENGTH: 49 amino acids
        (B) TYPE: amino acid
        (D) TOPOLOGY: linear (ii) MOLECULE TYPE: protein (xi) SEQUENCE DESCRIPTION: SEQ ID NO: 54:

```
Met Glu Glu Lys Leu Lys Ala Met Glu Glu Lys Leu Lys Ala Met Glu
  1               5                  10                  15

Glu Lys Leu Lys Ala Met Glu Glu Lys Leu Lys Ala Met Glu Glu Lys
                20                  25                  30

Leu Lys Ala Met Glu Glu Lys Leu Lys Ala Met Glu Glu Lys Met Lys
            35                  40                  45

Ala
```

(2) INFORMATION FOR SEQ ID NO: 55:

(i) SEQUENCE CHARACTERISTICS:
        (A) LENGTH: 97 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: E. coli
        (G) CELL TYPE: DH5 alpha (vii) IMMEDIATE SOURCE:
        (B) CLONE: 84-H3

(ix) FEATURE:
        (A) NAME/KEY: CDS
        (B) LOCATION: 2..88
        (D) OTHER INFORMATION: /function= "synthetic
            storage protein
            /product= "protein"
            /gene= "ssp"
            /standard_name=
            "5.5.5.5"

(xi) SEQUENCE DESCRIPTION: SEQ ID NO: 55:

```
C ATG GAG GAG AAG ATG AAG GCG ATG GAG GAG AAG ATG AAG GCG ATG        46
  Met Glu Glu Lys Met Lys Ala Met Glu Glu Lys Met Lys Ala Met
    1               5                  10                  15

GAG GAG AAG ATG AAG GCG ATG GAA GAG AAG ATG AAG GCG TGATAGGTAC       95
Glu Glu Lys Met Lys Ala Met Glu Glu Lys Met Lys Ala
                20                  25

CG                                                                   97
```

(2) INFORMATION FOR SEQ ID NO: 56:

(i) SEQUENCE CHARACTERISTICS:
        (A) LENGTH: 28 amino acids
        (B) TYPE: amino acid
        (D) TOPOLOGY: linear (ii) MOLECULE TYPE: protein (xi) SEQUENCE DESCRIPTION: SEQ ID NO: 56:

```
Met Glu Glu Lys Met Lys Ala Met Glu Glu Lys Met Lys Ala Met Glu
  1               5                  10                  15

Glu Lys Met Lys Ala Met Glu Glu Lys Met Lys Ala
                20                  25
```

(2) INFORMATION FOR SEQ ID NO: 57:

(i) SEQUENCE CHARACTERISTICS:
        (A) LENGTH: 97 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
             (B) STRAIN: E. coli
             (G) CELL TYPE: DH5 alpha (vii) IMMEDIATE SOURCE:
             (B) CLONE: 86-H23

(ix) FEATURE:
             (A) NAME/KEY: CDS
             (B) LOCATION: 2..88
             (D) OTHER INFORMATION: /function= "synthetic
                 storage protein
                 /product= "protein"
                 /gene= "ssp"
                 /standard_name=
                 "5.8.8.5"

(xi) SEQUENCE DESCRIPTION: SEQ ID NO: 57:

```
C ATG GAG GAG AAG ATG AAG GCG ATG GAG GAG AAG CTG AAG AAG ATG          46
  Met Glu Glu Lys Met Lys Ala Met Glu Glu Lys Leu Lys Lys Met
   1               5                  10                  15

GAG GAG AAG CTG AAG AAG ATG GAA GAG AAG ATG AAG GCG TGATAGGTAC         95
Glu Glu Lys Leu Lys Lys Met Glu Glu Lys Met Lys Ala
             20                  25

CG                                                                     97
```

(2) INFORMATION FOR SEQ ID NO: 58:

(i) SEQUENCE CHARACTERISTICS:
            (A) LENGTH: 28 amino acids
            (B) TYPE: amino acid
            (D) TOPOLOGY: linear (ii) MOLECULE TYPE: protein (xi) SEQUENCE DESCRIPTION: SEQ ID NO: 58:

```
Met Glu Glu Lys Met Lys Ala Met Glu Glu Lys Leu Lys Lys Met Glu
 1               5                  10                  15

Glu Lys Leu Lys Lys Met Glu Glu Lys Met Lys Ala
            20                  25
```

(2) INFORMATION FOR SEQ ID NO: 59:

(i) SEQUENCE CHARACTERISTICS:
            (A) LENGTH: 112 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (B) STRAIN: E. coli
            (G) CELL TYPE: DH5 alpha (vii) IMMEDIATE SOURCE:
            (B) CLONE: 88-2

(ix) FEATURE:
            (A) NAME/KEY: CDS
            (B) LOCATION: 2..103
            (D) OTHER INFORMATION: /function= "synthetic
                storage protein
                /product= "protein"
                /gene= "ssp"
                /standard_name=
                "5.9.9.9.5"

(xi) SEQUENCE DESCRIPTION: SEQ ID NO: 59:

```
C ATG GAG GAG AAG ATG AAG GCG AAG AAG CTG AAG TGG ATG GAG GAG           46
  Met Glu Glu Lys Met Lys Ala Lys Lys Leu Lys Trp Met Glu Glu
   1               5                  10                  15

AAG CTG AAG TGG ATG GAG GAG AAG CTG AAG TGG ATG GAA GAG AAG ATG         94
Lys Leu Lys Trp Met Glu Glu Lys Leu Lys Trp Met Glu Glu Lys Met
            20                  25                  30

AAG GCG TGATAGGTAC CG                                                   112
Lys Ala
```

(2) INFORMATION FOR SEQ ID NO: 60:

(i) SEQUENCE CHARACTERISTICS:
        (A) LENGTH: 33 amino acids
        (B) TYPE: amino acid
        (D) TOPOLOGY: linear (ii) MOLECULE TYPE: protein (xi) SEQUENCE DESCRIPTION: SEQ ID NO: 60:

```
Met Glu Glu Lys Met Lys Ala Lys Lys Leu Lys Trp Met Glu Lys
 1               5                  10                  15

Leu Lys Trp Met Glu Glu Lys Leu Lys Trp Met Glu Glu Lys Met Lys
            20                  25                  30

Ala
```

(2) INFORMATION FOR SEQ ID NO: 61:

(i) SEQUENCE CHARACTERISTICS:
        (A) LENGTH: 118 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: E. coli
        (G) CELL TYPE: DH5 alpha (vii) IMMEDIATE SOURCE:
        (B) CLONE: 90-H8

(ix) FEATURE:
        (A) NAME/KEY: CDS
        (B) LOCATION: 2..109
        (D) OTHER INFORMATION: /function= "synthetic
            storage protein
            /product= "protein"
            /gene= "ssp"
            /standard_name=
            "5.10.10.10.5"

(xi) SEQUENCE DESCRIPTION: SEQ ID NO: 61:

```
C ATG GAG GAG AAG ATG AAG GCG ATG GAG GAG AAG ATG AAG AAG ATG           46
  Met Glu Glu Lys Met Lys Ala Met Glu Glu Lys Met Lys Lys Met
   1               5                  10                  15

GAG GAG AAG ATG AAG AAG ATG GAG GAG AAG ATG AAG AAG ATG GAA GAG         94
Glu Glu Lys Met Lys Lys Met Glu Glu Lys Met Lys Lys Met Glu Glu
            20                  25                  30

AAG ATG AAG GCG TGATAGGTAC CG                                           118
Lys Met Lys Ala
            35
```

(2) INFORMATION FOR SEQ ID NO: 62:

(i) SEQUENCE CHARACTERISTICS:
        (A) LENGTH: 35 amino acids
        (B) TYPE: amino acid (D) TOPOLOGY: linear (ii) MOLECULE TYPE: protein (xi) SEQUENCE DESCRIPTION: SEQ ID NO: 62:

Met Glu Glu Lys Met Lys Ala Met Glu Glu Lys Met Lys Met Glu
  1               5                  10                  15

Glu Lys Met Lys Lys Met Glu Glu Lys Met Lys Lys Met Glu Glu Lys
                20                  25                  30

Met Lys Ala
        35

(2) INFORMATION FOR SEQ ID NO: 63:

(i) SEQUENCE CHARACTERISTICS:
            (A) LENGTH: 97 base pairs
            (B) TYPE: nucleic acid
            (C) STRANDEDNESS: double
            (D) TOPOLOGY: linear (ii) MOLECULE TYPE: DNA (genomic)

(vi) ORIGINAL SOURCE:
            (B) STRAIN: E. coli
            (G) CELL TYPE: DH5 alpha (vii) IMMEDIATE SOURCE:
            (B) CLONE: 92-2

(ix) FEATURE:
            (A) NAME/KEY: CDS
            (B) LOCATION: 2..88
            (D) OTHER INFORMATION: /function= "synthetic
                storage protein
                /product= "protein"
                /gene= "ssp"
                /standard_name=
                "5.11.11.5"

(xi) SEQUENCE DESCRIPTION: SEQ ID NO: 63:

C ATG GAG GAG AAG ATG AAG GCG ATG GAG GAG AAG ATG AAG TGG ATG        46
  Met Glu Glu Lys Met Lys Ala Met Glu Glu Lys Met Lys Trp Met
    1               5                  10                  15

GAG GAG AAG ATG AAG TGG ATG GAA GAG AAG ATG AAG GCG TGATAGGTAC       95
Glu Glu Lys Met Lys Trp Met Glu Glu Lys Met Lys Ala
                20                  25

CG                                                                   97

(2) INFORMATION FOR SEQ ID NO: 64:

(i) SEQUENCE CHARACTERISTICS:
            (A) LENGTH: 28 amino acids
            (B) TYPE: amino acid
            (D) TOPOLOGY: linear (ii) MOLECULE TYPE: protein (xi) SEQUENCE DESCRIPTION: SEQ ID NO: 64:

Met Glu Glu Lys Met Lys Ala Met Glu Glu Lys Met Lys Trp Met Glu
  1               5                  10                  15

Glu Lys Met Lys Trp Met Glu Glu Lys Met Lys Ala
                20                  25

(2) INFORMATION FOR SEQ ID NO: 65:

(i) SEQUENCE CHARACTERISTICS:
            (A) LENGTH: 84 base pairs
            (B) TYPE: nucleic acid

```
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..84
            (D) OTHER INFORMATION: /product= "synthetic
                oligonucleotide"
                /standard_name= "SM
                96"

(xi) SEQUENCE DESCRIPTION: SEQ ID NO: 65:

GATGGAGGAA AAGATGAAGG CGATGGAGGA GAAAATGAAA GCTATGGAGG AAAAGATGAA      60

AGCGATGGAG GAGAAAATGA AGGC                                            84

(2) INFORMATION FOR SEQ ID NO: 66:

(i) SEQUENCE CHARACTERISTICS:
            (A) LENGTH: 84 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 1..84
            (D) OTHER INFORMATION: /product= "synthetic
                oligonucleotide"
                /standard_name= "SM
                97"

(xi) SEQUENCE DESCRIPTION: SEQ ID NO: 66:

ATCGCCTTCA TTTTCTCCTC CATCGCTTTC ATCTTTTCCT CCATAGCTTT CATTTTCTCC      60

TCCATCGCCT TCATCTTTTC CTCC                                            84

(2) INFORMATION FOR SEQ ID NO: 67:

(i) SEQUENCE CHARACTERISTICS:
            (A) LENGTH: 28 amino acids
            (B) TYPE: amino acid
            (C) STRANDEDNESS: unknown
            (D) TOPOLOGY: unknown (ii) MOLECULE TYPE: protein (ix) FEATURE:
            (A) NAME/KEY: Protein
            (B) LOCATION: 1..28
            (D) OTHER INFORMATION: /label= name
                /note= "(SSP 5)4"

(xi) SEQUENCE DESCRIPTION: SEQ ID NO: 67:

Met Glu Glu Lys Met Lys Ala Met Glu Glu Lys Met Lys Ala Met Glu
1               5                   10                  15

Glu Lys Met Lys Ala Met Glu Glu Lys Met Lys Ala
            20                  25

(2) INFORMATION FOR SEQ ID NO: 68:

(i) SEQUENCE CHARACTERISTICS:
            (A) LENGTH: 84 base pairs
            (B) TYPE: nucleic acid
            (C) STRANDEDNESS: single
            (D) TOPOLOGY: linear (ii) MOLECULE TYPE: DNA (genomic)
```

```
    (ix) FEATURE:
        (A) NAME/KEY:  misc_feature
        (B) LOCATION:  1..84
        (D) OTHER INFORMATION:  /product= "synthetic
            oligonucleotide"
            /standard_name= "SM
            98"

(xi) SEQUENCE DESCRIPTION: SEQ ID NO: 68:

GATGGAGGAA AAGCTGAAAG CGATGGAGGA GAAACTCAAG GCTATGGAAG AAAAGCTTAA      60

AGCGATGGAG GAGAAACTGA AGGC                                            84

(2) INFORMATION FOR SEQ ID NO: 69:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY:  misc_feature
        (B) LOCATION:  1..84
        (D) OTHER INFORMATION:  /product= "synthetic
            oligonucleotide"
            /standard_name= "SM
            99"

(xi) SEQUENCE DESCRIPTION: SEQ ID NO: 69:

ATCGCCTTCA GTTTCTCCTC CTACGCTTTA AGCTTTTCTT CCATAGCCTT GAGTTTCTCC      60

TCCATCGCTT TCAGCTTTTC CTCC                                            84

(2) INFORMATION FOR SEQ ID NO: 70:

(i) SEQUENCE CHARACTERISTICS:
        (A) LENGTH: 28 amino acids
        (B) TYPE: amino acid
        (C) STRANDEDNESS: unknown
        (D) TOPOLOGY: unknown (ii) MOLECULE TYPE: protein (ix) FEATURE:
        (A) NAME/KEY:  Protein
        (B) LOCATION:  1..28
        (D) OTHER INFORMATION:  /label= name
            /note= "(SSP 7)4"

(xi) SEQUENCE DESCRIPTION: SEQ ID NO: 70:

Met Glu Glu Lys Leu Lys Ala Met Glu Glu Lys Leu Lys Ala Met Glu
1               5                   10                  15

Glu Lys Leu Lys Ala Met Glu Glu Lys Leu Lys Ala
            20                  25

(2) INFORMATION FOR SEQ ID NO: 71:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY:  misc_feature
        (B) LOCATION:  1..84
```

(D) OTHER INFORMATION: /product= "synthetic
            oligonucleotide"
            /standard_name= "SM
            100"

(xi) SEQUENCE DESCRIPTION: SEQ ID NO: 71:

GATGGAGGAA AAGCTTAAGA AGATGGAAGA AAAGCTGAAA TGGATGGAGG AGAAACTCAA    60

AAAGATGGAG GAAAAGCTTA AATG                                          84

(2) INFORMATION FOR SEQ ID NO: 72:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..84
        (D) OTHER INFORMATION: /product= "synthetic
            oligonucleotide"
            /standard_name= "SM
            101"

(xi) SEQUENCE DESCRIPTION: SEQ ID NO: 72:

ATCCATTTAA GCTTTTCCTC CTACTTTTTG AGTTTCTCCT CCATCCATTT CAGCTTTTCT    60

TCCATCTTCT TAAGCTTTTC CTCC                                          84

(2) INFORMATION FOR SEQ ID NO: 73:

(i) SEQUENCE CHARACTERISTICS:
        (A) LENGTH: 28 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO: 73:

Met Glu Glu Lys Leu Lys Lys Met Glu Glu Lys Leu Lys Trp Met Glu
1               5                   10                  15

Glu Lys Leu Lys Lys Met Glu Glu Lys Leu Lys Trp
            20                  25

(2) INFORMATION FOR SEQ ID NO: 74:

(i) SEQUENCE CHARACTERISTICS:
        (A) LENGTH: 243 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: E. coli
        (G) CELL TYPE: DH5 alpha (vii) IMMEDIATE SOURCE:
        (B) CLONE: 2-9

(ix) FEATURE:
        (A) NAME/KEY: CDS
        (B) LOCATION: 2..235
        (D) OTHER INFORMATION: /function= "synthetic
            storage protein
            /product= "protein"

/gene= "ssp"
/standard_name=
"7.7.7.7.7.7.8.9.8.9.5"

(xi) SEQUENCE DESCRIPTION: SEQ ID NO: 74:

| | | | | | | | | | | | | | | | | |
|---|---|---|---|---|---|---|---|---|---|---|---|---|---|---|---|---|
| C | ATG | GAG | GAG | AAG | CTG | AAG | GCG | ATG | GAG | GAG | AAG | CTG | AAG | GCG | ATG | 46 |
| | Met | Glu | Glu | Lys | Leu | Lys | Ala | Met | Glu | Glu | Lys | Leu | Lys | Ala | Met | |
| | 1 | | | | 5 | | | | | 10 | | | | | 15 | |

| | | | | | | | | | | | | | | | |
|---|---|---|---|---|---|---|---|---|---|---|---|---|---|---|---|
| GAG | GAG | AAG | CTG | AAG | GCG | ATG | GAG | GAG | AAG | CTG | AAG | GCG | ATG | GAG | GAG | 94 |
| Glu | Glu | Lys | Leu | Lys | Ala | Met | Glu | Glu | Lys | Leu | Lys | Ala | Met | Glu | Glu |
| | | | 20 | | | | | 25 | | | | | 30 | | |

| | | | | | | | | | | | | | | | |
|---|---|---|---|---|---|---|---|---|---|---|---|---|---|---|---|
| AAG | CTG | AAG | GCG | ATG | GAG | GAG | AAG | CTG | AAG | GCG | ATG | GAG | GAA | AAG | CTT | 142 |
| Lys | Leu | Lys | Ala | Met | Glu | Glu | Lys | Leu | Lys | Ala | Met | Glu | Glu | Lys | Leu |
| | | 35 | | | | | 40 | | | | | 45 | | | |

| | | | | | | | | | | | | | | | |
|---|---|---|---|---|---|---|---|---|---|---|---|---|---|---|---|
| AAG | AAG | ATG | GAA | GAA | AAG | CTG | AAA | TGG | ATG | GAG | GAG | AAA | CTC | AAA | AAG | 190 |
| Lys | Lys | Met | Glu | Glu | Lys | Leu | Lys | Trp | Met | Glu | Glu | Lys | Leu | Lys | Lys |
| | 50 | | | | | 55 | | | | | 60 | | | | |

| | | | | | | | | | | | | |
|---|---|---|---|---|---|---|---|---|---|---|---|---|
| ATG | GAG | GAA | AAG | CTT | AAA | TGG | ATG | GAA | GAG | AAG | ATG | AAG | GCG | TGATAGGT | 242 |
| Met | Glu | Glu | Lys | Leu | Lys | Trp | Met | Glu | Glu | Lys | Met | Lys | Ala | | |
| 65 | | | | | 70 | | | | | 75 | | | | | |

C                                                                                    243

(2) INFORMATION FOR SEQ ID NO: 75:

(i) SEQUENCE CHARACTERISTICS:
        (A) LENGTH: 77 amino acids
        (B) TYPE: amino acid
        (D) TOPOLOGY: linear (ii) MOLECULE TYPE: protein (xi) SEQUENCE DESCRIPTION: SEQ ID NO: 75:

Met Glu Glu Lys Leu Lys Ala Met Glu Glu Lys Leu Lys Ala Met Glu
 1               5                  10                  15

Glu Lys Leu Lys Ala Met Glu Glu Lys Leu Lys Ala Met Glu Glu Lys
            20                  25                  30

Leu Lys Ala Met Glu Glu Lys Leu Lys Ala Met Glu Glu Lys Leu Lys
            35                  40                  45

Lys Met Glu Glu Lys Leu Lys Trp Met Glu Glu Lys Leu Lys Lys Met
     50                  55                  60

Glu Glu Lys Leu Lys Trp Met Glu Glu Lys Met Lys Ala
 65                 70                  75

(2) INFORMATION FOR SEQ ID NO: 76:

(i) SEQUENCE CHARACTERISTICS:
        (A) LENGTH: 175 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: E. coli
        (G) CELL TYPE: DH5 alpha (vii) IMMEDIATE SOURCE:
        (B) CLONE: 5-1

(ix) FEATURE:
        (A) NAME/KEY: CDS
        (B) LOCATION: 2..172
        (D) OTHER INFORMATION: /function= "synthetic
            storage protein
            /product= "protein"

```
                /gene= "ssp"
                /standard_name=
                "5.5.5.7.7.7.7.5"

(xi) SEQUENCE DESCRIPTION: SEQ ID NO: 76:

C ATG GAG GAG AAG ATG AAG GCG ATG GAG GAG AAG ATG AAG GCG ATG           46
  Met Glu Glu Lys Met Lys Ala Met Glu Glu Lys Met Lys Ala Met
   1               5                  10                  15

GAG GAG AAG ATG AAG GCG ATG GAG GAA AAG CTG AAA GCG ATG GAG GAG         94
Glu Glu Lys Met Lys Ala Met Glu Glu Lys Leu Lys Ala Met Glu Glu
                 20                  25                  30

AAA CTC AAG GCT ATG GAA GAA AAG CTT AAA GCG ATG GAG GAG AAA CTG        142
Lys Leu Lys Ala Met Glu Glu Lys Leu Lys Ala Met Glu Glu Lys Leu
            35                  40                  45

AAG GCC ATG GAA GAG AAG ATG AAG GCG TGATAG                             175
Lys Ala Met Glu Glu Lys Met Lys Ala
        50                  55

(2) INFORMATION FOR SEQ ID NO: 77:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO: 77:

Met Glu Glu Lys Met Lys Ala Met Glu Glu Lys Met Lys Ala Met Glu
 1               5                  10                  15

Glu Lys Met Lys Ala Met Glu Glu Lys Leu Lys Ala Met Glu Glu Lys
                 20                  25                  30

Leu Lys Ala Met Glu Glu Lys Leu Lys Ala Met Glu Glu Lys Leu Lys
            35                  40                  45

Ala Met Glu Glu Lys Met Lys Ala
        50                  55

(2) INFORMATION FOR SEQ ID NO: 78:

(i) SEQUENCE CHARACTERISTICS:
        (A) LENGTH: 187 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: E. coli
        (G) CELL TYPE: DH5 alpha (ix) FEATURE:
        (A) NAME/KEY:  CDS
        (B) LOCATION:  3..173
        (D) OTHER INFORMATION:   /function= "synthetic
            storage protein
            /product= "protein"
            /gene= "ssp"
            /standard_name=
            "SSP-3-5"

(xi) SEQUENCE DESCRIPTION: SEQ ID NO: 78:

CC ATG GAG GAG AAG CTG AAG GCG ATG GAG GAG AAG CTG AAG GCG ATG          47
   Met Glu Glu Lys Leu Lys Ala Met Glu Glu Lys Leu Lys Ala Met
    1               5                  10                  15

GAG GAG AAG CTG AAG GCG ATG GAG GAG AAG CTG AAG GCG ATG GAG GAG         95
Glu Glu Lys Leu Lys Ala Met Glu Glu Lys Leu Lys Ala Met Glu Glu
```

147 148

-continued

```
                   20                  25                  30
AAG CTG AAG GCG ATG GAG GAG AAG CTG AAG GCG ATG GAG GAA AAG ATG       143
Lys Leu Lys Ala Met Glu Glu Lys Leu Lys Ala Met Glu Glu Lys Met
                35                  40                  45

AAG GCG ATG GAA GAG AAG ATG AAG GCG TGATAGGTAC CGAATTC                187
Lys Ala Met Glu Glu Lys Met Lys Ala
        50                  55
```

(2) INFORMATION FOR SEQ ID NO: 79:

(i) SEQUENCE CHARACTERISTICS:
      (A) LENGTH: 56 amino acids
      (B) TYPE: amino acid
      (D) TOPOLOGY: linear (ii) MOLECULE TYPE: protein (xi) SEQUENCE DESCRIPTION: SEQ ID NO: 79:

```
Met Glu Glu Lys Leu Lys Ala Met Glu Glu Lys Leu Lys Ala Met Glu
 1               5                  10                  15

Glu Lys Leu Lys Ala Met Glu Glu Lys Leu Lys Ala Met Glu Glu Lys
                20                  25                  30

Leu Lys Ala Met Glu Glu Lys Leu Lys Ala Met Glu Glu Lys Met Lys
                35                  40                  45

Ala Met Glu Glu Lys Met Lys Ala
                50                  55
```

(2) INFORMATION FOR SEQ ID NO: 80:

(i) SEQUENCE CHARACTERISTICS:
      (A) LENGTH: 61 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: 1..61
      (D) OTHER INFORMATION: /product= "synthetic
          oligonucleotide"
          /standard_name= "SM
          107"

(xi) SEQUENCE DESCRIPTION: SEQ ID NO: 80:

```
CATGGAGGAG AAGATGAAAA AGCTCGAAGA GAAGATGAAG GTCATGAAGT GATAGGTACC     60
G                                                                     61
```

(2) INFORMATION FOR SEQ ID NO: 81:

(i) SEQUENCE CHARACTERISTICS:
      (A) LENGTH: 61 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: misc_feature
      (B) LOCATION: 1..61
      (D) OTHER INFORMATION: /product= "synthetic
          ligonucleotide"
          /standard_name= "SM
          106"

(xi) SEQUENCE DESCRIPTION: SEQ ID NO: 81:

```
AATTCGGTAC CTATCACTTC ATGACCTTCA TCTTCTCTTC GAGCTTTTTC ATCTTCTCCT    60

C                                                                   61
```

(2) INFORMATION FOR SEQ ID NO: 82:

(i) SEQUENCE CHARACTERISTICS:
        (A) LENGTH: 16 amino acids
        (B) TYPE: amino acid
        (C) STRANDEDNESS: unknown
        (D) TOPOLOGY: unknown (ii) MOLECULE TYPE: protein (ix) FEATURE:
        (A) NAME/KEY: Protein
        (B) LOCATION: 1..16
        (D) OTHER INFORMATION: /label= name
           /note= "pSK34 base
           gene"

(xi) SEQUENCE DESCRIPTION: SEQ ID NO: 82:

```
Met Glu Glu Lys Met Lys Lys Leu Glu Glu Lys Met Lys Val Met Lys
1               5                   10                  15
```

(2) INFORMATION FOR SEQ ID NO: 83:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..63
        (D) OTHER INFORMATION: /product= "synthetic
           oligonucleotide"
           /standard_name= "SM
           110"

(xi) SEQUENCE DESCRIPTION: SEQ ID NO: 83:

```
GCTGGAAGAA AAGATGAAGG CTATGGAGGA CAAGATGAAA TGGCTTGAGG AAAAGATGAA    60

GAA                                                                 63
```

(2) INFORMATION FOR SEQ ID NO: 84:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..63
        (D) OTHER INFORMATION: /product= "synthetic
           oligonucleotide"
           /standard_name= "SM
           111"

(xi) SEQUENCE DESCRIPTION: SEQ ID NO: 84:

```
AGCTTCTTCA TCTTTTCCTC AAGCCATTTC ATCTTGTCCT CCATAGCCTT CATCTTTTCT    60

TCC                                                                 63
```

(2) INFORMATION FOR SEQ ID NO: 85:

(i) SEQUENCE CHARACTERISTICS:
       (A) LENGTH: 37 amino acids
       (B) TYPE: amino acid
       (D) TOPOLOGY: linear (ii) MOLECULE TYPE: protein (xi) SEQUENCE DESCRIPTION: SEQ ID NO: 85:

Met Glu Glu Lys Met Lys Lys Leu Glu Glu Lys Met Lys Ala Met Glu
 1               5                  10                  15

Asp Lys Met Lys Trp Leu Glu Glu Lys Met Lys Lys Leu Glu Glu Lys
            20                  25                  30

Met Lys Val Met Lys
        35

(2) INFORMATION FOR SEQ ID NO: 86:

(i) SEQUENCE CHARACTERISTICS:
       (A) LENGTH: 37 amino acids
       (B) TYPE: amino acid
       (D) TOPOLOGY: linear (ii) MOLECULE TYPE: protein (xi) SEQUENCE DESCRIPTION: SEQ ID NO: 86:

Met Glu Glu Lys Met Lys Lys Leu Glu Glu Lys Met Lys Ala Met Glu
 1               5                  10                  15

Asp Lys Met Lys Trp Leu Glu Glu Lys Met Lys Lys Leu Glu Glu Lys
            20                  25                  30

Met Lys Val Met Lys
        35

(2) INFORMATION FOR SEQ ID NO: 87:

(i) SEQUENCE CHARACTERISTICS:
       (A) LENGTH: 62 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: misc_feature
       (B) LOCATION: 1..62
       (D) OTHER INFORMATION: /product= "synthetic
           oligonucletide"
           /standard_name= "SM
           112"

(xi) SEQUENCE DESCRIPTION: SEQ ID NO: 87:

GCTCGAAGAA AGATGAAGGC AATGGAAGAC AAAATGAAGT GGCTTGAGGA GAAAATGAAG    60

AA                                                                  62

(2) INFORMATION FOR SEQ ID NO: 88:

(i) SEQUENCE CHARACTERISTICS:
       (A) LENGTH: 62 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: misc_feature (B) LOCATION: 1..62
            (D) OTHER INFORMATION: /product= "synthetic
                oligonucleotide"
                /standard_name= "SM
                113"

(xi) SEQUENCE DESCRIPTION: SEQ ID NO: 88:

AGCTTCTTCA TTTTCTCCTC AAGCCACTTC ATTTTGTCTT CCATTGCCTT CATCTTTCTT        60

CG                                                                       62

(2) INFORMATION FOR SEQ ID NO: 89:

(i) SEQUENCE CHARACTERISTICS:
        (A) LENGTH: 37 amino acids
        (B) TYPE: amino acid
        (D) TOPOLOGY: linear (ii) MOLECULE TYPE: protein (xi) SEQUENCE DESCRIPTION: SEQ ID NO: 89:

Met Glu Glu Lys Met Lys Lys Leu Lys Glu Met Ala Lys Met Lys
 1               5                  10                  15

Asp Glu Met Trp Lys Leu Lys Glu Glu Met Lys Lys Leu Glu Glu Lys
                20                  25                  30

Met Lys Val Met Lys
        35

(2) INFORMATION FOR SEQ ID NO: 90:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..63
        (D) OTHER INFORMATION: /product= "synthetic
            oligonucleotide"
            /standard_name= "SM
            114"

(xi) SEQUENCE DESCRIPTION: SEQ ID NO: 90:

GCTCAAGGAG GAAATGGCTA AGATGAAAGA CGAAATCTGG AAACTGAAAG AGGAAATGAA        60

GAA                                                                      63

(2) INFORMATION FOR SEQ ID NO: 91:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..63
        (D) OTHER INFORMATION: /product= "synthetic
            oligonucleotide"
            /standard_name= "SM
            115"

(xi) SEQUENCE DESCRIPTION: SEQ ID NO: 91:

```
AGCTTCTTCA TTTCCTCTTT CAGTTTCCAC ATTTCGTCTT TCATCTTAGC CATTTCCTCC    60

TTG                                                                  63
```

(2) INFORMATION FOR SEQ ID NO: 92:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO: 92:

```
Met Glu Glu Lys Met Lys Lys Leu Lys Glu Glu Met Ala Lys Met Lys
 1               5                  10                  15

Asp Glu Met Trp Lys Leu Lys Glu Glu Met Lys Lys Leu Glu Glu Lys
             20                  25                  30

Met Lys Val Met Glu Glu Lys Met Lys Lys Leu Glu Glu Lys Met Lys
         35                  40                  45

Ala Met Glu Asp Lys Met Lys Trp Leu Glu Glu Lys Met Lys Lys Leu
     50                  55                  60

Glu Glu Lys Met Lys Val Met Glu Glu Lys Met Lys Lys Leu Glu Glu
 65                  70                  75                  80

Lys Met Lys Ala Met Glu Asp Lys Met Lys Trp Leu Glu Glu Lys Met
                 85                  90                  95

Lys Lys Leu Glu Glu Lys Met Lys Val Met Lys
            100                 105
```

(2) INFORMATION FOR SEQ ID NO: 93:

(i) SEQUENCE CHARACTERISTICS:
        (A) LENGTH: 839 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 93:

```
GGATCCCCCG GGCTGCAGGA ATTCTACGTA CCATATAGTA AGACTTTGTA TATAAGACGT    60

CACCTCTTAC GTGCATGGTT ATATGTGACA TGTGCAGTGA CGTTGTACCA TATAGTAAG   120

CTTTGTATAT AAGACGTCAC CTCTTACGTG CATGGTTATA TGTGACATGT GCAGTGACG   180

TAACCGCACC CTCCTTCCCG TCGTTTCCCA TCTCTTCCTC CTTTAGAGCT ACCACTATA   240

AAATCAGGGC TCATTTTCTC GCTCCTCACA GGCTCATCAG CACCCCGGCA GTGCCACCC   300

GACTCCCTGC ACCTGCCATG GGTACGCTAG CCCGGGAGAT CTGACAAAGC AGCATTAGT   360

CGTTGATCGG TGGAAGACCA CTCGTCAGTG TTGAGTTGAA TGTTTGATCA ATAAAATAC   420

GCAATGCTGT AAGGGTTGTT TTTTATGCCA TTGATAATAC ACTGTACTGT TCAGTTGTT   480

AACTCTATTT CTTAGCCATG CCAGTGCTTT TCTTATTTTG AATAACATTA CAGCAAAAA   540

TTGAAAGACA AAAAAANNNN NCCCCGAACA GAGTGCTTTG GGTCCCAAGC TTCTTTAGA   600

TGTGTTCGGC GTTCCCCCTA AATTTCTCCC CTATATCTCA CTCACTTGTC ACATCAGCG   660

TCTCTTTCCC CTATATCTCC ACGCTCTACA GCAGTTCCAC CTATATCAAA CCTCTATAC   720

CCACCACAAC AATATTATAT ACTTTCATCT TCACCTAACT CATGTACCTT CCAATTTTT   780

TCTACTAATA ATTATTTACG TGCACAGAAA CTTAGGCAAG GGAGAGAGAG AGCGGTACC   839
```

(2) INFORMATION FOR SEQ ID NO: 94:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 94:

CTAGAAGCCT CGGCAACGTC AGCAACGGCG GAAGAATCCG GTG                43

(2) INFORMATION FOR SEQ ID NO: 95:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 95:

CATGCACCGG ATTCTTCCGC CGTTGCTGAC GTTGCCGAGG CTT                43

(2) INFORMATION FOR SEQ ID NO: 96:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 96:

GATCCCATGG CGCCCCTTAA GTCCACCGCC AGCCTCCCCG TCGCCCGCCG CTCCT    55

(2) INFORMATION FOR SEQ ID NO: 97:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 97:

CTAGAGGAGC GGCGGGCGAC GGGGAGGCTG GCGGTGGACT TAAGGGGCGC CATGG    55

(2) INFORMATION FOR SEQ ID NO: 98:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 98:

CATGGCGCCC ACCGTGATGA TGGCCTCGTC GGCCACCGCC GTCGCTCCGT TCCAGGGGC    59

(2) INFORMATION FOR SEQ ID NO: 99:

(i) SEQUENCE CHARACTERISTICS:
        (A) LENGTH: 59 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 99:

TTAAGCCCCT GGAACGGAGC GACGGCGGTG GCCGACGAGG CCATCATCAC GGTGGGCGC    59

(2) INFORMATION FOR SEQ ID NO: 100:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 100:

GCGCCCACCG TGATGA    16

(2) INFORMATION FOR SEQ ID NO: 101:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 101:

CACCGGATTC TTCCGC    16

(2) INFORMATION FOR SEQ ID NO: 102:

(i) SEQUENCE CHARACTERISTICS:
        (A) LENGTH: 372 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 102:

GTAAGATTGG TAAAGTCCAG CAAGAAAATG AGATAAAAGA GAAGCCTGAA ATGACGAAAA    60

AATCAGGTGT TTTGATTCTT GGTGCTGGAC GTGTGTNTCG CCCAGCTGCT GATTTCCTA    120

CTTCAGTTAG AACCATTTCG TCACAGCAAT GGTACAAAAC ATATTTCGGA GCAGACTCT    180

AAGAGAAAAC AGATGTTCAT GTGATTGTCG CGTCTCTGTA TCTTAAGGAT GCCAAAGAG    240

CGGTTGAAGG TATTTCAGAT GTAGAAGCAG TTCGGCTAGA TGTATCTGAT AGTGAAAGT    300

TCCTTAAGTA TGTTTCTCAG GTTGATGTTG TCCTAAGTTT ATTACCTGCA AGTTGTCAT    360

CTTGTTGTAG CA    372

(2) INFORMATION FOR SEQ ID NO: 103:

(i) SEQUENCE CHARACTERISTICS:
        (A) LENGTH: 323 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 103:

-continued

```
GGAAGCACAC TGCGACTCTT TTGGAATTCG GGGACATCAA GAATGGACAA ACAACAACCG      60

CTATGGCCAA GACTGTTGGG ATCCCTGCAG CCATTGGAGC TCTGCTGTTA ATTGAAGAC      120

AGATCAAGAC AAGAGGAGTC TTAAGGCCTC TCGAAGCAGA GGTGTATTTG CCAGCTTTG      180

ATATATTGCA AGCATATGGT ATAAAGCTGA TGGAGAAGGC AGAATGATCA AGAACTCT       240

TATATTGTTT CTNTCTATAA CTTGGAGTTG GAGACAAAGC TGAAGGAGNC AGNGCCATT      300

GACCAGCAAA AAAAGGAGGA GGA                                             323
```

(2) INFORMATION FOR SEQ ID NO: 104:

(i) SEQUENCE CHARACTERISTICS:
        (A) LENGTH: 123 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 104:

```
Lys Ile Gly Lys Val Gln Gln Glu Asn Glu Ile Lys Glu Lys Pro Glu
1               5                   10                  15

Met Thr Lys Lys Ser Gly Val Leu Ile Leu Gly Ala Gly Arg Val Xaa
            20                  25                  30

Arg Pro Ala Ala Asp Phe Leu Ala Ser Val Arg Thr Ile Ser Ser Gln
        35                  40                  45

Gln Trp Tyr Lys Thr Tyr Phe Gly Ala Asp Ser Glu Glu Lys Thr Asp
    50                  55                  60

Val His Val Ile Val Ala Ser Leu Tyr Leu Lys Asp Ala Lys Glu Thr
65                  70                  75                  80

Val Glu Gly Ile Ser Asp Val Glu Ala Val Arg Leu Asp Val Ser Asp
                85                  90                  95

Ser Glu Ser Leu Leu Lys Tyr Val Ser Gln Val Asp Val Val Leu Ser
            100                 105                 110

Leu Leu Pro Ala Ser Cys His Ala Cys Cys Ser
        115                 120
```

(2) INFORMATION FOR SEQ ID NO: 105:

(i) SEQUENCE CHARACTERISTICS:
        (A) LENGTH: 74 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 105:

```
Lys His Thr Ala Thr Leu Leu Glu Phe Gly Asp Ile Lys Asn Gly Gln
1               5                   10                  15

Thr Thr Thr Ala Met Ala Lys Thr Val Gly Ile Pro Ala Ala Ile Gly
            20                  25                  30

Ala Leu Leu Leu Ile Glu Asp Lys Ile Lys Thr Arg Gly Val Leu Arg
        35                  40                  45

Pro Leu Glu Ala Glu Val Tyr Leu Pro Ala Leu Asp Ile Leu Gln Ala
    50                  55                  60

Tyr Gly Ile Lys Leu Met Glu Lys Ala Glu
65                  70
```

```
-continued (2) INFORMATION FOR SEQ ID NO: 106:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 106:

ATTCCCCATG GTTTCGCCGA CGAAT                                            25

(2) INFORMATION FOR SEQ ID NO: 107:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 107:

CTCTCGGTAC CTAGTACCTA CTGATCAAC                                        29

(2) INFORMATION FOR SEQ ID NO: 108:

(i) SEQUENCE CHARACTERISTICS:
        (A) LENGTH: 56 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 108:

Met Glu Glu Lys Leu Lys Ala Met Glu Glu Lys Leu Lys Ala Met Glu
1               5                   10                  15

Glu Lys Leu Lys Ala Met Glu Glu Lys Leu Lys Ala Met Glu Glu Lys
            20                  25                  30

Leu Lys Ala Met Glu Glu Lys Leu Lys Ala Met Glu Glu Lys Met Lys
        35                  40                  45

Ala Met Glu Glu Lys Met Lys Ala
    50                  55
```